US011344510B2

(12) United States Patent
Kruegel

(10) Patent No.: US 11,344,510 B2
(45) Date of Patent: May 31, 2022

(54) ARYLCYCLOHEXYLAMINE DERIVATIVES AND THEIR USE IN THE TREATMENT OF PSYCHIATRIC DISORDERS

(71) Applicant: Gilgamesh Pharmaceuticals, Inc., New York, NY (US)

(72) Inventor: Andrew Carry Kruegel, Secaucus, NJ (US)

(73) Assignee: Gilgamesh Pharmaceuticals, Inc., New York, NY (US)

( * ) Notice: Subject to any disclaimer, the term of this patent is extended or adjusted under 35 U.S.C. 154(b) by 0 days.

(21) Appl. No.: 17/510,108

(22) Filed: Oct. 25, 2021

(65) Prior Publication Data

US 2022/0041540 A1 Feb. 10, 2022

Related U.S. Application Data

(63) Continuation of application No. PCT/US2020/067235, filed on Dec. 28, 2020.

(60) Provisional application No. 63/093,830, filed on Oct. 20, 2020, provisional application No. 63/037,044, filed on Jun. 10, 2020, provisional application No. 62/953,611, filed on Dec. 26, 2019.

(51) Int. Cl.
*A61K 31/135* (2006.01)
*C07C 225/20* (2006.01)

(52) U.S. Cl.
CPC .......... *A61K 31/135* (2013.01); *C07C 225/20* (2013.01); *C07C 2601/14* (2017.05)

(58) Field of Classification Search
CPC ........................... C07C 225/20; A61K 31/135
See application file for complete search history.

(56) References Cited

U.S. PATENT DOCUMENTS

| 8,288,406 B2 | 10/2012 | Frormann et al. |
| 2012/0095217 A1 | 4/2012 | Ritter et al. |
| 2012/0122948 A1 | 5/2012 | Soubhye et al. |
| 2018/0021326 A1 | 1/2018 | Stamets |
| 2018/0221396 A1 | 8/2018 | Chadeayne |

FOREIGN PATENT DOCUMENTS

| CA | 1100516 A | 5/1981 |
| CA | 1105938 A | 7/1981 |
| CN | 104276993 A | 1/2015 |
| CN | 110343050 A | 10/2019 |
| CN | 112174851 A | 1/2021 |
| CN | 113234036 A | 8/2021 |
| DE | 1668550 A1 | 7/1971 |
| DE | 2723937 A1 | 12/1977 |
| EP | 1956016 A1 | 8/2008 |
| GB | 853775 A | 11/1960 |
| KR | 20190120859 A | 10/2019 |

(Continued)

OTHER PUBLICATIONS

Wang et al, Mol Pharmaceutics 2019 (first published Dec. 27, 2018), vol. 16, pp. 898-906. (Year: 2018).*

(Continued)

*Primary Examiner* — Craig D Ricci
*Assistant Examiner* — Janet L Coppins
(74) *Attorney, Agent, or Firm* — Goodwin Procter LLP

(57) ABSTRACT

Provided herein are arylcyclohexylamine derivatives and their use in the treatment of psychiatric disorders.

2 Claims, 11 Drawing Sheets

(56) References Cited

FOREIGN PATENT DOCUMENTS

| | | |
|---|---|---|
| WO | WO-2004000205 A2 | 12/2003 |
| WO | WO-2004000845 A1 | 12/2003 |
| WO | WO-2004000849 A2 | 12/2003 |
| WO | WO-2004043949 A1 | 5/2004 |
| WO | WO-2004043967 A1 | 5/2004 |
| WO | WO-2005063769 A1 | 7/2005 |
| WO | WO-2007017289 A2 | 2/2007 |
| WO | WO-2008071455 A1 | 6/2008 |
| WO | WO-2010081036 A2 | 7/2010 |
| WO | WO-2010136546 A1 | 12/2010 |
| WO | WO-2012013343 A1 | 2/2012 |
| WO | WO-2018064465 A1 | 4/2018 |
| WO | WO-2019077332 A1 | 4/2019 |
| WO | WO-2019081764 A1 | 5/2019 |
| WO | WO-2019129815 A1 | 7/2019 |
| WO | WO-2019160057 A1 | 8/2019 |
| WO | WO-2019/192602 A1 | 10/2019 |
| WO | WO-2019220139 A1 | 11/2019 |
| WO | WO-2020120539 A1 | 6/2020 |
| WO | WO-2020181194 A1 | 9/2020 |
| WO | WO-2021134086 A1 | 7/2021 |

OTHER PUBLICATIONS

Adamowicz Piotr et al., "Simple and rapid screening procedure for 143 new psychoactive substances by liquid chromatography-tandem mass spectrometry : Simple and rapid screening procedure for 143 new psychoactive substances", Drug Testing and Analysis, vol. 8 (7) 652-667 (2016).

Brandt Simon D. et al., "Analytical chemistry of synthetic routes to psychoactive tryptamines : Part II. Characterisation of the Speeter and Anthony synthetic route to N,N-dialkylated tryptamines using GC-EI-ITMS, ESI-TQ-MS-MS and NMR", Analyst, vol. 130(3) 330 (2005).

Cozzi, Nicholas V, and Paul F Daley. "Receptor binding profiles and quantitative structure-affinity relationships of some 5-substituted-N,N-diallyltryptamines." *Bioorganic & medicinal chemistry letters* vol. 26,3 (2016): 959-964.

Davidsen et al. "Ketamine analogues: Comparative toxicokinetic in vitro-in vivo extrapolation and quantification of 2-fluorodeschloroketamine in forensic blood and hair samples", J. Pharm Biomed Anal. 180:113049 (2020).

Dinger, Julia et al. "Cytochrome P450 inhibition potential of new psychoactive substances of the tryptamine class." Toxicology Letters vol. 241 (2016): 82-94.

Folprechtova et al. "Enantioselective potential of teicoplanin- and vancomycin-based superficially porous particles-packed columns for supercritical fluid chromatography"Journal of Chromatography A, 1612, 460687 (2020).

Han, Yixin et al. "Simple Enantioselective Syntheses of (2R,6R)-Hydroxynorketamine and Related Potential Rapid-Onset Antidepressants." *Organic letters* vol. 19,19 (2017): 5224-5227.

Hägele, JS, Hubner, E-M, Schmid, MG. Determination of the chiral status of different novel psychoactive substance classes by capillary electrophoresis and ß-cyclodextrin derivatives. Chirality. 2020; 32 1191-1207.

Krotulski et al. "Sample Mining and Data Mining: Combined Real-Time and Retrospective Approaches for the Identification of Emerging Novel Psychoactive Substances", Journal of Forensic Sciences 65(2), 550-562 (2020).

Lednicer D, VonVoigtlander PF, Emmert DE "4-Amino-4-arylcyclohexanones and their derivatives, a novel class of analgesics. 1. Modification of the aryl ring" J Med Chem vol. 23(4): 424-30 (1980).

Mestria et al. "Method development for the identification of methoxpropamine, 2-fluoro-deschloroketamine and deschloroketamine and their main metabolites in blood and hair and forensic application", Forensic Sci Int. 323:110817 (2021).

Michely, Julian A et al. "Biotransformation and detectability of the new psychoactive substances N,N-diallyltryptamine (DALT) derivatives 5-fluoro-DALT, 7-methyl-DALT, and 5,6-methylenedioxy-DALT in urine using GC-MS, LC-MSn, and LC-HR-MS/MS." *Analytical and bioanalytical chemistry* vol. 409,6 (2017): 1681-1695.

Michely, Julian A et al. "Dried urine spots—A novel sampling technique for comprehensive LC-MSn drug screening." *Analytica chimica acta* vol. 982 (2017): 112-121.

N-Ethyl-N-methyl-1H-indole-3-ethanamine. Accessed on SciFinder. 1 page.

Pelchowicz, Z. et al. "N-Alkylated 5-fluorotryptamines." Journal of the Chemical Society (1961): 5418-21.

Pelletier et al. "New psychoactive substance cocktail in an intensive care intoxication case elucidated by molecular networking", Clinical Toxicology (2021).

Porpiglia, Nadia et al. "Chiral separation and determination of ketamine and norketamine in hair by capillary electrophoresis." *Forensic science international* vol. 266 (2016): 304-310.

Ryosuke et al. "Studies on generic analytical conditions of illicit drugs using supercritical fluid chromatography-mass spectrometry", Masashi Kanzei Chuo Bunsekishoho, 58, 45-79 (2019).

Schotten et al. "A machine-assisted approach for the preparation of follow-on pharmaceutical compound libraries" Reaction Chemistry & Engineering vol. 3(2), 210-215 (2018).

Shao et al. "Presence of the ketamine analog of 2-fluorodeschloroketamine residues in wastewater" Drug Test Anal. Sep;13(9):1650-1657 (2021).

Soubhye Jalal et al., "Conclusions", Pharmaceutical and Clinical Research, vol. 66(8) 1122-1132 (2014).

Soubhye, Jalal et al. "Hybrid molecules inhibiting myeloperoxidase activity and serotonin reuptake: a possible new approach of major depressive disorders with inflammatory syndrome." *The Journal of pharmacy and pharmacology* vol. 66,8 (2014): 1122-32.

Soubhye, Jalal et al. "Structure-based design, synthesis, and pharmacological evaluation of 3-(aminoalkyl)-5-fluoroindoles as myeloperoxidase inhibitors." *Journal of medicinal chemistry* vol. 53,24 (2010): 8747-59.

Stefanescu, Paul "Syntheses of new indole compounds analogous to bufotenine", Revistade Chimie (Bucharest, Romania), 19(11), 639-42 (1968).

Tang et al. "Emergence of new psychoactive substance 2-fluorodeschloroketamine: Toxicology and urinary analysis in a cluster of patients exposed to ketamine and multiple analogues", Forensic Sci Int. 312:110327 (2020).

Valentin Magne et al., "Synthesis of Spiroindolenines via Regioselective Gold(I)-Catalyzed Cyclizations of N -Propargyl Tryptamines", Advanced Synthesis and Catalysis, vol. 359 (22) 4036-4042 (2017).

Wang et al. "Halogen Substitution Influences Ketamine Metabolism by Cytochrome P450 2B6: In Vitro and Computational Approaches", Mol Pharm 16(2):898-906 (2019).

Wang, Shiyu; Li, Changxi "Synthesis of anesthetic compound 2-(o-fluorophenyl)-2-methylaminocyclohexanone hydrochloride (F-ketamine)", Beijing Daxue Xuebao, Ziran Kexueban (2), 116-19 (1987).

West et al. "Early Warning System for Illicit Drug Use at Large Public Events: Trace Residue Analysis of Discarded Drug Packaging Samples", J Am Soc Mass Spectrom. vol 32(10):2604-2614(2021).

Kuhnz et al., "Predicting the Oral Bioavailability of 19-nortestosterone Progestins in vivo from Their Metabolic Stability in Human Liver Microsomal Preparations in vitro", Drug Metabolism and Disposition, vol. 26 (11) 1120-1127 (1998).

Lipton, Stuart A, "Failures and Successes of NMDA Receptor Antagonists: Molecular Basis for the Use of Open-channel Blockers like Memantine in the Treatment of Acute and Chronic Neurologic Insults", NeuroRx, vol. 1 (1) 101-110 (2004).

Maurer et al., "Current Use of PSMA-PET in Prostate Cancer Management", Nat Rev Urol., vol. 13 (4) 226-235 (2016).

Obach, Scott R, "Prediction of Human Clearance of Twenty-nine Drugs from Hepatic Microsomal Intrinsic Clearance Data: An

(56) References Cited

OTHER PUBLICATIONS

Axamination of in vitro Half-life Approach and Nonspecific Binding to Microsomes", Drug Metab Dispos, vol. 27 (11) 1350-1359 (1999).
Olivares et al., "N-methyl D-aspartate (NMDA) Receptor Antagonists and Memantine Treatment for Alzheimer's Disease, Vascular Dementia and Parkinson's Disease", Curr Alzheimer Res, vol. 9 (6) 746-758 (2012).

\* cited by examiner

ARYLCYCLOHEXYLAMINE DERIVATIVES AND THEIR USE IN THE TREATMENT OF PSYCHIATRIC DISORDERS

RELATED APPLICATIONS

This application is a continuation of International Application No. PCT/US2020/067235, filed Dec. 28, 2020, which claims priority to U.S. Provisional Application No. 62/953,611, filed Dec. 26, 2019; U.S. Provisional Application No. 63/037,044, filed Jun. 10, 2020; and U.S. Provisional Patent Application No. 63/093,830, filed Oct. 20, 2020, each of which are incorporated herein by reference in their entirety.

BACKGROUND

Approximately one third of patients with major depressive disorder (MDD) fail to achieve remission of their symptoms, even after multiple rounds of treatment with several known classes of antidepressants, including selective serotonin reuptake inhibitors (SSRIs) (Rush et al. 2006). This high prevalence of treatment-resistant depression (TRD) makes clear the need for new, more efficacious pharmacotherapies for depression that will target new mechanisms and/or patient populations. In recent years, ketamine, a drug long used as a dissociative anesthetic, has attracted considerable attention for its secondary use as a rapid-acting antidepressant with robust efficacy, even in patients with TRD (Zarate et al. 2006; Berman et al. 2000). The antidepressant effects of the drug are also notable in that they persist for days or weeks after a single administration. Importantly, the S enantiomer of ketamine (S-ket) has recently been approved by the United States Food and Drug Administration as a treatment for depression Unfortunately, the potent dissociative anesthetic effects of ketamine and S-ket make these drugs attractive to recreational drug users and limit the broad clinical utility of these compounds by restricting their use to circumstances under the direct supervision of a medical provider. Given that the primary molecular target of ketamine is the N-methyl-D-aspartate receptor (NMDAR), inhibition of which is responsible for the drugs anesthetic effects, many have proposed that inhibition of this target is also responsible for the antidepressant effects of ketamine. Such a mechanism suggests that the antidepressant effects and dissociative effects of ketamine might be inseparable at the mechanistic level. However, a number of lines of evidence question this hypothesis (Aleksandrova et al. 2017). First, the R enantiomer of ketamine (R-ket), has been found to be more efficacious and longer lasting as an antidepressant in rodent models than S-ket, despite the fact that R-ket has a weaker binding affinity for NMDAR than S-ket (Zhang et al. 2014). Similarly, the ketamine metabolite (2R,6R)-hydroxynorketamine (HNK) has been shown to induce antidepressant effects in rodent models, but only weakly binds NMDAR and does not engage this receptor in vivo at dose levels that induce antidepressant effects (Zanos et al. 2016; Lumsden et al. 2019; Morris et al. 2017). Accordingly, both R-ket and HNK may induce antidepressant effects while limiting the dissociative effects of ketamine However, other strategies proposed to attenuate the dissociative effects of ketamine, for example, by targeting the NR2B subunit of NMDAR or utilizing a compound with low-trapping properties, have met with poor results. For example, a number of such structurally distinct NMDAR antagonists (e.g. memantine, MK-0657, and lanicemine), although in some cases reducing dissociation, have been found to be less efficacious and/or shorter acting than ketamine in treating depression (Zanos et al. 2016; Qu et al. 2017; Cerecor 2019; Kadriu et al. 2019; Lepow et al. 2017). Likewise, agonists with higher affinity for NMDAR (e.g. MK-801) or targeting alternative binding sites on the channel (e.g. rapastinel), have also met with failure (Yang et al. 2016; Al Idrus 2019). Accordingly, the precise molecular mechanisms underpinning the antidepressant effects of ketamine remain poorly understood and may involve other as-yet-unidentified targets. Further, the antidepressant effects of NMDAR modulators and the magnitude of their concomitant dissociative effects are in general highly unpredictable. At the same time, these findings have raised the exciting possibility that the antidepressant effects of ketamine might in fact be separable from its dissociative anesthetic effects.

In addition to its dissociative side effects, the use of ketamine for depression treatment is further limited by the drug's poor oral bioavailability (Clements et al. 1982). Accordingly, for the treatment of MDD, ketamine is used almost entirely by the intravenous (i.v.) route. The practical challenges of i.v. administration further necessitate the use of ketamine under the supervision of a medical provider in a clinic or hospital setting. The inability to use ketamine by an oral route of administration is thus a major shortcoming that has limited the drug's broad adoption and increased medical costs associated with its use. Although other NMDAR antagonists have been developed that are orally bioavailable, to date none have reached the market, nor have they demonstrated the robust clinical efficacy of ketamine as an antidepressant. Therefore, there remains an acute need for novel antidepressants of the ketamine class that possess robust efficacy, decreased dissociative side effects, and increased oral bioavailability. A drug that retained the antidepressant activity of ketamine while also decreasing its dissociative effects and increasing oral bioavailability would provide a treatment option that was simpler to administer and potentially viable for at home use by virtue of its reduced dissociative effects and concomitant reduced abuse potential.

SUMMARY OF THE INVENTION

The present disclosure, at least in part, provides arylcyclohexylamine compounds and compositions of single enantiomers or enantiomerically enriched mixtures of arylcyclohexylamines having significantly higher oral bioavailability, higher antidepressant potency, and/or greater therapeutic index between antidepressant effects and side effects, compared to ketamine.

For example, the disclosure provides for compounds having increased oral bioavailability, e.g., by having structural components that provide increased resistance to hepatic metabolism as compared to ketamine. This can be seen, for example, in their greater stability in both rodent and human liver microsome preparations. Importantly, despite such increases in oral bioavailability, disclosed compounds retain substantially short half-lives, in contrast to the more typical observation that increased hepatic stability may result in slow clearance. A short half-life may be desirable since therapeutic efficacy of such compounds may not depend on sustained receptor occupancy. Instead, pulsatile engagement of NMDAR (or other) signaling may be sufficient to induce therapeutic effects that last well beyond (days or weeks) the elimination of the drug (hours), thereby limiting overall exposure and reducing the duration of any dissociative or other negative side effects. Further, in some embodiments, provided herein are compounds with increased antidepressant potency as a secondary effect of increased exposure, particularly after oral dosing and while retaining the high brain permeability of ketamine Such compounds may be more potent as antidepressants even in cases where the in vitro affinity at NMDAR is similar to or lower than that of ketamine. Further, compounds provided herein may exhibit increased therapeutic index between antidepressant effects and dissociative side effects, as a consequence of NMDAR binding affinity of ~1-5 μM, as determined though displacement of the radioligand [$^3$H]MK-801 from NMDAR-containing membranes isolated from rat cortex. In certain embodiments, this affinity range may be useful in balancing the antidepressant efficacy and side effects, likely due to the rapid off kinetics of such compounds. For example, compounds with too high an affinity at NMDAR (<1 μM), for example racemic ketamine and S-ket, exhibit pronounced dissociative effects that restrict their use to physician-supervised settings and increase their abuse liability. Further, high affinity at NMDAR may also decrease therapeutic efficacy in depression (e.g., both MK-801 and S-ket appear to exhibit weaker and less durable antidepressant effects than racemic ketamine and R-ket, which have lower affinities). In contrast, compounds with too low an affinity at NMDAR (>5 μM) may lose antidepressant efficacy, even when doses are appropriately scaled to account for such lower affinity. Further, even if efficacious, the very high doses required with such low potency compounds may exacerbate toxicological challenges or result in the introduction of undesirable off targets (as selectivity over other weak binding partners decreases).

In one aspect, provided herein is a compound having the general structure (I):

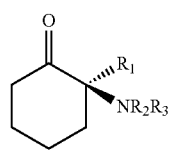

(I)

wherein R1 is selected from the group consisting of phenyl, optionally substituted thiazole, optionally substituted thiophene, optionally substituted pyridine, a moiety of general formula (II);

wherein when R1 is phenyl then R2 and R3 are independently selected from H, CD3, branched or cyclo C3 alkyl, C4-C10 alkyl, C2-C10 halo-alkyl, —R$_4$—O—R$_5$; wherein R4 is a C2-C10 alkylene and R5 is selected from H and C1-C10 alkyl; wherein D represents a deuterium-enriched —H site; provided that one or more of R2 and R3 is different than H; or R2 and R3 are independently selected from C2-C10 alkyl; C2-C10 halo-alkyl, —R$_4$—O—R$_5$; wherein R4 is a C2-C10 alkylene and R5 is selected from H and C1-C10 alkyl; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms;

wherein when R1 is a moiety of general formula (II):

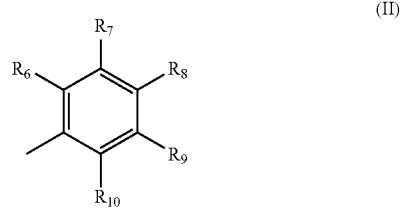

(II)

R2 and R3 are independently selected from H, C1-C10 alkyl, C2-C10 halo-alkyl, —R$_4$—O—R$_5$; wherein R4 is a C2-C10 alkylene and R5 is selected from H and C1-C10 alkyl; provided that one or more of R2 and R3 is different than H; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms; and wherein R6, R7, R8, R9 and R10 are independently selected from H, OH, halogen (selected from F, Cl, Br, I), —OR11, C1-C10 alkyl, C2-C10 alkenyl, C2-C10 alkynyl, CN, CF$_3$, OCF$_3$, NO$_2$, —NR12R13, —SR14, —SO$_2$R15, —CO$_2$R16, —C(=O)NR17R18; wherein R11, R12, R13, R14, R15, R16, R17 and R18 are each independently selected from H, C1-C10 alkyl, C2-C10 alkenyl, C2-C10 alkynyl, aryl, heteroaryl, —C(=O)H, —C(=O)alkyl, —C(=O)aryl, —C(=O)heteroaryl;

provided that one or more of R6-R10 is different than H; or provided that when R6 is C1 and R7-R10 are H or when R7 is C1 and R6, R8-R10 are H, and R2 or R3 is H, then the other of R2 or R3 is C3-C10 alkyl, C2-C10 halo-alkyl, or —R$_4$—O—R$_5$; or provided that when R7 is OH and R6, R8-R10 are H, and R2 or R3 is H, then the other of R2 or R3 is straight or branched C3-C10 alkyl, C2-C10 halo-alkyl, or —R$_4$—O—R$_5$; or provided that when R6, R7, or R8 is OMe and the other of R6-R10 are each H, and R2 or R3 is H, then the other of R2 or R3 is C3-C10 alkyl, C2-C10 halo-alkyl, or —R$_4$—O—R$_5$;

wherein when R1 is selected from thiazole, thiophene, pyridine, each optionally substituted with one or more OH, halogen (selected from F, Cl, Br, I), —OR19, C1-C10 alkyl, C2-C10 alkenyl, C2-C10 alkynyl, CN, CF$_3$, OCF$_3$, NO$_2$, —NR2OR21, —SR22, —SO$_2$R23, —CO$_2$R24, —C(=O)NR25R26; wherein R19, R20, R21, R22, R23, R24, R25 and R26 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl;

R2 and R3 are independently selected from H, C1-C10 alkyl, C2-C10 halo-alkyl, C2-C10 alkenyl, C2-C10 alkynyl, —R$_4$—O—R$_5$; wherein R4 is a C2-C10 alkylene and R5 is selected from H and C1-C10 alkyl; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms.

In some embodiments, a compound provided herein has the general structure (Ia):

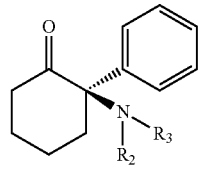

(Ia)

wherein R2 and R3 are independently selected from H, branched or cyclo C3 alkyl, C4-C10 alkyl, C2-C10 halo-alkyl, —R$_4$—O—R$_5$; wherein R4 is a C2-C10 alkylene and R5 is selected from H and C1-C10 alkyl; provided that one or more of R2 and R3 is different than H; or R2 and R3 are independently selected from C2-C10 alkyl, C2-C10 halo-alkyl, —R$_4$—O—R$_5$;
wherein R4 is a C2-C10 alkylene and R5 is selected from H and C1-C10 alkyl; or R2 and R3 together with the nitrogen ring they are connected to form a C3-C9 cycloheteroalkyl ring; said ring optionally substituted by one or more C1-C10 alkyl or interrupted by one or more additional nitrogen or oxygen atoms.

In some embodiments, a compound provided herein has the general structure (Ib):

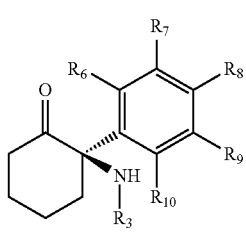

(Ib)

wherein R3 is a C1-C10 alkyl, C2-C10 halo-alkyl, or —R$_4$—O—R$_5$; wherein R4 is a C2-C10 alkylene and R5 is selected from H and C1-C10 alkyl; and wherein R6, R7, R8, R9 and R10 are independently selected from H, OH, halogen (selected from F, Cl, Br, I), —OR11, C1-C10 alkyl, C2-C10 alkenyl, C2-C10 alkynyl, CN, CF$_3$, OCF$_3$, NO$_2$, —NR12R13, —SR14, —SO$_2$R15, —CO$_2$R16, —C(=O)NR17R18; wherein R11, R12, R13, R14, R15, R16, R17 and R18 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl, provided that one or more of R6-R10 is different than H; or provided that when R6 is Cl and R7-R10 are H or when R7 is Cl and R6, R8-R10 are H, then R3 is C3-C10 alkyl, C2-C10 halo-alkyl, or —R$_4$—O—R$_5$; or provided that when R7 is OH and R6, R8-R10 is H, then R3 is C3-C10 alkyl, C2-C10 halo-alkyl, or —R$_4$—O—R$_5$; or provided that when R6, R7, or R8 is OMe, and the other of R6-R10 are H, then R3 is C3-C10 alkyl, C2-C10 halo-alkyl, or —R$_4$—O—R$_5$.

In some embodiments, a compound provided herein has the general structure (I), wherein R1 is selected from thiazole, thiophene, pyridine; each optionally substituted with one or more OH, halogen (selected from F, Cl, Br, I), —OR19, C1-C10 alkyl, C2-C10 alkenyl, C2-C10 alkynyl, CN, CF$_3$, OCF$_3$, NO$_2$, —NR20R21, —SR22, —SO$_2$R23, —CO$_2$R24, —C(=O)NR25R26; wherein R19, R20, R21, R22, R23, R24, R25 and R26 are each independently selected from H, C1-C10 alkyl, C2-C10 alkenyl, C2-C10 alkynyl, aryl, heteroaryl, C(=O)H, C(=O)alkyl, C(=O) aryl, C(=O)heteroaryl; R2 and R3 are independently selected from H, C1-C10 alkyl, C2-C10 halo-alkyl, C2-C10 alkenyl, C2-C10 alkynyl, —R$_4$—O—R$_5$; wherein R4 is a C2-C10 alkylene and R5 is selected from H and C1-C10 alkyl; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms.

In some embodiments, a compound provided herein has the general structure (Ia):

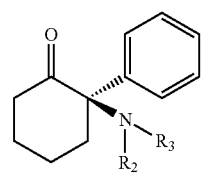

(Ia)

wherein R2 and R3 are independently selected from H, branched or cyclo C3 alkyl, C4-C10 alkyl, C2-C10 halo-alkyl, —R$_4$—O—R$_5$; wherein R4 is a C2-C10 alkylene and R5 is selected from H and C1-C10 alkyl; provided that at least one of R2 and R3 is different than H.

In some embodiments, a compound provided herein has the general structure (Ia):

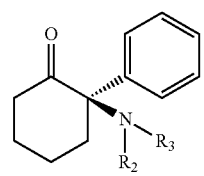

(Ia)

wherein R2 and R3 are independently selected from C2-C10 alkyl, C2-C10 halo-alkyl, —R$_4$—O—R$_5$; wherein R4 is a C2-C10 alkylene and R5 is selected from H and C1-C10 alkyl.

In some embodiments, a compound provided herein has the general structure (Ia):

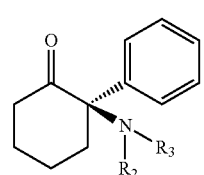

(Ia)

wherein R2 and R3 together with the nitrogen ring they are attached to form a C3-C9 cycloheteroalkyl ring; said ring optionally substituted by one or more C1-C10 alkyl or interrupted by one or more additional nitrogen or oxygen atoms.

In some embodiments, a compound provided herein has the general structure (Ia):

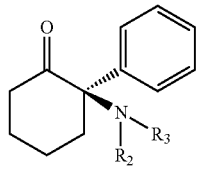
(Ia)

wherein R2 is H and R3 is selected from branched or cyclo C3 alkyl, C4-C5 alkyl, C2-C5 fluoro-alkyl, —R$_4$—O—R$_5$; wherein R4 is a C2-C5 alkylene and R5 is selected from H and C1-C5 alkyl.

In some embodiments, a compound provided herein has the general structure (Ia):

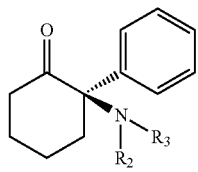
(Ia)

wherein R2 and R3 are independently selected from C2-C5 alkyl, C2-C5 fluoro-alkyl, —R$_4$—O—R$_5$; wherein R4 is a C2-C5 alkylene and R5 is selected from H and C1-C5 alkyl.

In some embodiments, a compound provided herein has the general structure (Ia):

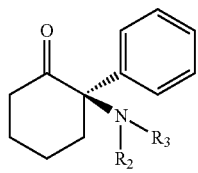
(Ia)

wherein R2 and R3 together with the nitrogen ring they are attached to form a C3-C6 cycloheteroalkyl ring; said ring optionally substituted by one or more C1-C2 alkyl or interrupted by one or more additional nitrogen or oxygen atoms.

In some embodiments, a compound provided herein has the general structure (Ib):

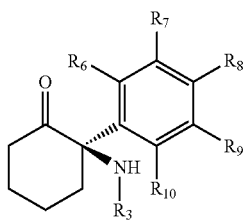
(Ib)

wherein one or more of R6, R7, R8, R9 and R10 is OH, R3 is selected from C1-C10 alkyl, C2 C10 halo-alkyl, —R$_4$—O—R$_5$; wherein R4 is a C2-C10 alkylene and R5 is selected from H and C1-C10 alkyl; provided that when R7 is OH, and R6, R8-R10 are H, then R3 is C3-C10 alkyl.

In some embodiments, a compound provided herein has the general structure (Ib):

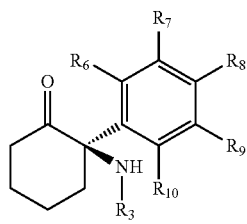
(Ib)

wherein one or more of R6, R7, R8, R9 and R10 is halogen (selected from F, Cl, Br, I), R3 is selected from C1-C10 alkyl, C2-C10 halo-alkyl, —R$_4$—O—R$_5$; wherein R4 is a C2-C10 alkylene and R5 is selected from H and C1-C10 alkyl; provided that when R6 is Cl and R7-R10 are H or when R7 is Cl and R6, R8-R10 are H, then R3 is C3-C10 alkyl.

In some embodiments, a compound provided herein has the general structure (Ib):

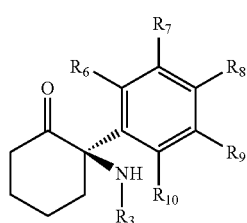
(Ib)

wherein one or more of R6, R7, R8, R9 and R10 is OMe, R3 is selected from C1-C10 alkyl, C2-C10 halo-alkyl, —R$_4$—O—R$_5$; wherein R4 is a C2-C10 alkylene and R5 is selected from H and C1-C10 alkyl; provided that when R6, R7 or R8 is OMe and the other of R6-R10 are H, then R3 is C3-C10 alkyl.

In some embodiments, a compound provided herein has the general structure (Ib):

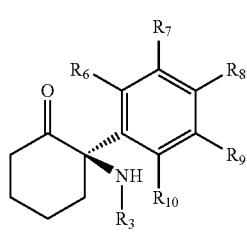
(Ib)

wherein one or more of R6, R7, R8, R9 and R10 is F, R3 is selected from C1-C10 alkyl, C2-C10 halo-alkyl, —R$_4$—O—R$_5$; wherein R4 is a C2-C10 alkylene and R5 is selected from H and C1-C10 alkyl.

In some embodiments, a compound provided herein has the general structure (Ib):

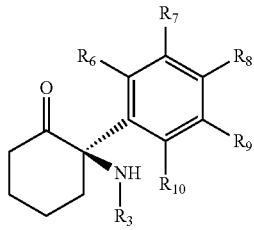
(Ib)

wherein one or more of R6, R7, R8, R9 and R10 is Me, R3 is selected from C1-C10 alkyl, C2-C10 halo-alkyl, —R4—O—R5; wherein R4 is a C2-C10 alkylene and R5 is selected from H and C1-C10 alkyl.

In some embodiments, a compound provided herein has the general structure (Ib):

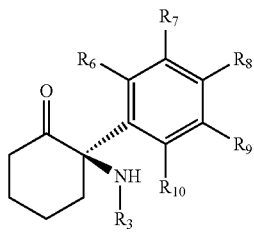
(Ib)

wherein one or more of R6, R7, R8, R9 and R10 is OH, R3 is selected from C1-C5 alkyl, C2-C5 fluoro-alkyl, —R4—O—R5; wherein R4 is a C2-C5 alkylene and R5 is selected from H and C1-C5 alkyl; provided that when R7 is OH, and R6, R8-R10 are H, then R3 is C3-C5 alkyl.

In some embodiments a compound provided herein has the general structure (Ib):

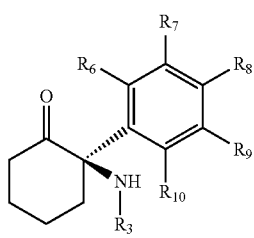
(Ib)

wherein one or more of R6, R7, R8, R9 and R10 is OMe, R3 is selected from C1-C5 alkyl, C2-C5 fluoro-alkyl, —R4—O—R5; wherein R4 is a C2-C5 alkylene and R5 is selected from H and C1-C5 alkyl; provided that when R6, R7 or R8 is OMe and the other of R6-R10 are H, then R3 is C3-C5 alkyl.

In some embodiments, a compound provided herein has the general structure (Ib):

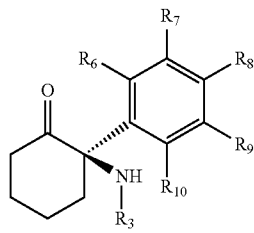
(Ib)

wherein one or more of R6, R7, R8, R9 and R10 is F, R3 is selected from C1-C5 alkyl, C2-C5 fluoro-alkyl, —R4—O—R5; wherein R4 is a C2-C5 alkylene and R5 is selected from H and C1-C5 alkyl.

In some embodiments, a compound provided herein has the general structure (Ib):

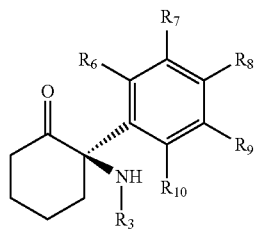
(Ib)

wherein one or more of R6, R7, R8, R9 and R10 is Me, R3 is selected from C1-C5 alkyl, C2-C5 fluoro-alkyl, —R4—O—R5; wherein R4 is a C2-C5 alkylene and R5 is selected from H and C1-C5 alkyl.

In some embodiments, a compound provided herein has the general structure (Ic):

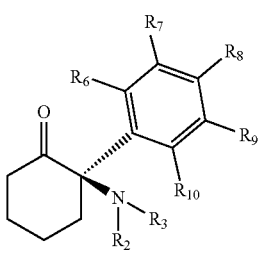
(Ic)

wherein one or more of R6, R7, R8, R9 and R10 is OH, R2 and R3 are independently selected from C1-C5 alkyl, C2-C5 fluoro-alkyl, —R4—O—R5; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, a compound provided herein has the general structure (Ic):

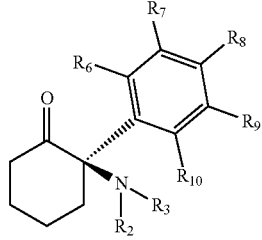
(Ic)

wherein one or more of R6, R7, R8, R9 and R10 is OMe, R2 and R3 are independently selected from C1-C5 alkyl, C2-C5 fluoro-alkyl, —$R_4$—O—$R_5$; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, a compound provided herein has the general structure (Ic):

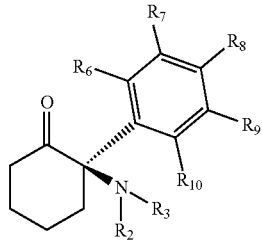
(Ic)

wherein one or more of R6, R7, R8, R9 and R10 is F, R2 and R3 are independently selected from C1-C5 alkyl, C2-C5 fluoro-alkyl, —$R_4$—O—$R_5$; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, a compound provided herein has the general structure (Ic):

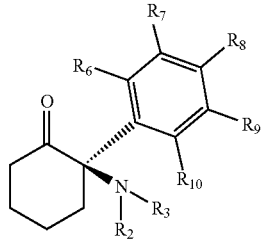
(Ic)

wherein one or more of R6, R7, R8, R9 and R10 is Me, R2 and R3 are independently selected from C1-C5 alkyl, C2-C5 fluoro-alkyl, —$R_4$—O—$R_5$; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, a compound provided herein is selected from:

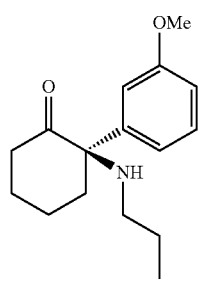
15R

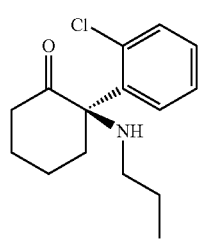
16R

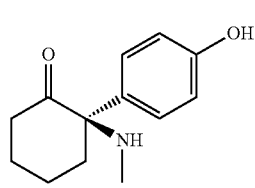
17R

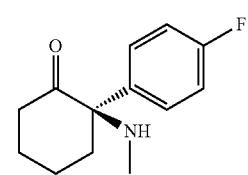
18R

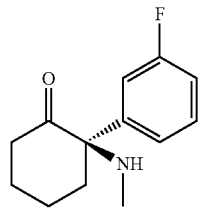
19R

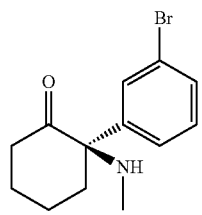
20R

| | | |
|---|---|---|
| 21R | 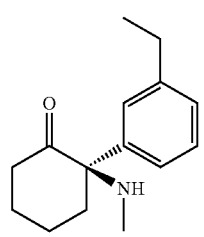 | 28R 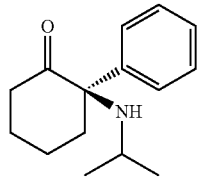 |
| 22R | 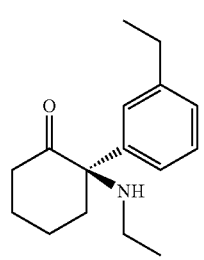 | 29R 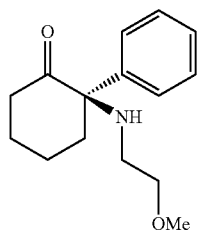 |
| 23R | 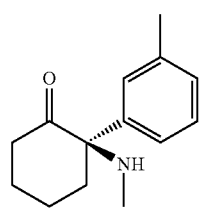 | 30R 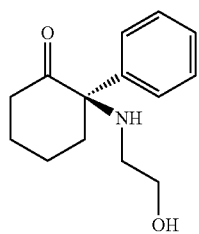 |
| 24R | 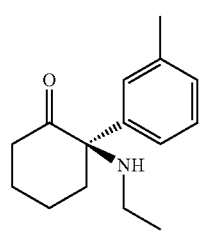 | 31R 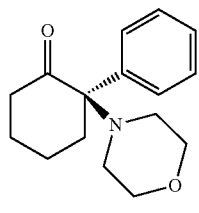 |
| 25R | 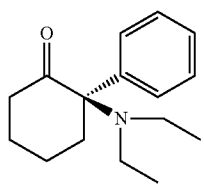 | 32R 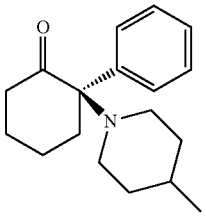 |
| 26R | 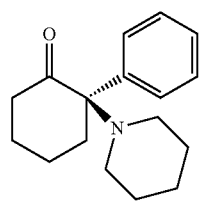 | 33R 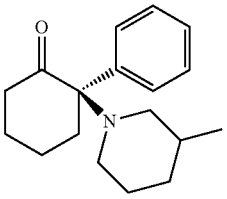 |
| 27R | 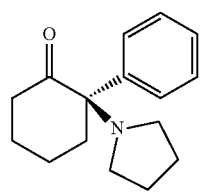 | 34R 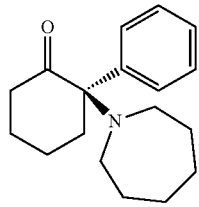 |

-continued
35R 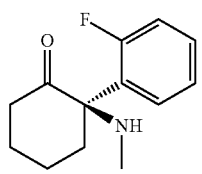
36R 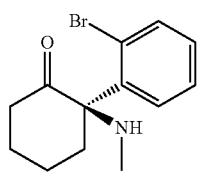
37R 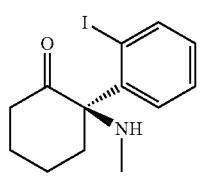
38R 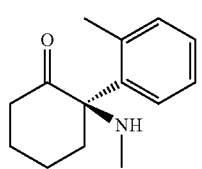
39R 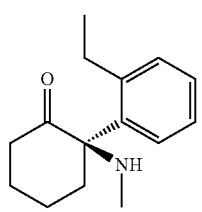
42R 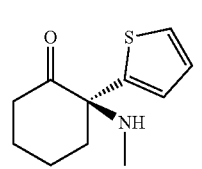
43R 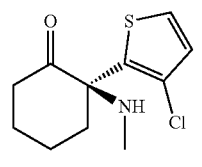
44R 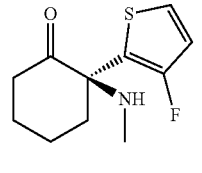
45R 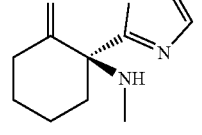
-continued
46R 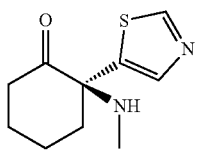
47R 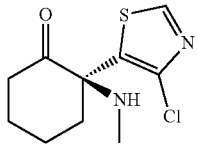
48R 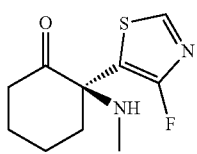
49R 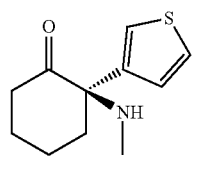
50R 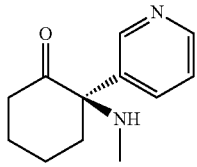
51R 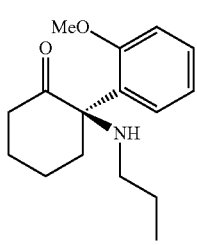
54R 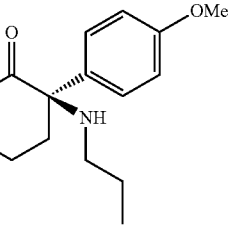
77R 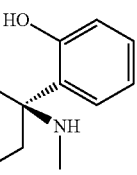

-continued
82R 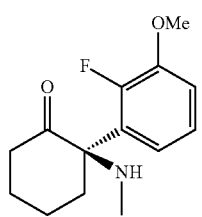
83R 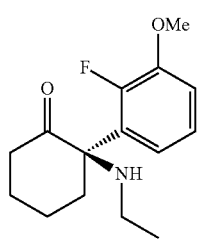
84R 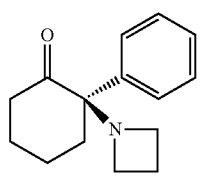
85R 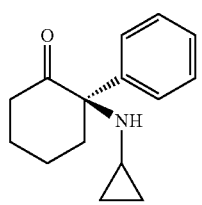
86R 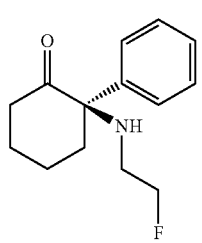
or a pharmaceutically acceptable salt or ester thereof.
In some embodiments, a compound provided herein is selected from:
38R 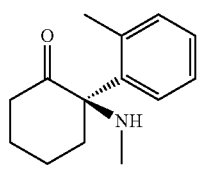
77R 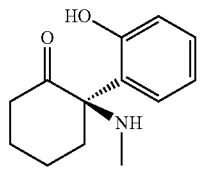
-continued
19R 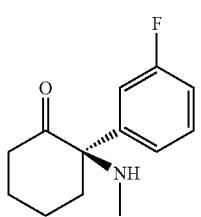
26R 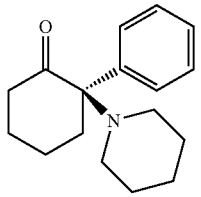
27R 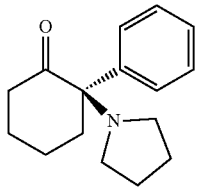
85R 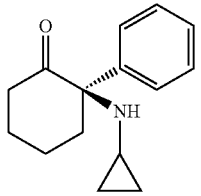
86R 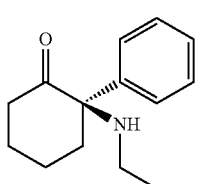
29R 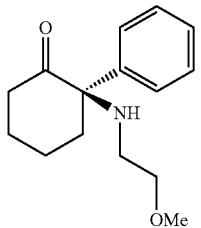
30R 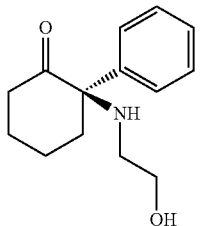

-continued

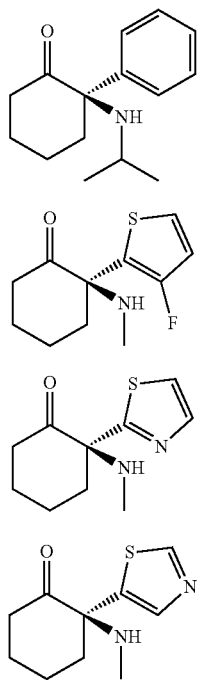

28R

44R

45R

46R

In another aspect, provided herein are compositions comprising a carrier and a compound having the structure:

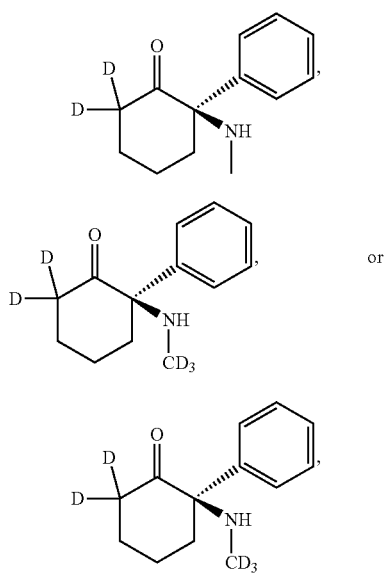

87R 88R, or

92R wherein D represents a deuterium-enriched H-site.

In some embodiments, each D represents a deuterium-enriched —H site and the level of deuterium at each deuterium-enriched —H site of the compound is 0.02% to 100%. In some embodiments, each D represents a deuterium-enriched —H site and the level of deuterium at each deuterium-enriched —H site of the compound is 20%-100%, 50%-100%, 70%-100%, 90%-100%, 97%-100%, or 99%-100%.

In another aspect, provided herein is a compound having the general structure (III):

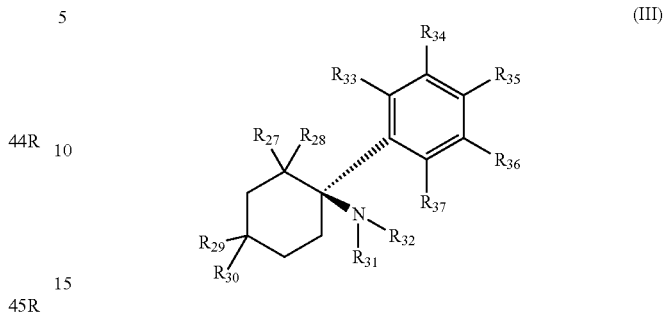

(III)

wherein R31 and R32 are each H, C1-C10 alkyl, C2-C10 halo-alkyl, —R38-O—R39; wherein R38 is a C2-C10 alkylene and R39 is selected from H and C1-C10 alkyl; or R31 and R32 together with the nitrogen atom they are attached to form a C3-C6 cycloheteroalkyl ring; said ring optionally substituted by one or more straight or branched C1-C10 alkyl or interrupted by one or more additional nitrogen or oxygen atoms; and wherein R27, R28, R29, R30 are each independently selected from H, straight or branched C1-C10 alkyl, F, or R27 and R28 or R29 and R30 together with the carbon atom they are attached to form a cycloalkyl ring or together with the carbon they are attached to and one or more heteroatoms form a cycloheteroalkyl ring; and wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(=O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl; provided that at least one of R27, R28, R29, or R30 is different than H; or provided that when one of R27 and R28 is Me and the other of R27 and R28 is H, then R32 is C2-C10 alkyl, C2-C10 halo-alkyl, or —R$_{38}$—O—R$_{39}$.

In some embodiments a compound provided herein has the general structure (III):

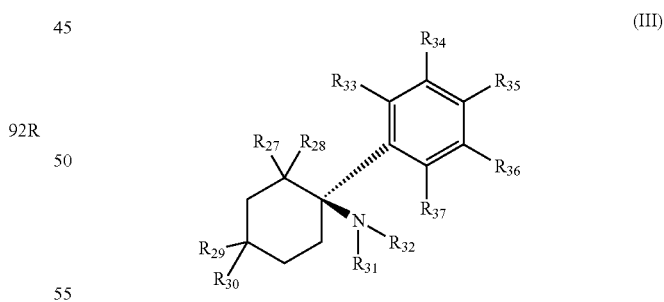

(III)

wherein R31 and R32 are each H, C1-C10 alkyl, C2-C10 halo-alkyl, —R$_{38}$—O—R$_{39}$; wherein R38 is a C2-C10 alkylene and R39 is selected from H and C1-C10 alkyl; or R31 and R32 together with the nitrogen atom they are attached to form a C3-C6 cycloheteroalkyl ring; said ring optionally substituted by one or more straight or branched C1-C2 alkyl or interrupted by one or more additional nitrogen or oxygen atoms; and wherein R27 and R28 are fluorine and R29 and R30 are H; and wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(=O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl.

In some embodiments, a compound provided herein has the general structure (III):

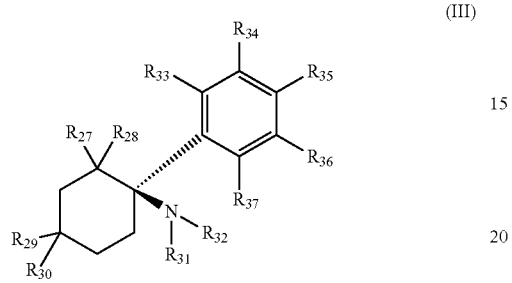

(III)

wherein R31 and R32 are each H, C1-C10 alkyl, C2-C10 halo-alkyl, —R38-O—R39; wherein R38 is a C2-C10 alkylene and R39 is selected from H and C1-C10 alkyl; or R31 and R32 together with the nitrogen atom they are attached to form a C3-C6 cycloheteroalkyl ring; said ring optionally substituted by one or more straight or branched C1-C2 alkyl or interrupted by one or more additional nitrogen or oxygen atoms; and wherein R27 and R28 together with the carbon they are attached to and an oxygen atom form an oxetane ring; and wherein R29 and R30 are H; and wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(=O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl.

In some embodiments, a compound provided herein is selected from:

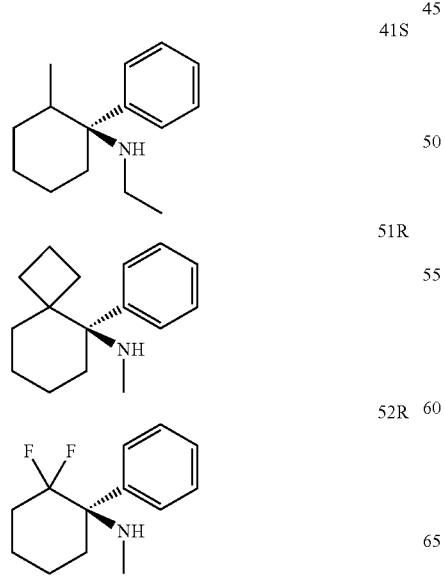

41S

51R

52R

-continued

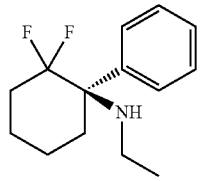

70R

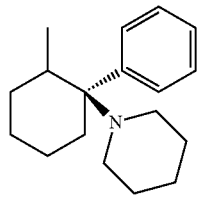

71R

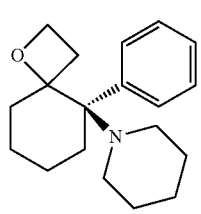

72R

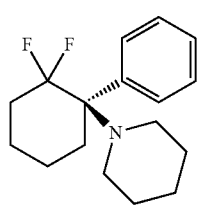

73R

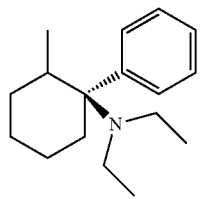

74R

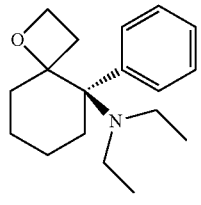

75R

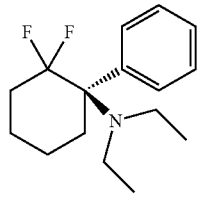

76R

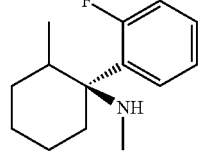

57S

58R 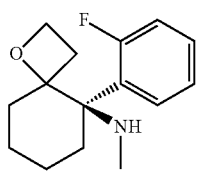

59R 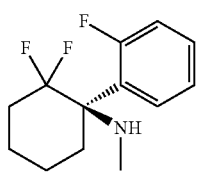

60S 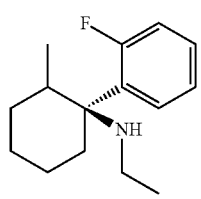

61R 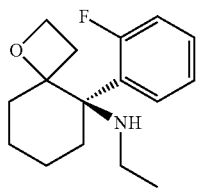

62 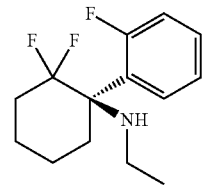

63S 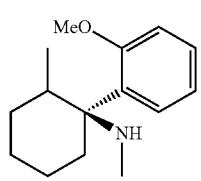

64R 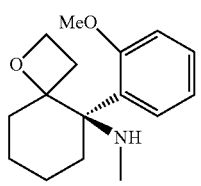

65R 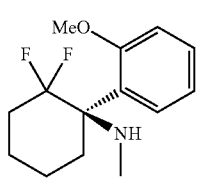

66S 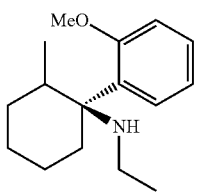

67R 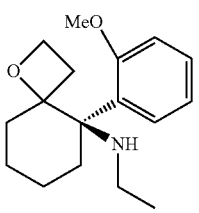

68R 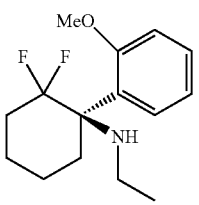

69R 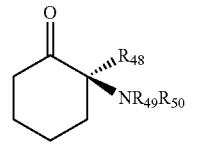

In another aspect, provided herein is a pharmaceutical composition comprising one or more compound. In some embodiments, a composition described herein (e.g., a pharmaceutical composition) is an oral composition.

In another aspect, provided herein is a method of treating depression, a mood disorder, an anxiety disorder, or a substance use disorder and any symptom or disorders associated therewith in a subject in need thereof, the method generally comprising administering to the subject a compound of structure (IV):

(IV)

wherein R48 is selected from the group consisting of: phenyl, thiazole, thiophene, pyridine, or a moiety of general formula (V);

(V)

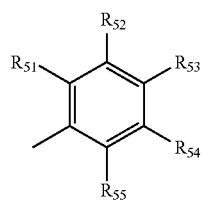

wherein R51, R52, R53, R54 and R55 are each independently selected from H, OH, halogen (selected from F, Cl, Br, I), OMe, C1-C10 alkyl; R49 and R50 are each independently selected from H and C1-C10 alkyl; or R49 and R50 together with the nitrogen atom they are connected to from a C3-C9 cycloheteroalkyl ring optionally substituted with one or more C1-C10 alkyl, provided that when R51 is Cl and R52-R55 are H, and R49 or R50 is H, then the other of R49 or R50 is C2-C10 alkyl.

In some embodiments, a compound provided herein is selected from:

1R

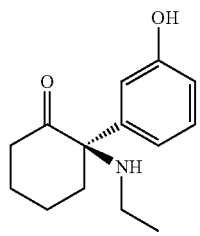

2R

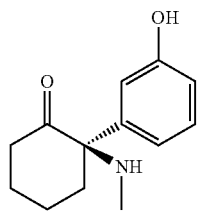

3R

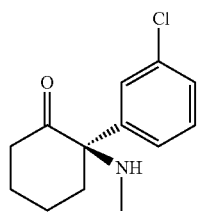

4R

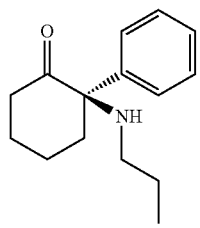

5R

6R

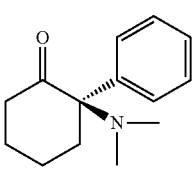

7R

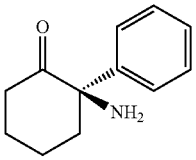

8R

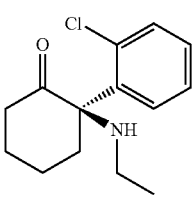

9R

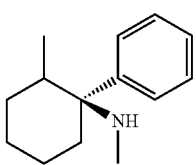

10R

11R

12R

13S

14R

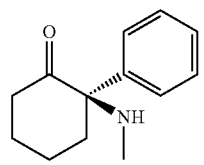

55R

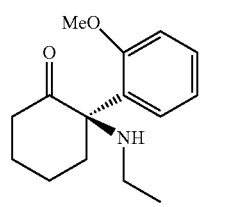

56R

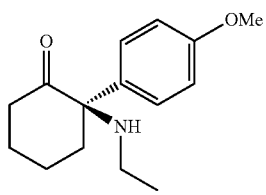

78R

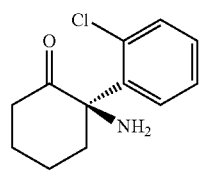

In some embodiments, a compound provided herein is selected from:

14R

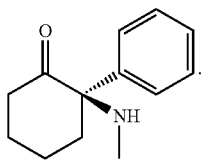

In another aspect, provided herein is method of treating depression, a mood disorder, an anxiety disorder, or a substance use disorder and any symptom or disorders associated therewith in a subject in need thereof, the method generally comprising administering to the subject the compound:

13R

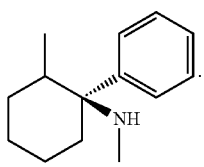

In another aspect, provided herein is a composition comprising a compound having the general structure (VI):

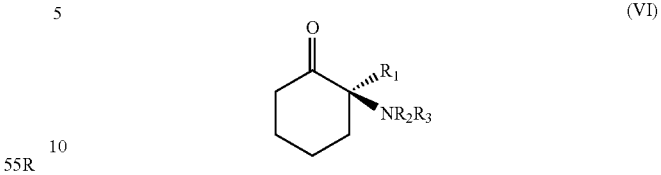

wherein R1 is selected from the group consisting of phenyl, optionally substituted thiazole, optionally substituted thiophene, optionally substituted pyridine, a moiety of general formula (VII);

wherein when R1 is phenyl;

R2 and R3 are independently selected from H, CD3, branched or cyclo C3 alkyl, C4-C10 alkyl, C2-C10 haloalkyl, —R4—O—R5; wherein R4 is a C2-C10 alkylene and R5 is selected from H and C1-C10 alkyl; wherein D represents a deuterium-enriched —H site; and wherein at least one of R2 and R3 is other than H; or R2 and R3 are independently selected from C2-C10 alkyl; C2-C10 halo-alkyl, —R4—O—R5; wherein R4 is a C2-C10 alkylene and R5 is selected from H and C1-C10 alkyl; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms;

wherein when R1 is a moiety of general formula (VII):

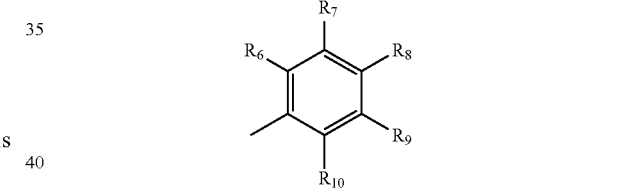

R2 and R3 are independently selected from H, C1-C10 alkyl, C2-C10 halo-alkyl, —R4—O—R5;

wherein R4 is a C2-C10 alkylene and R5 is selected from H and C1-C10 alkyl; and wherein at least one of R2 and R3 is other than H; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms; and R6, R7, R8, R9 and R10 are independently selected from H, OH, halogen (selected from F, Cl, Br, I), —OR11, C1-C10 alkyl, C2-C10 alkenyl, C2-C10 alkynyl, CN, CF3, OCF3, NO2, —NR12R13, —SR14, —SO2R15, —CO2R16, —C(=O)NR17R18; wherein R11, R12, R13, R14, R15, R16, R17 and R18 are each independently selected from H, C1-C10 alkyl, C2-C10 alkenyl, C2-C10 alkynyl, aryl, heteroaryl, —C(=O)H, —C(=O)alkyl, —C(=O)aryl, —C(=O)heteroaryl; wherein at least one of R6-R10 is other than H; and wherein neither R6 nor R10 is halogen; provided that when R7 is Cl and R6, R8-R10 are H, and R2 or R3 is H, then the other of R2 or R3 is C3-C10 alkyl, C2-C10 halo-alkyl, or —R4—O—R5; or provided that when R7 is OH and R6, R8-R10 are H, and R2 or R3 is H, then the other of R2 or R3 is C3-C10 alkyl, C2-C10 halo-alkyl, or —R4—O—R5; or provided that when R6, R7, or R8 is OMe and the other of R6-R10 are each H, and R2 or R3 is H, then the other of R2 or R3 is C3-C10 alkyl, C2-C10 halo-alkyl, or —R$_4$—O—R$_5$;

wherein when R1 is selected from thiazole, thiophene, and pyridine, each optionally substituted with one or more OH, halogen (selected from F, Cl, Br, I), —OR19, C1-C10 alkyl, C2-C10 alkenyl, C2-C10 alkynyl, CN, CF$_3$, OCF$_3$, NO$_2$, —NR2OR21, —SR22, —SO$_2$R23, —CO$_2$R24, —C(═O)NR25R26; wherein R19, R20, R21, R22, R23, R24, R25 and R26 are each independently selected from H, C1-C10 alkyl, C2-C10 alkenyl, C2-C10 alkynyl, aryl, heteroaryl, C(═O)H, C(═O)alkyl, C(═O)aryl, C(═O)heteroaryl;

R2 and R3 are independently selected from H, C1-C10 alkyl, C2-C10 halo-alkyl, C2-C10 alkenyl, C2-C10 alkynyl, —R$_4$—O—R$_5$; wherein R4 is a C2-C10 alkylene and R5 is selected from H and C1-C10 alkyl; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms;

or a pharmaceutically acceptable salt or ester of the compound, wherein the composition is enriched in the compound over its opposite enantiomer.

In another aspect, is a composition comprising a carrier and a compound having the structure:

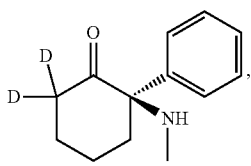
87R

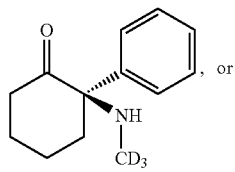
88R, or

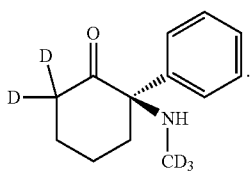
92R wherein D represents a deuterium-enriched —H site, and wherein the composition is enriched in the compound over its opposite enantiomer.

In another aspect, provided herein is a composition comprising a compound having the general structure (VIII)

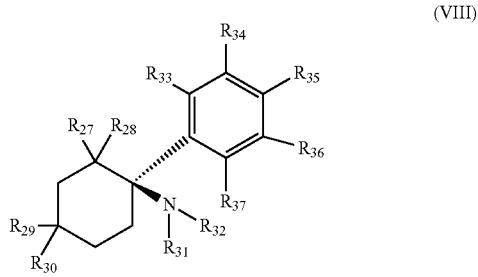
(VIII)

wherein R31 and R32 are independently selected from H, C1-C10 alkyl, C2-C10 halo-alkyl, —R$_{38}$—O—R$_{39}$; wherein R38 is a C2-C10 alkylene and R39 is selected from H and C1-C10 alkyl; or R31 and R32 together with the nitrogen atom they are attached to form a C3-C6 cycloheteroalkyl ring; said ring optionally substituted by one or more straight or branched C1-C10 alkyl or interrupted by one or more additional nitrogen or oxygen atoms; and wherein R27, R28, R29, R30 are each independently selected from H, straight or branched C1-C10 alkyl, F; wherein at least one of R27, R28, R29, or R30 is other than H; or R27 and R28 or R29 and R30 together with the carbon atom they are attached to form a cycloalkyl ring or together with the carbon they are attached to and one or more heteroatoms form a cycloheteroalkyl ring; and wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF3, OCF3, NO2, —NR41R42, —SR43, —SO$_2$R44, —CO$_2$R45, —C(═O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(═O)H, C(═O)alkyl, C(═O)aryl, C(═O)heteroaryl;

provided that when one of R27 and R28 is Me, the other of R27 and R28 is H, R29-R30 and R33-R37 are each H, and R31 or R32 is H, then the other of R31 or R32 is C2-C10 alkyl, C2-C10 halo-alkyl, or —R$_{38}$—O—R$_{39}$;

or a pharmaceutically acceptable salt or ester of the compound, wherein the composition is enriched in the compound over its opposite enantiomer.

In another aspect, provided herein is a method of treating depression, anxious depression, a mood disorder, an anxiety disorder, or a substance use disorder and any symptom or disorders associated therewith in a subject in need thereof, the method generally comprising administering to the subject a compound of structure (IX):

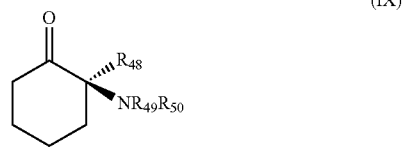
(IX)

wherein R48 is selected from the group consisting of: phenyl, thiazole, thiophene, pyridine, or a moiety of general formula (X);

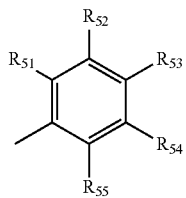

(X)

wherein R51 and R55 are independently selected from H, OH, OMe, C1-C10 alkyl; and
wherein R52, R53, and R54 are each independently selected from H, OH, halogen (selected from F, Cl, Br, I), OMe, C1-C10 alkyl; and
wherein R49 and R50 are each independently selected from H and C1-C10 alkyl; or R49 and R50 together with the nitrogen atom they are connected to from a C3-C9 cycloheteroalkyl ring optionally substituted with one or more C1-C10 alkyl;
or a pharmaceutically acceptable salt or ester of the compound, wherein the compound is enriched over its opposite enantiomer.

In another aspect, provided herein is a method of treating depression, anxious depression, a mood disorder, an anxiety disorder, or a substance use disorder and any symptom or disorders associated therewith in a subject in need thereof, the method generally comprising administering to the subject the compound:

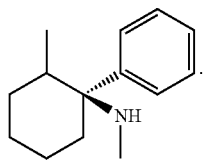

13S

In another aspect, provided herein is a composition comprising a compound having the general structure (XI):

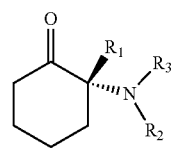

(XI)

wherein R1 is selected from the group consisting of phenyl, optionally substituted thiazole, optionally substituted thiophene, optionally substituted pyridine, a moiety of general formula (XII);
wherein when R1 is phenyl;
R2 and R3 are independently selected from H, CD₃, branched or cyclo C3 alkyl, C4-C10 alkyl, C2-C10 halo-alkyl, —R₄—O—R₅; wherein R4 is a C2-C10 alkylene and R5 is selected from H and C1-C10 alkyl; wherein D represents a deuterium-enriched —H site; and wherein at least one of R2 and R3 is other than H; or
R2 and R3 are independently selected from C2-C10 alkyl; C2-C10 halo-alkyl, —R₄—O—R₅;
wherein R4 is a C2-C10 alkylene and R5 is selected from H and C1-C10 alkyl; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms;
wherein when R1 is a moiety of general formula (XII):

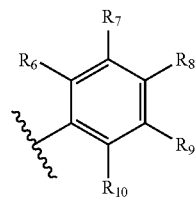

(XII)

R2 and R3 are independently selected from H, C1-C10 alkyl, C2-C10 halo-alkyl, —R₄—O—R₅;
wherein R4 is a C2-C10 alkylene and R5 is selected from H and C1-C10 alkyl; and wherein at least one of R2 and R3 is other than H; or
R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms; and
R6, R7, R8, R9 and R10 are independently selected from H, OH, halogen (selected from F, Cl, Br, I), —OR11, C1-C10 alkyl, C2-C10 alkenyl, C2-C10 alkynyl, CN, CF₃, OCF₃, NO₂, —NR12R13, —SR14, —SO₂R15, —CO₂R16, —C(═O)NR17R18; wherein R11, R12, R13, R14, R15, R16, R17 and R18 are each independently selected from H, C1-C10 alkyl, C2-C10 alkenyl, C2-C10 alkynyl, aryl, heteroaryl, —C(═O)H, —C(═O)alkyl, —C(═O)aryl, —C(═O)heteroaryl;
wherein at least one of R6-R10 is other than H; and wherein neither R6 nor R10 is halogen;
provided that when R7 is Cl and R6, R8-R10 are H, and R2 or R3 is H, then the other of R2 or R3 is C3-C10 alkyl, C2-C10 halo-alkyl, or —R₄—O—R₅; or
provided that when R7 is OH and R6, R8-R10 are H, and R2 or R3 is H, then the other of R2 or R3 is C3-C10 alkyl, C2-C10 halo-alkyl, or —R₄—O—R₅; or
provided that when R6, R7, or R8 is OMe and the other of R6-R10 are each H, and R2 or R3 is H, then the other of R2 or R3 is C3-C10 alkyl, C2-C10 halo-alkyl, or —R₄—O—R₅;
wherein when R1 is selected from thiazole, thiophene, and pyridine, each optionally substituted with one or more OH, halogen (selected from F, Cl, Br, I), —OR19, C1-C10 alkyl, C2-C10 alkenyl, C2-C10 alkynyl, CN, CF₃, OCF₃, NO₂, —NR20R21, —SR22, —SO₂R23, —CO₂R24, —C(═O) NR25R26; wherein R19, R20, R21, R22, R23, R24, R25 and R26 are each independently selected from H, C1-C10 alkyl, C2-C10 alkenyl, C2-C10 alkynyl, aryl, heteroaryl, C(═O) H, C(═O)alkyl, C(═O)aryl, C(═O)heteroaryl;
R2 and R3 are independently selected from H, C1-C10 alkyl, C2-C10 halo-alkyl, C2-C10 alkenyl, C2-C10 alkynyl, —R₄—O—R₅; wherein R4 is a C2-C10 alkylene and R5 is selected from H and C1-C10 alkyl; or
R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms;

or a pharmaceutically acceptable salt or ester of the compound, wherein the composition is enriched in the compound over its opposite enantiomer.

In another aspect, provided herein is a composition comprising a carrier and a compound having the structure:

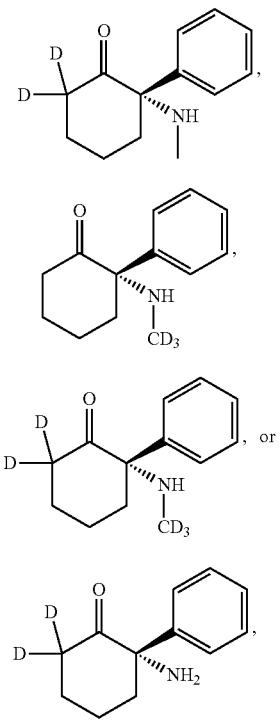

87S, 88S, 92S, 142S wherein D represents a deuterium-enriched —H site, and wherein the composition is enriched in the compound over its opposite enantiomer.

In another aspect, provided herein is a composition comprising a compound having the general structure (XIII):

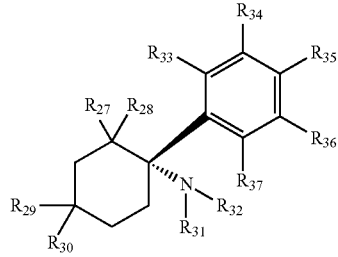

(XIII)

wherein R31 and R32 are independently selected from H, C1-C10 alkyl, C2-C10 halo-alkyl, —R$_{38}$—O—R$_{39}$; wherein R38 is a C2-C10 alkylene and R39 is selected from H and C1-C10 alkyl; or
R31 and R32 together with the nitrogen atom they are attached to form a C3-C6 cycloheteroalkyl ring; said ring optionally substituted by one or more straight or branched C1-C10 alkyl or interrupted by one or more additional nitrogen or oxygen atoms; and
wherein R27, R28, R29, R30 are each independently selected from H, straight or branched C1-C10 alkyl, F; wherein at least one of R27, R28, R29, or R30 is other than H; or R27 and R28 or R29 and R30 together with the carbon atom they are attached to form a cycloalkyl ring or together with the carbon they are attached to and one or more heteroatoms form a cycloheteroalkyl ring; and
wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(=O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl;
provided that when one of R27 and R28 is Me, the other of R27 and R28 is H, R29-R30 and R33-R37 are each H, and R31 or R32 is H, then the other of R31 or R32 is C2-C10 alkyl, C2-C10 halo-alkyl, or —R$_{38}$—O—R$_{39}$;
or a pharmaceutically acceptable salt or ester of the compound, wherein the composition is enriched in the compound over its opposite enantiomer. In another aspect, provided herein is a method of treating depression, anxious depression, a mood disorder, an anxiety disorder, or a substance use disorder and any symptom or disorders associated therewith in a subject in need thereof, the method generally comprising administering to the subject a compound of structure (XIV):

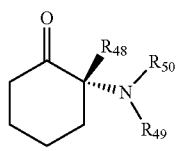

(XIV)

wherein R48 is selected from the group consisting of: phenyl, thiazole, thiophene, pyridine, or a moiety of general formula (XV);

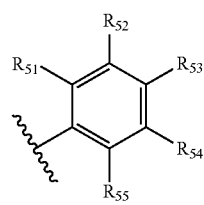

(XV)

wherein R51 and R55 are independently selected from H, OH, OMe, C1-C10 alkyl; and
wherein R52, R53, and R54 are each independently selected from H, OH, halogen (selected from F, Cl, Br, I), OMe, C1-C10 alkyl; and
wherein R49 and R50 are each independently selected from H and C1-C10 alkyl; or R49 and R50 together with the nitrogen atom they are connected to from a C3-C9 cycloheteroalkyl ring optionally substituted with one or more C1-C10 alkyl;
or a pharmaceutically acceptable salt or ester of the compound, wherein the compound is enriched over its opposite enantiomer.

In another aspect, provided herein is a method of treating depression, anxious depression, a mood disorder, an anxiety disorder, or a substance use disorder and any symptom or disorders associated therewith in a subject in need thereof, the method generally comprising administering to the subject the compound:

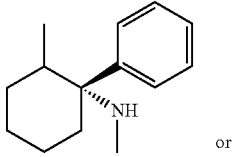

13R

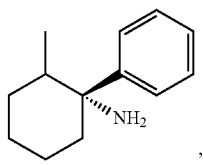

14IR or a pharmaceutically acceptable salt or ester of the compound, wherein the compound is enriched over its opposite enantiomer.

In another aspect, provided herein is a compound having the general structure (XVI):

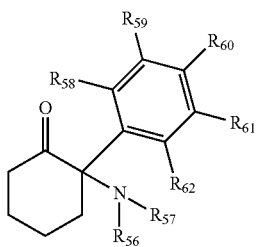

(XVI)

wherein R56 and R57 together with the nitrogen atom they are connected to form a monocyclic or bicyclic C3-C8 cycloheteroalkyl ring, said ring optionally substituted by one or more C1-C3 alkyl, F, OH, OMe, or =O, and optionally interrupted by one or more additional nitrogen or oxygen atoms; and wherein R58, R59, R60, R61, and R62 are each independently selected from H, OH, halogen (selected from F, Cl, Br, I), —OR63, —O—C(=O)R64, C1-C10 alkyl, C2-C10 alkenyl, C2-C10 alkynyl, CN, $CF_3$, $OCF_3$, $NO_2$, —NR65R66, —NH—C(=O)R67, —SR68, —$SO_2$R69, —$CO_2$R70, —C(=O)NR71R72; wherein R63, R64, R65, R66, R67, R68, R69, R70, R71, and R72 are each independently selected from H, C1-C10 alkyl, C2-C10 alkenyl, C2-C10 alkynyl, aryl, heteroaryl;

provided that when R56 and R57 together with the nitrogen atom they are connected to form an unsubstituted piperidine ring, then at least one of R58, R59, R60, R61, and R62 is other than H; or a pharmaceutically acceptable salt or ester thereof.

In another aspect, provided herein is a compound having the general structure (XVII):

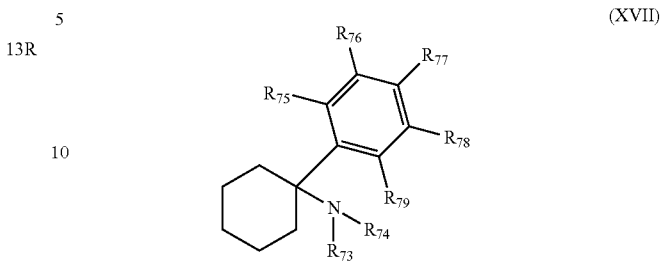

(XVII)

wherein R73 and R74 together with the nitrogen atom they are connected to form an azetidine ring, said ring optionally substituted by one or more C1-C3 alkyl, F, OH, or OMe; and wherein R75, R76, R77, R78, and R79 are each independently selected from H, OH, halogen (selected from F, Cl, Br, I), —OR80, —O—C(=O)R81, C1-C10 alkyl, C2-C10 alkenyl, C2-C10 alkynyl, CN, $CF_3$, $OCF_3$, $NO_2$, —NR82R83, —NH—C(=O)R84, —SR85, —$SO_2$R86, —$CO_2$R87, —C(=O)NR88R89; wherein R80, R81, R82, R83, R84, R85, R86, R87, R88, and R89 are each independently selected from H, C1-C10 alkyl, C2-C10 alkenyl, C2-C10 alkynyl, aryl, heteroaryl;

or a pharmaceutically acceptable salt or ester thereof.

In another aspect, provided herein is a method of treating depression, anxious depression, a mood disorder, an anxiety disorder, or a substance use disorder and any symptom or disorders associated therewith in a subject in need thereof, the method generally comprising administering to the subject a compound disclosed herein.

In another aspect, provided herein is a method of treating depression or anxious depression in a subject in need thereof, the method generally comprising administering to the subject a compound disclosed herein.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings, which are briefly described below. It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

Figure 1:
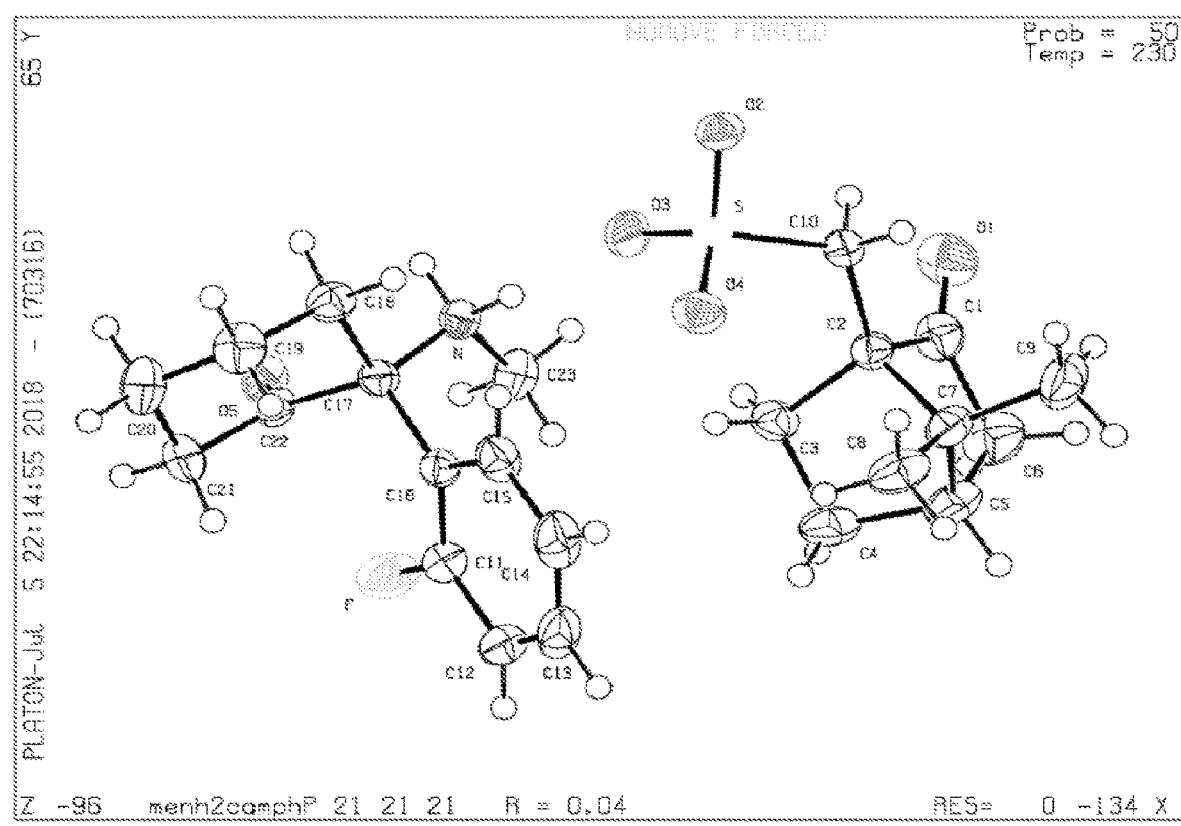
FIG. 1. The x-ray crystal structure of a 35R (1R)-(-)-camphorsulfonate crystal grown in toluene.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one aspect, provided herein is a compound having the general structure (I):

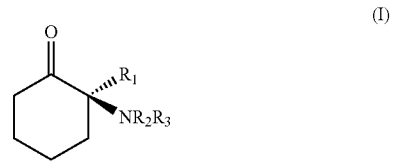

wherein R1 is selected from the group consisting of phenyl, optionally substituted thiazole, optionally substituted thiophene, optionally substituted pyridine, a moiety of general formula (II);

wherein when R1 is phenyl then R2 and R3 are independently selected from H, CD3, branched or cyclo C3 alkyl, C4-C10 alkyl, C2-C10 halo-alkyl, —R4—O—R5; wherein R4 is a C2-C10 alkylene and R5 is selected from H and C1-C10 alkyl; wherein D represents a deuterium-enriched —H site; provided that one or more of R2 and R3 is different than H; or R2 and R3 are independently selected from C2-C10 alkyl; C2-C10 halo-alkyl, —R4—O—R5;
wherein R4 is a C2-C10 alkylene and R5 is selected from H and C1-C10 alkyl; or
R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms;
wherein when R1 is a moiety of general formula (II):

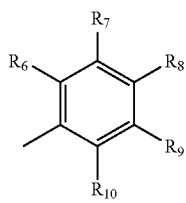

(II)

R2 and R3 are independently selected from H, C1-C10 alkyl, C2-C10 halo-alkyl, —R4—O—R5; wherein R4 is a C2-C10 alkylene and R5 is selected from H and C1-C10 alkyl; provided that one or more of R2 and R3 is different than H; or
R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms; and
wherein R6, R7, R8, R9 and R10 are independently selected from H, OH, halogen (selected from F, Cl, Br, I), —OR11, C1-C10 alkyl, C2-C10 alkenyl, C2-C10 alkynyl, CN, $CF_3$, $OCF_3$, $NO_2$, —NR12R13, —SR14, —$SO_2$R15, —$CO_2$R16, —C(=O)NR17R18; wherein R11, R12, R13, R14, R15, R16, R17 and R18 are each independently selected from H, C1-C10 alkyl, C2-C10 alkenyl, C2-C10 alkynyl, aryl, heteroaryl, —C(=O)H, —C(=O)alkyl, —C(=O)aryl, —C(=O)heteroaryl;
provided that one or more of R6-R10 is different than H; or provided that when R6 is Cl and R7-R10 are H or when R7 is Cl and R6, R8-R10 are H, and R2 or R3 is H, then the other of R2 or R3 is C3-C10 alkyl, C2-C10 halo-alkyl, or —R4—O—R5; or
provided that when R7 is OH and R6, R8-R10 are H, and R2 or R3 is H, then the other of R2 or R3 is straight or branched C3-C10 alkyl, C2-C10 halo-alkyl, or —R4—O—R5; or
provided that when R6, R7, or R8 is OMe and the other of R6-R10 are each H, and R2 or R3 is H, then the other of R2 or R3 is C3-C10 alkyl, C2-C10 halo-alkyl, or —R4—O—R5;
wherein when R1 is selected from thiazole, thiophene, pyridine, each optionally substituted with one or more OH, halogen (selected from F, Cl, Br, I), —OR19, C1-C10 alkyl, C2-C10 alkenyl, C2-C10 alkynyl, CN, $CF_3$, $OCF_3$, $NO_2$, —NR20R21, —SR22, —$SO_2$R23, —$CO_2$R24, —C(=O)NR25R26; wherein R19, R20, R21, R22, R23, R24, R25 and R26 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl;
R2 and R3 are independently selected from H, C1-C10 alkyl, C2-C10 halo-alkyl, C2-C10 alkenyl, C2-C10 alkynyl, —R4—O—R5; wherein R4 is a C2-C10 alkylene and R5 is selected from H and C1-C10 alkyl; or
R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms.

In some embodiments, a compound provided herein has the general structure (Ia):

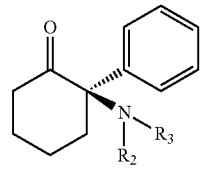

(Ia)

wherein R2 and R3 are independently selected from H, branched or cyclo C3 alkyl, C4-C10 alkyl, C2-C10 halo-alkyl, —R4—O—R5; wherein R4 is a C2-C10 alkylene and R5 is selected from H and C1-C10 alkyl; provided that one or more of R2 and R3 is different than H; or R2 and R3 are independently selected from C2-C10 alkyl, C2-C10 halo-alkyl, —R4—O—R5;
wherein R4 is a C2-C10 alkylene and R5 is selected from H and C1-C10 alkyl; or R2 and R3 together with the nitrogen ring they are connected to form a C3-C9 cycloheteroalkyl ring; said ring optionally substituted by one or more C1-C10 alkyl or interrupted by one or more additional nitrogen or oxygen atoms.

In some embodiments, a compound provided herein has the general structure (Ib):

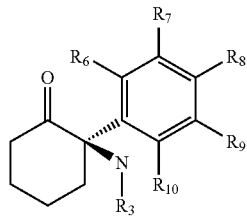

(Ib)

wherein R3 is a C1-C10 alkyl, C2-C10 halo-alkyl, or —R4—O—R5; wherein R4 is a C2-C10 alkylene and R5 is selected from H and C1-C10 alkyl; and wherein R6, R7, R8, R9 and R10 are independently selected from H, OH, halogen (selected from F, Cl, Br, I), —OR11, C1-C10 alkyl, C2-C10 alkenyl, C2-C10 alkynyl, CN, $CF_3$, $OCF_3$, $NO_2$, —NR12R13, —SR14, —$SO_2$R15, —$CO_2$R16, —C(=O) NR17R18; wherein R11, R12, R13, R14, R15, R16, R17 and R18 are each independently selected from H, C1-C10 alkyl, C2-C10 alkenyl, C2-C10 alkynyl, aryl, heteroaryl, C(=O) H, C(=O)alkyl, C(=O)aryl, C(=O)heteroaryl, provided that one or more of R6-R10 is different than H; or provided that when R6 is Cl and R7-R10 are H or when R7 is Cl and R6, R8-R10 are H, then R3 is C3-C10 alkyl, C2-C10 halo-alkyl, or —R4—O—R5; or
provided that when R7 is OH and R6, R8-R10 is H, then R3 is C3-C10 alkyl, C2-C10 halo-alkyl, or —R4—O—R5; or
provided that when R6, R7, or R8 is OMe, and the other of R6-R10 are H, then R3 is C3-C10 alkyl, C2-C10 halo-alkyl, or —R4—O—R5.

In some embodiments, a compound provided herein has the general structure (I), wherein R1 is selected from thiazole, thiophene, pyridine; each optionally substituted with one or more OH, halogen (selected from F, Cl, Br, I), —OR19, C1-C10 alkyl, C2-C10 alkenyl, C2-C10 alkynyl, CN, CF$_3$, OCF$_3$, NO$_2$, —NR20R21, —SR22, —SO$_2$R23, —CO$_2$R24, —C(=O)NR25R26; wherein R19, R20, R21, R22, R23, R24, R25 and R26 are each independently selected from H, C1-C10 alkyl, C2-C10 alkenyl, C2-C10 alkynyl, aryl, heteroaryl, C(=O)H, C(=O)alkyl, C(=O) aryl, C(=O)heteroaryl; R2 and R3 are independently selected from H, C1-C10 alkyl, C2-C10 halo-alkyl, C2-C10 alkenyl, C2-C10 alkynyl, —R$_4$—O—R$_5$; wherein R4 is a C2-C10 alkylene and R5 is selected from H and C1-C10 alkyl; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms.

In some embodiments, a compound provided herein has the general structure (Ia):

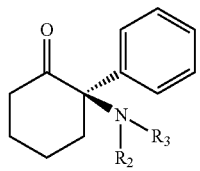

(Ia)

wherein R2 and R3 are independently selected from H, branched or cyclo C3 alkyl, C4-C10 alkyl, C2-C10 halo-alkyl, —R$_4$—O—R$_5$; wherein R4 is a C2-C10 alkylene and R5 is selected from H and C1-C10 alkyl; provided that at least one of R2 and R3 is different than H.

In some embodiments, a compound provided herein has the general structure (Ia):

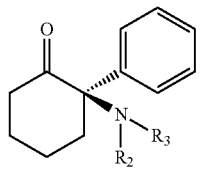

(Ia)

wherein R2 and R3 are independently selected from C2-C10 alkyl, C2-C10 halo-alkyl, —R$_4$—O—R$_5$; wherein R4 is a C2-C10 alkylene and R5 is selected from H and C1-C10 alkyl.

In some embodiments, a compound provided herein has the general structure (Ia):

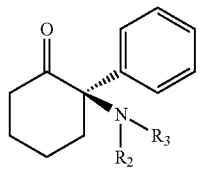

(Ia)

wherein R2 and R3 together with the nitrogen ring they are attached to form a C3-C9 cycloheteroalkyl ring; said ring optionally substituted by one or more C1-C10 alkyl or interrupted by one or more additional nitrogen or oxygen atoms.

In some embodiments, a compound provided herein has the general structure (Ia):

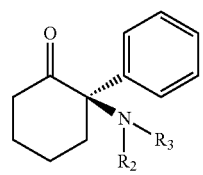

(Ia)

wherein R2 is H and R3 is selected from branched or cyclo C3 alkyl, C4-C5 alkyl, C2-C5 fluoro-alkyl, —R$_4$—O—R$_5$; wherein R4 is a C2-C5 alkylene and R5 is selected from H and C1-C5 alkyl.

In some embodiments, a compound provided herein has the general structure (Ia):

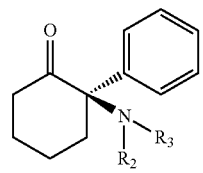

(Ia)

wherein R2 and R3 are independently selected from C2-C5 alkyl, C2-C5 fluoro-alkyl, —R$_4$—O—R$_5$; wherein R4 is a C2-C5 alkylene and R5 is selected from H and C1-C5 alkyl.

In some embodiments, a compound provided herein has the general structure (Ia):

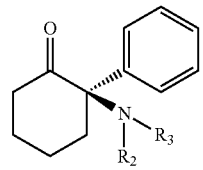

(Ia)

wherein R2 and R3 together with the nitrogen ring they are attached to form a C3-C6 cycloheteroalkyl ring; said ring optionally substituted by one or more C1-C2 alkyl or interrupted by one or more additional nitrogen or oxygen atoms.

In some embodiments, a compound provided herein has the general structure (Ib):

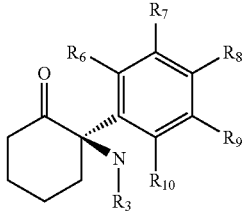

wherein one or more of R6, R7, R8, R9 and R10 is OH, R3 is selected from C1-C10 alkyl, C2-C10 halo-alkyl, —R4—O—R5; wherein R4 is a C2-C10 alkylene and R5 is selected from H and C1-C10 alkyl; provided that when R7 is OH, and R6, R8-R10 are H, then R3 is C3-C10 alkyl.

In some embodiments, a compound provided herein has the general structure (Ib):

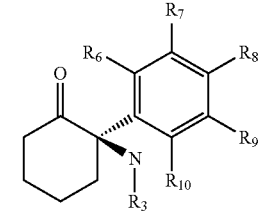

wherein one or more of R6, R7, R8, R9 and R10 is halogen (selected from F, Cl, Br, I), R3 is selected from C1-C10 alkyl, C2-C10 halo-alkyl, —R4—O—R5; wherein R4 is a C2-C10 alkylene and R5 is selected from H and C1-C10 alkyl; provided that when R6 is Cl and R7-R10 are H or when R7 is Cl and R6, R8-R10 are H, then R3 is C3-C10 alkyl.

In some embodiments, a compound provided herein has the general structure (Ib):

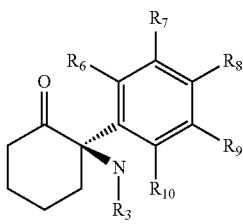

wherein one or more of R6, R7, R8, R9 and R10 is OMe, R3 is selected from C1-C10 alkyl, C2-C10 halo-alkyl, —R4—O—R5; wherein R4 is a C2-C10 alkylene and R5 is selected from H and C1-C10 alkyl; provided that when R6, R7 or R8 is OMe and the other of R6-R10 are H, then R3 is C3-C10 alkyl.

In some embodiments, a compound provided herein has the general structure (Ib):

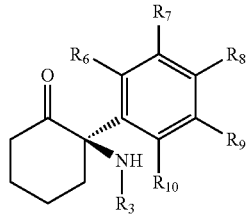

wherein one or more of R6, R7, R8, R9 and R10 is F, R3 is selected from C1-C10 alkyl, C2-C10 halo-alkyl, —R4—O—R5; wherein R4 is a C2-C10 alkylene and R5 is selected from H and C1-C10 alkyl.

In some embodiments, a compound provided herein has the general structure (Ib):

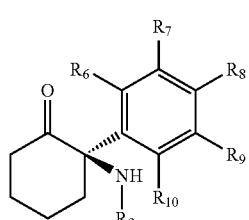

wherein one or more of R6, R7, R8, R9 and R10 is Me, R3 is selected from C1-C10 alkyl, C2-C10 halo-alkyl, —R4—O—R5; wherein R4 is a C2-C10 alkylene and R5 is selected from H and C1-C10 alkyl.

In some embodiments, a compound provided herein has the general structure (Ib):

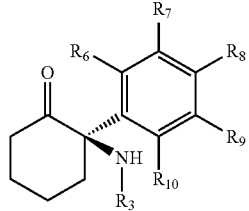

wherein one or more of R6, R7, R8, R9 and R10 is OH, R3 is selected from C1-C5 alkyl, C2-C5 fluoro-alkyl, —R4—O—R5; wherein R4 is a C2-C5 alkylene and R5 is selected from H and C1-C5 alkyl; provided that when R7 is OH, and R6, R8-R10 are H, then R3 is C3-C5 alkyl.

In some embodiments, a compound provided herein has the general structure (Ib):

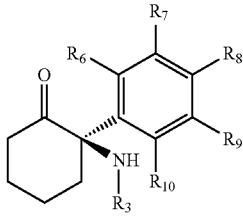

(Ib)

wherein one or more of R6, R7, R8, R9 and R10 is OMe, R3 is selected from C1-C5 alkyl, C2-C5 fluoro-alkyl, —R$_4$—O—R$_5$; wherein R4 is a C2-C5 alkylene and R5 is selected from H and C1-C5 alkyl; provided that when R6, R7 or R8 is OMe and the other of R6-R10 are H, then R3 is C3-C5 alkyl.

In some embodiments, a compound provided herein has the general structure (Ib):

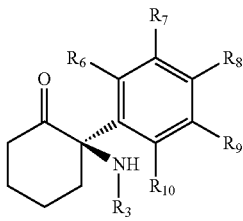

(Ib)

wherein one or more of R6, R7, R8, R9 and R10 is F, R3 is selected from C1-C5 alkyl, C2-C5 fluoro-alkyl, —R$_4$—O—R$_5$; wherein R4 is a C2-C5 alkylene and R5 is selected from H and C1-C5 alkyl.

In some embodiments, a compound provided herein has the general structure (Ib):

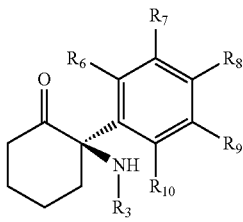

(Ib)

wherein one or more of R6, R7, R8, R9 and R10 is Me, R3 is selected from C1-C5 alkyl, C2-C5 fluoro-alkyl, —R$_4$—O—R$_5$; wherein R4 is a C2-C5 alkylene and R5 is selected from H and C1-C5 alkyl.

In some embodiments, a compound provided herein has the general structure (Ic):

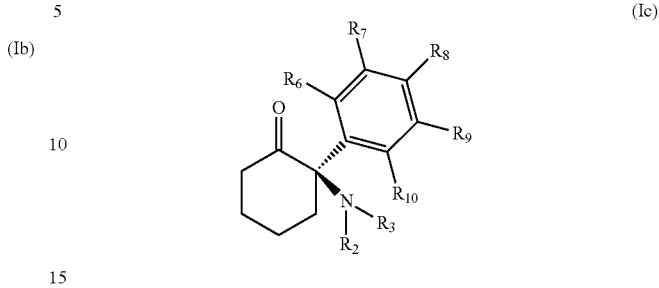

(Ic)

wherein one or more of R6, R7, R8, R9 and R10 is OH, R2 and R3 are independently selected from C1-C5 alkyl, C2-C5 fluoro-alkyl, —R$_4$—O—R$_5$; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, a compound provided herein has the general structure (Ic):

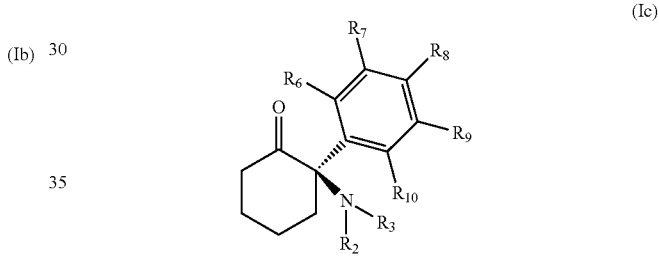

(Ic)

wherein one or more of R6, R7, R8, R9 and R10 is OMe, R2 and R3 are independently selected from C1-C5 alkyl, C2-C5 fluoro-alkyl, —R$_4$—O—R$_5$; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, a compound provided herein has the general structure (Ic):

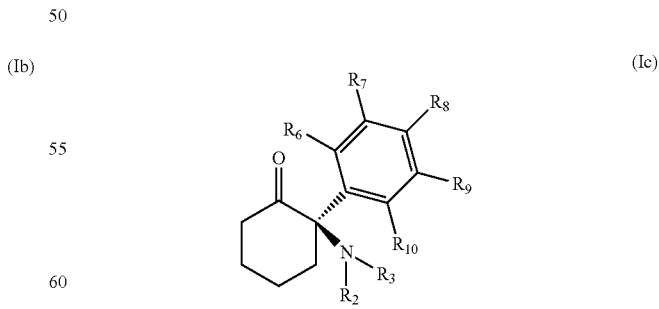

(Ic)

wherein one or more of R6, R7, R8, R9 and R10 is F, R2 and R3 are independently selected from C1-C5 alkyl, C2-C5 fluoro-alkyl, —R$_4$—O—R$_5$; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, a compound provided herein has the general structure (Ic):

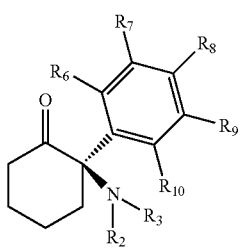

(Ic)

wherein one or more of R6, R7, R8, R9 and R10 is Me, R2 and R3 are independently selected from C1-C5 alkyl, C2-C5 fluoro-alkyl, —R$_4$—O—R$_5$; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, a compound provided herein is selected from:

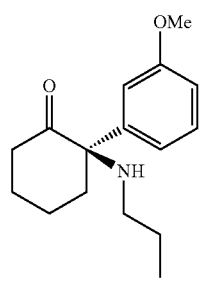

15R

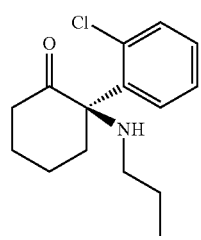

16R

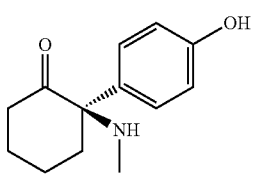

17R

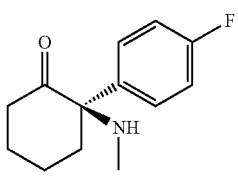

18R

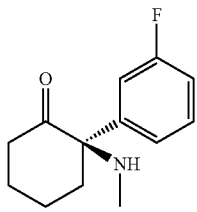

19R

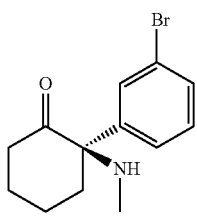

20R

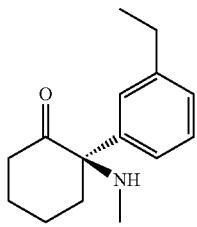

21R

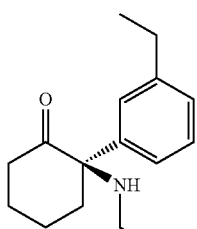

22R

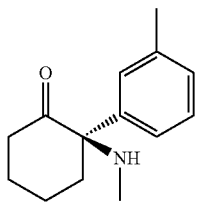

23R

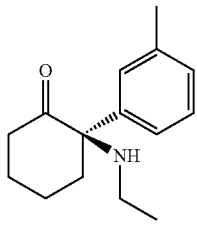

24R

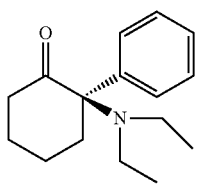

25R

26R 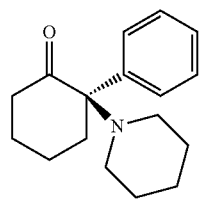
27R 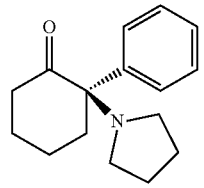
28R 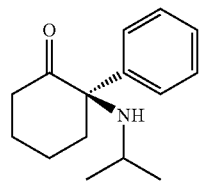
29R 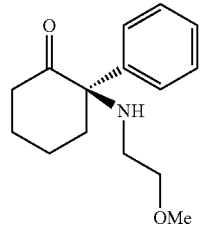
30R 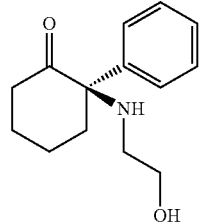
31R 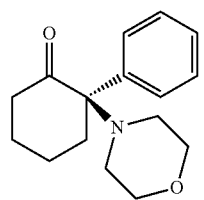
32R 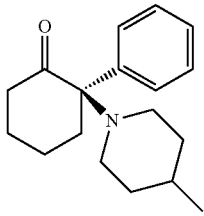
33R 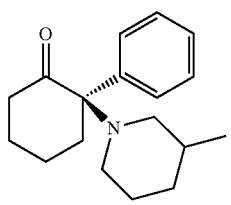
34R 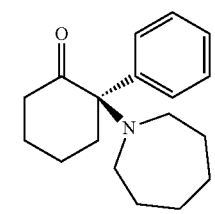
35R 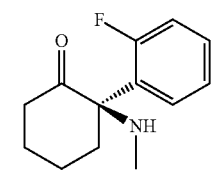
36R 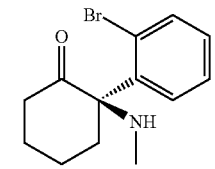
37R 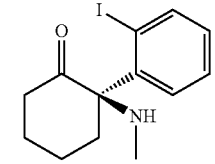
38R 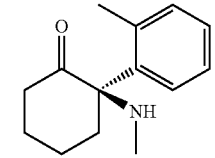
39R 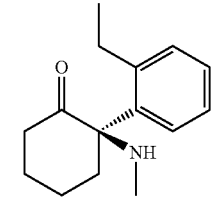
42R 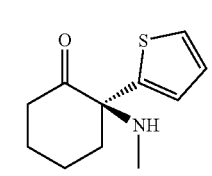

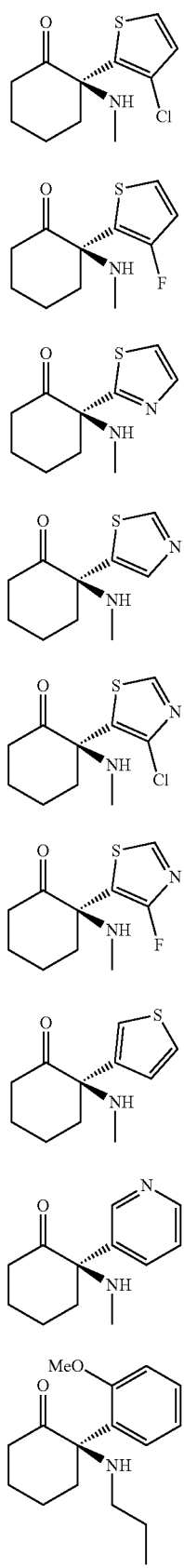
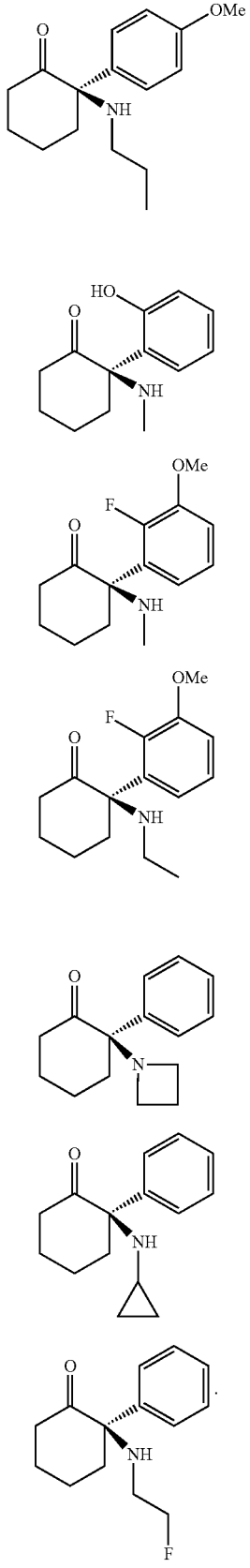

In some embodiments, a compound provided herein is selected from:
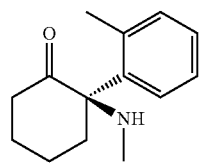
38R
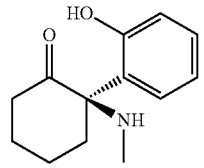
77R
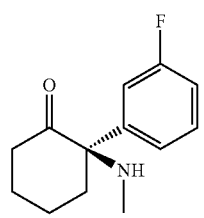
19R
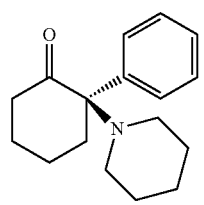
26R
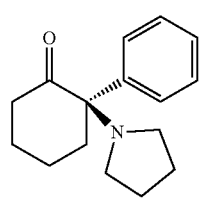
27R
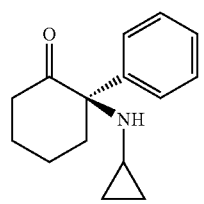
85R
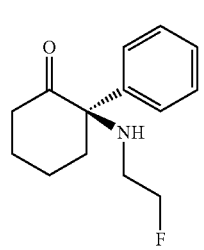
86R
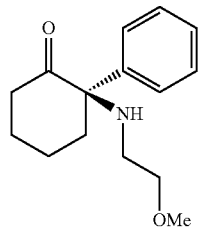
29R
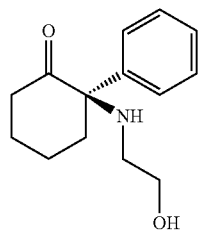
30R
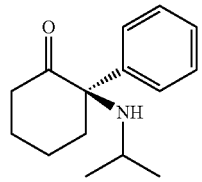
28R
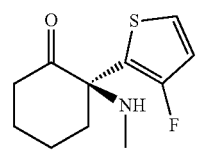
44R
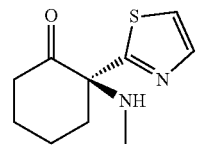
45R
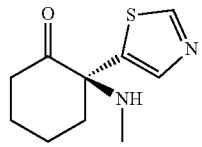
46R
In another aspect, provided herein are compositions comprising a carrier and a compound having the structure:
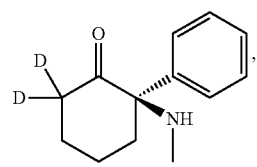
87R
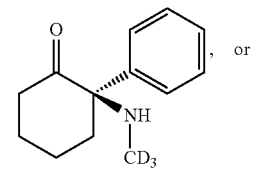
88R
or -continued

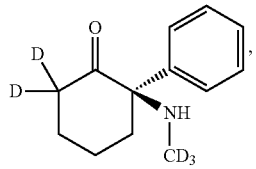

92R wherein D represents a deuterium-enriched H-site.

In some embodiments, each D represents a deuterium-enriched —H site and the level of deuterium at each deuterium-enriched —H site of the compound is 0.02% to 100%. In some embodiments, each D represents a deuterium-enriched —H site and the level of deuterium at each deuterium-enriched —H site of the compound is 20%-100%, 50%-100%, 70%-100%, 90%-100%, 97%-100%, or 99%-100%.

In another aspect, provided herein is a compound having the general structure (III):

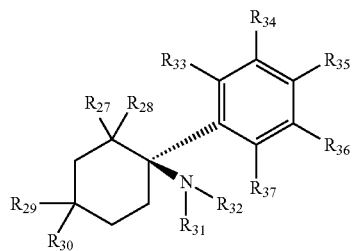

(III)

wherein R31 and R32 are each H, C1-C10 alkyl, C2-C10 halo-alkyl, —R$_{38}$—O—R$_{39}$; wherein R38 is a C2-C10 alkylene and R39 is selected from H and C1-C10 alkyl; or R31 and R32 together with the nitrogen atom they are attached to form a C3-C6 cycloheteroalkyl ring; said ring optionally substituted by one or more straight or branched C1-C10 alkyl or interrupted by one or more additional nitrogen or oxygen atoms; and wherein R27, R28, R29, R30 are each independently selected from H, straight or branched C1-C10 alkyl, F, or R27 and R28 or R29 and R30 together with the carbon atom they are attached to form a cycloalkyl ring or together with the carbon they are attached to and one or more heteroatoms form a cycloheteroalkyl ring; and wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(═O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(═O)H, C(═O)alkyl, C(═O)aryl, C(═O)heteroaryl; provided that at least one of R27, R28, R29, or R30 is different than H; or provided that when one of R27 and R28 is Me and the other of R27 and R28 is H, then R32 is C2-C10 alkyl, C2-C10 halo-alkyl, or —R$_{38}$—O—R$_{39}$.

In some embodiments a compound provided herein has the general structure (III):

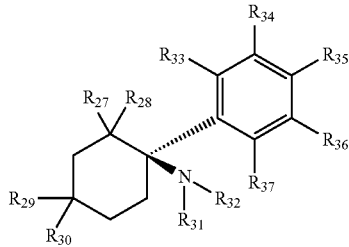

(III)

wherein R31 and R32 are each H, C1-C10 alkyl, C2-C10 halo-alkyl, —R$_{38}$—O—R$_{39}$; wherein R38 is a C2-C10 alkylene and R39 is selected from H and C1-C10 alkyl; or R31 and R32 together with the nitrogen atom they are attached to form a C3-C6 cycloheteroalkyl ring; said ring optionally substituted by one or more straight or branched C1-C2 alkyl or interrupted by one or more additional nitrogen or oxygen atoms; and wherein R27 and R28 are fluorine and R29 and R30 are H; and wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(═O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(═O)H, C(═O)alkyl, C(═O)aryl, C(═O)heteroaryl.

In some embodiments, a compound provided herein has the general structure (III):

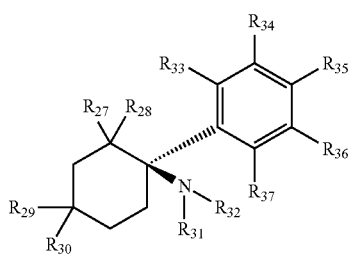

(III)

wherein R31 and R32 are each H, C1-C10 alkyl, C2-C10 halo-alkyl, —R$_{38}$—O—R$_{39}$; wherein R38 is a C2-C10 alkylene and R39 is selected from H and C1-C10 alkyl; or R31 and R32 together with the nitrogen atom they are attached to form a C3-C6 cycloheteroalkyl ring; said ring optionally substituted by one or more straight or branched C1-C2 alkyl or interrupted by one or more additional nitrogen or oxygen atoms; and wherein R27 and R28 together with the carbon they are attached to and an oxygen atom form an oxetane ring; and wherein R29 and R30 are H; and wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(═O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(═O)H, C(═O)alkyl, C(═O)aryl, C(═O)heteroaryl.

In some embodiments, a compound provided herein is selected from:
41S
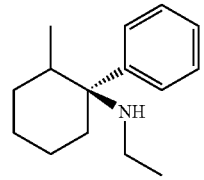
51R
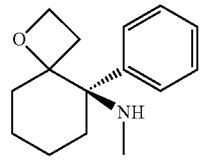
52R
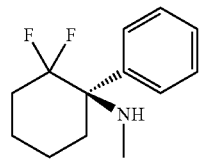
70R
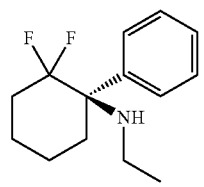
71S
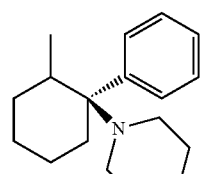
72R
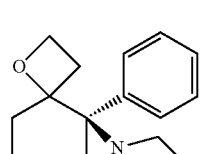
73R
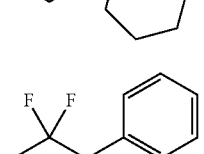
74R
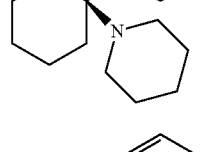
-continued
75R
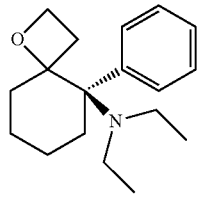
76R
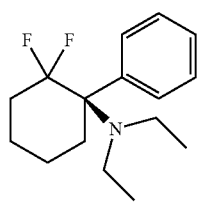
57S
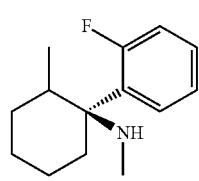
58R
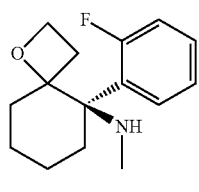
59R
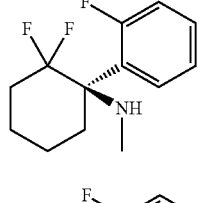
60S
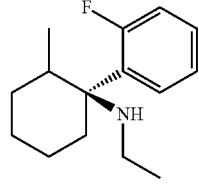
61R
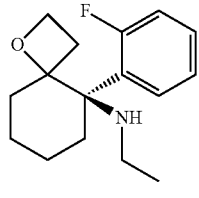
62
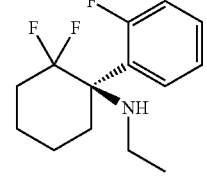

63S 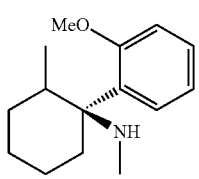

64R 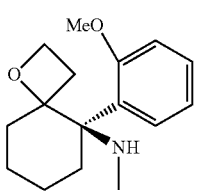

65R 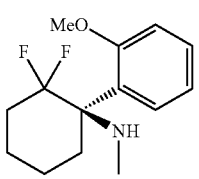

66S 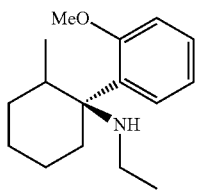

67R 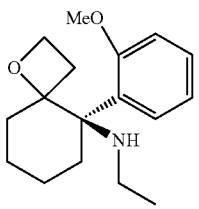

68R 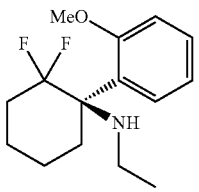

69R 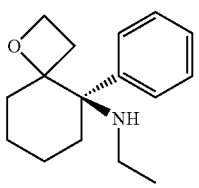

In another aspect, provided herein is a method of treating depression, a mood disorder, an anxiety disorder, or a substance use disorder and any symptom or disorders associated therewith in a subject in need thereof, the method generally comprising administering to the subject a compound of structure (IV):

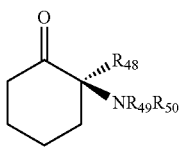

wherein R48 is selected from the group consisting of: phenyl, thiazole, thiophene, pyridine, or a moiety of general formula (V);

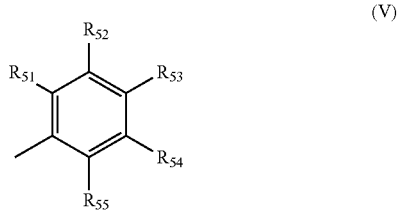

wherein R51, R52, R53, R54 and R55 are each independently selected from H, OH, halogen (selected from F, Cl, Br, I), OMe, C1-C10 alkyl;

R49 and R50 are each independently selected from H and C1-C10 alkyl; or R49 and R50 together with the nitrogen atom they are connected to from a C3-C9 cycloheteroalkyl ring optionally substituted with one or more C1-C10 alkyl, provided that when R51 is Cl and R52-R55 are H, and R49 or R50 is H, then the other of R49 or R50 is C2-C10 alkyl.

In some embodiments, a compound provided herein is selected from:

1R 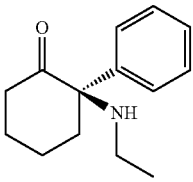 [SMILES: CCNC1(c2ccccc2)CCCCC1=O]

2R 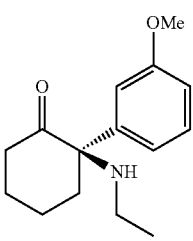

3R 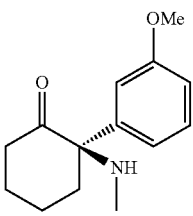 [SMILES: CNC1(c2cccc(OC)c2)CCCCC1=O]

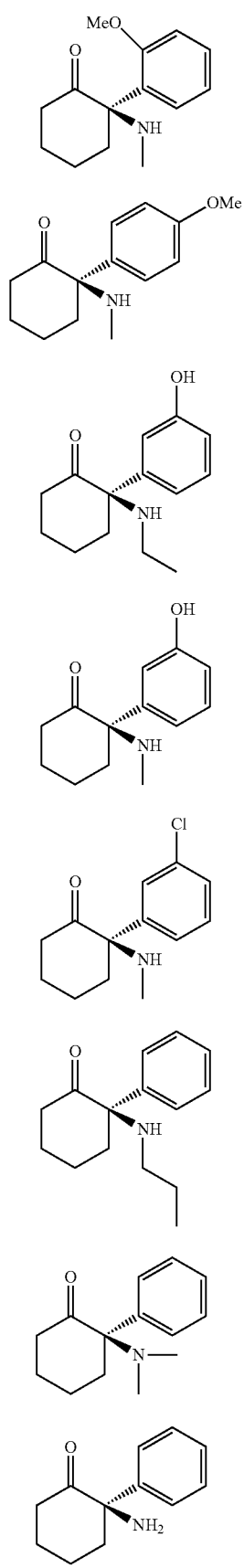
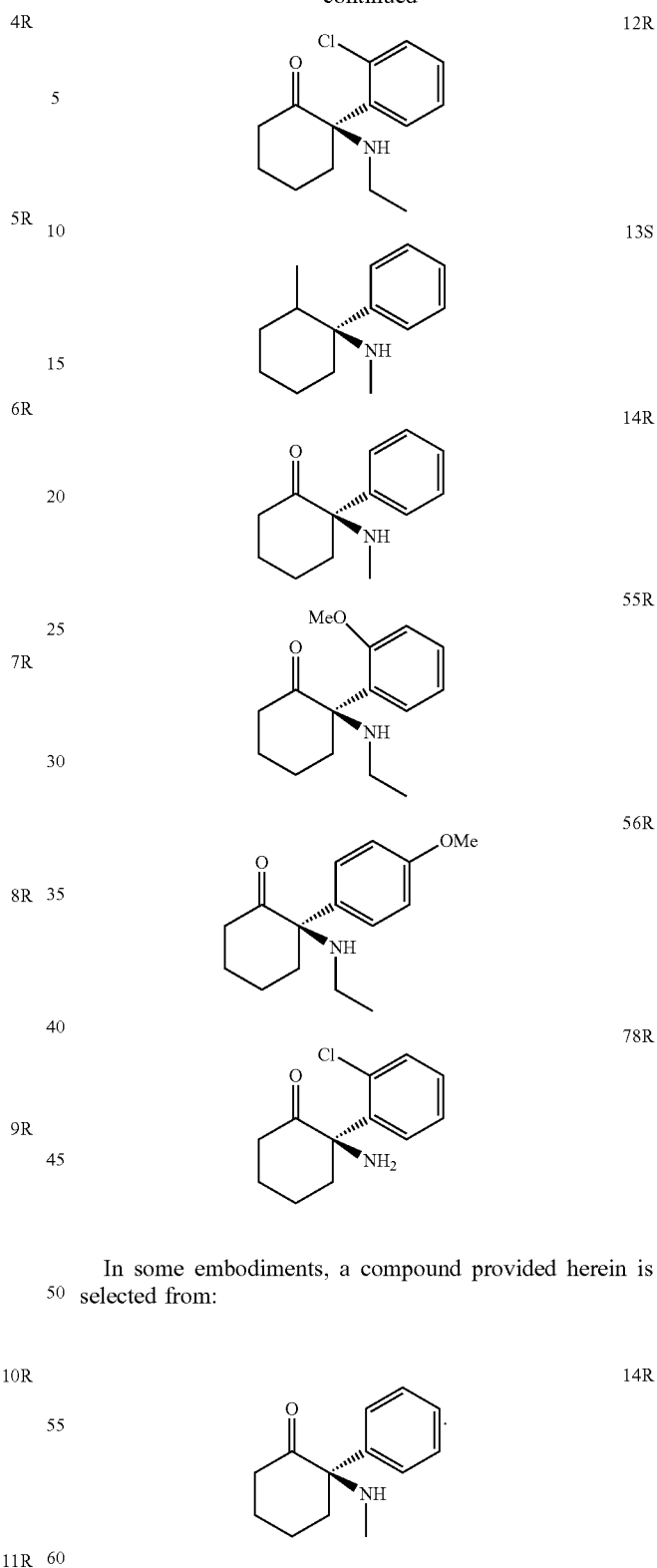
In some embodiments, a compound provided herein is selected from:
In another aspect, provided herein is method of treating depression, a mood disorder, an anxiety disorder, or a substance use disorder and any symptom or disorders associated therewith in a subject in need thereof, the method generally comprising administering to the subject the compound:

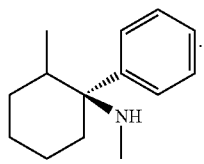

In another aspect, provided herein is a composition comprising a compound having the general structure (VI):

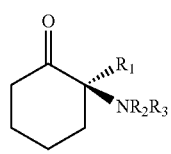

(VI)

wherein R1 is selected from the group consisting of phenyl, optionally substituted thiazole, optionally substituted thiophene, optionally substituted pyridine, a moiety of general formula (VII);
wherein when R1 is phenyl;
R2 and R3 are independently selected from H, $CD_3$, branched or cyclo C3 alkyl, C4-C10 alkyl, C2-C10 halo-alkyl, $-R_4-O-R_5$; wherein R4 is a C2-C10 alkylene and R5 is selected from H and C1-C10 alkyl; wherein D represents a deuterium-enriched —H site; and wherein at least one of R2 and R3 is other than H; or
R2 and R3 are independently selected from C2-C10 alkyl; C2-C10 halo-alkyl, $-R_4-O-R_5$; wherein R4 is a C2-C10 alkylene and R5 is selected from H and C1-C10 alkyl; or
R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms;
wherein when R1 is a moiety of general formula (VII):

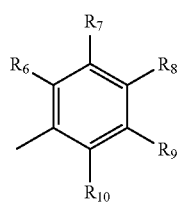

(VII)

R2 and R3 are independently selected from H, C1-C10 alkyl, C2-C10 halo-alkyl, $-R_4-O-R_5$; wherein R4 is a C2-C10 alkylene and R5 is selected from H and C1-C10 alkyl; and wherein at least one of R2 and R3 is other than H; or
R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms; and
R6, R7, R8, R9 and R10 are independently selected from H, OH, halogen (selected from F, Cl, Br, I), $-OR_{11}$, C1-C10 alkyl, C2-C10 alkenyl, C2-C10 alkynyl, CN, $CF_3$, $OCF_3$, $NO_2$, $-NR_{12}R_{13}$, $-SR_{14}$, $-SO_2R_{15}$, $-CO_2R_{16}$, $-C(=O)NR_{17}R_{18}$; wherein R11, R12, R13, R14, R15, R16, R17 and R18 are each independently selected from H, C1-C10 alkyl, C2-C10 alkenyl, C2-C10 alkynyl, aryl, heteroaryl, $-C(=O)H$, $-C(=O)$alkyl, $-C(=O)$aryl, $-C(=O)$heteroaryl; wherein at least one of R6-R10 is other than H; and wherein neither R6 nor R10 is halogen;

provided that when R7 is Cl and R6, R8-R10 are H, and R2 or R3 is H, then the other of R2 or R3 is C3-C10 alkyl, C2-C10 halo-alkyl, or $-R_4-O-R_5$; or provided that when R7 is OH and R6, R8-R10 are H, and R2 or R3 is H, then the other of R2 or R3 is C3-C10 alkyl, C2-C10 halo-alkyl, or $-R_4-O-R_5$; or provided that when R6, R7, or R8 is OMe and the other of R6-R10 are each H, and R2 or R3 is H, then the other of R2 or R3 is C3-C10 alkyl, C2-C10 halo-alkyl, or $-R_4-O-R_5$;

wherein when R1 is selected from thiazole, thiophene, and pyridine, each optionally substituted with one or more OH, halogen (selected from F, Cl, Br, I), $-OR_{19}$, C1-C10 alkyl, C2-C10 alkenyl, C2-C10 alkynyl, CN, $CF_3$, $OCF_3$, $NO_2$, $-NR_{20}R_{21}$, $-SR_{22}$, $-SO_2R_{23}$, $-CO_2R_{24}$, $-C(=O)NR_{25}R_{26}$; wherein R19, R20, R21, R22, R23, R24, R25 and R26 are each independently selected from H, C1-C10 alkyl, C2-C10 alkenyl, C2-C10 alkynyl, aryl, heteroaryl, $C(=O)H$, $C(=O)$alkyl, $C(=O)$aryl, $C(=O)$heteroaryl;

R2 and R3 are independently selected from H, C1-C10 alkyl, C2-C10 halo-alkyl, C2-C10 alkenyl, C2-C10 alkynyl, $-R_4-O-R_5$; wherein R4 is a C2-C10 alkylene and R5 is selected from H and C1-C10 alkyl; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms;

or a pharmaceutically acceptable salt or ester of the compound, wherein the composition is enriched in the compound over its opposite enantiomer.

In some embodiments, the compound has the general structure (VIa):

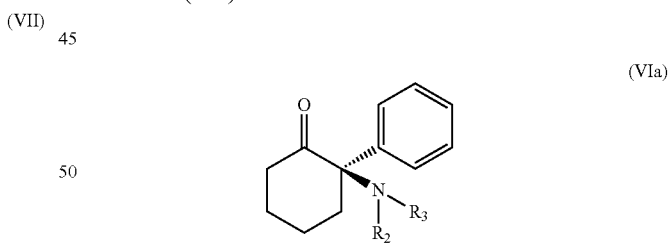

(VIa)

wherein R2 and R3 are independently selected from H, branched or cyclo C3 alkyl, C4-C10 alkyl, C2-C10 halo-alkyl, $-R_4-O-R_5$; wherein R4 is a C2-C10 alkylene and R5 is selected from H and C1-C10 alkyl; and wherein at least one of R2 and R3 is other than H; or R2 and R3 are independently selected from C2-C10 alkyl, C2-C10 halo-alkyl, $-R_4-O-R_5$; wherein R4 is a C2-C10 alkylene and R5 is selected from H and C1-C10 alkyl; or R2 and R3 together with the nitrogen ring they are connected to form a C3-C9 cycloheteroalkyl ring; said ring optionally substituted by one or more C1-C10 alkyl or interrupted by one or more additional nitrogen or oxygen atoms.

In some embodiments, the compound has the general structure (VIb):

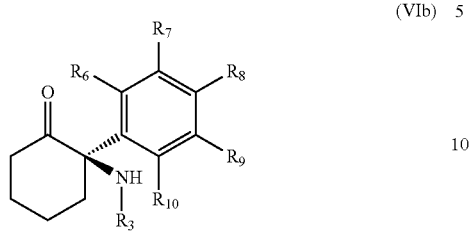
(VIb)

wherein R3 is a C1-C10 alkyl, C2-C10 halo-alkyl, or —R4—O—R5; wherein R4 is a C2-C10 alkylene and R5 is selected from H and C1-C10 alkyl; and wherein R6, R7, R8, R9 and R10 are independently selected from H, OH, halogen (selected from F, Cl, Br, I), —OR11, C1-C10 alkyl, C2-C10 alkenyl, C2-C10 alkynyl, CN, CF3, OCF3, NO2, —NR12R13, —SR14, —SO2R15, —CO2R16, —C(=O)NR17R18; wherein R11, R12, R13, R14, R15, R16, R17 and R18 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl; wherein at least one of R6-R10 is other than H; and wherein neither R6 nor R10 is halogen;

provided that when R7 is Cl and R6, R8-R10 are H, then R3 is C3-C10 alkyl, C2-C10 halo-alkyl, or —R4—O—R5; or provided that when R7 is OH and R6, R8-R10 is H, then R3 is C3-C10 alkyl, C2-C10 halo-alkyl, or —R4—O—R5; or provided that when R6, R7, or R8 is OMe, and the other of R6-R10 are H, then R3 is C3-C10 alkyl, C2-C10 halo-alkyl, or —R4—O—R5.

In some embodiments, the compound has the general structure (VI):

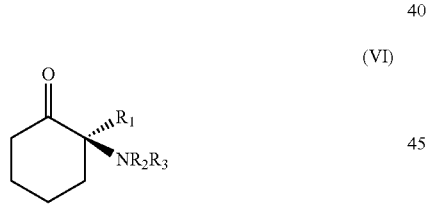
(VI)

wherein R1 is selected from thiazole, thiophene, and pyridine; each optionally substituted with one or more OH, halogen (selected from F, Cl, Br, I), —OR19, C1-C10 alkyl, C2-C10 alkenyl, C2-C10 alkynyl, CN, CF3, OCF3, NO2, —NR2OR21, —SR22, —SO2R23, —CO2R24, —C(=O)NR25R26; wherein R19, R20, R21, R22, R23, R24, R25 and R26 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl; and wherein R2 and R3 are independently selected from H, C1-C10 alkyl, C2-C10 halo-alkyl, C2-C10 alkenyl, C2-C10 alkynyl, —R4—O—R5; wherein R4 is a C2-C10 alkylene and R5 is selected from H and C1-C10 alkyl; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms.

In some embodiments, the compound has the general structure (VIa):

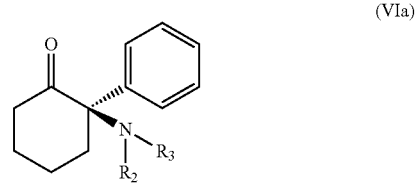
(VIa)

wherein R2 and R3 are independently selected from H, branched or cyclo C3 alkyl, C4-C10 alkyl, C2-C10 halo-alkyl, —R4—O—R5; wherein R4 is a C2-C10 alkylene and R5 is selected from H and C1-C10 alkyl; wherein at least one of R2 and R3 is other than H.

In some embodiments, the compound has the general structure (VIa):

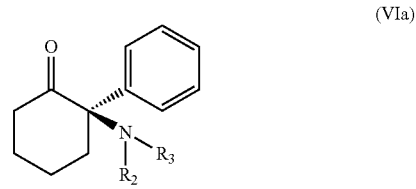
(VIa)

wherein R2 and R3 are independently selected from C2-C10 alkyl, C2-C10 halo-alkyl, —R4—O—R5; wherein R4 is a C2-C10 alkylene and R5 is selected from H and C1-C10 alkyl.

In some embodiments, the compound has the general structure (VIa):

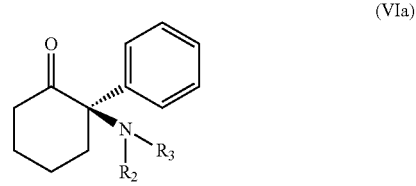
(VIa)

wherein R2 and R3 together with the nitrogen ring they are attached to form a C3-C9 cycloheteroalkyl ring; said ring optionally substituted by one or more C1-C10 alkyl or interrupted by one or more additional nitrogen or oxygen atoms.

In some embodiments, the compound has the general structure (VIa):

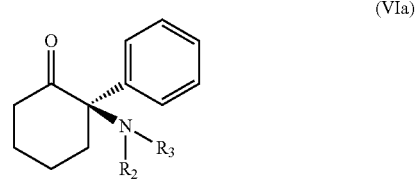
(VIa)

wherein R2 is H and R3 is selected from branched or cyclo C3 alkyl, C4-C5 alkyl, C2-C5 fluoro-alkyl, —R4—O—R5;

wherein R4 is a C2-C5 alkylene and R5 is selected from H and C1-C5 alkyl.

In some embodiments, the compound has the general structure (VIa):

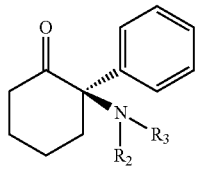

(VIa)

wherein R2 and R3 are independently selected from C2-C5 alkyl, C2-C5 fluoro-alkyl, —R$_4$—O—R$_5$; wherein R4 is a C2-C5 alkylene and R5 is selected from H and C1-C5 alkyl.

In some embodiments, the compound has the general structure (VIa):

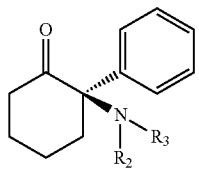

(VIa)

wherein R2 and R3 together with the nitrogen ring they are attached to form a C3-C6 cycloheteroalkyl ring; said ring optionally substituted by one or more C1-C2 alkyl or interrupted by one or more additional nitrogen or oxygen atoms.

In some embodiments, the compound has the general structure (VIb):

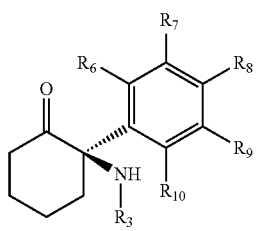

(VIb)

wherein one or more of R6, R7, R8, R9 and R10 is OH; and
wherein R3 is selected from C1-C10 alkyl, C2-C10 halo-alkyl, —R$_4$—O—R$_5$; wherein R4 is a C2-C10 alkylene and R5 is selected from H and C1-C10 alkyl;
provided that when R7 is OH, and R6, R8-R10 are H, then R3 is C3-C10 alkyl, C2-C10 halo-alkyl, or —R$_4$—O—R$_5$.

In some embodiments, the compound has the general structure (VIb):

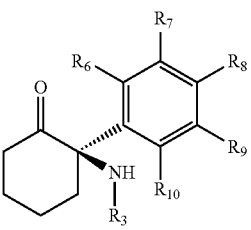

(VIb)

wherein one or more of R7, R8, and R9 is halogen (selected from F, Cl, Br, I); and
wherein R3 is selected from C1-C10 alkyl, C2-C10 halo-alkyl, —R$_4$—O—R$_5$; wherein R4 is a C2-C10 alkylene and R5 is selected from H and C1-C10 alkyl;
provided that when R7 is Cl and R6, R8-R10 are H, then R3 is C3-C10 alkyl, C2-C10 halo-alkyl, or —R$_4$—O—R$_5$.

In some embodiments, the compound has the general structure (VIb):

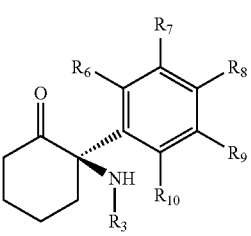

(VIb)

wherein one or more of R6, R7, R8, R9 and R10 is OMe; and
wherein R3 is selected from C1-C10 alkyl, C2-C10 halo-alkyl, —R$_4$—O—R$_5$; wherein R4 is a C2-C10 alkylene and R5 is selected from H and C1-C10 alkyl;
provided that when R6, R7 or R8 is OMe and the other of R6-R10 are H, then R3 is C3-C10 alkyl, C2-C10 halo-alkyl, or —R4-O—R5.

In some embodiments, the compound has the general structure (VIb):

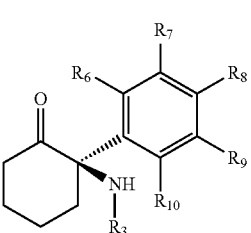

(VIb)

wherein one or more of R7, R8, and R9 is F; and
wherein R3 is selected from C1-C10 alkyl, C2-C10 halo-alkyl, —R$_4$—O—R$_5$; wherein R4 is a C2-C10 alkylene and R5 is selected from H and C1-C10 alkyl.

In some embodiments, the compound has the general structure (VIb):

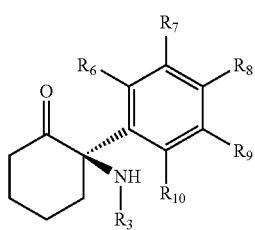

(VIb)

wherein one or more of R6, R7, R8, R9 and R10 is Me; and
wherein R3 is selected from C1-C10 alkyl, C2-C10 halo-alkyl, —R$_4$—O—R$_5$; wherein R4 is a C2-C10 alkylene and R5 is selected from H and C1-C10 alkyl.

In some embodiments, the compound has the general structure (VIb):

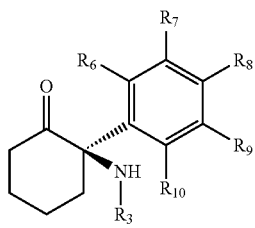

(VIb)

wherein one or more of R6, R7, R8, R9 and R10 is OH; and
wherein R3 is selected from C1-C5 alkyl, C2-C5 fluoro-alkyl, —R$_4$—O—R$_5$; wherein R4 is a C2-C5 alkylene and R5 is selected from H and C1-C5 alkyl;
provided that when R7 is OH, and R6, R8-R10 are H, then R3 is C3-C5 alkyl, C2-C5 fluoro-alkyl, or —R4-O—R5.

In some embodiments, the compound has the general structure (VIb):

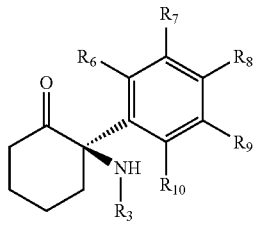

(VIb)

wherein one or more of R6, R7, R8, R9 and R10 is OMe; and
wherein R3 is selected from C1-C5 alkyl, C2-C5 fluoro-alkyl, —R$_4$—O—R$_5$; wherein R4 is a C2-C5 alkylene and R5 is selected from H and C1-C5 alkyl;
provided that when R6, R7 or R8 is OMe and the other of R6-R10 are H, then R3 is C3-C5 alkyl, C2-C5 fluoro-alkyl, or —R$_4$—O—R$_5$.

In some embodiments, the compound has the general structure (VIb):

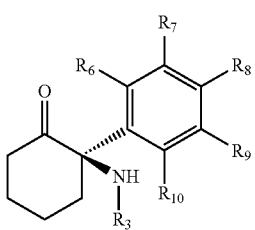

(VIb)

wherein one or more of R7, R8, or R9 is F; and
wherein R3 is selected from C1-C5 alkyl, C2-C5 fluoro-alkyl, —R$_4$—O—R$_5$; wherein R4 is a C2-C5 alkylene and R5 is selected from H and C1-C5 alkyl.

In some embodiments, the compound has the general structure (VIb):

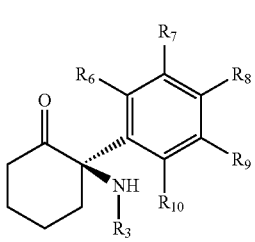

(VIb)

wherein one or more of R6, R7, R8, R9 and R10 is Me; and
wherein R3 is selected from C1-C5 alkyl, C2-C5 fluoro-alkyl, —R$_4$—O—R$_5$; wherein R4 is a C2-C5 alkylene and R5 is selected from H and C1-C5 alkyl.

In some embodiments, the compound has the general structure (VIc):

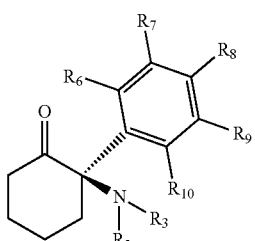

(VIc)

wherein one or more of R6, R7, R8, R9 and R10 is OH; and
wherein R2 and R3 are independently selected from C1-C5 alkyl, C2-C5 fluoro-alkyl, —R$_4$—O—R$_5$; wherein R4 is a C2-C5 alkylene and R5 is selected from H and C1-C5 alkyl; or
R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, the compound has the general structure (VIc):

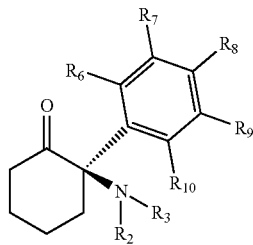
(VIc)

wherein one or more of R6, R7, R8, R9 and R10 is OMe; and
wherein R2 and R3 are independently selected from C1-C5 alkyl, C2-C5 fluoro-alkyl, —R4—O—R5; wherein R4 is a C2-C5 alkylene and R5 is selected from H and C1-C5 alkyl; or
R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, the compound has the general structure (VIc):

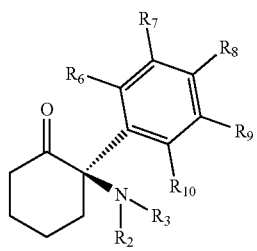
(VIc)

wherein one or more of R7, R8, and R9 is F; and
wherein R2 and R3 are independently selected from C1-C5 alkyl, C2-C5 fluoro-alkyl, —R4—O—R5; wherein R4 is a C2-C5 alkylene and R5 is selected from H and C1-C5 alkyl; or
R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, the compound has the general structure (VIc):

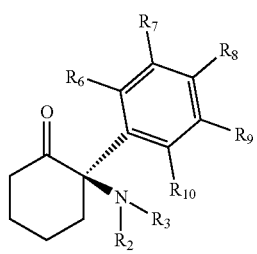
(VIc)

wherein one or more of R6, R7, R8, R9 and R10 is Me; and
wherein R2 and R3 are independently selected from C1-C5 alkyl, C2-C5 fluoro-alkyl, —R4—O—R5; wherein R4 is a C2-C5 alkylene and R5 is selected from H and C1-C5 alkyl; or
R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, the compound is selected from:

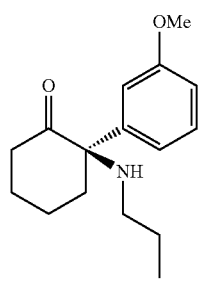
15R

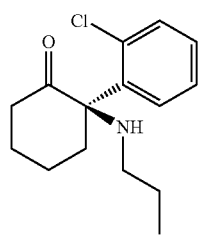
16R

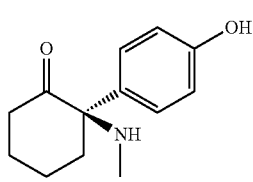
17R

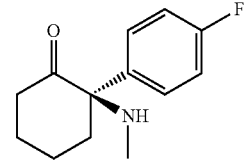
18R

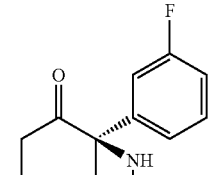
19R

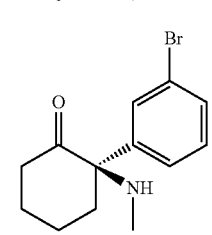
20R

73
-continued
21R 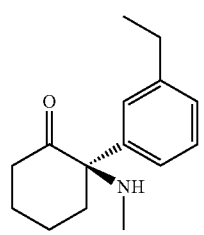
22R 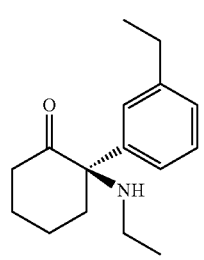
23R 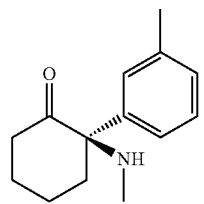
24R 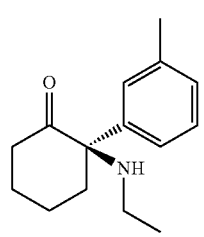
25R 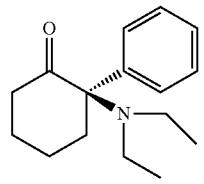
26R 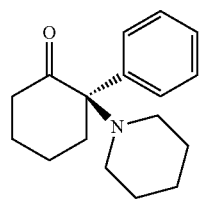
27R 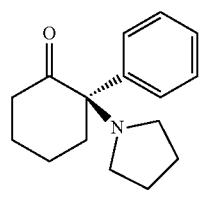
74
-continued
28R 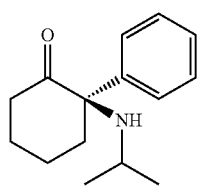
29R 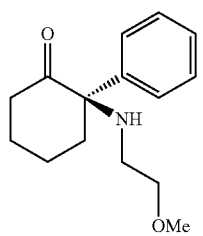
30R 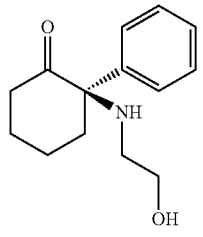
31R 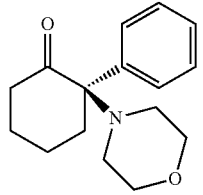
32R 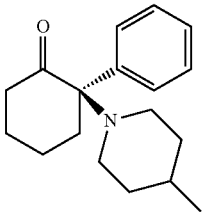
33R 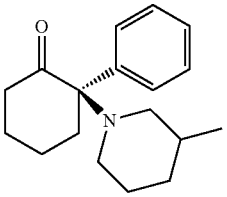
34R 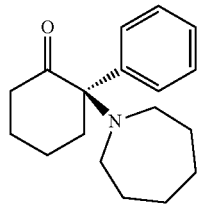

| | |
|---|---|
| 38R 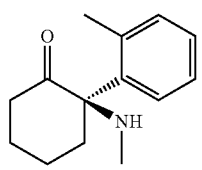 [SMILES: CN[C@@]1(c2ccccc2C)CCCCC1=O] | 49R 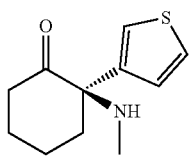 |
| 39R 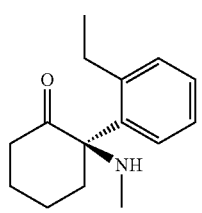 | 50R 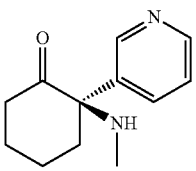 |
| 42R 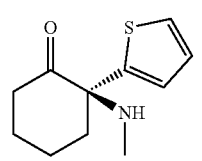 | 53R 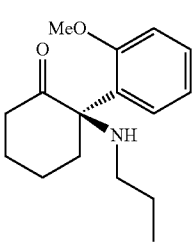 |
| 43R 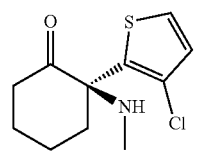 | 54R 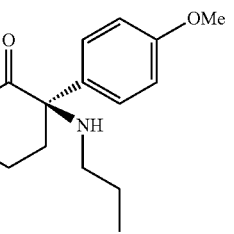 |
| 44R 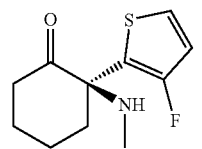 | 77R 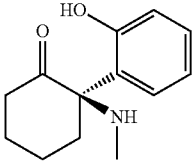 |
| 45R 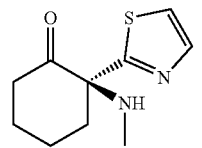 | 84R 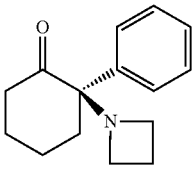 |
| 46R 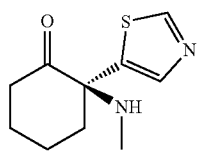 | 85R 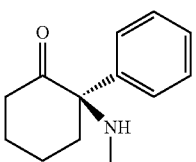 |
| 47R 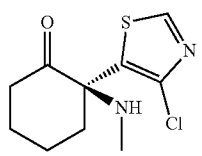 | 86R 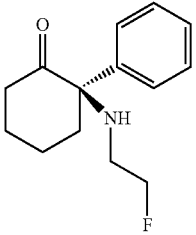 |
| 48R 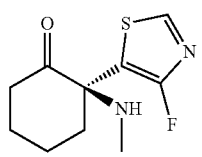 | |

114R
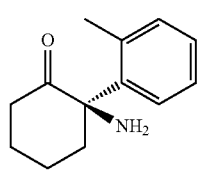
115R
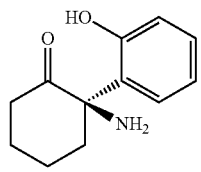
116R
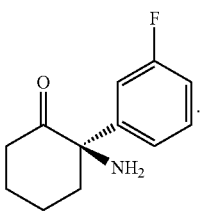
In some embodiments, the compound is selected from:
38R
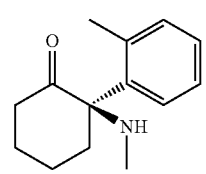
77R
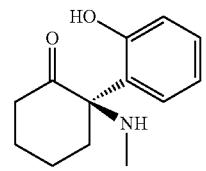
19R
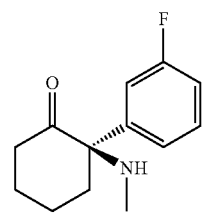
26R
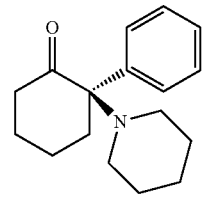
27R
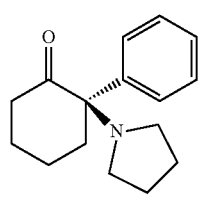
85R
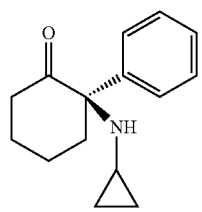
86R
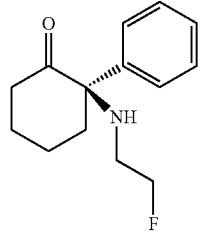
29R
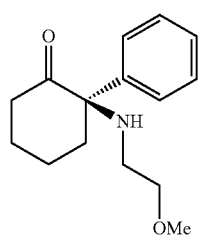
30R
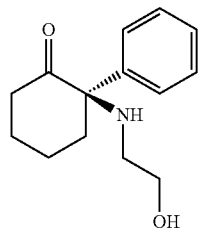
28R
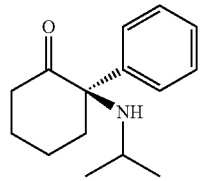
44R
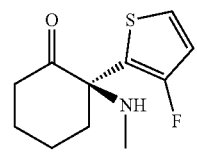

-continued

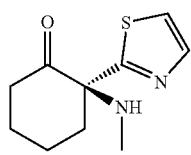
45R

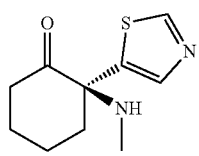
46R

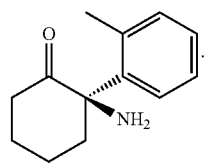
114R

In another aspect, provided herein is a composition comprising a carrier and a compound having the structure:

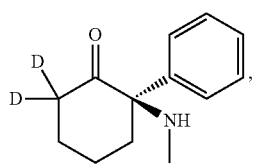
87R

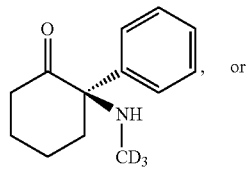
88R, or

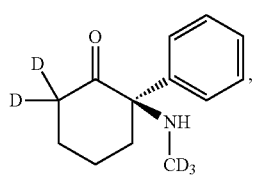
92R wherein D represents a deuterium-enriched —H site, and wherein the composition is enriched in the compound over its opposite enantiomer.

In some embodiments, each D represents a deuterium-enriched —H site and the level of deuterium at each deuterium-enriched —H site of the compound is 0.02% to 100%.

In some embodiments, each D represents a deuterium-enriched —H site and the level of deuterium at each deuterium-enriched —H site of the compound is 20%-100%, 50%-100%, 70%-100%, 90%-100%, 97%-100%, or 99%-100%.

In another aspect, provided herein a composition comprising a compound having the general structure (VIII):

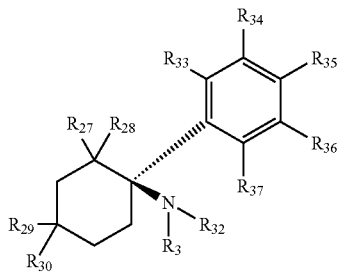
(VIII)

wherein R31 and R32 are independently selected from H, C1-C10 alkyl, C2-C10 halo-alkyl, —R38—O—R39; wherein R38 is a C2-C10 alkylene and R39 is selected from H and C1-C10 alkyl; or R31 and R32 together with the nitrogen atom they are attached to form a C3-C6 cycloheteroalkyl ring; said ring optionally substituted by one or more straight or branched C1-C10 alkyl or interrupted by one or more additional nitrogen or oxygen atoms; and wherein R27, R28, R29, R30 are each independently selected from H, straight or branched C1-C10 alkyl, F; wherein at least one of R27, R28, R29, or R30 is other than H; or R27 and R28 or R29 and R30 together with the carbon atom they are attached to form a cycloalkyl ring or together with the carbon they are attached to and one or more heteroatoms form a cycloheteroalkyl ring; and wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(=O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl;

provided that when one of R27 and R28 is Me, the other of R27 and R28 is H, R29-R30 and R33-R37 are each H, and R31 or R32 is H, then the other of R31 or R32 is C2-C10 alkyl, C2-C10 halo-alkyl, or —R38—O—R39;

or a pharmaceutically acceptable salt or ester of the compound, wherein the composition is enriched in the compound over its opposite enantiomer.

In some embodiments, the compound has the general structure (VIII):

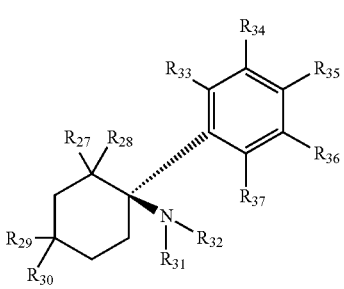
(VIII)

wherein R31 and R32 are independently selected from H, C1-C10 alkyl, C2-C10 halo-alkyl, —R38—O—R39; wherein R38 is a C2-C10 alkylene and R39 is selected from H and C1-C10 alkyl; or R31 and R32 together with the nitrogen atom they are attached to form a C3-C6 cycloheteroalkyl ring; said ring optionally substituted by one or more straight or branched C1-C2 alkyl or interrupted by one or more additional nitrogen or oxygen atoms; and wherein R27 and R28 are fluorine and R29 and R30 are H; and wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(=O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl.

In some embodiments, the compound has the general structure (VIII):

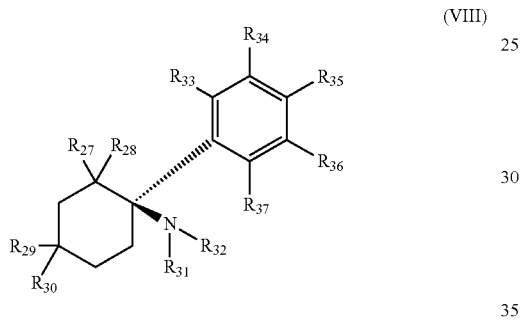

(VIII)

wherein R31 and R32 are independently selected from H, C1-C10 alkyl, C2-C10 halo-alkyl, —R38—O—R39; wherein R38 is a C2-C10 alkylene and R39 is selected from H and C1-C10 alkyl; or R31 and R32 together with the nitrogen atom they are attached to form a C3-C6 cycloheteroalkyl ring; said ring optionally substituted by one or more straight or branched C1-C2 alkyl or interrupted by one or more additional nitrogen or oxygen atoms; and wherein R27 and R28 together with the carbon they are attached to and an oxygen atom form an oxetane ring; and wherein R29 and R30 are H; and wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(=O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl.

In some embodiments, the compound is selected from:

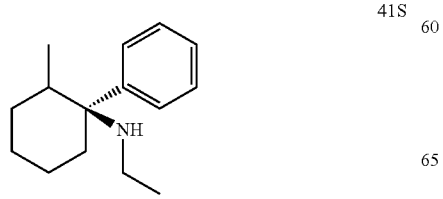

41S

-continued

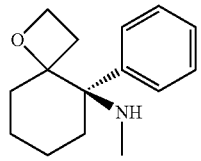

51R

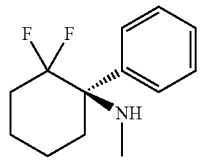

52R

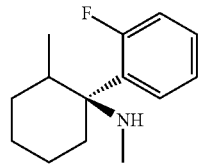

57S

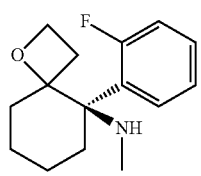

58R

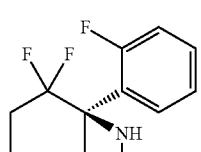

59R

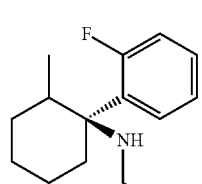

60S

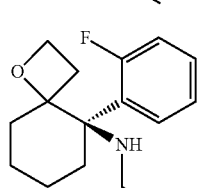

61R

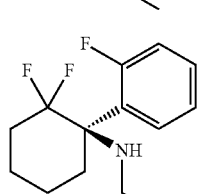

62R

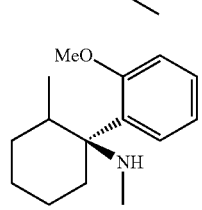

63S

-continued
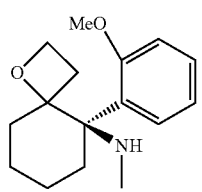 64R
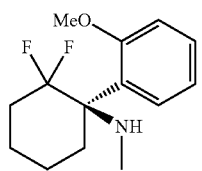 65R
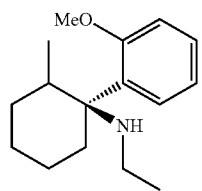 66S
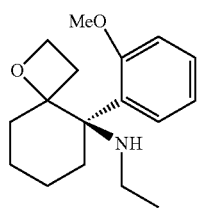 67R
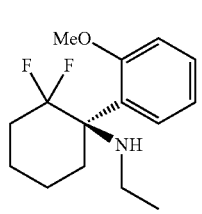 68R
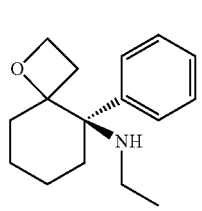 69R
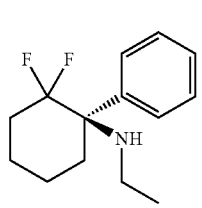 70R
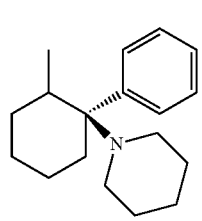 71S
-continued
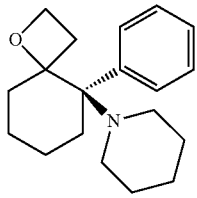 72R
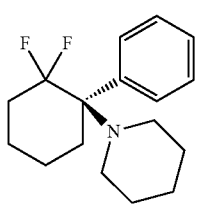 73R
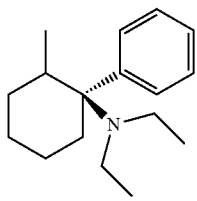 74R
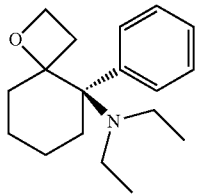 75R
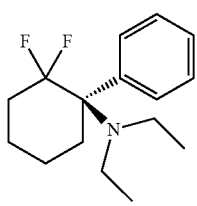 76R
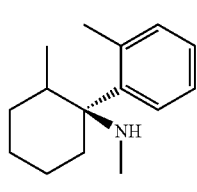 93S
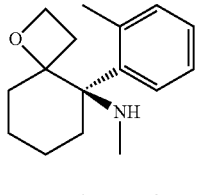 94R
95R 96S 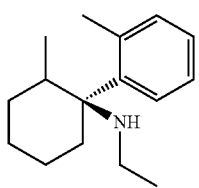

97R 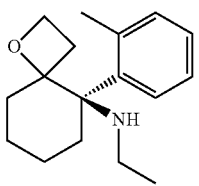

98R 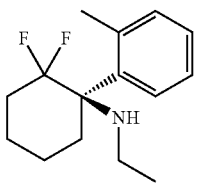

99S 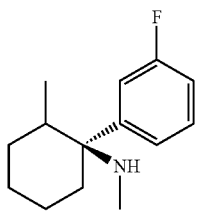

100R 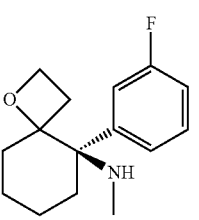

106R 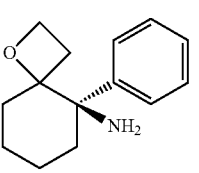

107R 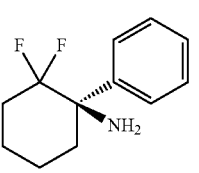

108S 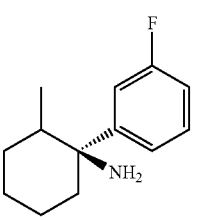

109R 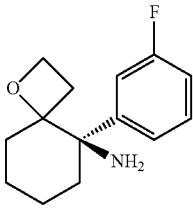

110R 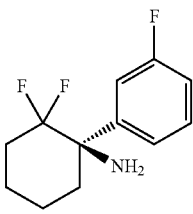

111S 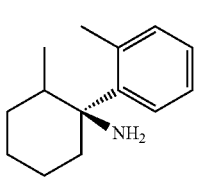

112R 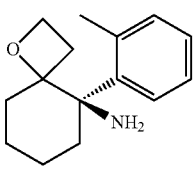

113R 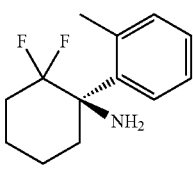

In some embodiments, the compound is selected from:

51R 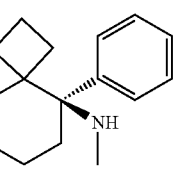 or

52R 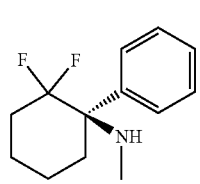

In some embodiments, the optical purity of the compound is >5%, >25%, >50%, >75%, >90%, >95%, >97%, >98%, or >99%.

In another aspect, provided herein is a method of treating depression, anxious depression, a mood disorder, an anxiety disorder, or a substance use disorder and any symptom or disorders associated therewith in a subject in need thereof, the method comprising administering to the subject a composition comprising a compound of structure (IX):

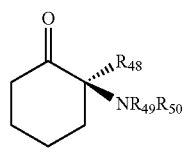

(IX)

wherein R48 is selected from the group consisting of: phenyl, thiazole, thiophene, pyridine, or a moiety of general formula (X);

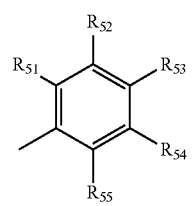

(X)

wherein R51 and R55 are independently selected from H, OH, OMe, C1-C10 alkyl; and wherein R52, R53, and R54 are each independently selected from H, OH, halogen (selected from F, Cl, Br, I), OMe, C1-C10 alkyl; and wherein R49 and R50 are each independently selected from H and C1-C10 alkyl; or R49 and R50 together with the nitrogen atom they are connected to from a C3-C9 cycloheteroalkyl ring optionally substituted with one or more C1-C10 alkyl;

or a pharmaceutically acceptable salt or ester of the compound, wherein the compound is enriched over its opposite enantiomer.

In some embodiments, the compound is selected from:

1R

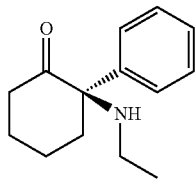

2R

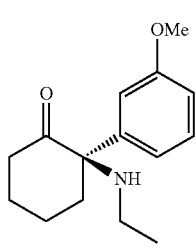

3R

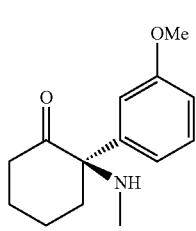

4R

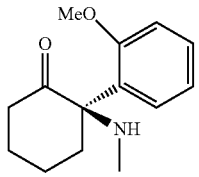

5R

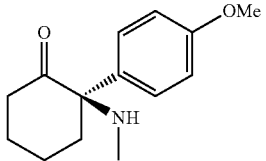

6R

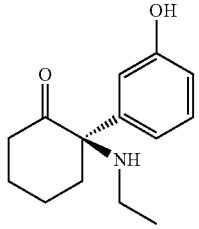

7R

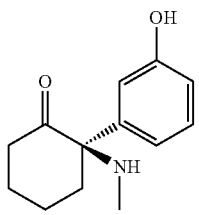

8R

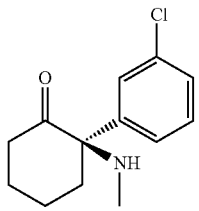

9R

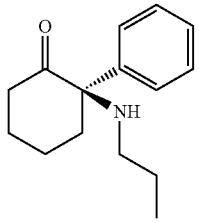

10R

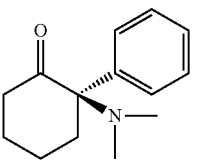

11R

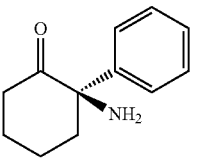

-continued

13R
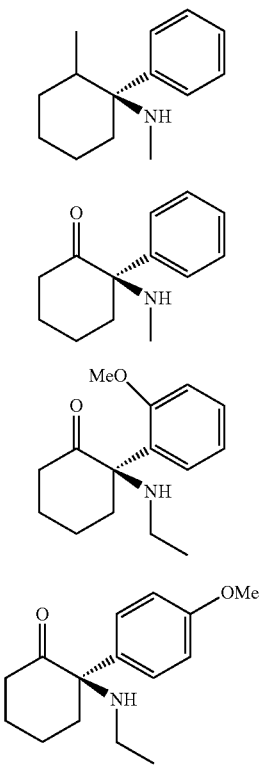
14R

55R

56R

In some embodiments, the compound has the structure:

14R
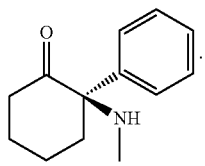

In some embodiments, the disorder to be treated in the subject is depression or anxious depression. In some embodiments, the composition is orally administered.

In another aspect, provided herein is a method of treating depression, anxious depression, a mood disorder, an anxiety disorder, or a substance use disorder and any symptom or disorders associated therewith in a subject in need thereof, the method comprising administering to the subject a composition comprising the compound:

13S
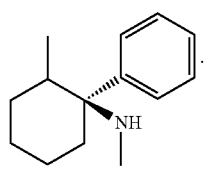

or a pharmaceutically acceptable salt or ester of the compound, wherein the compound is enriched over its opposite enantiomer.

In another aspect, provided herein is a composition comprising a compound having the general structure (XI):

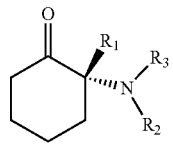

(XI)

wherein R1 is selected from the group consisting of phenyl, optionally substituted thiazole, optionally substituted thiophene, optionally substituted pyridine, a moiety of general formula (XII);
wherein when R1 is phenyl;
R2 and R3 are independently selected from H, $CD_3$, branched or cyclo C3 alkyl, C4-C10 alkyl, C2-C10 halo-alkyl, —$R_4$—O—$R_5$; wherein R4 is a C2-C10 alkylene and R5 is selected from H and C1-C10 alkyl; wherein D represents a deuterium-enriched —H site; and wherein at least one of R2 and R3 is other than H; or
R2 and R3 are independently selected from C2-C10 alkyl; C2-C10 halo-alkyl, —$R_4$—O—$R_5$;
wherein R4 is a C2-C10 alkylene and R5 is selected from H and C1-C10 alkyl; or
R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms;
wherein when R1 is a moiety of general formula (XII):

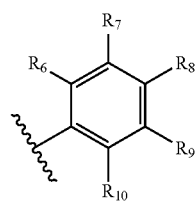

(XII)

R2 and R3 are independently selected from H, C1-C10 alkyl, C2-C10 halo-alkyl, —$R_4$—O—$R_5$; wherein R4 is a C2-C10 alkylene and R5 is selected from H and C1-C10 alkyl; and wherein at least one of R2 and R3 is other than H; or
R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms; and
R6, R7, R8, R9 and R10 are independently selected from H, OH, halogen (selected from F, Cl, Br, I), —OR11, C1-C10 alkyl, C2-C10 alkenyl, C2-C10 alkynyl, CN, $CF_3$, $OCF_3$, $NO_2$, —NR12R13, —SR14, —$SO_2$R15, —$CO_2$R16, —C(=O)NR17R18; wherein R11, R12, R13, R14, R15, R16, R17 and R18 are each independently selected from H, C1-C10 alkyl, C2-C10 alkenyl, C2-C10 alkynyl, aryl, heteroaryl, —C(=O)H, —C(=O)alkyl, —C(=O)aryl, —C(=O)heteroaryl; wherein at least one of R6-R10 is other than H; and wherein neither R6 nor R10 is halogen; provided that when R7 is Cl and R6, R8-R10 are H, and R2 or R3 is H, then the other of R2 or R3 is C3-C10 alkyl, C2-C10 halo-alkyl, or —R$_4$—O—R$_5$; or provided that when R7 is OH and R6, R8-R10 are H, and R2 or R3 is H, then the other of R2 or R3 is C3-C10 alkyl, C2-C10 halo-alkyl, or —R$_4$—O—R$_5$; or provided that when R6, R7, or R8 is OMe and the other of R6-R10 are each H, and R2 or R3 is H, then the other of R2 or R3 is C3-C10 alkyl, C2-C10 halo-alkyl, or —R$_4$—O—R$_5$;

wherein when R1 is selected from thiazole, thiophene, and pyridine, each optionally substituted with one or more OH, halogen (selected from F, Cl, Br, I), —OR19, C1-C10 alkyl, C2-C10 alkenyl, C2-C10 alkynyl, CN, CF$_3$, OCF$_3$, NO$_2$, —NR20R21, —SR22, —SO$_2$R23, —CO$_2$R24, —C(═O)NR25R26; wherein R19, R20, R21, R22, R23, R24, R25 and R26 are each independently selected from H, C1-C10 alkyl, C2-C10 alkenyl, C2-C10 alkynyl, aryl, heteroaryl, C(═O)H, C(═O)alkyl, C(═O)aryl, C(═O)heteroaryl;

R2 and R3 are independently selected from H, C1-C10 alkyl, C2-C10 halo-alkyl, C2-C10 alkenyl, C2-C10 alkynyl, —R$_4$—O—R$_5$; wherein R4 is a C2-C10 alkylene and R5 is selected from H and C1-C10 alkyl; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms;

or a pharmaceutically acceptable salt or ester of the compound, wherein the composition is enriched in the compound over its opposite enantiomer.

In some embodiments, the compound has the general structure (XIa):

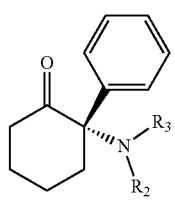

(XIa)

wherein R2 and R3 are independently selected from H, branched or cyclo C3 alkyl, C4-C10 alkyl, C2-C10 halo-alkyl, —R$_4$—O—R$_5$; wherein R4 is a C2-C10 alkylene and R5 is selected from H and C1-C10 alkyl; and wherein at least one of R2 and R3 is other than H; or R2 and R3 are independently selected from C2-C10 alkyl, C2-C10 halo-alkyl, —R$_4$—O—R$_5$;

wherein R4 is a C2-C10 alkylene and R5 is selected from H and C1-C10 alkyl; or

R2 and R3 together with the nitrogen ring they are connected to form a C3-C9 cycloheteroalkyl ring; said ring optionally substituted by one or more C1-C10 alkyl or interrupted by one or more additional nitrogen or oxygen atoms.

In some embodiments, the compound has the general structure (XIb):

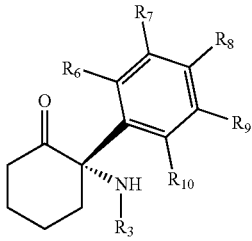

(XIb)

wherein R3 is a C1-C10 alkyl, C2-C10 halo-alkyl, or —R$_4$—O—R$_5$; wherein R4 is a C2-C10 alkylene and R5 is selected from H and C1-C10 alkyl; and wherein R6, R7, R8, R9 and R10 are independently selected from H, OH, halogen (selected from F, Cl, Br, I), —OR11, C1-C10 alkyl, C2-C10 alkenyl, C2-C10 alkynyl, CN, CF$_3$, OCF$_3$, NO$_2$, —NR12R13, —SR14, —SO$_2$R15, —CO$_2$R16, —C(═O)NR17R18; wherein R11, R12, R13, R14, R15, R16, R17 and R18 are each independently selected from H, C1-C10 alkyl, C2-C10 alkenyl, C2-C10 alkynyl, aryl, heteroaryl, C(═O)H, C(═O)alkyl, C(═O)aryl, C(═O)heteroaryl; wherein at least one of R6-R10 is other than H; and wherein neither R6 nor R10 is halogen;

provided that when R7 is Cl and R6, R8-R10 are H, then R3 is C3-C10 alkyl, C2-C10 halo-alkyl, or —R$_4$—O—R$_5$; or provided that when R7 is OH and R6, R8-R10 is H, then R3 is C3-C10 alkyl, C2-C10 halo-alkyl, or —R$_4$—O—R$_5$; or provided that when R6, R7, or R8 is OMe, and the other of R6-R10 are H, then R3 is C3-C10 alkyl, C2-C10 halo-alkyl, or —R$_4$—O—R$_5$.

In some embodiments, the compound has the general structure (XI):

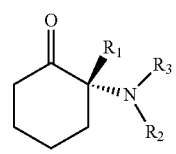

(XI)

wherein R1 is selected from thiazole, thiophene, and pyridine; each optionally substituted with one or more OH, halogen (selected from F, Cl, Br, I), —OR19, C1-C10 alkyl, C2-C10 alkenyl, C2-C10 alkynyl, CN, CF$_3$, OCF$_3$, NO$_2$, —NR20R21, —SR22, —SO$_2$R23, —CO$_2$R24, —C(═O)NR25R26; wherein R19, R20, R21, R22, R23, R24, R25 and R26 are each independently selected from H, C1-C10 alkyl, C2-C10 alkenyl, C2-C10 alkynyl, aryl, heteroaryl, C(═O)H, C(═O)alkyl, C(═O)aryl, C(═O)heteroaryl; and wherein R2 and R3 are independently selected from H, C1-C10 alkyl, C2-C10 halo-alkyl, C2-C10 alkenyl, C2-C10 alkynyl, —R$_4$—O—R$_5$; wherein R4 is a C2-C10 alkylene and R5 is selected from H and C1-C10 alkyl; or R2 and R3 together with the nitrogen atom they are connected to form a C3-C9 cycloheteroalkyl ring; said ring optionally substituted by one or more C1-C10 alkyl or interrupted by one or more additional nitrogen or oxygen atoms.

In some embodiments, the compound has the general structure (XIa):

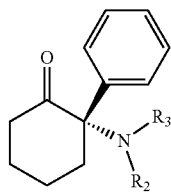

(XIa)

wherein R2 and R3 are independently selected from H, branched or cyclo C3 alkyl, C4-C10 alkyl, C2-C10 halo-alkyl, —R₄—O—R₅; wherein R4 is a C2-C10 alkylene and R5 is selected from H and C1-C10 alkyl; wherein at least one of R2 and R3 is other than H.

In some embodiments, the compound has the general structure (XIa):

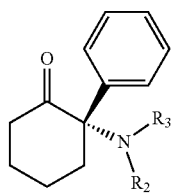

(XIa)

wherein R2 and R3 are independently selected from C2-C10 alkyl, C2-C10 halo-alkyl, —R₄—O—R₅; wherein R4 is a C2-C10 alkylene and R5 is selected from H and C1-C10 alkyl.

In some embodiments, the compound has the general structure (XIa):

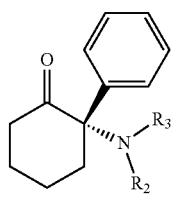

(XIa)

wherein R2 and R3 together with the nitrogen ring they are attached to form a C3-C9 cycloheteroalkyl ring; said ring optionally substituted by one or more C1-C10 alkyl or interrupted by one or more additional nitrogen or oxygen atoms.

In some embodiments, the compound has the general structure (XIa):

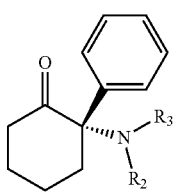

(XIa)

wherein R2 is H and R3 is selected from branched or cyclo C3 alkyl, C4-C5 alkyl, C2-C5 fluoro-alkyl, —R₄—O—R₅; wherein R4 is a C2-C5 alkylene and R5 is selected from H and C1-C5 alkyl.

In some embodiments, the compound has the general structure (XIa):

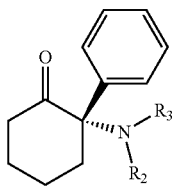

(XIa)

wherein R2 and R3 are independently selected from C2-C5 alkyl, C2-C5 fluoro-alkyl, —R₄—O—R₅; wherein R4 is a C2-C5 alkylene and R5 is selected from H and C1-C5 alkyl.

In some embodiments, the compound has the general structure (XIa):

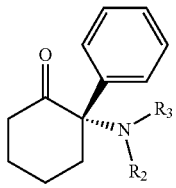

(XIa)

wherein R2 and R3 together with the nitrogen ring they are attached to form a C3-C6 cycloheteroalkyl ring; said ring optionally substituted by one or more C1-C2 alkyl or interrupted by one or more additional nitrogen or oxygen atoms.

In some embodiments, the compound has the general structure (XIb):

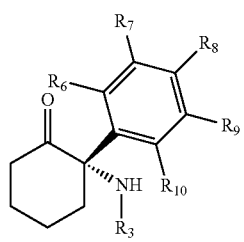

(XIb)

wherein one or more of R6, R7, R8, R9 and R10 is OH; and wherein R3 is selected from C1-C10 alkyl, C2-C10 halo-alkyl, —R₄—O—R₅; wherein R4 is a C2-C10 alkylene and R5 is selected from H and C1-C10 alkyl;

provided that when R7 is OH, and R6, R8-R10 are H, then R3 is C3-C10 alkyl, C2-C10 halo-alkyl, or —R₄—O—R₅.

In some embodiments, the compound has the general structure (XIb):

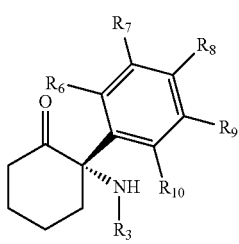
(XIb)

wherein one or more of R7, R8, and R9 is halogen (selected from F, Cl, Br, I); and wherein R3 is selected from C1-C10 alkyl, C2-C10 halo-alkyl, —R$_4$—O—R$_5$; wherein R4 is a C2-C10 alkylene and R5 is selected from H and C1-C10 alkyl;

provided that when R7 is Cl and R6, R8-R10 are H, then R3 is C3-C10 alkyl, C2-C10 halo-alkyl, or —R$_4$—O—R$_5$.

In some embodiments, the compound has the general structure (XIb):

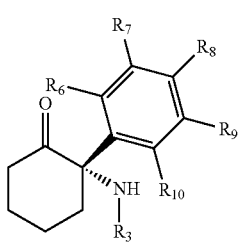
(XIb)

wherein one or more of R6, R7, R8, R9 and R10 is OMe; and wherein R3 is selected from C1-C10 alkyl, C2-C10 halo-alkyl, —R$_4$—O—R$_5$; wherein R4 is a C2-C10 alkylene and R5 is selected from H and C1-C10 alkyl;

provided that when R6, R7 or R8 is OMe and the other of R6-R10 are H, then R3 is C3-C10 alkyl, C2-C10 halo-alkyl, or —R$_4$—O—R$_5$.

In some embodiments, the compound has the general structure (XIb):

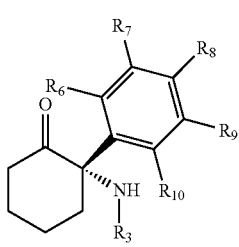
(XIb)

wherein one or more of R7, R8, and R9 is F; and wherein R3 is selected from C1-C10 alkyl, C2-C10 halo-alkyl, —R$_4$—O—R$_5$; wherein R4 is a C2-C10 alkylene and R5 is selected from H and C1-C10 alkyl.

In some embodiments, the compound has the general structure (XIb):

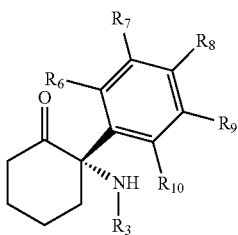
(XIb)

wherein one or more of R6, R7, R8, R9 and R10 is Me; and wherein R3 is selected from C1-C10 alkyl, C2-C10 halo-alkyl, —R$_4$—O—R$_5$; wherein R4 is a C2-C10 alkylene and R5 is selected from H and C1-C10 alkyl.

In some embodiments, the compound has the general structure (XIb):

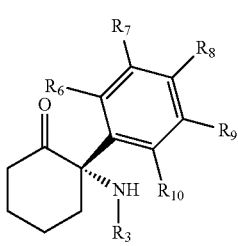
(XIb)

wherein one or more of R6, R7, R8, R9 and R10 is OH; and wherein R3 is selected from C1-C5 alkyl, C2-C5 fluoro-alkyl, —R$_4$—O—R$_5$; wherein R4 is a C2-C5 alkylene and R5 is selected from H and C1-C5 alkyl;

provided that when R7 is OH, and R6, R8-R10 are H, then R3 is C3-C5 alkyl, C2-C5 fluoro-alkyl, or —R$_4$—O—R$_5$.

In some embodiments, the compound has the general structure (XIb):

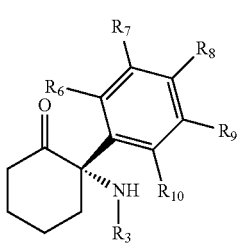
(XIb)

wherein one or more of R6, R7, R8, R9 and R10 is OMe; and wherein R3 is selected from C1-C5 alkyl, C2-C5 fluoro-alkyl, —R$_4$—O—R$_5$; wherein R4 is a C2-C5 alkylene and R5 is selected from H and C1-C5 alkyl;

provided that when R6, R7 or R8 is OMe and the other of R6-R10 are H, then R3 is C3-C5 alkyl, C2-C5 fluoro-alkyl, or —R$_4$—O—R$_5$.

In some embodiments, the compound has the general structure (XIb):

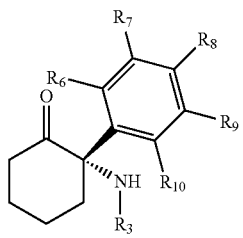
(XIb)

wherein one or more of R7, R8, or R9 is F; and wherein R3 is selected from C1-C5 alkyl, C2-C5 fluoro-alkyl, —R₄—O—R₅; wherein R4 is a C2-C5 alkylene and R5 is selected from H and C1-C5 alkyl.

In some embodiments, the compound has the general structure (XIb):

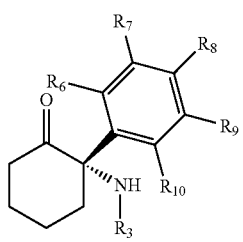
(XIb)

wherein one or more of R6, R7, R8, R9 and R10 is Me; and wherein R3 is selected from C1-C5 alkyl, C2-C5 fluoro-alkyl, —R₄—O—R₅; wherein R4 is a C2-C5 alkylene and R5 is selected from H and C1-C5 alkyl.

In some embodiments, the compound has the general structure (XIc):

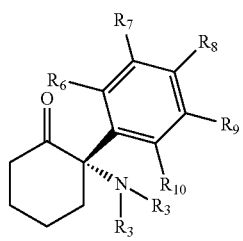
(XIc)

wherein one or more of R6, R7, R8, R9 and R10 is OH; and wherein R2 and R3 are independently selected from C1-C5 alkyl, C2-C5 fluoro-alkyl, —R₄—O—R₅; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, the compound has the general structure (XIc):

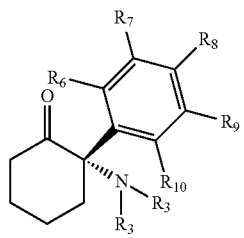
(XIc)

wherein one or more of R6, R7, R8, R9 and R10 is OMe; and wherein R2 and R3 are independently selected from C1-C5 alkyl, C2-C5 fluoro-alkyl, —R₄—O—R₅; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, the compound has the general structure (XIc):

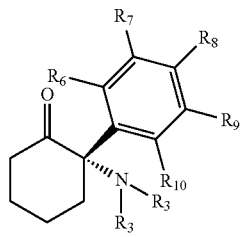
(XIc)

wherein one or more of R7, R8, and R9 is F; and
wherein R2 and R3 are independently selected from C1-C5 alkyl, C2-C5 fluoro-alkyl, —R₄—O—R₅; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, the compound has the general structure (XIc):

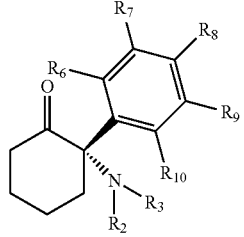
(XIc)

wherein one or more of R6, R7, R8, R9 and R10 is Me; and wherein R2 and R3 are independently selected from C1-C5 alkyl, C2-C5 fluoro-alkyl, —R₄—O—R₅; wherein R4 is a C2-C5 alkylene and R5 is selected from H and C1-C5 alkyl; or R2 and R3 together with the nitrogen atom they are connected to form a C3-C6 cycloheteroalkyl ring; said ring optionally substituted by one or more C1-C2 alkyl or interrupted by one or more additional nitrogen or oxygen atoms.

In some embodiments, the compound is selected from:

15S
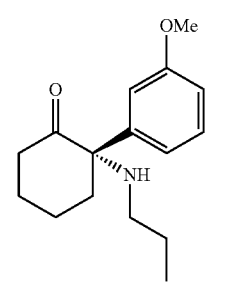

16S
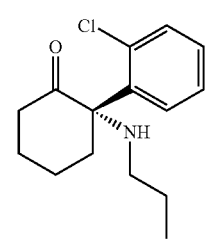

17S
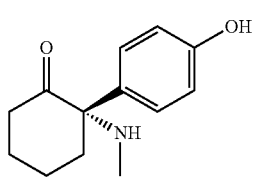

18S
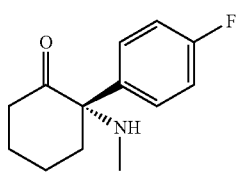

19S
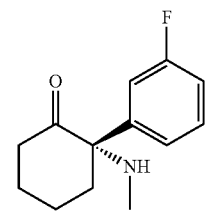

20S
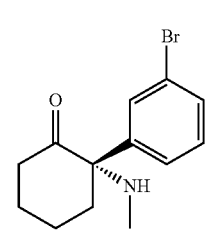

21S
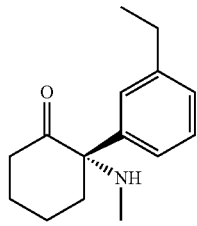

22S
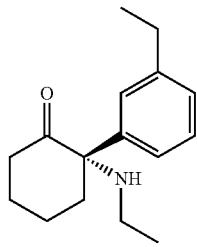

23S
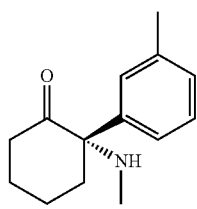

24S
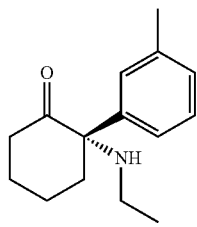

25S
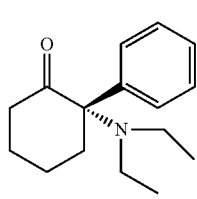

26S
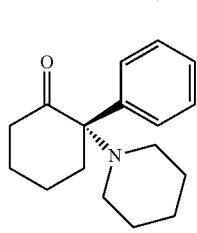

27S
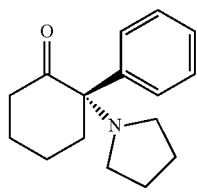

| 101 -continued | | 102 -continued | |
|---|---|---|---|
| 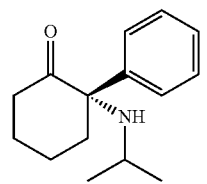 | 28S | 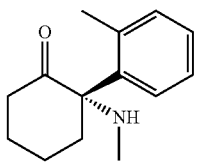 [SMILES: CN[C@]1(c2ccccc2C)CCCCC1=O] | 38S |
| 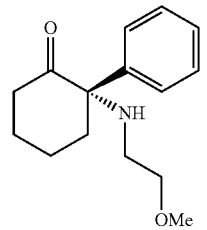 | 29S | 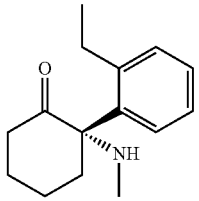 | 39S |
| 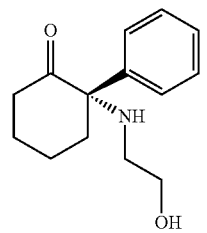 | 30S | 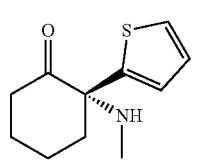 | 42S |
| 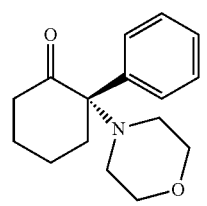 | 31S | 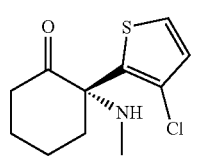 | 43S |
| 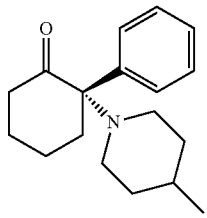 | 32S | 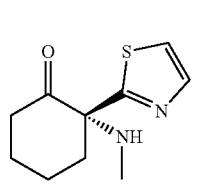 | 44S |
| 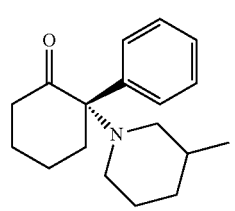 | 33S | 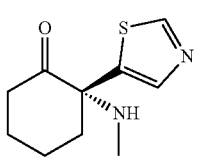 | 45S |
| 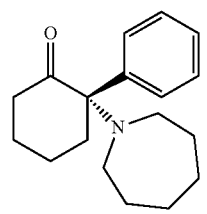 | 34S | 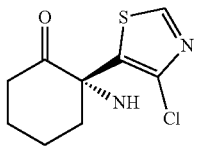 | 46S |
| | | 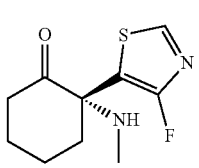 | 47S |
| | | | 48S |

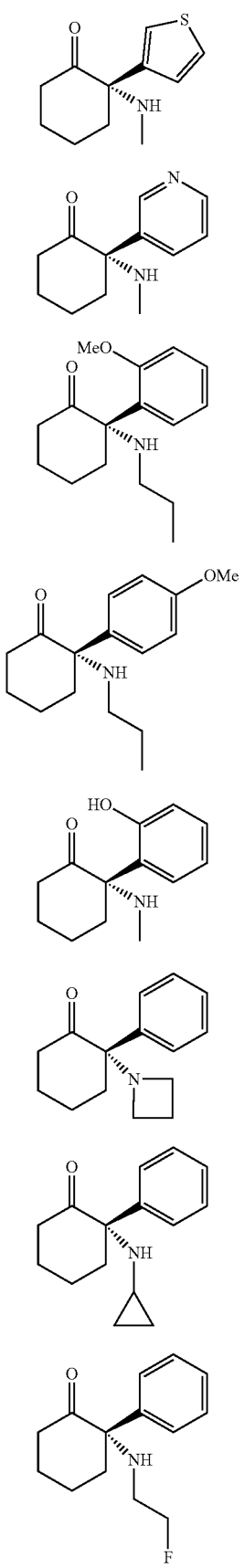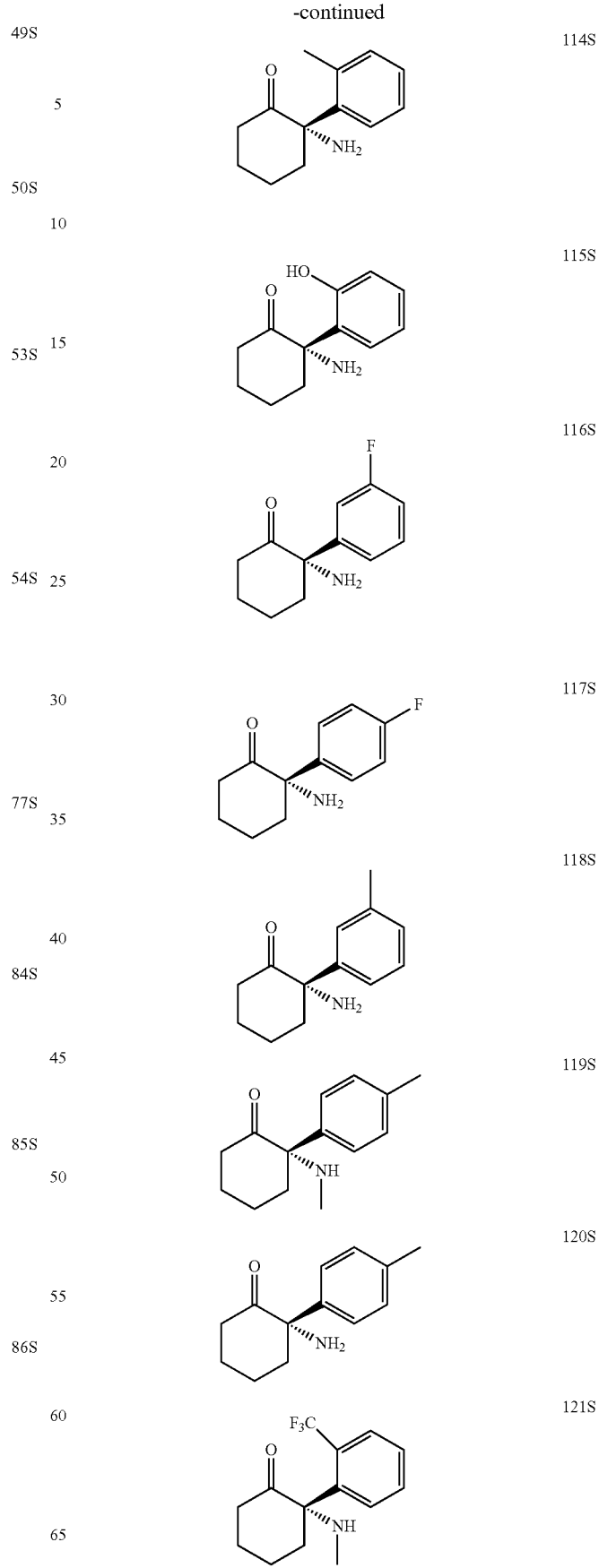

122S 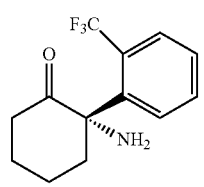
123S 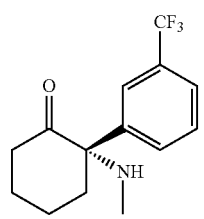
S124S 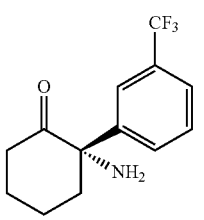
125S 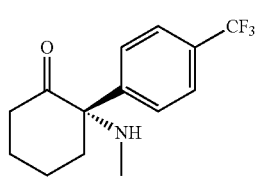
126S 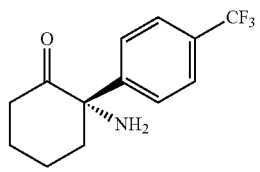
127S 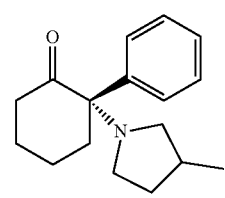
128S 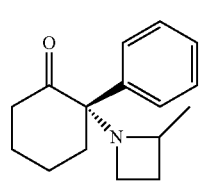
129S 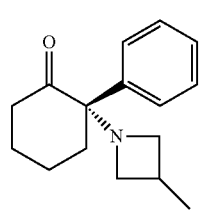
130S 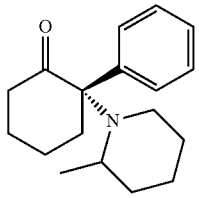
131S 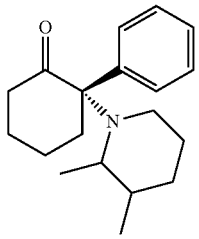
132S 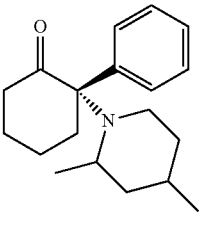
133S 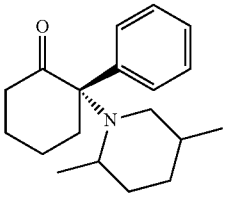
134S 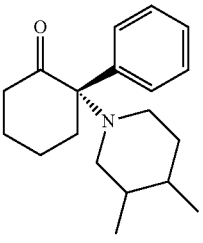
135S 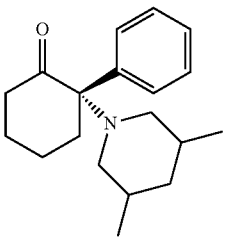
136S 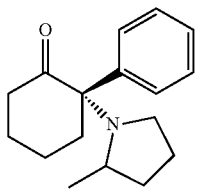

137S
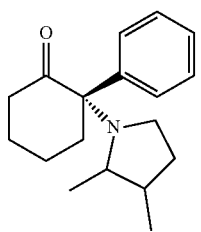
138S
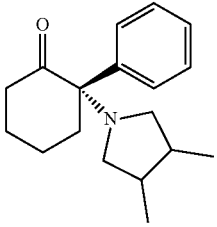
139S
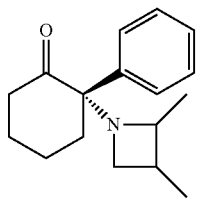
140S
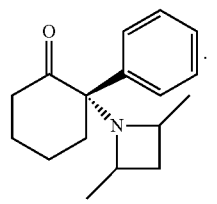
In some embodiments, the compound is selected from:
38S
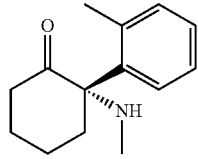
77S
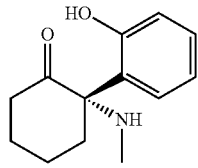
19S
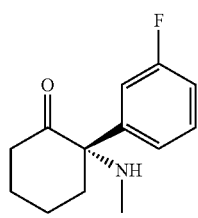
26S
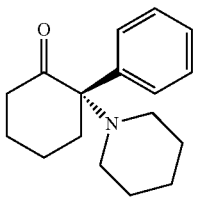
27S
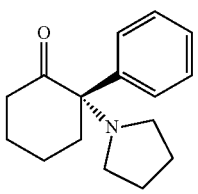
85S
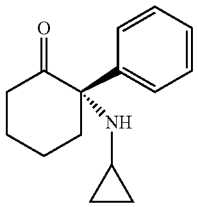
86S
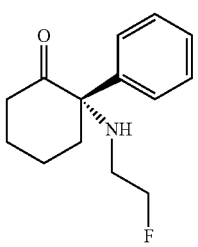
29S
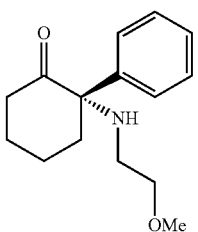 [SMILES: COCCN[C@]1(c2ccccc2)CCCCC1=O]
30S
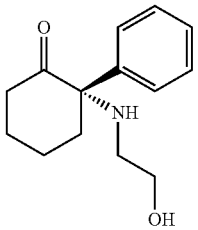 [SMILES: O=C1CCCC[C@]1(NCCO)c1ccccc1]
28S
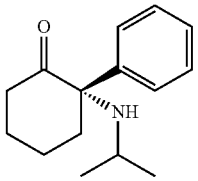

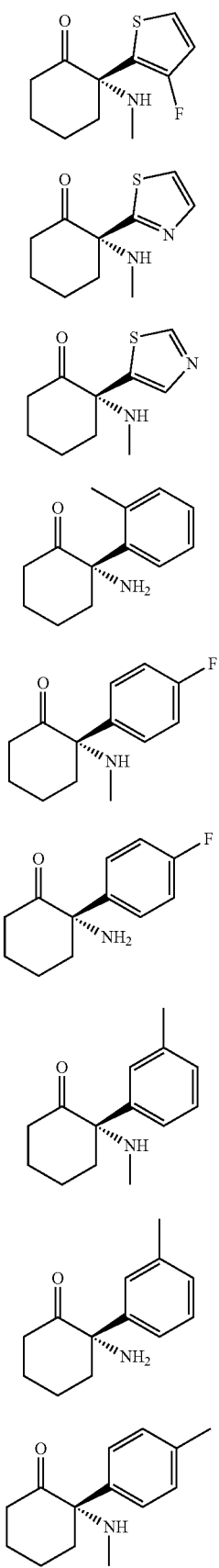
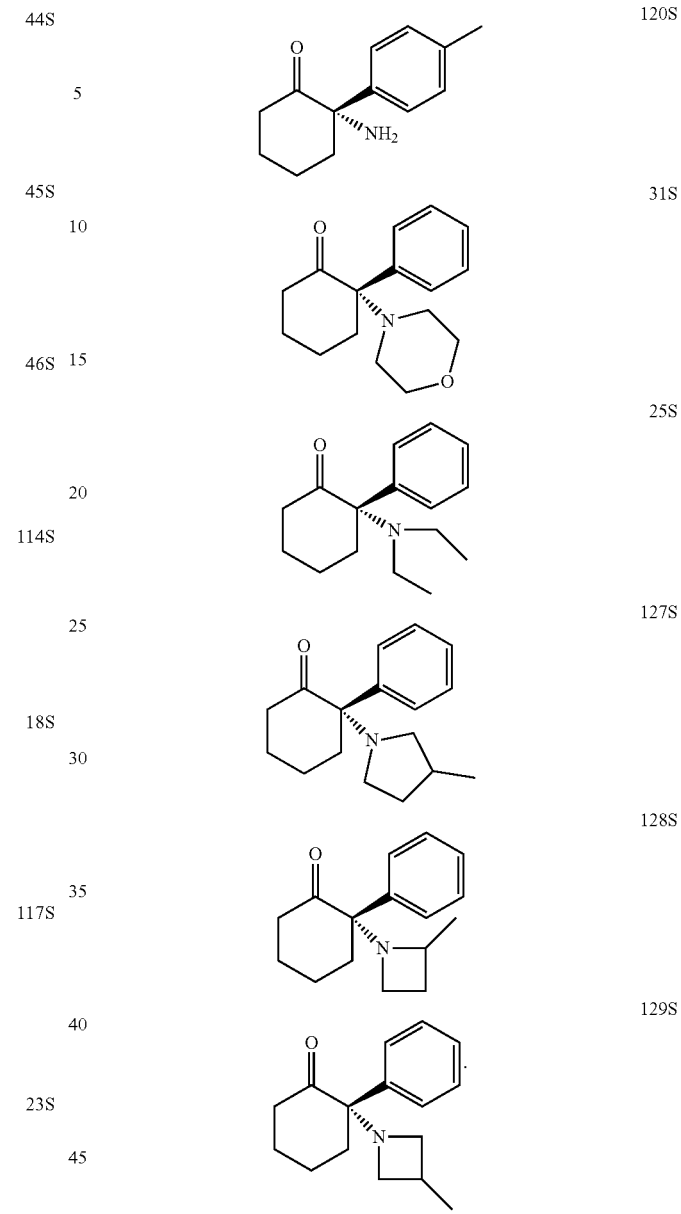
In another aspect, provided herein is a composition comprising a carrier and a compound having the structure:
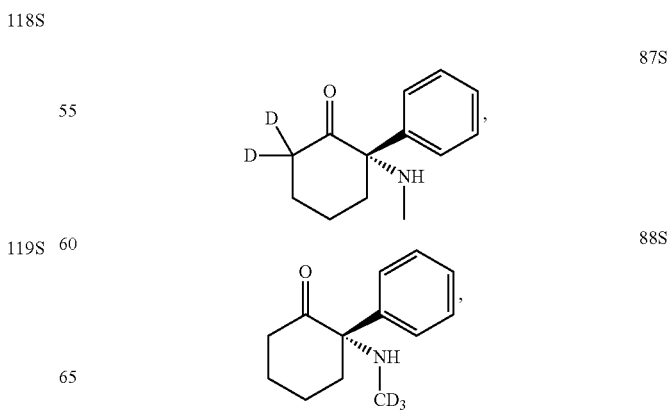

-continued

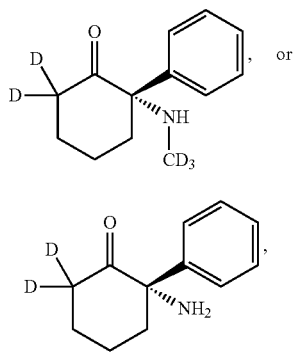

92S

142S wherein D represents a deuterium-enriched —H site, and wherein the composition is enriched in the compound over its opposite enantiomer.

In some embodiments, each D represents a deuterium-enriched —H site and the level of deuterium at each deuterium-enriched —H site of the compound is 0.02% to 100%.

In some embodiments, each D represents a deuterium-enriched —H site and the level of deuterium at each deuterium-enriched —H site of the compound is 20%-100%, 50%-100%, 70%-100%, 90%-100%, 97%-100%, or 99%-100%.

In another aspect, provided herein is a composition comprising a compound having the general structure (XIII):

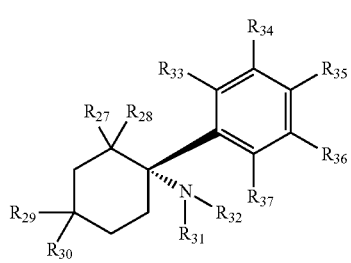

(XIII)

wherein R31 and R32 are independently selected from H, C1-C10 alkyl, C2-C10 halo-alkyl, —R38—O—R39; wherein R38 is a C2-C10 alkylene and R39 is selected from H and C1-C10 alkyl; or
R31 and R32 together with the nitrogen atom they are attached to form a C3-C6 cycloheteroalkyl ring; said ring optionally substituted by one or more straight or branched C1-C10 alkyl or interrupted by one or more additional nitrogen or oxygen atoms; and
wherein R27, R28, R29, R30 are each independently selected from H, straight or branched C1-C10 alkyl, F; wherein at least one of R27, R28, R29, or R30 is other than H; or
R27 and R28 or R29 and R30 together with the carbon atom they are attached to form a cycloalkyl ring or together with the carbon they are attached to and one or more heteroatoms form a cycloheteroalkyl ring; and
wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(=O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl;

provided that when one of R27 and R28 is Me, the other of R27 and R28 is H, R29-R30 and R33-R37 are each H, and R31 or R32 is H, then the other of R31 or R32 is C2-C10 alkyl, C2-C10 halo-alkyl, or —R38—O—R39;

or a pharmaceutically acceptable salt or ester of the compound, wherein the composition is enriched in the compound over its opposite enantiomer.

In some embodiments, the compound has the general structure (XIII):

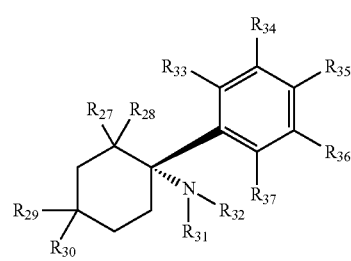

(XIII)

wherein R31 and R32 are independently selected from H, C1-C10 alkyl, C2-C10 halo-alkyl, —R38—O—R39; wherein R38 is a C2-C10 alkylene and R39 is selected from H and C1-C10 alkyl; or
R31 and R32 together with the nitrogen atom they are attached to form a C3-C6 cycloheteroalkyl ring; said ring optionally substituted by one or more straight or branched C1-C2 alkyl or interrupted by one or more additional nitrogen or oxygen atoms; and
wherein R27 and R28 are fluorine and R29 and R30 are H; and
wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(=O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl.

In some embodiments, the compound has the general structure (XIII):

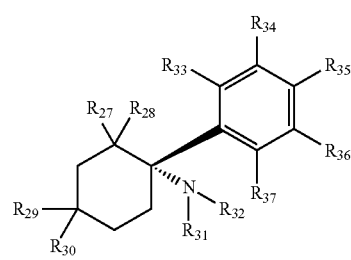

(XIII)

wherein R31 and R32 are independently selected from H, C1-C10 alkyl, C2-C10 halo-alkyl, —R38—O—R39; wherein R38 is a C2-C10 alkylene and R39 is selected from H and C1-C10 alkyl; or
R31 and R32 together with the nitrogen atom they are attached to form a C3-C6 cycloheteroalkyl ring; said ring optionally substituted by one or more straight or branched C1-C2 alkyl or interrupted by one or more additional nitrogen or oxygen atoms; and wherein R27 and R28 together with the carbon they are attached to and an oxygen atom form an oxetane ring; and wherein R29 and R30 are H; and wherein R33, R34, R35, R36 and R37 are each independently selected from H, OH, halogen (selected from F, Cl, Br, I), —OR40, C1-C10 alkyl, C2-C10 alkenyl, C2-C10 alkynyl, CN, CF$_3$, OCF$_3$, NO$_2$, —NR41R42, —SR43, —SO$_2$R44, —CO$_2$R45, —C(=O)NR46R47; wherein R40, R41, R42, R43, R44, R45, R46 and R47 are each independently selected from H, C1-C10 alkyl, C2-C10 alkenyl, C2-C10 alkynyl, aryl, heteroaryl, C(=O)H, C(=O)alkyl, C(=O)aryl, C(=O)heteroaryl.

In some embodiments, the compound is selected from:

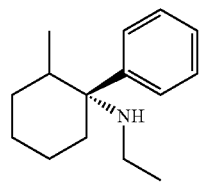
41R

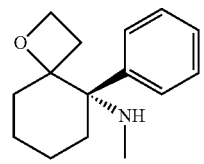
51S

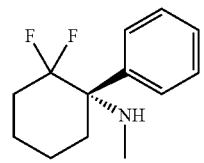
52S

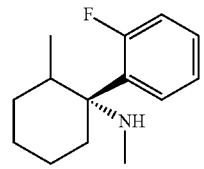
57S

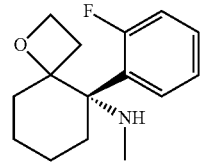
58S

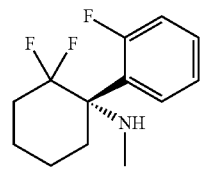
59S

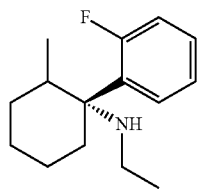
60R

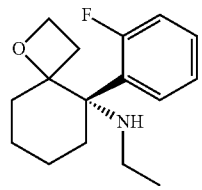
61S

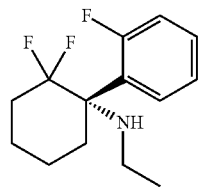
62S

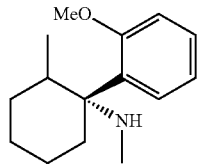
63R

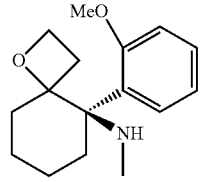
64S

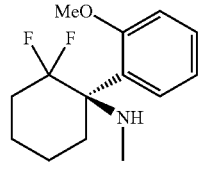
65S

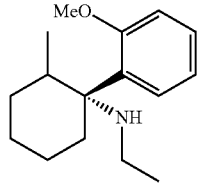
66R

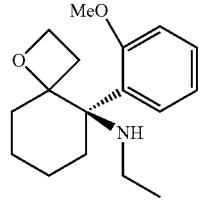
67S

-continued
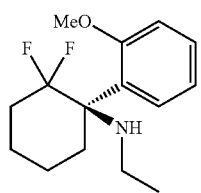 68S
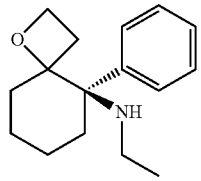 69S
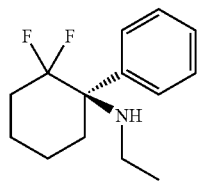 70S
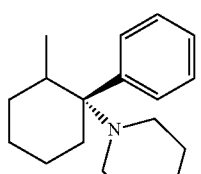 71R
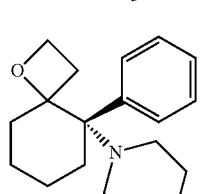 72S
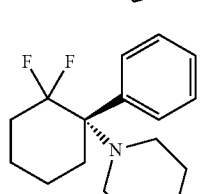 73S
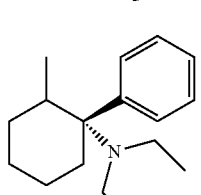 74R
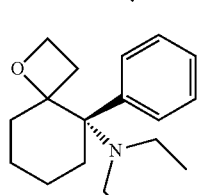 75S
-continued
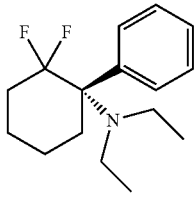 76S
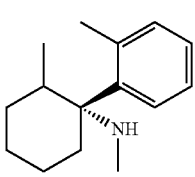 93R
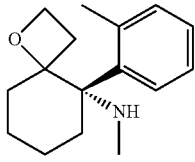 94S
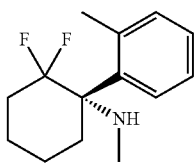 95S
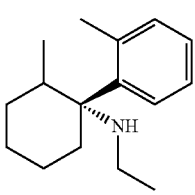 96R
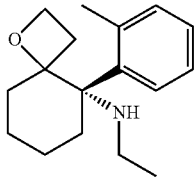 97S
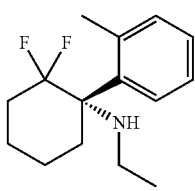 98S
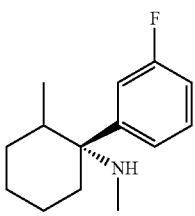 99R -continued
100S 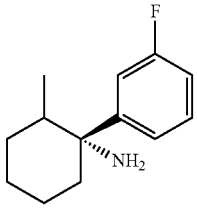
101S 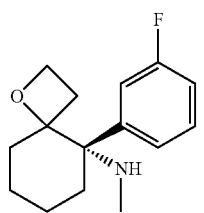
102R 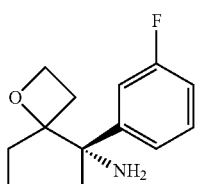
103S 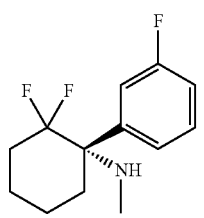
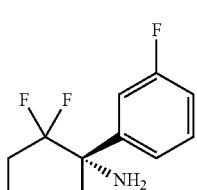 110S
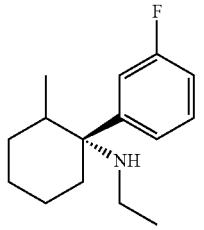 111R 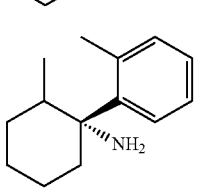
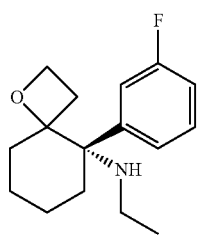 112S 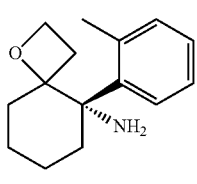
104S
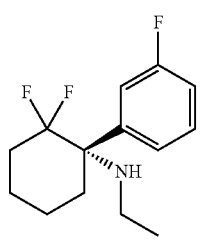 113S 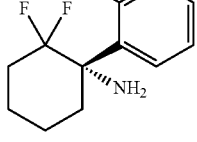
106S
In some embodiments, the compound is selected from:
51S
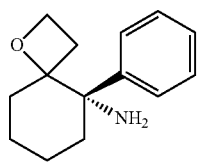 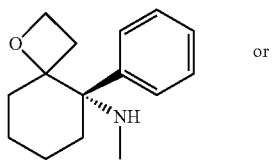 or
107S
52S
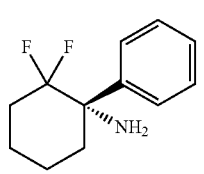 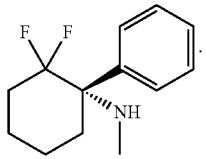
108R
109S In some embodiments, the optical purity of the compound is >5%, >25%, >50%, >75%, >90%, >95%, >97%, >98%, or >99%.

In some embodiments, a composition disclosed herein is a pharmaceutical composition.

In some embodiments, a composition disclosed is an oral composition.

In another aspect, provided herein is a method of treating depression, anxious depression, a mood disorder, an anxiety disorder, or a substance use disorder and any symptom or disorders associated therewith in a subject in need thereof, the method comprising administering to the subject a composition comprising a compound of structure (XIV):

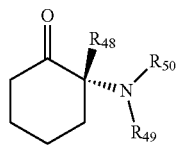

(XIV)

wherein R48 is selected from the group consisting of: phenyl, thiazole, thiophene, pyridine, or a moiety of general formula (XV);

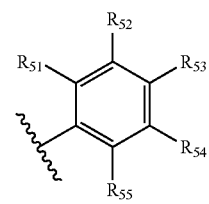

(XV)

wherein R51 and R55 are independently selected from H, OH, OMe, C1-C10 alkyl; and wherein R52, R53, and R54 are each independently selected from H, OH, halogen (selected from F, Cl, Br, I), OMe, C1-C10 alkyl; and wherein R49 and R50 are each independently selected from H and C1-C10 alkyl; or R49 and R50 together with the nitrogen atom they are connected to from a C3-C9 cyclo-heteroalkyl ring optionally substituted with one or more C1-C10 alkyl;

or a pharmaceutically acceptable salt or ester of the compound, wherein the compound is enriched over its opposite enantiomer.

In some embodiments, the compound is selected from:

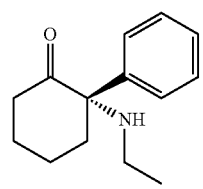

1S

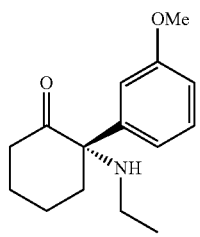

2S

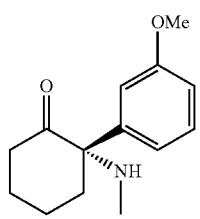

3S

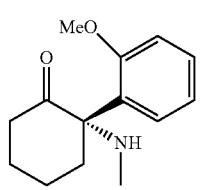

4S

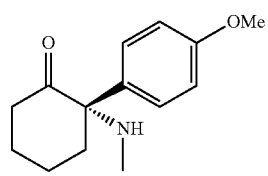

5S

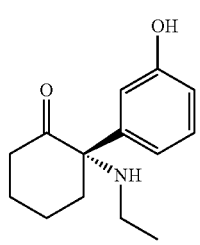

6S

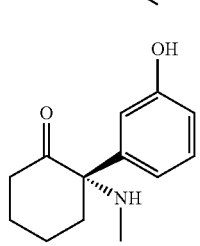

7S

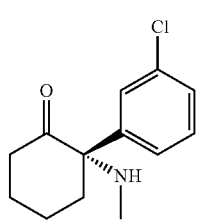

8S

-continued

9S

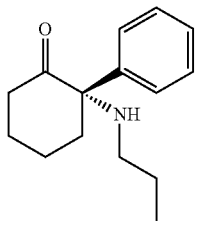

10S

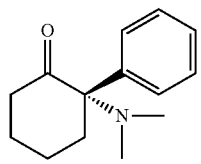

11S

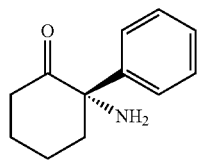

14S

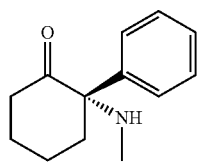

55S

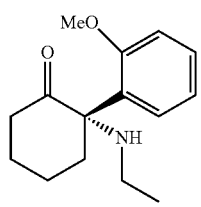

56S

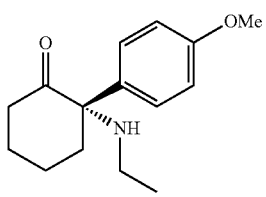

In some embodiments, the compound has the structure:

14S

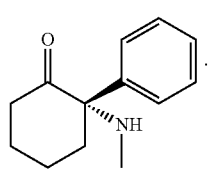

In some embodiments, the compound has the structure:

11S

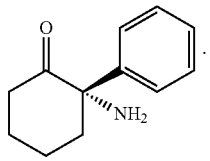

In some embodiments, the disorder to be treated in the subject is depression or anxious depression.

In some embodiments, the composition is orally administered.

In another aspect, provided herein is a method of treating depression, anxious depression, a mood disorder, an anxiety disorder, or a substance use disorder and any symptom or disorders associated therewith in a subject in need thereof, the method comprising administering to the subject a composition comprising the compound:

13R

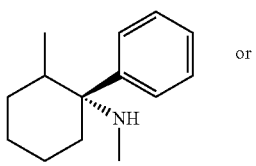

or

141R

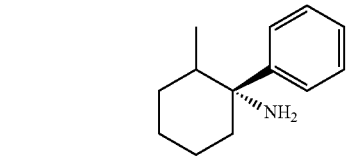

or a pharmaceutically acceptable salt or ester of the compound, wherein the compound is enriched over its opposite enantiomer.

In another aspect, provided herein is a compound having the general structure (XVI):

(XVI)

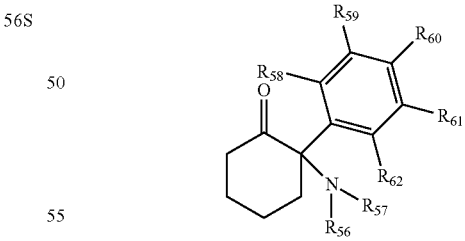

wherein R56 and R57 together with the nitrogen atom they are connected to form a monocyclic or bicyclic C3-C8 cycloheteroalkyl ring, said ring optionally substituted by one or more C1-C3 alkyl, F, OH, OMe, or =O, and optionally interrupted by one or more additional nitrogen or oxygen atoms; and wherein R58, R59, R60, R61, and R62 are each independently selected from H, OH, halogen (selected from F, Cl, Br, I), —OR63, —O—C(=O)R64, C1-C10 alkyl, C2-C10 alkenyl, C2-C10 alkynyl, CN, CF3, OCF3, NO2, —NR65R66, —NH—C(=O)R67, —SR68, —SO$_2$R69, —CO₂R70, —C(=O)NR71R72; wherein R63, R64, R65, R66, R67, R68, R69, R70, R71, and R72 are each independently selected from H, C1-C10 alkyl, C2-C10 alkenyl, C2-C10 alkynyl, aryl, heteroaryl;

provided that when R56 and R57 together with the nitrogen atom they are connected to form an unsubstituted piperidine ring, then at least one of R58, R59, R60, R61, and R62 is other than H; or a pharmaceutically acceptable salt or ester thereof.

In some embodiments, the compound wherein R56 and R57 together with the nitrogen atom they are connected to form a piperidine ring, said ring optionally substituted by one or more C1-C3 alkyl, F, OH, OMe, or =O; and wherein R58, R59, R60, R61, and R62 are each independently selected from H, OH, halogen (selected from F, Cl, Br, I), —OR63, —O—C(=O)R64, C1-C10 alkyl, C2-C10 alkenyl, C2-C10 alkynyl, CN, CF3, OCF3, NO2, —NR65R66, —NH—C(=O)R67, —SR68, —SO₂R69, —CO₂R70, —C(=O)NR71R72; wherein R63, R64, R65, R66, R67, R68, R69, R70, R71, and R72 are each independently selected from H, C1-C10 alkyl, C2-C10 alkenyl, C2-C10 alkynyl, aryl, heteroaryl;

provided that when R56 and R57 together with the nitrogen atom they are connected to form an unsubstituted piperidine ring, then at least one of R58, R59, R60, R61, and R62 is other than H;

or a pharmaceutically acceptable salt or ester thereof.

In some embodiments, the compound wherein R56 and R57 together with the nitrogen atom they are connected to form a pyrrolidine ring, said ring optionally substituted by one or more C1-C3 alkyl, F, OH, OMe, or =O; and wherein R58, R59, R60, R61, and R62 are each independently selected from H, OH, halogen (selected from F, Cl, Br, I), —OR63, —O—C(=O)R64, C1-C10 alkyl, C2-C10 alkenyl, C2-C10 alkynyl, CN, CF3, OCF3, NO2, —NR65R66, —NH—C(=O)R67, —SR68, —SO₂R69, —CO₂R70, —C(=O)NR71R72; wherein R63, R64, R65, R66, R67, R68, R69, R70, R71, and R72 are each independently selected from H, C1-C10 alkyl, C2-C10 alkenyl, C2-C10 alkynyl, aryl, heteroaryl;

or a pharmaceutically acceptable salt or ester thereof.

In some embodiments, the compound wherein R56 and R57 together with the nitrogen atom they are connected to form an azetidine ring, said ring optionally substituted by one or more C1-C3 alkyl, F, OH, OMe, or =O; and wherein R58, R59, R60, R61, and R62 are each independently selected from H, OH, halogen (selected from F, Cl, Br, I), —OR63, —O—C(=O)R64, C1-C10 alkyl, C2-C10 alkenyl, C2-C10 alkynyl, CN, CF3, OCF3, NO2, —NR65R66, —NH—C(=O)R67, —SR68, —SO₂R69, —CO₂R70, —C(=O)NR71R72; wherein R63, R64, R65, R66, R67, R68, R69, R70, R71, and R72 are each independently selected from H, C1-C10 alkyl, C2-C10 alkenyl, C2-C10 alkynyl, aryl, heteroaryl;

or a pharmaceutically acceptable salt or ester thereof.

In some embodiments, the compound wherein R56 and R57 together with the nitrogen atom they are connected to form an azetidine ring; said ring optionally substituted by one or more C1-C3 alkyl or F; and wherein R58, R59, R60, R61, and R62 are each independently selected from F, OH, halogen (selected from F, Cl, Br, I), —OR63, —O—C(=O)R64, C1-C3 alkyl, C2-C3 alkenyl, C2-C3 alkynyl, CN, CF3, OCF3, NO2, —NR65R66, —NH—C(=O)R67, —SR68, —SO₂R69, —CO₂R70, —C(=O)NR71R72; wherein R63, R64, R65, R66, R67, R68, R69, R70, R71, and R72 are each independently selected from H, C1-C3 alkyl, C2-C3 alkenyl, C2-C3 alkynyl;

or a pharmaceutically acceptable salt or ester thereof.

In some embodiments, the compound is selected from

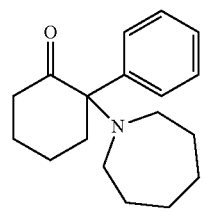

34rac

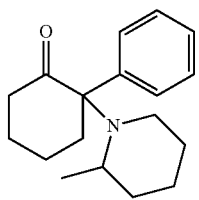

130rac

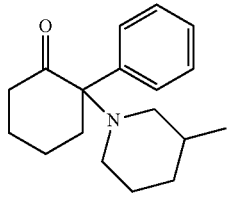

33rac

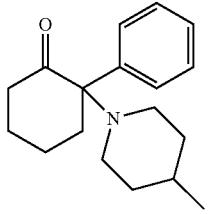

32rac

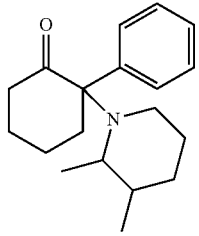

131rac

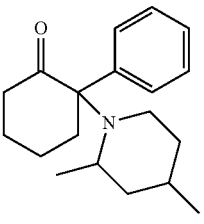

132rac

125
-continued
133rac
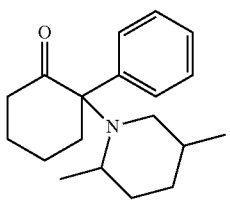
134rac
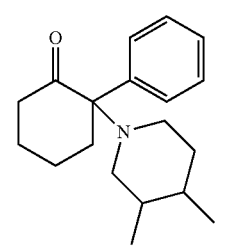
135rac
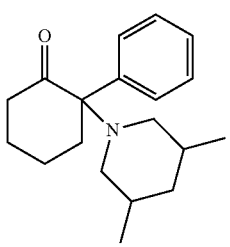
27rac
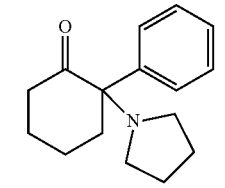
136rac
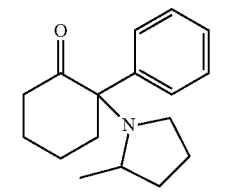
127rac
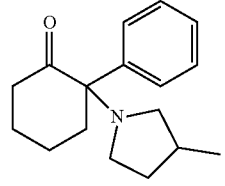
137rac
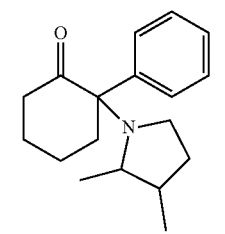
126
-continued
138rac
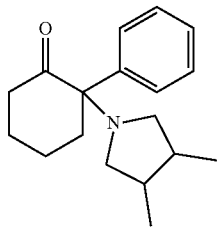
84rac
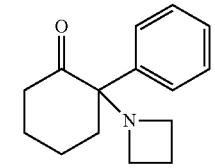
128rac
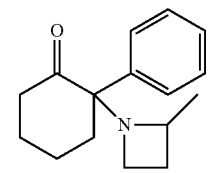
129rac
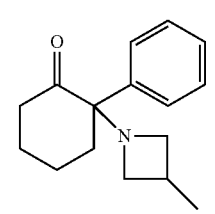
139rac
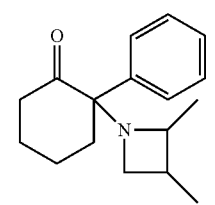
140rac
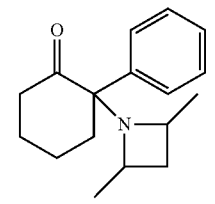
143rac
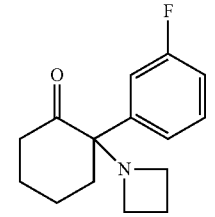
144rac
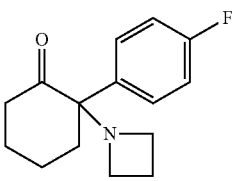

-continued

145rac

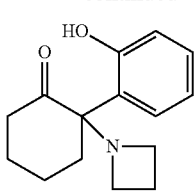

146rac

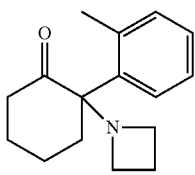

147rac

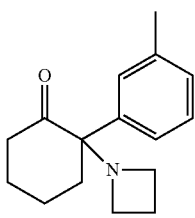

148rac

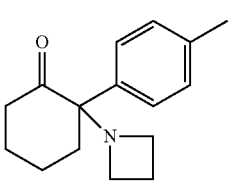

or a pharmaceutically acceptable salt or ester thereof, and/or a specific S- or R-isomer thereof.

In some embodiments, the compound has the structure:

84rac

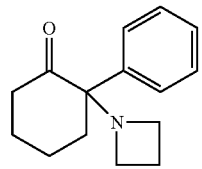

or a pharmaceutically acceptable salt thereof.

In another aspect, provided herein is a compound having the general structure (XVII):

(XVII)

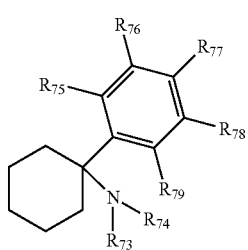

wherein R73 and R74 together with the nitrogen atom they are connected to form an azetidine ring, said ring optionally substituted by one or more C1-C3 alkyl, F, OH, or OMe; and wherein R75, R76, R77, R78, and R79 are each independently selected from H, OH, halogen (selected from F, Cl, Br, I), —OR80, —O—C(=O)R81, C1-C10 alkyl, C2-C10 alkenyl, C2-C10 alkynyl, CN, CF3, OCF3, NO2, —NR82R83, —NH—C(=O)R84, —SR85, —SO2R86, —CO2R87, —C(=O)NR88R89; wherein R80, R81, R82, R83, R84, R85, R86, R87, R88, and R89 are each independently selected from H, C1-C10 alkyl, C2-C10 alkenyl, C2-C10 alkynyl, aryl, heteroaryl;

or a pharmaceutically acceptable salt or ester thereof.

In some embodiments, the compound is selected from:

149

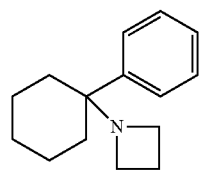

150rac

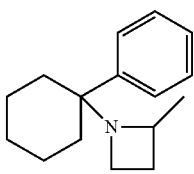

151

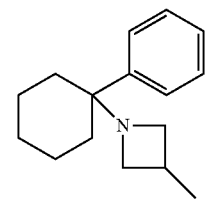

152rac

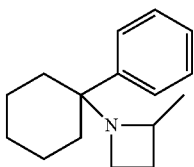

153rac

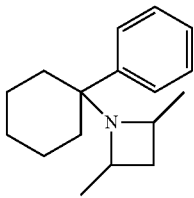

154

-continued
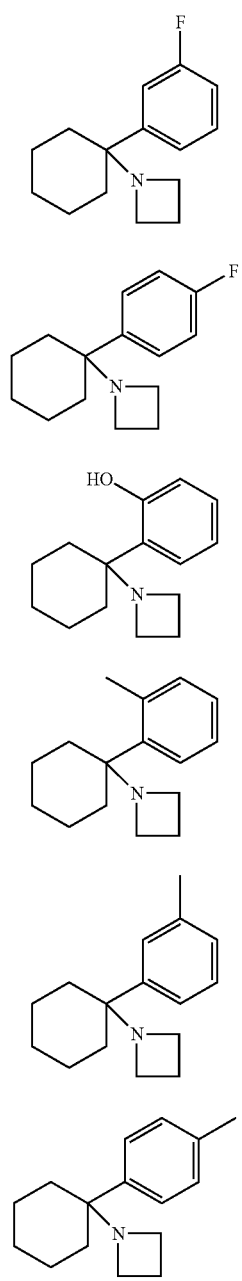
155
156
157
158
159
160
or a pharmaceutically acceptable salt or ester thereof, and/or a specific S- or R-isomer thereof.
In another aspect, provided herein is an isolated, substantially enantiomerically pure compound selected from the group consisting of:
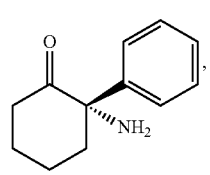
11S
-continued
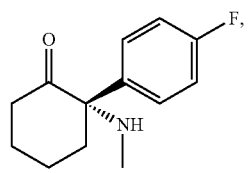
18S
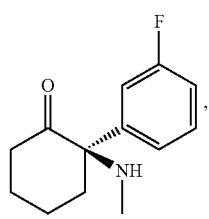
19R
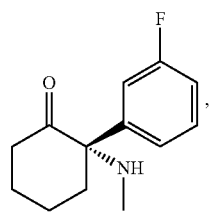
19S
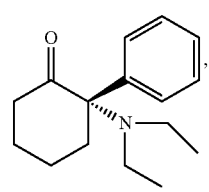
25S
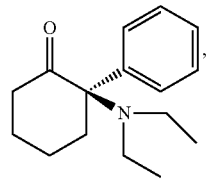
25R
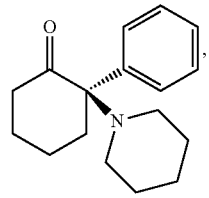
26R
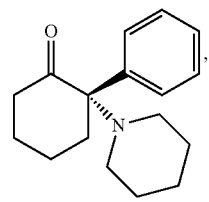
26S
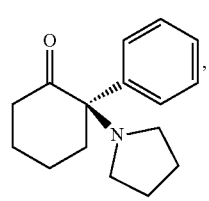
27R -continued
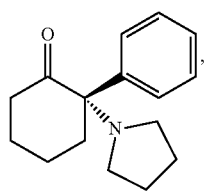 27S
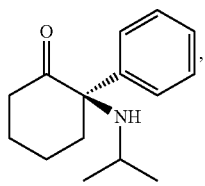 28R
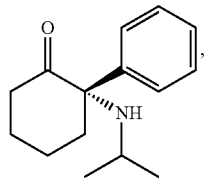 28S
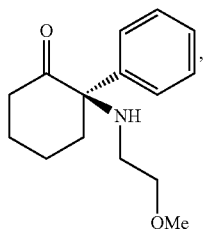 29R
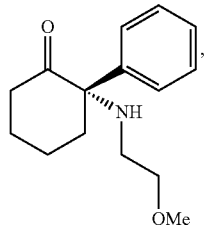 29S
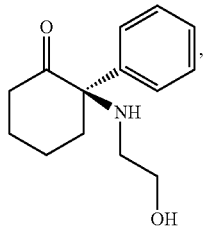 30R
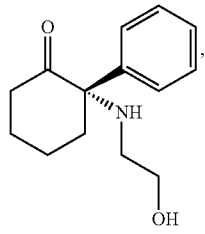 30S
-continued
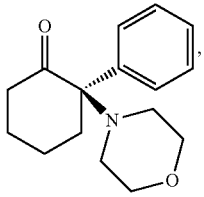 31R
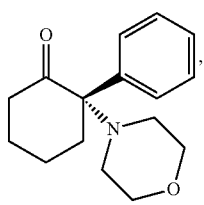 31S
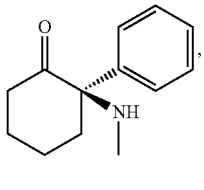 38R
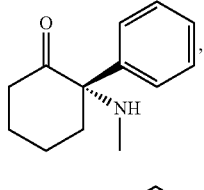 38S
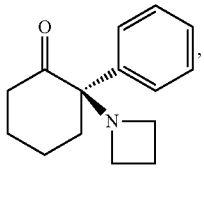 84R
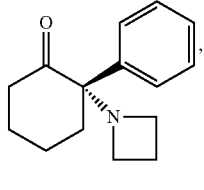 84S
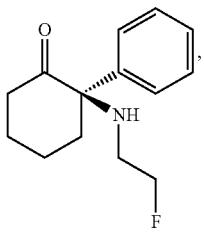 86R
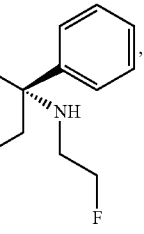 86S

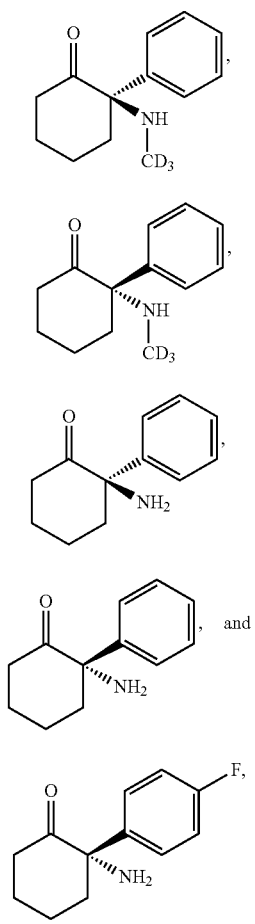
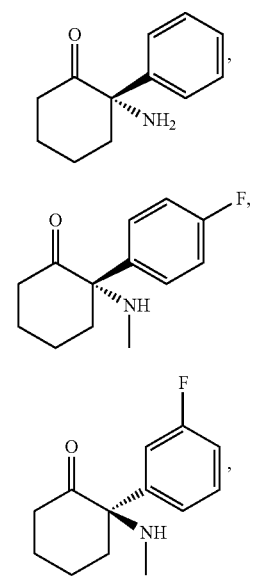
or a pharmaceutically acceptable salt thereof.
In another aspect, provided herein is an enantiomeric compound represented by
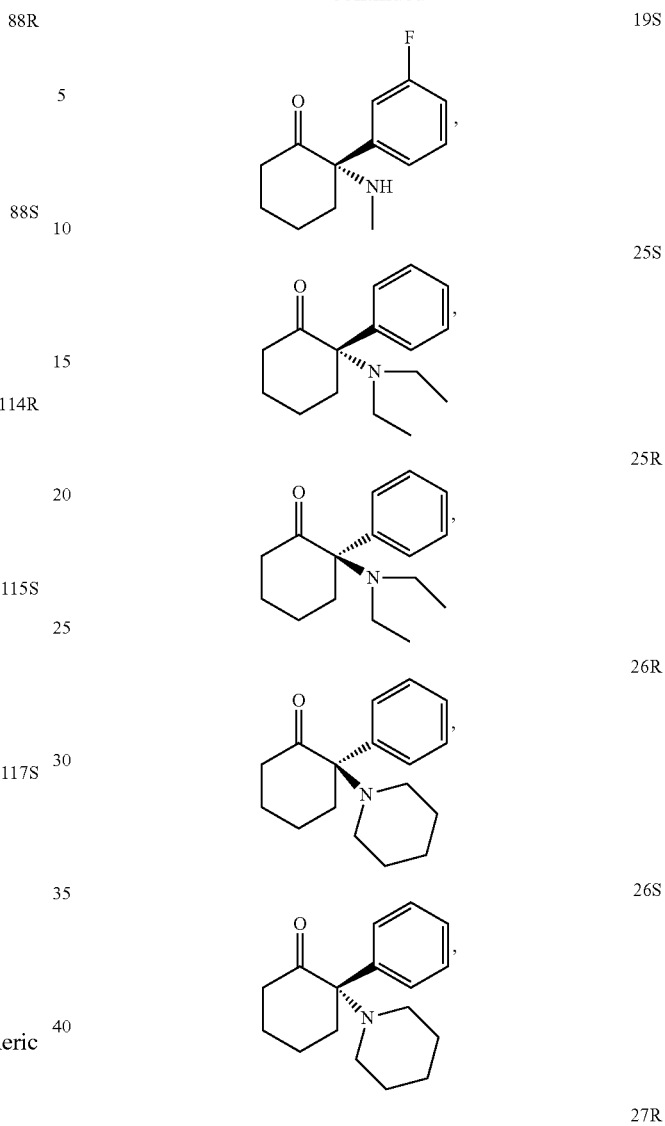
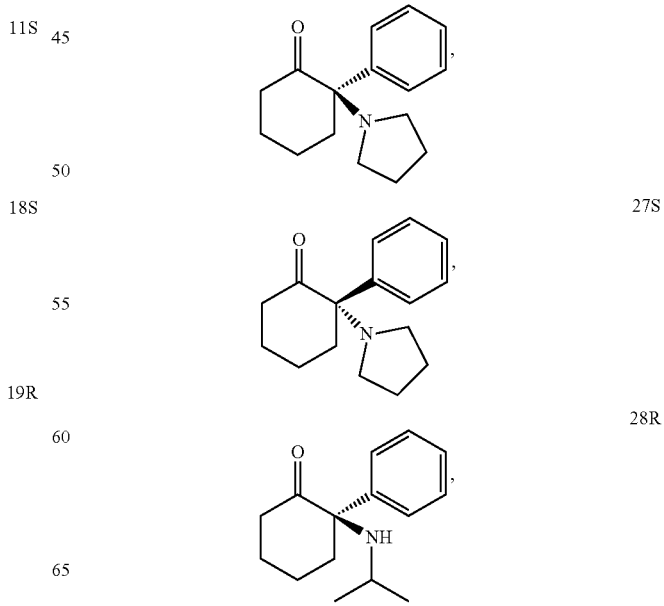

28S
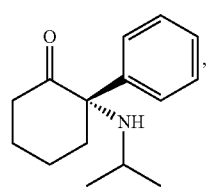
29R
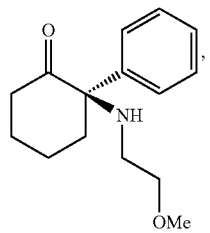
29S
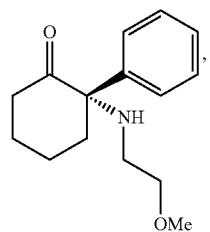
30R
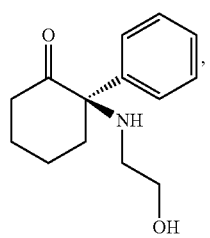
30S
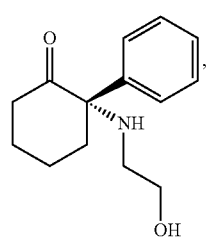
31R
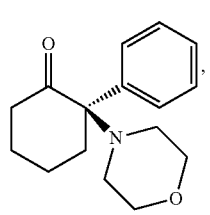
31S
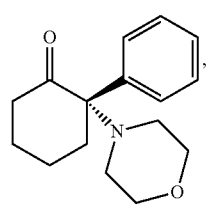
38R
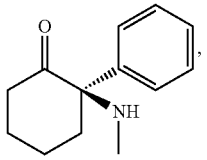
38S
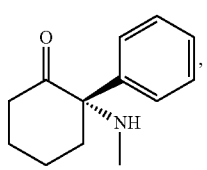
84R
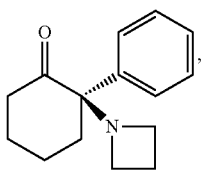
84S
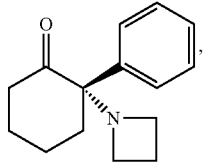
86R
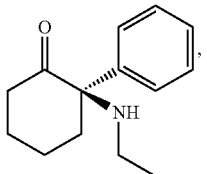
86S
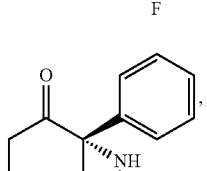
88R
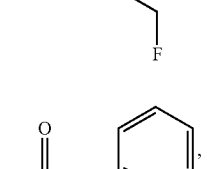
88S
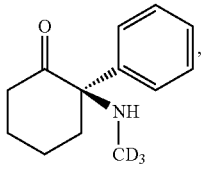

-continued
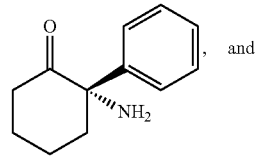
114R
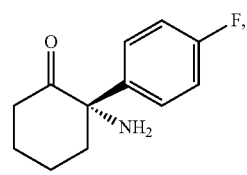
115S, and
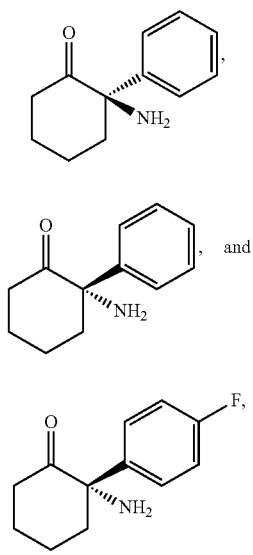
117S
or a pharmaceutically acceptable salt thereof, wherein the enantiomeric compound is present in an enantiomeric mixture having at least 90%, at least 95% or at least 99% of the enantiomeric compound.
In another aspect, provided herein is a compound selected from:
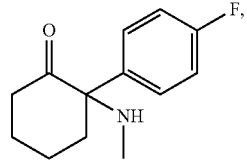
18rac
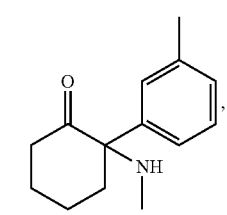
23rac
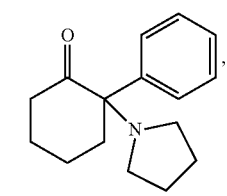
27rac
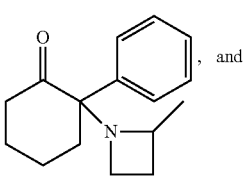
128mix, and
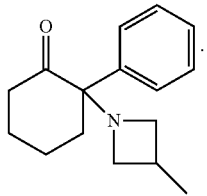
129rac
In some embodiments, the compound is selected from:
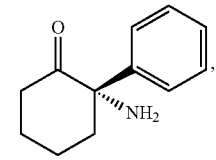
11S
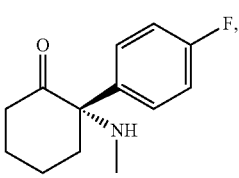
18S
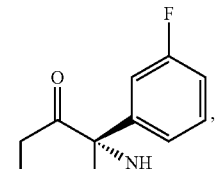
19S
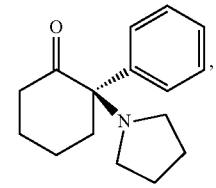
27R
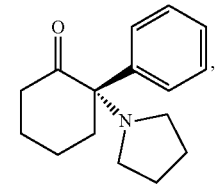
27S
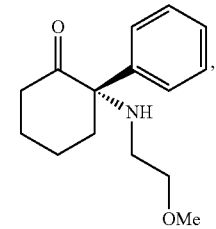
29S

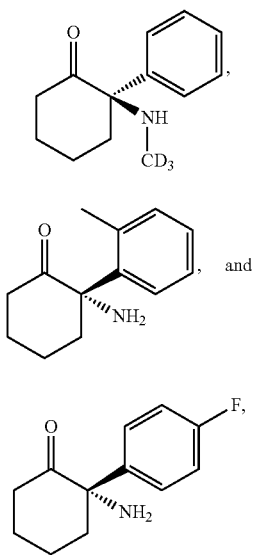

88R

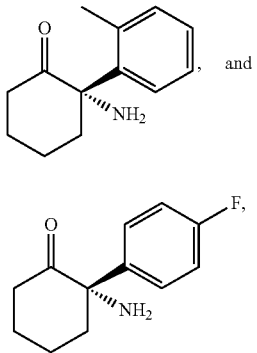, and

114S

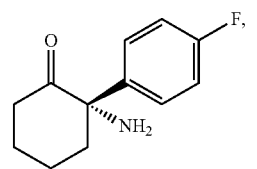

117S or a pharmaceutically acceptable salt thereof.

In some embodiments, the compound is

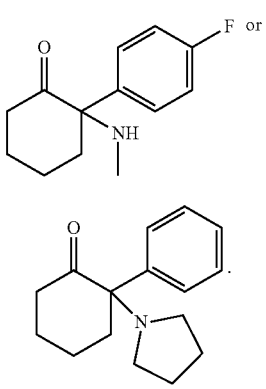 F or

18rac

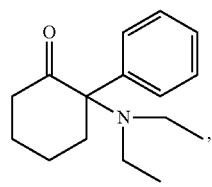.

27rac

In another aspect, provided herein is a composition comprising an enantiomeric mixture of a compound selected from the group consisting of:

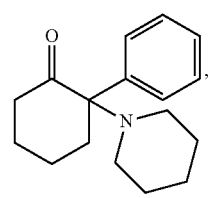,

25

26

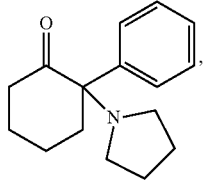,

27

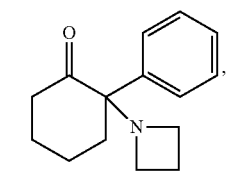,

38

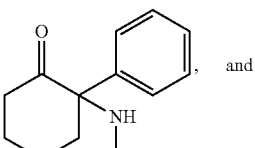,

84

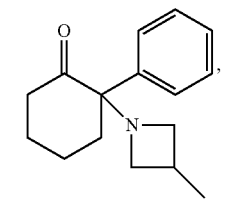,

88 and

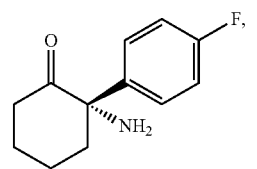

129 wherein the enantiomeric mixture has a significantly greater amount of the enantiomer having the lower binding affinity at the NMDA receptor MK-801 site.

In some embodiments, the compound is selected from the group consisting of:

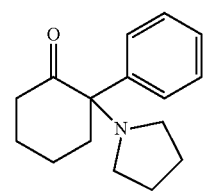 and

27

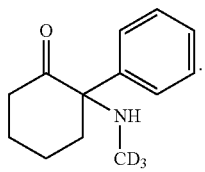.

88

In another aspect, provided herein is a composition comprising an enantiomeric mixture of a compound selected from the group consisting of:
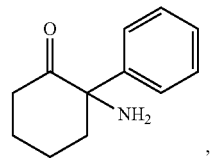
11
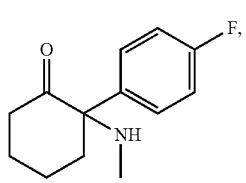
18
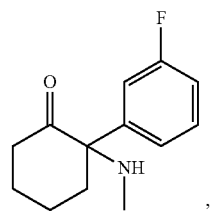
19
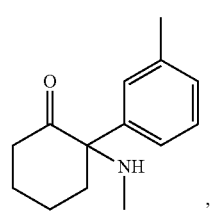
23
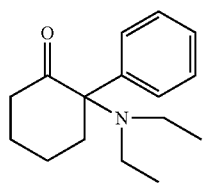
25
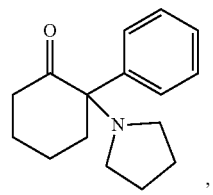
27
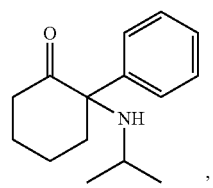
28
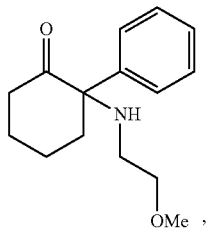
29
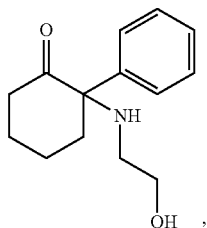
30
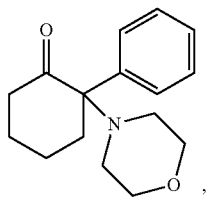
31
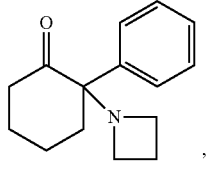
84
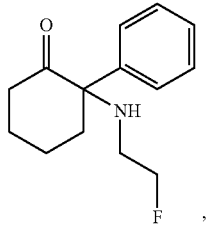
86
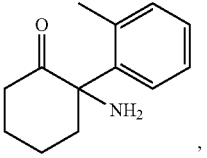
114
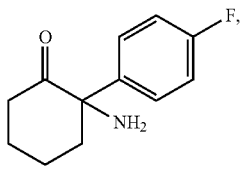
117

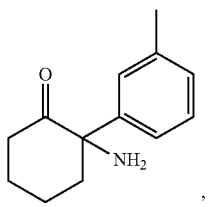
118

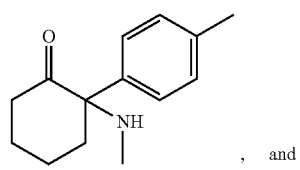
119
, and

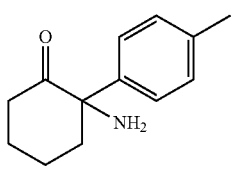
120
, wherein the enantiomeric mixture has a significantly greater amount of the enantiomer having the higher binding affinity at the NMDA receptor MK-801 site.

In another aspect, provided herein is a method of treating depression, anxious depression, a mood disorder, an anxiety disorder, or a substance use disorder and any symptom or disorders associated therewith in a subject in need thereof, the method comprising administering to the subject in need thereof an effective amount of a compound disclosed herein.

In some embodiments, the compound is selected from the group consisting of:

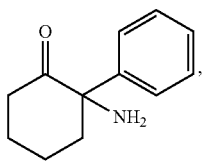
11rac

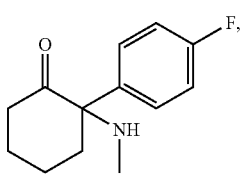
18rac

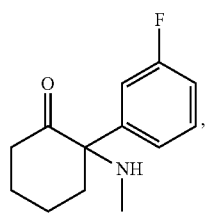
19rac

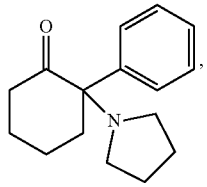
27rac

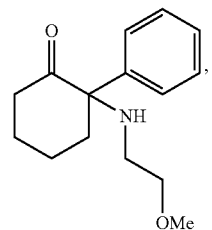
29rac

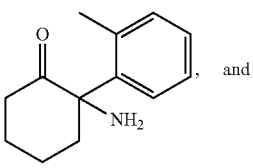
114rac, and

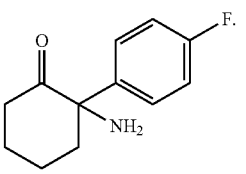
117rac

In another aspect, provided herein is a method of treating depression, anxious depression, a mood disorder, an anxiety disorder, or a substance use disorder and any symptom or disorders associated therewith in a subject in need thereof, the method comprising administering to the subject in need thereof an effective amount of a composition comprising an isolated, substantially enantiomerically pure compound selected from the group consisting of:

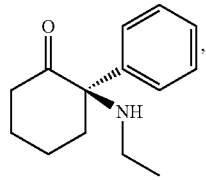
1R

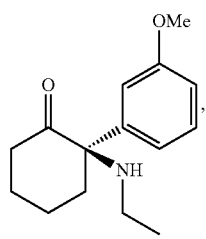
2R

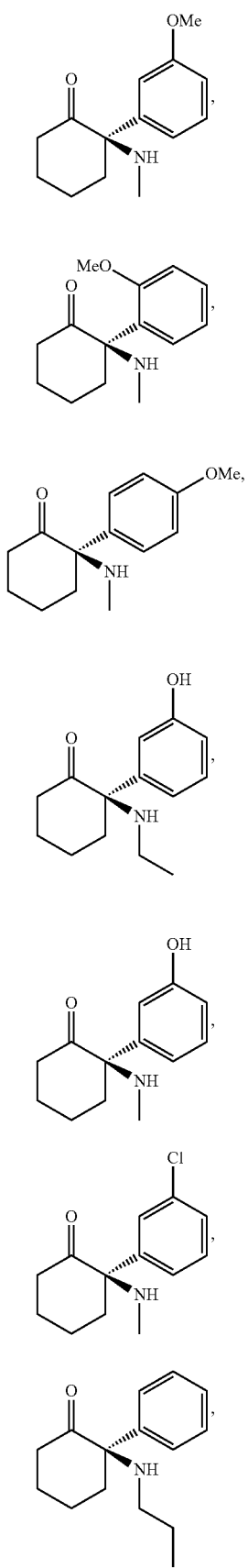
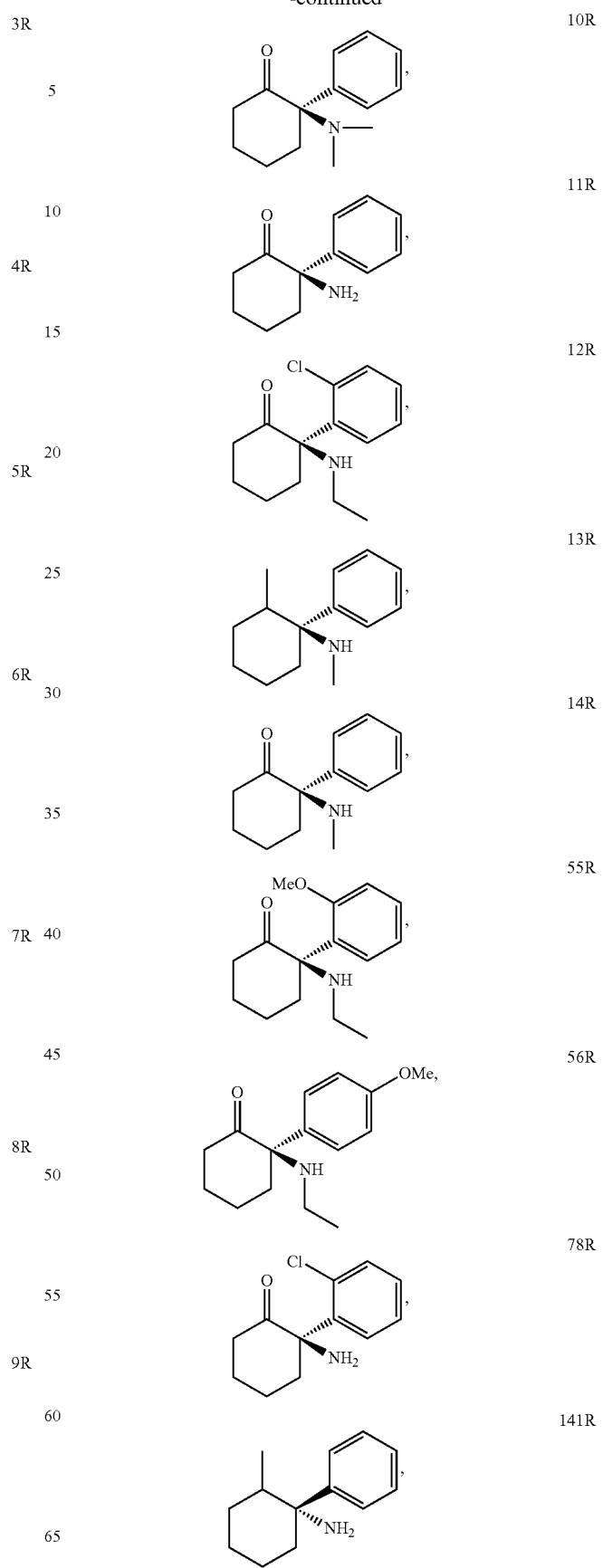

1S 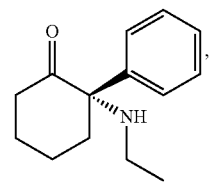
2S 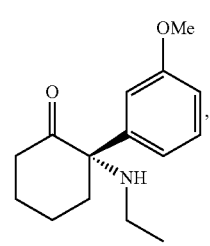
3S 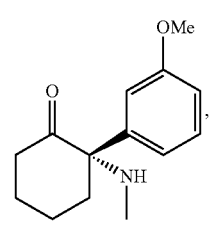
4S 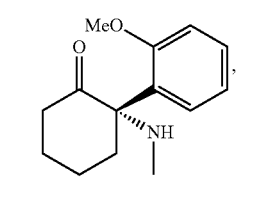
5S 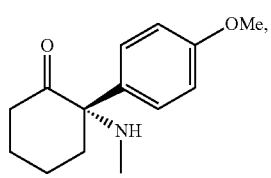
6S 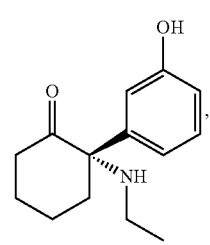
7S 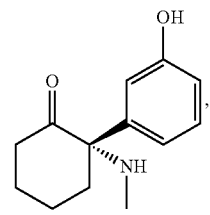
8S 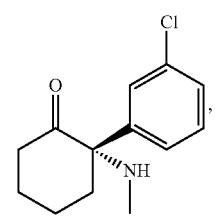
9S 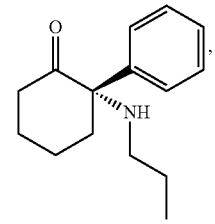
10S 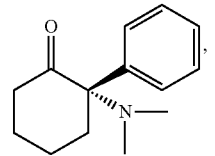
11S 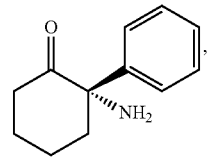
12S 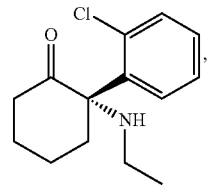
13S 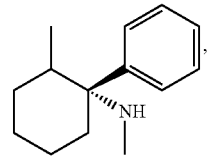
14S 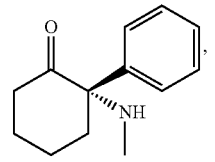
55S 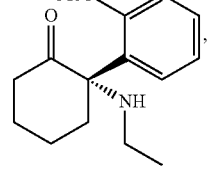

-continued

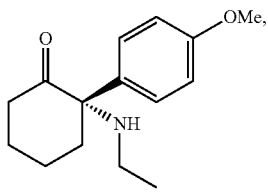
56S

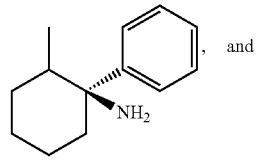
141S

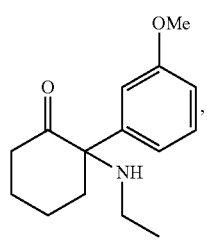
2rac or a pharmaceutically acceptable salt thereof.

In another aspect, provided herein is a method of treating depression, anxious depression, a mood disorder, an anxiety disorder, or a substance use disorder and any symptom or disorders associated therewith in a subject in need thereof, the method comprising administering to the subject in need thereof an effective amount of a composition comprising a compound selected from the group consisting of:

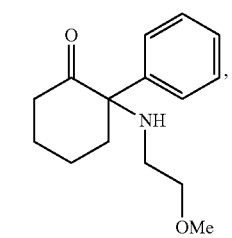
29rac

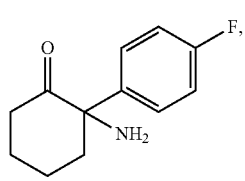
117rac

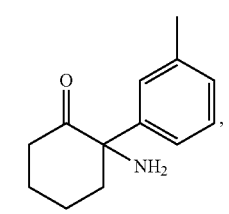
118rac

-continued

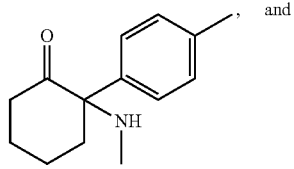
119rac

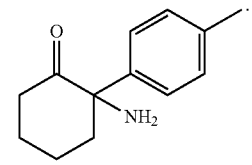
120rac

In some embodiments, the compound is selected from the group consisting of:

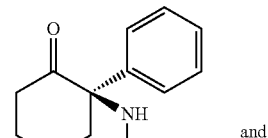

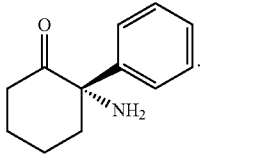

In another aspect, provided herein is an isolated, substantially enantiomerically pure compound represented by:

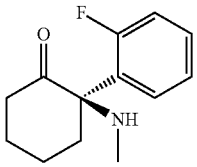
35R or a pharmaceutically acceptable salt thereof.

In another aspect, provided herein is a method of treating depression, anxious depression, a mood disorder, an anxiety disorder, or a substance use disorder and any symptom or disorders associated therewith in a subject in need thereof, the method comprising administering to the subject in need thereof an effective amount of a composition comprising an isolated, substantially enantiomerically pure compound represented by:

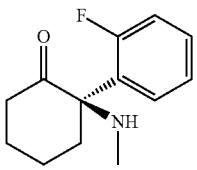
35R or a pharmaceutically acceptable salt thereof.

In another aspect, provided herein is a method of treating depression or anxious depression in a subject in need thereof, the method comprising administering to the subject in need thereof an effective amount of an isolated, substantially enantiomerically pure compound represented by:

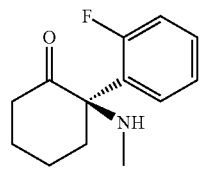
35R or a pharmaceutically acceptable salt thereof.

In another aspect, provided herein is a compound selected from:

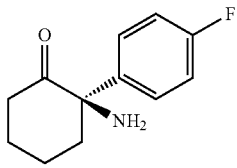
117R

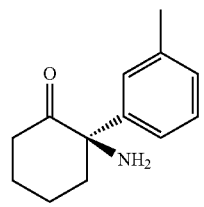
118R

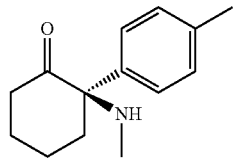
119R

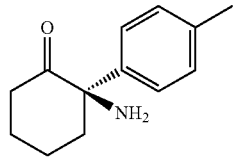
120R

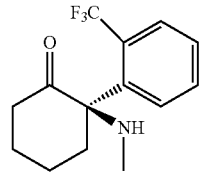
121R

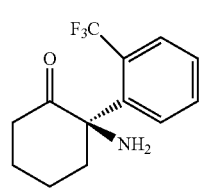
122R

-continued

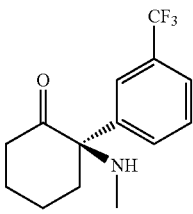 [SMILES: CN[C@@]1(c2cccc(F)c2)CCCCC1=O]
123R

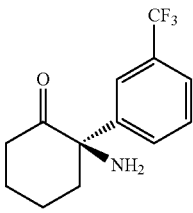
124R

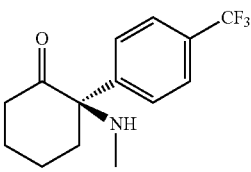
125R

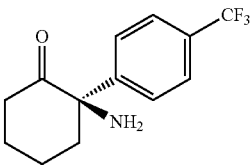
126R

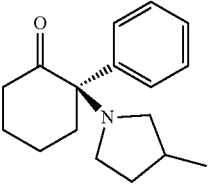
127R

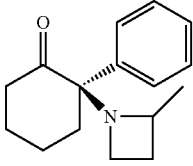
128R

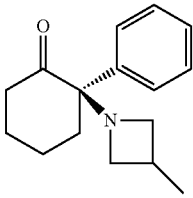
129R

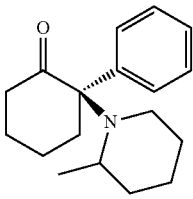
130R

131R 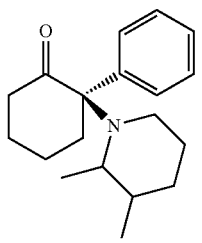

132R 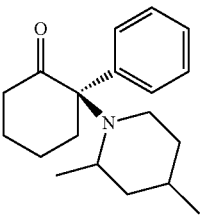

133R 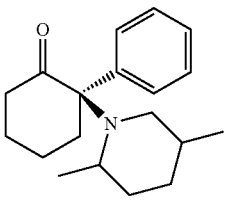

134R 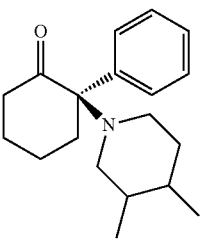

135R 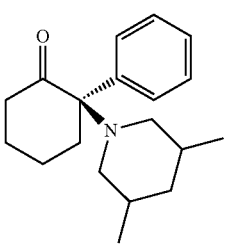

136R 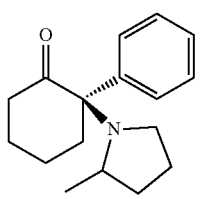

137R 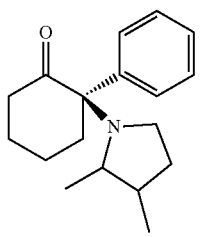

138R 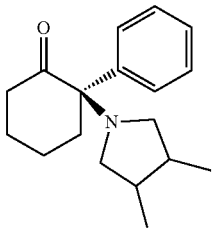

139R 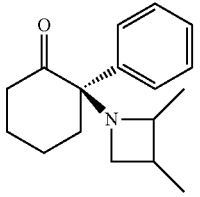

140R 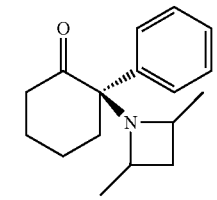

142R 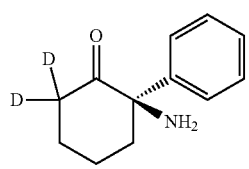

or a pharmaceutically acceptable salt thereof.

In another aspect, provided herein is a method of treating depression or anxious depression in a subject in need thereof, the method comprising administering to the subject in need thereof an effective amount of a compound disclosed herein.

In some embodiments, the compound is orally administered.

Provided herein are methods of treating a psychiatric disorder comprising administering to a subject in need thereof a therapeutically effective amount of a compound, or composition disclosed herein. Contemplated psychiatric disorders may include Depressive Disorders, e.g., Major Depressive Disorder, Persistent Depressive Disorder, Postpartum Depression, Premenstrual Dysphoric Disorder, Seasonal Affective Disorder, Psychotic Depression, Disruptive Mood Dysregulation Disorder, Substance/Medication-Induced Depressive Disorder, and Depressive Disorder Due to Another Medical Condition.

Also provided herein are compounds, methods, and compositions useful for treating refractory depression, e.g., patients suffering from a depressive disorder that does not, and/or has not, responded to adequate courses of at least one, or at least two, other antidepressant compounds or therapeutics. As used herein "depressive disorder" encompasses refractory depression.

In some embodiments, the compounds, methods, and compositions may be used to treat a psychiatric disorder including Bipolar and Related Disorders, e.g., Bipolar I Disorder, Bipolar II Disorder, Cyclothymic Disorder, Substance/Medication-Induced Bipolar and Related Disorder, and Bipolar and Related Disorder Due to Another Medical Condition.

In some embodiments, the compounds, methods, and compositions may be used to treat a psychiatric disorder including Substance-Related Disorders, e.g., preventing a substance use craving, diminishing a substance use craving, and/or facilitating substance use cessation or withdrawal. Substance use disorders involve abuse of psychoactive compounds such as alcohol, caffeine, cannabis, inhalants, opioids, sedatives, hypnotics, anxiolytics, stimulants, nicotine and tobacco. As used herein "substance" or "substances" are psychoactive compounds which can be addictive such as alcohol, caffeine, cannabis, hallucinogens, inhalants, opioids, sedatives, hypnotics, anxiolytics, stimulants, nicotine and tobacco. For example, the methods and compositions may be used to facilitate smoking cessation or cessation of opioid use.

In some embodiments, the compounds, methods, and compositions may be used to treat a psychiatric disorder including Anxiety Disorders, e.g., Separation Anxiety Disorder, Selective Mutism, Specific Phobia, Social Anxiety Disorder (Social Phobia), Panic Disorder, Panic Attack, Agoraphobia, Generalized Anxiety Disorder, Substance/Medication-Induced Anxiety Disorder. and Anxiety Disorder Due to Another Medical Condition.

In some embodiments, the compounds, methods, and compositions may be used to treat a psychiatric disorder including Obsessive-Compulsive and Related. Disorders, e.g., Obsessive-Compulsive Disorder, Body Dysmorphic Disorder, Hoarding Disorder, Trichotillomania (Hair-Pulling Disorder), Excoriation (Skin-Picking) Disorder, Substance/Medication-Induced Obsessive-Compulsive and Related Disorder, and Obsessive-Compulsive and Related Disorder Due to Another Medical Condition.

In some embodiments, the compounds, methods, and compositions may be used to treat a psychiatric disorder including Trauma—and Stressor-Related Disorders, e.g., Reactive Attachment Disorder, Disinhibited Social Engagement Disorder, Posttraumatic Stress Disorder, Acute Stress Disorder, and Adjustment Disorders.

In some embodiments, the compounds, methods, and compositions may be used to treat a psychiatric disorder including Feeding and Eating Disorders, e.g., Anorexia Nervosa, Bulimia Nervosa, Binge-Eating Disorder, Pica, Rumination Disorder, and Avoidant/Restrictive Food Intake Disorder.

In some embodiments, the compounds, methods, and compositions may be used to treat a psychiatric disorder including Neurocognitive Disorders, e.g., Delirium, Major Neurocognitive Disorder, Mild Neurocognitive Disorder, Major or Mild Neurocognitive Disorder Due to Alzheimer's Disease, Major or Mild Frontotemporal Neurocognitive Disorder, Major or Mild Neurocognitive Disorder With Lewy Bodies, Major or Mild Vascular Neurocognitive Disorder, Major or Mild Neurocognitive Disorder Due to Traumatic Brain Injury, Substance/Medication-Induced Major or Mild Neurocognitive Disorder, Major or Mild Neurocognitive Disorder Due to HIV Infection, Major or Mild Neurocognitive Disorder Due to Prion Disease, Major or Mild Neurocognitive Disorder Due to Parkinson's Disease, Major or Mild Neurocognitive Disorder Due to Huntington's Disease, Major or Mild Neurocognitive Disorder Due to Another Medical Condition, and Major or Mild Neurocognitive Disorder Due to Multiple Etiologies.

In some embodiments, the compounds, methods, and compositions may be used to treat a psychiatric disorder including Neurodevelopmental Disorders, e.g., Autism Spectrum Disorder, Attention-Deficit/Hyperactivity Disorder, Stereotypic Movement Disorder, Tic Disorders, Tourette's Disorder, Persistent (Chronic) Motor or Vocal Tic Disorder, and Provisional Tic Disorder.

In some embodiments, the compounds, methods, and compositions may be used to treat a psychiatric disorder including Personality Disorders, e.g., Borderline Personality Disorder.

In some embodiments, the compounds, methods, and compositions may be used to treat a psychiatric disorder including Sexual Dysfunctions, e.g., Delayed Ejaculation, Erectile Disorder, Female Orgasmic Disorder, Female Sexual Interest/Arousal Disorder, Genito-Pelvic Pain/Penetration Disorder, Male Hypoactive Sexual Desire Disorder, Premature (Early) Ejaculation, and Substance/Medication-Induced Sexual Dysfunction.

In some embodiments, the compounds, methods, and compositions may be used to treat a psychiatric disorder including Gender Dysphoria, e.g., Gender Dysphoria.

The terms "effective amount" or "therapeutically effective amount" refer to an amount of a compound, material, composition, medicament, or other material that is effective to achieve a particular pharmacological and/or physiologic effect including but not limited to reducing the frequency or severity of sadness or lethargy, depressed mood, anxious or sad feelings, diminished interest in all or nearly all activities, significant increased or decreased appetite leading to weight gain or weight loss, insomnia, irritability, fatigue, feelings of worthlessness, feelings of helplessness, inability to concentrate, and recurrent thoughts of death or suicide, or to provide a desired pharmacologic and/or physiologic effect, for example, reducing, inhibiting, or reversing one or more of the underlying pathophysiological mechanisms underlying the neurological dysfunction, modulating dopamine levels or signaling, modulating serotonin levels or signaling, modulating norepinephrine levels or signaling, modulating glutamate or GABA levels or signaling, modulating synaptic connectivity or neurogenesis in certain brain regions, or a combination thereof.

The term "therapeutic index" used in reference to any compound and its associated therapeutic effects and side effects refers to the ratio of the dose of said compound required to induce a particular negative side effect to the dose of said compound required to induce the desired therapeutic effect. For example, in the case of racemic ketamine, antidepressant therapeutic effects and dissociative side effects occur at similar doses and thus, the therapeutic index of this compound in this context is −1:1. In contrast, a compound disclosed herein might have an improved therapeutic index, for example 3:1, where a 3-fold higher dose is required to induce dissociative side effects relative to that needed for antidepressant therapeutic effects.

In some embodiments, methods include treating a psychiatric disorder by administering to a subject in need thereof a pharmaceutical composition including about 0.01 mg to about 400 mg of a compound disclosed herein. In some embodiments, doses may be, e.g., in the range of about 0.1 to 300 mg, 0.1 to 250 mg, 0.1 to 200 mg, 0.1 to 150 mg, 0.1 to 100 mg, 0.1 to 75 mg, 0.1 to 50 mg, 0.1 to 25 mg, 0.1 to 20 mg, 0.1 to 15 mg, 0.1 to 10 mg, 0.1 to 5 mg, 0.1 to 1 mg, 10 to 300 mg, 10 to 250 mg, 10 to 200 mg, 10 to 150 mg, 10 to 100 mg, 10 to 50 mg, 10 to 25 mg, 10 to 15 mg, 20 to 300 mg, 20 to 250 mg, 20 to 200 mg, 20 to 150 mg, 20 to 100 mg, 20 to 50 mg, 50 to 300 mg, 50 to 250 mg, 50 to 200 mg, 50 to 150 mg, 50 to 100 mg, 100 to 300 mg, 100 to 250 mg, 100 to 200 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 10 mg, 15 mg, 20 mg, 25 mg, 30, mg, 35 mg, 40 mg, 45 mg, 50 mg, 75 mg, 100 mg, 125 mg, 150 mg, 175 mg, 200 mg, 225 mg, 250 mg, 275 mg, 300 mg, and 400 mg being examples.

In some embodiments, dosages may include amounts of a compound disclosed herein or a pharmaceutically acceptable salt thereof in the range of about, e.g., 1 mg to 200 mg, 1 mg to 100 mg, 1 mg to 50 mg, 1 mg to 40 mg, 1 mg to 30 mg, 1 mg to 20 mg, 1 mg to 15 mg, 0.01 mg to 10 mg, 0.1 mg to 15 mg, 0.15 mg to 12.5 mg, or 0.2 mg to 10 mg, with doses of 0.1 mg, 0.2 mg, 0.3 mg, 0.4 mg, 0.5 mg, 0.6 mg, 0.7 mg, 0.8 mg, 0.9 mg, 1.5 mg, 1.0 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, 10 mg, 11 mg, 12 mg, 15 mg, 20 mg, 25 mg, 30 mg, 35 mg, 40 mg, 45 mg, 50 mg, 60 mg, 75 mg, 80 mg, 90 mg, 100 mg, 125 mg, 150 mg, and 200 mg being specific examples of doses.

Typically, dosages of a compound disclosed herein or a pharmaceutically acceptable salt thereof, are administered once, twice, three or four times daily, every other day, every three days, once weekly, or once a month to a patient in need thereof. In some embodiments, the dosage is about, e.g., 1-400 mg/day, or 1-300 mg/day, or 1-250 mg/day, or 1-200 mg/day, for example 300 mg/day, 250 mg/day, 200 mg/day, 150 mg/day, 100 mg/day, 75 mg/day, 50 mg/day, 25 mg/day, 20 mg/day, 10 mg/day, 5 mg/day, or 1 mg/day.

In some embodiments, pharmaceutical compositions for parenteral or inhalation, e.g., a spray or mist of a compound of the present invention or a pharmaceutically acceptable salt thereof, include a concentration of about 0.005 mg/mL to about 500 mg/mL. In some embodiments, the compositions include a compound disclosed herein or a pharmaceutically acceptable salt thereof, at a concentration of, e.g., about 0.05 mg/mL to about 50 mg/mL, about 0.05 mg/mL to about 100 mg/mL, about 0.005 mg/mL to about 500 mg/mL, about 0.1 mg/mL to about 50 mg/mL, about 0.1 mg/mL to about 10 mg/mL, about 0.05 mg/mL to about 25 mg/mL, about 0.05 mg/mL to about 10 mg/mL, about 0.05 mg/mL to about 5 mg/mL, or about 0.05 mg/mL to about 1 mg/mL.

In some embodiments, the composition includes a compound disclosed herein or a pharmaceutically acceptable salt thereof, at a concentration of, e.g., about 0.05 mg/mL to about 15 mg/mL, about 0.5 mg/mL to about 10 mg/mL, about 0.25 mg/mL to about 5 mg/mL, about 0.5 mg/mL to about 7 mg/mL, about 1 mg/mL to about 10 mg/mL, about 5 mg/mL to about 10 mg/mL, about 5 mg/mL to about 15 mg/mL, about 5 mg/mL to 25 mg/mL, about 5 mg/mL to 50 mg/mL, or about 10 mg/mL to 100 mg/mL. In some embodiments, the pharmaceutical compositions are formulated as a total volume of about, e.g., 10 mL, 20 mL, 25 mL, 50 mL, 100 mL, 200 mL, 250 mL, or 500 mL.

Typically, dosages may be administered to a subject once, twice, three or four times daily, every other day, every three days, twice weekly, once weekly, twice monthly, or once monthly. In some embodiments, a compound disclosed herein is administered to a subject once in the morning, or once in the evening. In some embodiments, a compound disclosed herein is administered to a subject once in the morning, and once in the evening. In some embodiments, a disclosed herein is administered to a subject three times a day (e.g., at breakfast, lunch, and dinner), at a dose, e.g., of 50 mg/administration (e.g., 150 mg/day).

In some embodiments, a compound disclosed herein is administered to a subject at a dose of 25 mg/day in one or more doses. In some embodiments, a compound disclosed herein is administered to a subject at a dose of 50 mg/day in one or more doses. In some embodiments, a compound disclosed herein is administered to a subject at a dose of 75 mg/day in one or more doses. In some embodiments, a compound disclosed herein is administered to a subject at a dose of 100 mg/day in one or more doses. In some embodiments, a compound disclosed herein is administered to a subject at a dose of 150 mg/day in one or more doses. In some embodiments, a compound disclosed herein is administered to a subject at a dose of 200 mg/day in one or more doses. In some embodiments, a compound disclosed herein is administered to a subject at a dose of 250 mg/day in one or more doses.

In some embodiments, the dosage of a compound disclosed herein is 0.01-100 mg/kg, 0.5-50 mg/kg, 0.5-10 mg/kg or 25-50 mg/kg once, twice, three times or four times daily. For example, in some embodiments, the dosage is 0.1 mg/kg, 0.25 mg/kg, 0.5 mg/kg, 1 mg/kg, 5 mg/kg, 7.5 mg/kg, or 10 mg/kg once, twice, three times or four times daily. In some embodiments, a subject is administered a total daily dose of 0.01 mg to 500 mg of a compound disclosed herein once, twice, three times, or four times daily. In some embodiments, the total amount administered to a subject in 24-hour period is, e.g., 5 mg, 10 mg, 20 mg, 25 mg, 30 mg, 35 mg, 40 mg, 45 mg, 50 mg, 60 mg, 75 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg. In some embodiments, the subject may be started at a low dose and the dosage is escalated. In some embodiments, the subject may be started at a high dose and the dosage is decreased.

In some embodiments, a compound or composition disclosed herein is administered to a patient under the supervision of a healthcare provider.

In some embodiments, a compound or composition disclosed herein is administered to a patient under the supervision of a healthcare provider at a clinic specializing in the delivery of psychoactive treatments.

In some embodiments, a compound or composition disclosed herein is administered to a patient under the supervision of a healthcare provider at a dose intended to induce a psychedelic experience in the subject.

In some embodiments, the administration to a patient under the supervision of a healthcare provider occurs periodically in order to maintain a therapeutic effect in the patient, e.g., every three days, twice weekly, once weekly, twice monthly, once monthly, thrice yearly, twice yearly, or once yearly.

In some embodiments, a compound or composition disclosed herein is administered by a patient on their own at home or otherwise away from the supervision of a healthcare provider.

In some embodiments, the administration by a patient on their own occurs periodically in order to maintain a therapeutic effect in the patient, e.g., daily, every other day, every three days, twice weekly, once weekly, twice monthly, or once monthly, In some embodiments, a compound or composition disclosed herein may be administered at specified intervals. For example, during treatment a patient may be administered a compound or composition at intervals of every, e.g., 1 year, 6 months, 90 days, 60 days, 30 days, 14 days, 7 days, 3 days, 24 hours, 12 hours, 8 hours, 6 hours, 5 hours, 4 hours, 3 hours, 2.5 hours, 2.25 hours, 2 hours, 1.75 hours, 1.5 hours, 1.25 hours, 1 hour, 0.75 hour, 0.5 hour, or 0.25 hour.

In some embodiments, a compound disclosed herein is in the form of a pharmaceutically acceptable salt thereof.

In some embodiments, a pharmaceutical composition comprises one or more of the compounds disclosed herein.

In some embodiments, a salt of the compound disclosed herein is used in any of the methods, uses, or compositions.

In some embodiments, a pharmaceutically acceptable salt of the compound disclosed herein is used in any of the methods, uses, or compositions.

In some embodiments, an ester of the compound disclosed herein is used in any of the methods, uses, or compositions.

Any of the compounds disclosed herein may be used in any of the disclosed methods, uses, or compositions.

Any of the compounds used in the disclosed methods, uses, or compositions may be replaced with any other compound disclosed herein.

Any of the disclosed generic compounds may be used in any of the disclosed methods, uses, or compositions.

The terms "about" or "approximately" as used herein mean within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, a range up to 10%, a range up to 5%, and/or a range up to 1% of a given value. Alternatively, particularly with respect to biological systems or processes, the term can mean within an order of magnitude, e.g., within 5-fold, or within 2-fold, of a value. "About" and "approximately" are used interchangeably herein.

In the context of the present invention the term "thiazole" should be understood to refer to a moiety having the structure

wherein its connection to the backbone of a compound disclosed herein is through any carbon atom of the ring.

In the context of the present invention the term "thiophene" should be understood to refer to a moiety having the structure

wherein its connection to the backbone of a compound disclosed herein is through any carbon atom of the ring In the context of the present disclosure the term "pyridine" should be understood to refer to a moiety having the structure

wherein its connection to the backbone of a compound disclosed herein is through any carbon atom of the ring.

In the context of the present invention the term "alkyl" should be understood to refer to a straight, branched or where possible, cyclo hydrocarbon chain, containing the indicated number of carbon atoms, wherein all the bonds connecting the atoms are sigma bonds.

In the context of the present invention the term "alkenyl" should be understood to refer to a straight, branched or where possible, cyclo hydrocarbon chain, containing the indicated number of carbon atoms, wherein at least one bond between two carbons of the chain is a double (pi) bond.

In the context of the present invention the term "alkynyl" should be understood to refer to a straight, branched or where possible, cyclo hydrocarbon chain, containing the indicated number of carbon atoms, wherein at least one bond connecting two carbon atoms of the chain is a triple bond.

In the context of the present invention the term "aryl" should be understood to refer to a C5 to C10 aromatic system having one or more rings.

In the context of the present disclosure the term "heteroaryl" should be understood to refer to an aromatic ring system wherein at least one carbon atom is replaced by a heteroatom selected from O, N, S.

In the context of the present disclosure the term "alkylene" should be understood to refer to a straight, branched or where possible, cyclo hydrocarbon chain, containing the indicated number of carbon atoms, wherein all the bonds connecting the atoms are sigma bonds, wherein two hydrogen atoms are removed, thus being able to connect with two open sigma bonds (valencies).

In the context of the present disclosure the term "heteroalkyl" should be understood to refer to a straight, branched or where possible, cyclo hydrocarbon chain, containing the indicated number of carbon atoms, wherein the chain is interrupted by at least one heteroatom (selected from O, N, S) and all the bonds connecting the atoms are sigma bonds. For example, azetidine is an example of a C3 cycloheteroalkyl, pyrrolidine is an example of a C4 cycloheteroalkyl, piperidine is an example of a C5 cycloheteroalkyl, and morpholine is an example of a C4 cycloheteroalkyl.

In the context of the present disclosure the term "haloalkyl" should be understood to refer to a straight, branched or where possible, cyclo hydrocarbon chain, containing the indicated number of carbon atoms, wherein all the bonds connecting the atoms are sigma bonds and at least one of the hydrogen atoms on the chain is replaced by a halogen atom selected from F, Cl, Br, I.

Compounds disclosed herein may include at least one asymmetric center. These centers are designated by the symbols "R" or "S," depending on the configuration of substituents around the chiral atom. Unless otherwise indicated in the structural formula, it should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

In some embodiments, a composition disclosed herein may be enriched in a specific enantiomer of any compound disclosed herein relative to the corresponding opposite enantiomer of that compound, such that the mixture is not racemic. In such cases, the subject mixture of isomers is understood to have an enantiomeric excess and optical purity >0%. The enantiomeric excess or optical purity of the isomeric mixture may be >0%, >5%, >25%, >50%, >75%, >90%, >95%, >97%, >98%, or >99%. The enantiomeric excess or optical purity of the isomeric mixture may 5-100%, 25-100%, 50-100%, 75-100%, 90-100%, 95-100%, 97-100%, 98-100%, or 99-100%. Thus, for example, contemplated herein is a composition including the S enantiomer of a compound substantially free of the R enantiomer, or the R enantiomer substantially free of the S enantiomer. Further, if the named compound includes more than one chiral center, the scope of the present disclosure also includes compositions including mixtures of varying proportions between the diastereomers, as well as compositions including one or more diastereomers substantially free of one or more of the other diastereomers. By "substantially free" it is meant that the composition includes less than 50%, 25%, 15%, 10%, 8%, 5%, 3%, 2%, or 1% of the minor enantiomer or diastereomer(s).

For clarity, in the context of the present disclosure, chemical structures of a compound depicted with a specific stereochemical orientation at any particular chiral center, as defined by wedge and dash notation, are intended to represent the specified stereoisomer of said compound in substantially pure form, or a mixture enriched in the stereoisomer(s) with the specified stereochemical orientation at the defined chiral center over the stereoisomer(s) with the opposite orientation at said chiral center.

The disclosure may also include any salt of a compound disclosed herein above and below, including any pharmaceutically acceptable salt, wherein a compound disclosed herein has a net charge (either positive or negative) and at least one counter ion (having a counter negative or positive charge) is added thereto to form said salt. The phrase "pharmaceutically acceptable salt(s)", as used herein, means those salts of compounds disclosed herein that are safe and effective for pharmaceutical use in mammals and that possess the desired biological activity. Pharmaceutically acceptable salts include salts of acidic or basic groups present in compounds disclosed herein. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds disclosed herein can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 *J. PHARM. SCI.* 1-19 (1977), incorporated herein by reference.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include $^{13}C$ and $^{14}C$.

It will be noted that any notation of a carbon in structures throughout this application, when used without further notation, are intended to represent all isotopes of carbon, such as $^{12}C$, $^{13}C$ or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In some embodiments, each D in a chemical structure represents a deuterium-enriched —H site and the level of deuterium at each deuterium-enriched —H site of the compound is 0.02% to 100%.

In some embodiments, each D in a chemical structure represents a deuterium-enriched —H site and the level of deuterium at each deuterium-enriched —H site of the compound is 20-100%, 50-100%, 70-100%, 90-100%, 95-100%, 97-100%, or 99-100%.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc., are to be chosen in conformity with well-known principles of chemical structure connectivity.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The present disclosure thus also relates to pharmaceutical compositions comprising a compound as defined herein below and above in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavoring agents, anti-oxidants, and wetting agents. Such auxiliary agents are suitably selected with respect to the intended form and route of administration and as consistent with conventional pharmaceutical practices.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

Tablets may contain the active ingredient compounds and suitable binders, lubricants, disintegrating agents, coloring agents, flavoring agents, flow-inducing agents, and melting agents. Gelatin capsules may contain the active ingredient compounds and powdered carriers, such as lactose, starch, cellulose derivatives, magnesium stearate, stearic acid, and the like. Similar diluents can be used to make compressed tablets. Compressed tablets can be sugar coated or film coated to mask any unpleasant taste and protect the tablet from the atmosphere, or enteric coated for selective disintegration in the gastrointestinal tract. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Liquid dosage forms for oral administration can contain coloring and flavoring to increase patient acceptance.

For parenteral administration, suitable compositions include aqueous and non-aqueous sterile solutions. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. The compositions may be presented in unit-dose or multi-dose containers, for example sealed vials and ampoules, and may be stored in a freeze-dried (lyophilized) condition requiring only the addition of sterile liquid carrier, for example water, prior to use. For transdermal administration, e.g. gels, patches or sprays can be contemplated. Compositions or formulations suitable for pulmonary administration e.g. by nasal inhalation, include fine dusts or mists which may be generated by means of metered dose pressurized aerosols, nebulizers or insufflators. Parenteral and intravenous forms may also include minerals and other materials to make them compatible with the type of injection or delivery system chosen.

The compounds used in the method of the present disclosure may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present disclosure may also be coupled to soluble polymers as targetable drug carriers or as prodrugs. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Pharmaceutical compositions herein may be provided with immediate release, delayed release, extended release, or modified release profiles. In some embodiments, pharmaceutical compositions with different drug release profiles may be combined to create a two-phase or three-phase release profile. For example, pharmaceutical compositions may be provided with an immediate release and an extended release profile. In some embodiments, pharmaceutical compositions may be provided with an extended release and delayed release profile. Such composition may be provided as pulsatile formulations, multilayer tablets, or capsules containing tablets, beads, granules, etc.

Pharmaceutical compositions herein may be provided with abuse deterrent features by techniques know in the art, for example, by making a tablet that is difficult to crush or to dissolve in water.

The invention further includes a pharmaceutical composition, as hereinbefore described, in combination with packaging material, including instructions for the use of the composition for a use as hereinbefore described.

The exact dose and regimen of administration of the composition will necessarily be dependent upon the type and magnitude of the therapeutic or nutritional effect to be achieved and may vary depending on factors such as the particular compound, formula, route of administration, or age and condition of the individual subject to whom the composition is to be administered.

Furthermore, in some embodiments a pharmaceutical composition disclosed herein may include a single enantiomer, diastereomer or structural isomer of a compound disclosed herein. In other embodiments, a pharmaceutical composition disclosed herein may include a mixture of at least one single enantiomer, diastereomer or structural isomer of a compound disclosed herein together with any other enantiomer, diastereomer or structural isomer of a compound disclosed herein. In further embodiments, said mixture is a racemic mixture. In other embodiments, said mixture is a non-racemic mixture (wherein one enantiomer or diastereomer is enriched in said non-racemic mixture).

The compounds used in the method of the present disclosure may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

Each embodiment disclosed herein is contemplated as being applicable to each of the other disclosed embodiments. Thus, all combinations of the various elements described herein are within the scope of the disclosure.

It can be appreciated that stereochemical designations (e.g., R- and S-configurations for certain provided compounds below) may differ upon determination by e.g., X-ray crystallography.

Example 1. Preparation and Characterization of Compounds 35 and 37

General Considerations. Reagents and solvents were obtained from commercial sources and were used without further purification unless otherwise stated (including anhydrous solvents). Reactions were monitored by TLC using solvent mixtures appropriate to each reaction. All column chromatography was performed on silica gel (40-63 μn). Preparative TLC was conducted on glass plates coated with a 1 mm silica layer. Nuclear magnetic resonance spectra were recorded on Bruker 400 or 500 MHz instruments. Chemical shifts are reported as δ values in ppm referenced to $CDCl_3$ ($^1H$ NMR=7.26 and $^{13}C$ NMR=77.16), MeOD ($^1H$ NMR=3.31 and $^{13}C$ NMR=49.00), or DMSO-$d_6$ ($^1H$ NMR=2.50 and $^{13}C$ NMR=39.52). Multiplicity is indicated as follows: s (singlet); d (doublet); t (triplet); p (pentet); dd (doublet of doublets); ddd (doublet of doublet of doublets); dddd (doublet of doublet of doublet of doublets); td (triplet of doublets); dt (doublet of triplets); m (multiplet); br (broad). All carbon peaks are rounded to one decimal place unless such rounding would cause two close peaks to become identical; in these cases, two decimal places are retained.

Scheme 1. Preparation of compounds 35rac, 35R, 35S, and 37rac.

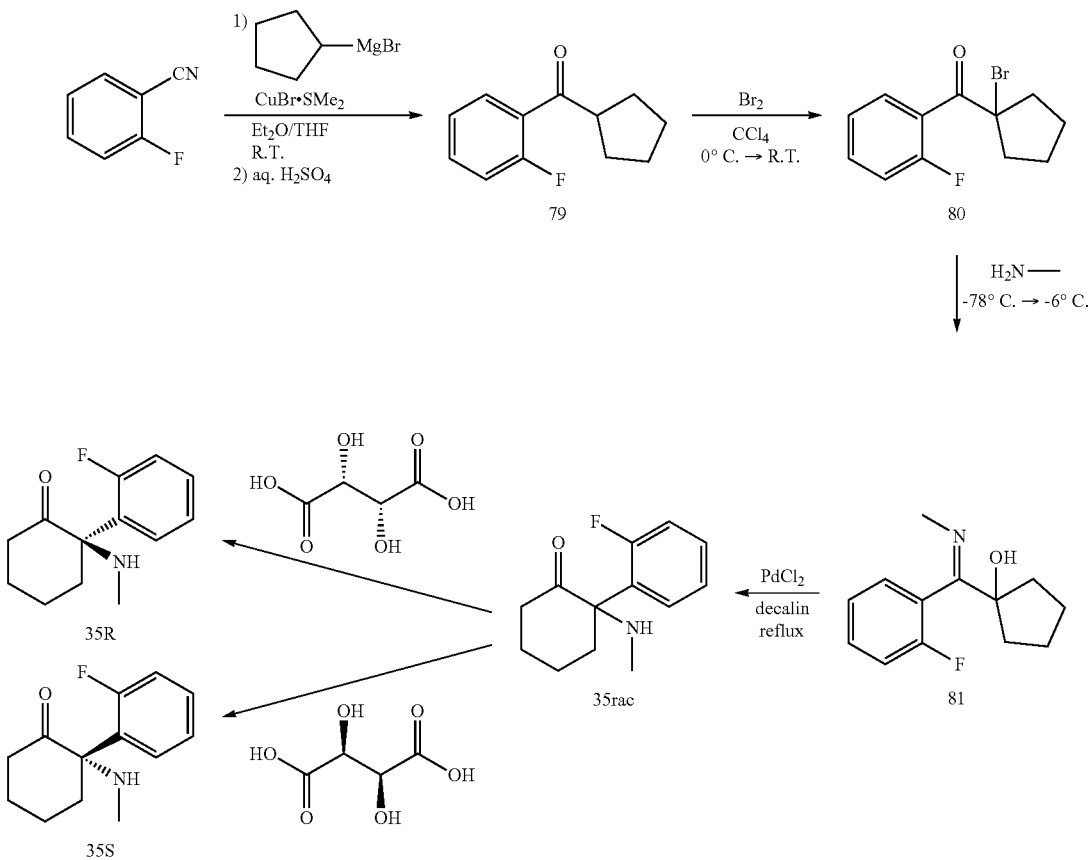

-continued

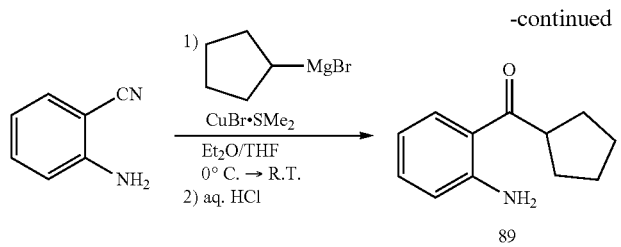

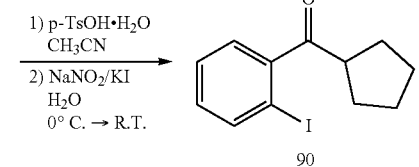

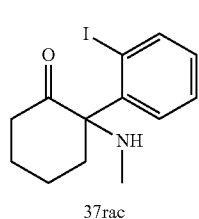

Cyclopentyl(2-fluorophenyl)methanone (79). To anhydrous THF (90 mL) under argon was added cyclopentylmagnesium bromide (2M in Et$_2$O; 30.00 mL, 60.00 mmol), 2-fluorobenzonitrile (5.43 mL, 6.06 g, 50.00 mmol), and CuBr.SMe$_2$ (206 mg, 1.00 mmol) and the mixture was left to stir at room temperature for 16 h. Note: On addition of the CuBr.SMe$_2$ the mixture turned from yellow to black and gas evolution occurred. At this time, water (20 mL) and 15% m/m aqueous H$_2$SO$_4$ (100 mL) were added and the mixture was stirred for 1 h. The reaction was then extracted with hexanes (3×50 mL) and the combined organics were washed with water (30 mL) and brine (30 mL), dried over Na$_2$SO$_4$, and concentrated in vacuo to give ketone 79 as a yellow-brown oil containing minor impurities (9.54 g, 99%). $^1$H NMR (500 MHz, CDCl$_3$) δ 7.79 (td, J=7.6, 1.9 Hz, 1H), 7.48 (dddd, J=9.0, 7.1, 5.0, 1.9 Hz, 1H), 7.21 (td, J=7.6, 1.1 Hz, 1H), 7.11 (ddd, J=11.2, 8.3, 1.0 Hz, 1H), 3.69-3.58 (m, 1H), 1.98-1.82 (m, 4H), 1.75-1.55 (m, 4H); $^{13}$C NMR (126 MHz, CDCl$_3$) δ 202.0 (d, J$_{C-F}$=3.8 Hz), 161.5 (d, J$_{C-F}$=253.8 Hz), 134.0 (d, J$_{C-F}$=9.0 Hz), 130.9 (d, J$_{C-F}$=2.9 Hz), 126.5 (d, J$_{C-F}$=13.1 Hz), 124.5 (d, J$_{C-F}$=3.3 Hz), 116.7 (d, J$_{C-F}$=24.0 Hz), 51.2 (d, J$_{C-F}$=5.9 Hz), 29.4, 26.2.

(1-Bromocyclopentyl)(2-fluorophenyl)methanone (80). To a solution of compound 79 (9.52 g, 49.52 mmol) in CCl$_4$ (50 mL) at 0° C. was added portionwise a solution of Br$_2$ (2.66 mL, 8.31 g, 52.00 mmol) in CCl$_4$ (50 mL) over 20 minutes. At the end of the addition, the mixture was allowed to warm to room temperature and stirred for 60 minutes. The reaction mixture was then diluted with CH$_2$Cl$_2$ (100 mL), washed with saturated aqueous Na$_2$S$_2$O$_3$ (50 mL), saturated aqueous NaHCO$_3$ (50 mL), and brine (50 mL), dried over Na$_2$SO$_4$, and concentrated in vacuo to give bromoketone 80 as a yellow-orange oil containing minor impurities (12.94 g, 96%). $^1$H NMR (500 MHz, CDCl$_3$) δ 7.76 (td, J=7.4, 1.8 Hz, 1H), 7.49-7.42 (m, 1H), 7.19 (td, J=7.6, 1.1 Hz, 1H), 7.12 (ddd, J=10.3, 8.3, 1.0 Hz, 1H), 2.46-2.33 (m, 4H), 2.10-1.99 (m, 2H), 1.89-1.79 (m, 2H); $^{13}$C NMR (126 MHz, CDCl$_3$) δ 196.9, 159.4 (d, J$_{C-F}$=252.1 Hz), 132.8 (d, J$_{C-F}$=8.5 Hz), 130.3 (d, J$_{C-F}$=2.8 Hz), 126.8 (d, J$_{C-F}$=15.0 Hz), 123.9 (d, J$_{C-F}$=3.6 Hz), 116.5 (d, J$_{C-F}$=22.2 Hz), 73.9, 40.5 (d, J$_{C-F}$=2.1 Hz), 23.4.

1-((2-Fluorophenyl)(methylimino)methyl)cyclopentan-1-ol (81). Liquid methylamine was freshly prepared as follows. Solid methylamine HCl (150 g) was treated dropwise with 50% m/m aqueous NaOH (200 g) and the evolved gas was passed through a drying tube containing NaOH pellets and condensed into a flask that was cooled to −78° C. and topped with a condenser containing dry ice/acetone. After all the NaOH solution had been added, the neutralization reaction was warmed to 80° C. to continue gas evolution. Once the required quantity of liquid methylamine had been collected, the reaction was carried out as follows. Compound 80 (12.89 g, 47.54 mmol) and liquid methylamine (50 mL) were combined at −78° C. under argon (Note: bromoketone too viscous to stir at this temperature so had to warm) and the resulting mixture was warmed to the boiling point of methylamine (−6° C.) and stirred with a spatula until all of the bromoketone had dissolved. The solution was then cooled back to −78° C. and stirred for 20 minutes and then at −6° C. for an additional 40 minutes. All methylamine was then carefully boiled off with a heat gun and the resulting residue dried in vacuo to give a sticky orange solid. This material was triturated with Et$_2$O (100 mL), filtered, and the filter cake washed with Et$_2$O (2×50 mL). The combined filtrates were concentrated in vacuo to give imine 81 as an oily orange solid containing minor impurities (10.32 g, 98%). $^1$H NMR (500 MHz, CDCl$_3$) δ 7.38 (dddd, J=8.3, 7.3, 5.4, 1.8 Hz, 1H), 7.20 (td, J=7.5, 1.1 Hz, 1H), 7.13 (ddd, J=9.3, 8.3, 1.0 Hz, 1H), 7.03 (ddd, J=7.4, 6.7, 1.8 Hz, 1H), 5.50 (br s, 1H), 3.01 (s, 3H), 1.97-1.83 (m, 3H), 1.74-1.62 (m, 3H), 1.62-1.49 (m, 2H); $^{13}$C NMR (126 MHz, CDCl$_3$) δ 171.3, 158.4 (d, J$_{C-F}$=246.3 Hz), 130.8 (d, J$_{C-F}$=7.8 Hz), 129.3 (d, J$_{C-F}$=4.4 Hz), 124.3 (d, J$_{C-F}$=3.5 Hz), 122.5 (d, J$_{C-F}$=19.5 Hz), 116.0 (d, J$_{C-F}$=21.9 Hz), 84.2, 39.8, 38.2 and 38.0 (conformers), 24.0 and 23.7 (conformers).

2-(2-Fluorophenyl)-2-(methylamino)cyclohexan-1-one (35rac). Compound 81 (10.20 g, 46.10 mmol) was dissolved in decalin (80 mL) and the mixture was brought to reflux under argon. After 1 h at reflux (dark-brown/black solution, slow conversion by TLC), PdCl$_2$ (245 mg, 1.38 mmol) was added and reflux was continued for an additional 2.5 h. The reaction mixture was cooled to room temperature, diluted with Et$_2$O (150 mL), and extracted with 2% m/m aqueous HCl (150 mL) and water (2×100 mL). The combined acidic aqueous extracts were washed with hexanes (100 mL) and Et$_2$O (100 mL), basified with 25% m/m aqueous NaOH, and extracted with Et$_2$O (3×100 mL). The combined organics were washed with water (50 mL) and brine (50 mL), dried over Na$_2$SO$_4$, and concentrated in vacuo to give a very dark-brown oil (6.69 g). This material was purified by column chromatography (8:2 hexanes:EtOAc+2% Et$_3$N, 1 column volume→7:3 hexanes:EtOAc+2% Et$_3$N, 4 column volumes) to provide a dark-brown oil still containing impurities (4.56 g). This material was further purified by additional column chromatography (1:1 hexanes:EtOAc, 2 column volumes→3:7 hexanes:EtOAc, 3 column volumes→EtOAc, 1 column volume) to give racemic 35 (35rac) as a viscous, pale-brown oil that slowly crystallized to a waxy solid (3.40 g, 33%). This material was converted to the HCl salt as follows. Freebase 35rac (3.40 g, 15.37 mmol) was dissolved in Et$_2$O (100 mL) and 2.0 M HCl in Et$_2$O (11.53 mL, 23.06 mmol) was added with stirring at room temperature. The resulting precipitate was collected by filtration, washed with Et$_2$O (3×), and dried to give 35rac HCl as a powdery white solid (3.98 g, quantitative recovery). Freebase: $^1$H NMR (400 MHz, CDCl$_3$) δ 7.40 (td, J=7.8, 1.8 Hz, 1H), 7.29 (dddd, J=8.1, 7.1, 5.1, 1.8 Hz, 1H), 7.19 (td, J=7.5, 1.3 Hz, 1H), 7.04 (ddd, J=11.5, 8.1, 1.3 Hz, 1H), 2.79-2.68 (m, 1H), 2.54-2.37 (m, 2H), 2.11 (s, 3H), 2.07 (s, 1H), 1.99-1.89 (m, 1H), 1.86-1.62 (m, 4H); $^{13}$C NMR (101 MHz, CDCl$_3$) δ 210.1, 161.2 (d, J$_{C-F}$=246.9 Hz), 129.5 (d, J$_{C-F}$=8.8 Hz), 128.9 (d, J$_{C-F}$=5.0 Hz), 127.3 (d, J$_{C-F}$=13.0 Hz), 124.3 (d, J$_{C-F}$=3.2 Hz), 116.4 (d, J$_{C-F}$=22.9 Hz), 68.5 (d, J$_{C-F}$=2.2 Hz), 39.5, 38.4, 29.4, 28.6, 22.1; HCl Salt: $^1$H NMR (400 MHz, DMSO-d$_6$) δ 10.29 (br s, 1H), 9.46 (br s, 1H), 7.85 (td, J=8.0, 1.7 Hz, 1H), 7.64 (dddd, J=8.6, 7.2, 5.3, 1.6 Hz, 1H), 7.45 (td, J=7.7, 1.3 Hz, 1H), 7.39 (ddd, J=12.0, 8.3, 1.2 Hz, 1H), 3.28 (dd, J=13.9, 2.9 Hz, 1H), 2.47-2.37 (m, 2H), 2.07-1.93 (m, 2H), 1.79 (dt, J=13.9, 3.2 Hz, 1H), 1.68-1.52 (m, 1H), 1.45 (qt, J=13.4, 3.5 Hz, 1H); $^{13}$C NMR (101 MHz, DMSO-d$_6$) δ 205.5, 160.7 (d, J$_{C-F}$=247.6 Hz), 133.2 (d, J$_{C-F}$=9.0 Hz), 130.9 (d, J$_{C-F}$=2.9 Hz), 125.7 (d, J$_{C-F}$=3.0 Hz), 118.2 (d, J$_{C-F}$=11.8 Hz), 116.8 (d, J$_{C-F}$=22.7 Hz), 68.7, 38.6 (d, J$_{C-F}$=1.8 Hz), 34.5, 28.3, 27.2, 21.1.

Chiral Separation of 35 Enantiomers (35R and 35S). The enantiomers of compound 35 were separated by crystallization of the diastereomeric hydrogen tartrate salts formed with L-(+)- and D-(−)-tartaric acid. Freebase 35rac (1.02 g, 4.61 mmol) was combined with L-(+)-tartaric acid (692 mg, 4.61 mmol) and water (2.75 mL), the mixture was gently warmed until a transparent brown solution was obtained, and this was left to stand at room temperature. After 16 h and then several hours in an acetone chamber (for vapor diffusion), no crystals had yet formed. Thus, acetone (5.5 mL) was added to the solution, and the entire mixture soon crystallized as a dense mass. The resulting crystals were collected by filtration, washed with minimal quantities of ice-cold 2:1 acetone:water (2×, some crystals dissolved) and ice-cold acetone (2×), and dried to give Crystals 1 (white needles, 344 mg, hydrogen L-tartrate salt, ~80:20 R:S). Crystals 1 were dissolved in water (1.5 mL) and placed in an acetone chamber (for vapor diffusion). After 84 h, the total volume of the solution was ~10-12 mL (so estimated ~6:1 acetone:water) and densely packed fine needle crystals had formed. These were collected by filtration, washed with room temperature acetone (2×), and dried to give Crystals 2 (fine white needles, 176 mg, hydrogen L-tartrate salt, R enantiomer, >95% e.e.). Over several hours, additional crystals formed in the filtrate from Crystals 2. These were collected after overnight standing, washed with room temperature acetone (2×), and dried to give Crystals 3 (fine white needles, 37.6 mg, hydrogen L-tartrate salt, R enantiomer, >95% e.e.). The concentrated filtrates from Crystals 1 and 3 (sticky, off-white foam, 1.48 g) were dissolved in water (1.5 mL), acetone (3.0 mL) was added, and the mixture was seeded with Crystals 3. After 2 h at room temperature, the resulting crystals were collected by filtration, washed with room temperature acetone (4×), and dried to give Crystals 4 (white needles, 690 mg, hydrogen L-tartrate salt, 48:52 R:S). The concentrated filtrate from Crystals 4 (white foam, 796 mg, hydrogen L-tartrate salt, 39:61 R:S) was enriched in the S enantiomer and was converted back to the freebase (nearly colorless waxy solid, 425 mg, 1.92 mmol). A quantity of this freebase (419 mg, 1.89 mmol) was combined with D-(−)-tartaric acid (284 mg, 1.89 mmol) and water (1.13 mL) and the mixture was gently warmed until a transparent brown solution was obtained. After cooling to room temperature, acetone (3.39 mL) was added and the mixture was left to stand for 2 h and then placed in an acetone chamber (for vapor diffusion) for 24 h. At this time, rosettes of blade-like crystals had formed, which appeared to be a different polymorph. These were collected by filtration, washed with ice-cold 3:1 acetone:H$_2$O (1×) and room temperature acetone (2×), and dried to give Crystals 5 (white crystals, 311 mg, hydrogen D-tartrate salt, 46.5:53.5 R:S) but enrichment in the S enantiomer had surprisingly decreased, likely due to crystallization as a different polymorph. However, fine needles soon formed in the filtrate of Crystals 5, which appeared to be the same polymorph as in earlier crystallizations. These were collected by filtration, washed with room temperature acetone (3×), and dried to give Crystals 6 (fine white needles, 159 mg, hydrogen D-tartrate salt, S enantiomer, >95% e.e.). Additional fine needles soon formed in the filtrate of Crystals 6. These were collected by filtration, washed with room temperature acetone (3×), and dried to give Crystals 7 (fine white needles, 54.8 mg, hydrogen D-tartrate salt, S enantiomer, >95% e.e.). Crystals 5 were dissolved in water (1.0 mL) and placed in an acetone chamber (for vapor diffusion) over the weekend. After this time, so crystals had yet formed, so the solution was seeded with Crystals 6. Within 30 minutes crystals began to form and after 2 h standing at room temperature, these were collected by filtration, washed with room temperature acetone (3×), and dried to give Crystals 8 (fine white needles, 150 mg, hydrogen D-tartrate salt, 33:77 R:S). The e.e. of all crystal crops was determined by chiral HPLC (Daicel Chiralcel AD column, 4.6 mm ID, 97:3 hexanes:iPrOH+0.30% Et$_2$NH, 1 mL/min, 4 mg/mL sample concentration, 20 µL injection volume; 35R t$_R$=12.7 min, 35S t$_R$=11.7 min) of samples that had been converted back to the freebase form. Hydrogen Tartrate Salt (identical for both R and S enantiomers): $^1$H NMR (500 MHz, DMSO-d$_6$) δ 7.52 (td, J=7.8, 1.8 Hz, 1H), 7.37 (tdd, J=7.5, 5.2, 1.8 Hz, 1H), 7.25 (td, J=7.6, 1.3 Hz, 1H), 7.16 (ddd, J=11.8, 8.2, 1.3 Hz, 1H), 4.20 (s, 2H), 2.54 (td, J=9.2, 4.7 Hz, 1H), 2.42-2.35 (m, 1H), 2.31-2.24 (m, 1H), 2.02 (s, 3H), 1.96-1.86 (m, 1H), 1.86-1.72 (m, 3H), 1.59-1.50 (m, 1H); $^1$H NMR (500 MHz, Methanol-d$_4$) δ 7.76 (td, J=7.9, 1.7 Hz, 1H), 7.67-7.61 (m, 1H), 7.47 (td, J=7.7, 1.2 Hz, 1H), 7.32 (ddd, J=11.8, 8.3, 1.2 Hz, 1H), 4.40 (s, 2H), 3.27-3.20 (m, 1H), 2.55-2.49 (m, 2H), 2.36 (s, 3H), 2.15-2.07 (m, 1H), 1.96-1.85 (m, 2H), 1.83-1.65 (m, 2H).

(R)-2-(2-Fluorophenyl)-2-(methylamino)cyclohexan-1-one (35R). t$_R$=12.7 min (Daicel Chiralcel AD column, 4.6 mm ID, 97:3 hexanes:iPrOH+0.30% Et$_2$NH, 1 mL/min, 4 mg/mL sample concentration, 20 µL injection volume).

(S)-2-(2-Fluorophenyl)-2-(methylamino)cyclohexan-1-one (35S). $t_R$=11.7 min (Daicel Chiralcel AD column, 4.6 mm ID, 97:3 hexanes:iPrOH+0.30% Et$_2$NH, 1 mL/min, 4 mg/mL sample concentration, 20 µL injection volume).

Assignment of Absolute Configuration of 35 Enantiomers (35R and 35S). X-ray quality crystals were grown as follows. A quantity Crystals 2 (20.5 mg, 0.055 mmol) was dissolved in water (10 mL), basified with 5% m/m aqueous NaOH, and extracted with Et$_2$O (3×10 mL). The combined organics were washed with water (2×5 mL) and brine (5 mL), dried over Na$_2$SO$_4$, and concentrated to give the corresponding freebase (11.6 mg, 0.052 mmol). This material was split into two vials (5.8 mg, 0.026 mmol each) and (1S)-(+)-camphorsulfonic acid (6.1 mg, 0.026 mmol; (+)-CSA) was added to one vial and (1R)-(−)-camphorsulfonic acid (6.1 mg, 0.026 mmol; (−)-CSA) was added to the other. Water (0.2 mL) was also added to each vial and the mixtures were gently warmed and stirred to homogenize and then concentrated in vacuo to give the diastereomeric camphorsulfonate salts. These salts were dissolved in minimal toluene and the solutions were allowed to slowly evaporate at room temperature in 4 mL vials with the caps left slightly ajar. Under these conditions, the (−)-CSA salt yielded crystals of acceptable quality for structural assignment by single-crystal x-ray diffraction. The absolute configuration was assigned both by anomalous dispersion and by reference to the known configuration of the (−)-CSA counterion and showed that Crystals 2 had the R configuration (R factor=0.0387). Crystallographic parameters are shown in Table 1 and a graphical representation of the determined crystal structure is shown in FIG. 1. With the absolute configuration of Crystals 2 known, it was possible to determine the configuration and e.e. of the other crops of crystals by chiral HPLC, as indicated above.

Grignard reagent over 5 minutes, a thick yellow precipitate formed and the mixture became difficult to stir. Additional anhydrous THF (45 mL) was added to attempt to reduce the viscosity and improve stirring, but this was largely ineffective. Accordingly, the remaining ⅔ of the Grignard reagent was added over 5 minutes and the mixture was swirled by hand to mix as completely as possible during the addition and then allowed to warm to room temperature. Once at room temperature, additional anhydrous THF (40 mL) was added and the mixture swirled more, which resulted in sufficient thinning of the thick, pale-yellow slurry to allow stirring. After 3 h stirring at room temperature, the reaction was poured into a mixture of ice (150 g) and 10% aqueous HCl (100 mL) and the resulting biphasic yellow solution was left to stand with occasional mixing until TLC showed complete hydrolysis of the imine intermediate. The hydrolyzed mixture was basified to pH 7-8 with solid NaHCO$_3$ and extracted with Et$_2$O (3×100 mL). The combined organics were washed with saturated aqueous NaHCO$_3$ (50 mL) and brine (50 mL), dried over Na$_2$SO$_4$, and concentrated in vacuo to give a yellow oil that slowly crystallized to a waxy yellow solid (7.37 g). This material was purified by column chromatography (9:1 hexanes:EtOAc) to give pure aminoketone 89 as a waxy, lemon-yellow solid (6.72 g, 89%). $^1$H NMR (500 MHz, CDCl$_3$) δ 7.79 (d, J=8.4 Hz, 1H), 7.25 (t, J=7.8 Hz, 1H), 6.69-6.61 (m, 2H), 6.27 (br s, 2H), 3.72 (p, J=8.0 Hz, 1H), 1.97-1.86 (m, 4H), 1.80-1.70 (m, 2H), 1.70-1.60 (m, 2H); $^{13}$C NMR (126 MHz, CDCl$_3$) δ 205.6, 150.8, 134.0, 131.5, 118.0, 117.5, 115.8, 46.8, 30.5, 26.5.

Cyclopentyl(2-iodophenyl)methanone (90). To a solution of aminoketone 89 (6.68 g, 35.30 mmol) in CH$_3$CN (141 mL) under argon was added p-toluenesulfonic acid monohydrate (20.14 g, 105.9 mmol) and the yellow solution was cooled to 0° C. A solution of NaNO$_2$ (4.87 g, 70.60 mmol)

TABLE 1

Crystallographic parameters of a 35R (1R)-(−)-camphorsulfonate crystal grown in toluene.

| Bond precision: | C—C = 0.0035 A | | Wavelength = 0.71073 | |
|---|---|---|---|---|
| Cell: | a = 6.882(3) | | b = 17.775(7) | c = 19.070(8) |
| | alpha = 90 | | beta = 90 | gamma = 90 |
| Temperature: | 230K | | | |

| | Calculated | Reported |
|---|---|---|
| Volume | 2332.8(17) | 2132.9(16) |
| Space group | P 21 21 21 | P 21 21 21 |
| Hall group | P 2ac 2ab | P 2ac 2ab |
| Moiety formula | C13 H17 F N O, C10 H15 O4 S | ? |
| Sum formula | C23 H32 F N O5 S | C23 H32 F N O5 S |
| Mr | 453.56 | 453.55 |
| Dx, g cm − 3 | 1.291 | 1.291 |
| Z | 4 | 4 |
| Mu (mm − 1) | 0.180 | 0.180 |
| F000 | 968.0 | 968.0 |
| F000' | 968.99 | |
| h, k, lmax | 9, 25, 27 | 9, 25, 27 |
| Nref | 7066 [3990] | 7054 |
| Tmin, Tmax | 0.977, 0.991 | 0.949, 0-999 |
| Tmin' | 0.959 | |
| Correction method = # Reported T Limits: Tmin = 0.949 Tmax = 0.999 AbsCorr = NUMERICAL | | |
| Data completeness = 1.77/1.00 | | Theta(max) = 30.449 |
| R(reflections)= 0.0387 (5991) | | wR2(reflections) = 0.0899(7054) |
| S = 1.031 | | Npar = 291 |

(2-Aminophenyl)(cyclopentyl)methanone (89). To a solution of 2-aminobenzonitrile (4.73 g, 40.00 mmol) in anhydrous THF (15 mL) at 0° C. under argon was added cyclopentylmagnesium bromide (2M in Et$_2$O; 60.00 mL, 120.00 mmol). After addition of approximately ⅓ of the and KI (14.65 g, 88.26 mmol) in water (21 mL) was added portionwise over ~30 minutes (~1 mL/min) while maintaining the temperature at <5° C. During the addition, effervescence was observed and the mixture rapidly became dark orange-brown, then nearly black (hard to stir at this stage), and then dark orang-brown again. After completing the addition, the mixture was allowed to warm to room temperature and stirred for 2 hours. At this time, TLC showed that the mixture was still mostly starting material and that no additional progress was occurring, so the reaction was quenched. The mixture was poured into water (200 mL), saturated aqueous NaHCO$_3$ (50 mL) and saturated aqueous Na$_2$S$_2$O$_3$ (50 mL) were added, and the mixture was extracted with Et$_2$O (3×100 mL). The combined organics were washed with water (50 mL), 5% aqueous HCl (50 mL), water (2×50 mL), saturated aqueous NaHCO$_3$ (25 mL), and brine (25 mL), dried over Na$_2$SO$_4$, and concentrated in vacuo to give a yellow-orange oil (7.70 g). This material was purified by column chromatography (40:1 hexanes:Et$_2$O, 2 column volumes→30:1 hexanes:Et$_2$O, 3 column volumes→5:1 hexanes:Et$_2$O, 2 column volumes) to give residual starting material 89 as a waxy, yellow solid (3.96 g, 59%) and iodoketone 90 as a yellow oil (3.42 g, 32%). $^1$H NMR (400 MHz, CDCl$_3$) δ 7.90 (d, J=7.9 Hz, 1H), 7.39 (td, J=7.5, 1.1 Hz, 1H), 7.32 (dd, J=7.6, 1.8 Hz, 1H), 7.10 (td, J=7.6, 1.8 Hz, 1H), 3.54 (p, J=7.9 Hz, 1H), 2.00-1.81 (m, 4H), 1.81-1.68 (m, 2H), 1.68-1.56 (m, 2H); $^{13}$C NMR (101 MHz, CDCl$_3$) δ 207.8, 145.7, 140.4, 131.3, 128.0, 127.8, 91.6, 50.5, 29.7, 26.3.

(1-Bromocyclopentyl)(2-iodophenyl)methanone (91). To a solution of iodoketone 90 (1.71 g, 5.70 mmol) in CCl$_4$ (5.8 mL) at 0° C. was added a solution of Br$_2$ (0.307 mL, 957 mg, 5.99 mmol) in CCl$_4$ (5.8 mL) portionwise over 20 minutes. At the end of the addition, the mixture was allowed to warm to room temperature and stirred for 40 minutes. The reaction mixture was then diluted with CH$_2$Cl2 (20 mL), washed with saturated aqueous Na$_2$S$_2$O$_3$ (10 mL), saturated aqueous NaHCO$_3$ (10 mL), and brine (10 mL), dried over Na$_2$SO$_4$, and concentrated in vacuo to give compound 91 as a yellow oil (2.14 g, 99%). $^1$H NMR (500 MHz, CDCl$_3$) δ 7.89 (dd, J=7.9, 1.1 Hz, 1H), 7.70 (dd, J=7.7, 1.7 Hz, 1H), 7.38 (td, J=7.6, 1.1 Hz, 1H), 7.12 (td, J=7.7, 1.6 Hz, 1H), 2.46-2.30 (m, 4H), 2.11-2.00 (m, 2H), 1.93-1.83 (m, 2H); $^{13}$C NMR (101 MHz, CDCl$_3$) δ 201.1, 144.7, 140.0, 131.1, 127.8, 127.7, 92.3, 73.5, 41.0, 23.4.

2-(2-Iodophenyl)-2-(methylamino)cyclohexan-1-one (37rac). Liquid methylamine was freshly prepared as follows. Solid methylamine HCl (30 g) was treated dropwise with 50% m/m aqueous NaOH (40 g) and the evolved gas was passed through a drying tube containing NaOH pellets and condensed into a flask topped with a condenser containing dry ice/acetone. Once the required quantity of liquid methylamine had been collected, the reaction was carried out as follows. Compound 91 (2.12 g, 5.59 mmol) and liquid methylamine (4.5 mL) were combined at −10° C. under argon and the resulting mixture was stirred for 1 h. All methylamine was then carefully boiled off and the resulting residue dried in vacuo to give a pale-yellow solid (2.40 g). This material was triturated with Et$_2$O (10 mL), filtered, and the filter cake washed with Et$_2$O (2×5 mL). The combined filtrates were concentrated in vacuo to give crude 1-((2-iodophenyl)(methylimino)methyl)cyclopentan-1-ol as a waxy yellow solid (1.78 g). A quantity (1.76 g) of this material was dissolved in decalin (9.5 mL) and the yellow solution was brought to reflux under argon for 2 h. The reaction mixture (now dark-brown) was then cooled to room temperature, diluted with Et$_2$O (20 mL), and extracted with 2% aqueous HCl (20 mL) and water (2×20 mL). The combined aqueous extracts were washed with hexanes (20 mL) and Et$_2$O (20 mL), basified to pH 9-10 with aqueous NaOH, and extracted with Et$_2$O (3×20 mL). The combined organics were washed with water (10 mL) and brine (10 mL), dried over Na$_2$SO$_4$, and concentrated in vacuo to give a viscous yellow oil (690 mg). This material was purified by column chromatography (8:2 hexanes:EtOAc, 4 column volumes→7:3 hexanes:EtOAc, 4 column volumes) to provide a nearly colorless oil that slowly crystallized to an off-white solid still containing impurities (0.31 g). This material was further purified by additional column chromatography (20:1 hexanes:EtOAc+2% Et$_3$N, 2 column volumes→9:1 hexanes:EtOAc+2% Et$_3$N, 2 column volumes→5.67:1 hexanes:EtOAc+2% Et$_3$N, 2 column volumes) to give racemic 37 (37rac) as a nearly colorless oil that slowly crystallized to a waxy white solid (267 mg, 15% over 2 steps). This material was converted to the HCl salt as follows. Freebase 37rac (267 mg, 0.811 mmol) was dissolved in Et$_2$O (5 mL) and 2.0 M HCl in Et$_2$O (0.61 mL, 1.22 mmol) was added with stirring at room temperature. The mixture was concentrated in vacuo, the resulting solids triturated with hexanes, and the mixture concentrated again to give 37rac HCl as a powdery off-white solid (281 mg, 95% recovery). Freebase: NMR (500 MHz, CDCl$_3$) δ 7.90 (d, J=7.8 Hz, 1H), 7.52 (dd, J=7.9, 1.7 Hz, 1H), 7.36 (t, J=7.6 Hz, 1H), 6.94 (td, J=7.6, 1.7 Hz, 1H), 2.76-2.66 (m, 1H), 2.54-2.44 (m, 2H), 2.18-2.08 (m, 2H), 2.07 (s, 3H), 1.94-1.84 (m, 1H), 1.83-1.75 (m, 3H); $^{13}$C NMR (126 MHz, CDCl$_3$) δ 207.6, 142.5, 142.2, 129.8, 128.9, 127.9, 98.3, 72.2, 39.9, 38.9, 29.3, 26.9, 21.7; HCl Salt: $^1$H NMR (500 MHz, DMSO-d$_6$) δ 9.89 (br s, 1H), 8.84 (br s, 1H), 8.12 (d, J=7.7 Hz, 1H), 7.85 (d, J=8.1 Hz, 1H), 7.64 (t, J=7.5 Hz, 1H), 7.26 (t, J=7.4 Hz, 1H), 3.43-3.29 (presumed m, 1H; buried under H$_2$O peak as shown by COSY), 2.65-2.53 (m, 2H), 2.25 (s, 3H), 2.09-1.99 (m, 1H), 1.88 (td, J=13.7, 3.4 Hz, 1H), 1.77 (br d, J=13.9 Hz, 1H), 1.74-1.64 (m, 1H), 1.55-1.42 (m, 1H).

Example 2: Preparation of Compounds 14S and 14R

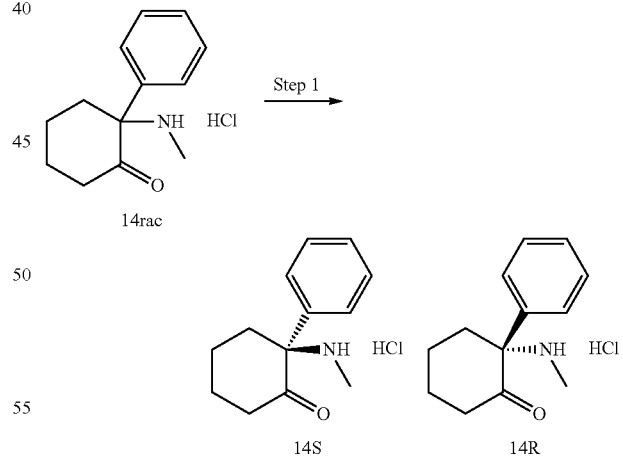

Step 1: Preparation of (S)-2-(methylamino)-2-phenylcyclohexan-1-one (14S) and (R)-2-(methylamino)-2-phenylcyclohexan-1-one (14R)

To a solution of 2-(methylamino)-2-phenylcyclohexan-1-one hydrochloride (1.4 g, 1.97 mmol) (14rac) stirred at RT in dry methanol (20 mL) was added NaOH (0.25 g, 6.26 mmol) and the reaction mixture was stirred for 30 min. The mixture was filtered and the filtrate was concentrated in vacuo. After evaporation, the residue was separated by chiral chromatography using a 250×20 mm, 5 μm Chiralpak AD-H column eluting with 90-5-5 Hexane-IPA-MeOH at a flow rate of 12 mL/min Samples were separated and combined to give product freebases, which were acidified with HCl in dioxane and concentrated to provide the HCl salts. Obtained were 0.475 g of ENT-1 2-(methylamino)-2-phenylcyclohexan-1-one hydrochloride, $t_R$=18.150 min (for freebase) (assigned here as the S isomer, 14S); m/z [M+H]$^+$ 204.0; $^1$H NMR (DMSO-d$_6$, 400 MHz) (for HCl): δ (ppm) 9.98 (s, 1H), 9.34 (s, 1H), 7.55 (m, 3H), 7.42 (d, J=7.1 Hz, 2H), 3.17 (d, J=13.1 Hz, 1H), 2.40 (m, 1H), 2.30 (m, 1H), 2.12 (m, 1H), 2.10 (s, 3H), 1.97 (m, 1H), 1.86 (m, 1H), 1.59 (m, 2H); and 0.470 g of ENT-2 2-(methylamino)-2-phenylcyclohexan-1-one hydrochloride, $t_R$=27.830 min (for freebase) (assigned here as the R isomer. 14R): m/z [M+H]$^+$ 204.1; $^1$H NMR (DMSO-d$_6$, 400 MHz) (for HCl): δ (ppm) 10.00 (s, 1H), 9.34 (s, 1H), 7.54 (m, 3H), 7.41 (d, J=6.9 Hz, 2H), 3.15 (d, J=13.8 Hz, 1H), 2.39 (m, 1H), 2.29 (m, 1H), 2.14 (m, 1H), 2.12 (s, 3H), 1.96 (m, 1H), 1.85 (m, 1H), 1.60 (m, 2H).

Example 3: Preparation of Compounds 29R and 29S

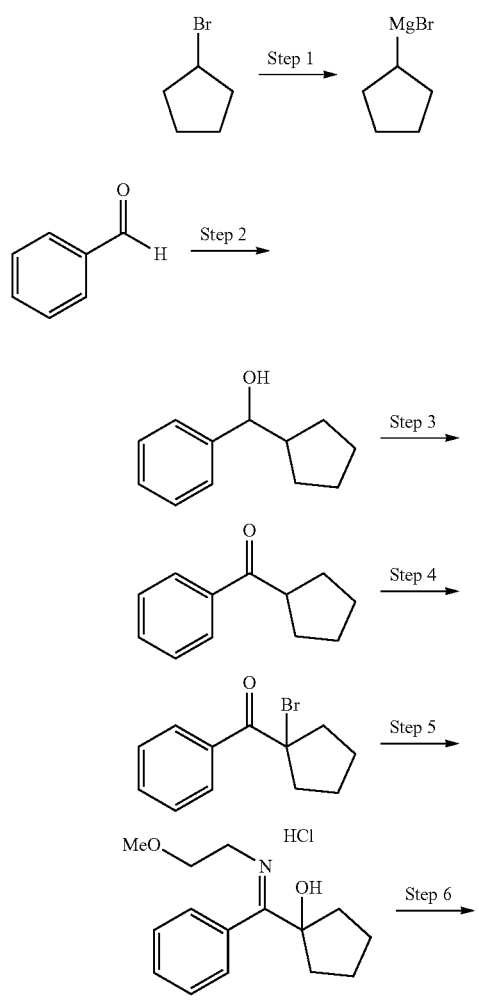

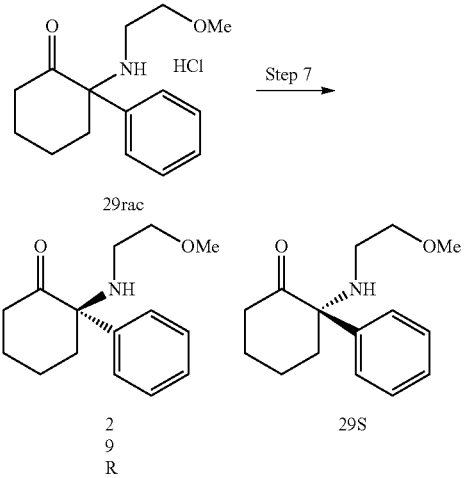

Step 1: Preparation of 0.8 M Cyclopentylmagnesium Bromide Solution in THF

To a stirred solution of bromocyclopentane (83 g, 560 mmol) in THF (700 mL) was added a catalytic amount of iodine and ethyl iodide. Magnesium turnings (17.5 g, 672 mmol) were added and the reaction mixture was refluxed with stirring for 5 h then cooled to RT to obtain cyclopentylmagnesium bromide in THF which was used directly in the next step.

Step 2: Preparation of cyclopentyl(phenyl)methanol

To a RT solution of cyclopentylmagnesium bromide in THF (0.8 M, 700 mL, 560 mmol, 1.5 eq.) was added dropwise a solution of benzaldehyde (40.3 g, 380 mmol) in THF (200 mL). The reaction mixture was stirred overnight at r.t. The mixture was cooled with an ice-water bath and then treated dropwise with a solution of NH$_2$Cl (50 g) in water (500 mL). The resulting mixture was extracted with ethyl acetate (3×400 mL). The combined organic layers were washed with water, dried over anhydrous Na$_2$SO$_4$ and evaporated under reduced pressure. Purification of the residue via column chromatography on silica gel (500 g SiO$_2$/25 g of reaction mixture, hexanes/MTBE 20/1→1/1) afforded 27 g of cyclopentyl(phenyl)methanol (40% yield). $^1$H NMR (400 MHz, Chloroform-d) δ 7.35-7.19 (m, 5H), 4.39 (d, J=8.4 Hz, 1H), 2.21 (h, J=8.2 Hz, 1H), 1.93-1.81 (m, 1H), 1.71-1.41 (m, 5H), 1.36 (dtd, J=11.4, 7.4, 3.7 Hz, 1H), 1.14 (dq, J=12.4, 8.1 Hz, 1H).

Step 3: Preparation of cyclopentyl(phenyl)methanone

To a solution of cyclopentyl(phenyl)methanol (27 g, 153 mmol) in dry dichloromethane (250 mL) was stirred, cooled with ice-water bath, and treated with Dess-Martin Periodinane (DMP, 97.5 g, 230 mmol). The reaction mixture was stirred overnight at RT, diluted with an aqueous solution of sodium bicarbonate (75 g, 500 mL) and extracted with dichloromethane twice. The combined organic layers were dried over anhydrous Na$_2$SO$_4$ and evaporated under reduced pressure. Purification of the residue via column chromatography on silica gel (100 g SiO$_2$/10 g of reaction mixture, hexanes/DCM 10/1) afforded 17 g of cyclopentyl(phenyl)

methanone (59% yield). ¹H NMR (400 MHz, DMSO-d₆) δ 7.98 (d, J=7.7 Hz, 2H), 7.62 (t, J=7.3 Hz, 1H), 7.52 (t, J=7.6 Hz, 2H), 1.94-1.82 (m, 2H), 1.75 (q, J=6.8 Hz, 2H), 1.71-1.56 (m, 4H).

Step 4: Preparation of (1-bromocyclopentyl)(phenyl)methanone

To a solution of cyclopentyl(phenyl)methanone (17 g, 90 mmol) in a mixture of dry ethyl acetate (75 mL) and dry CHCl₃ (75 mL) was added copper(II) bromide (60 g, 270 mmol) and the reaction mixture was stirred under reflux overnight. The mixture was cooled to RT and filtered. The filtrate was concentrated in vacuo to obtain 22 g of (1-bromocyclopentyl)(phenyl)methanone (96.6% yield), which was used in the next step without further purification.

Step 5: Preparation of 1-(((2-methoxyethyl)imino) (phenyl)methyl)cyclopentan-1-ol hydrochloride To a solution of (1-bromocyclopentyl)(phenyl)methanone (22 g, 86.9 mmol) in dry methanol (220 mL) was added 2-methoxyethylamine (19.6 g, 260.7 mmol) and the reaction mixture was stirred at RT for 48 h. The mixture was evaporated under reduced pressure, diluted with water (300 mL) and ethyl acetate (300 mL). The separated organic layer was dried over anhydrous Na₂SO₄ and evaporated under reduced pressure to obtain 16 g of 1-(((2-methoxyethyl)imino)(phenyl)methyl)cyclopentan-1-ol. The compound was stirred in dioxane (1 M) and treated with HCl/dioxane (1.05 eq.) and then evaporated under reduced pressure to obtain 1-(((2-methoxyethyl)imino)(phenyl)methyl)cyclopentan-1-olhydrochloride. ¹H NMR (500 MHz, Chloroform-d) δ 7.98 (dd, J=7.6, 1.9 Hz, 1H), 7.50-7.31 (m, 3H), 7.05 (dt, J=5.8, 1.7 Hz, 1H), 3.57 (td, J=6.0, 2.6 Hz, 1H), 3.35-3.22 (m, 3H), 2.43-2.32 (m, 1H), 2.09-1.97 (m, 1H), 1.89 (dddd, J=22.6, 10.8, 5.5, 2.8 Hz, 4H), 1.65 (ddt, J=11.1, 5.6, 2.7 Hz, 1H), 1.52 (ddt, J=7.8, 5.3, 2.9 Hz, 1H).

Step 6: Preparation of 2-((2-methoxyethyl)amino)-2-phenylcyclohexan-1-one (29rac)

To stirred Dowtherm (90 mL, 294 mmol), heated to 200° C. with an oil bath, was added in portions 1-(((2-methoxyethyl)imino)(phenyl)methyl)cyclopentan-1-ol hydrochloride. The reaction mixture was heated at 180° C. for 15 min, cooled to RT and diluted with CHCl₃ (250 mL) and water (150 mL). The separated aqueous layer was washed with CHCl₃ (2×200 mL) and evaporated under reduced pressure. The residue was recrystallized (5 mL of EtOH+few drops of MeOH per 1 g of crude product) to obtain 3.2 g of 2-((2-methoxyethyl)amino)-2-phenylcyclohexan-1-one hydrochloride (29rac). m/z [M+H]⁺248.3; ¹H NMR (DMSO-d₆, 400 MHz): δ (ppm) 9.39 (s, 2H), 7.46 (m, 3H), 7.39 (m, J=7.0 Hz, 2H), 3.44 (m, 2H), 3.34 (m, 1H), 3.19 (s, 3H), 3.01 (m, 1H), 2.41 (m, 2H), 2.31 (m, 1H), 2.12 (m, 1H), 1.90 (m, 1H), 1.82 (m, 1H), 1.64 (q, J=12.4, 12.3, 12.3 Hz, 1H), 1.51 (q, J=12.4, 12.4, 12.3 Hz, 1H).

Step 7: Preparation of (R)-2-((2-methoxyethyl)amino)-2-phenylcyclohexan-1-one (29R) and (S)-2-((2-methoxyethyl)amino)-2-phenylcyclohexan-1-one (29S)

The HCl salt of 29rac was basified with aqueous NaHCO₃, extracted with CH₂Cl₂, and the organic extracts were concentrated to provide the freebase (850 mg). This material was separated into the enantiomers by SFC (column: DAICEL CHIRALCEL OD (250 mm*30 mm, 10 µm); mobile phase: A: CO₂, B: 0.1% NH₃H₂O in ETOH, B %: 17%; multi-injection process with 1.2 min spacing between injections) to afford ENT-1, RT=1.080 min (241 mg) (assigned here as the S isomer, 29S) and ENT-2, RT=1.236 min (184 mg) (assigned here as the R isomer, 29R). Retention times were determined using the following chiral analytical method: column: Chiralpak OD-3, 100×4.6 mm I.D., 3 µm; mobile phase: A: CO₂, B: EtOH (0.1% IPAm, v/v); gradient: (Time (min)/A %/B %), (0.0/95/5, 0.5/95/5, 2.0/60/40, 3.0/60/40, 3.6/95/5, 4.0/95/5); flow rate: 3.4 mL/min; column temp.: 35° C.; ABPR: 1800 psi.

Example 4: Preparation of Compounds 30R and 30S

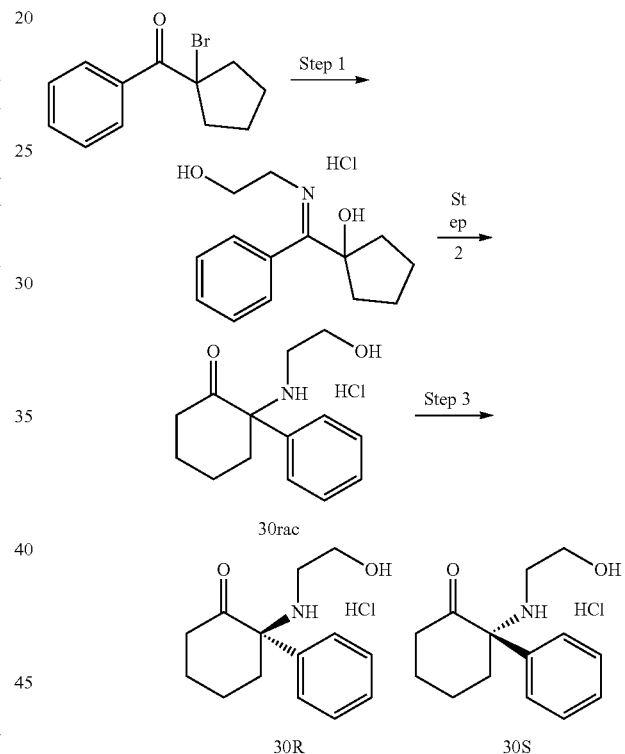

Step 1: Preparation of 1-(((2-hydroxyethyl)imino) (phenyl)methyl)cyclopentan-1-ol hydrochloride To a solution of (1-bromocyclopentyl)(phenyl)methanone (17 g, 67.15 mmol) in dry methanol (170 mL) was added 2-aminoethanol (12.3 g, 201.45 mmol) and the reaction mixture was stirred at RT for 48 h. Upon completion, the mixture was evaporated under reduced pressure, diluted with water (300 mL), and extracted with ethyl acetate (300 mL). The separated organic layer was dried over anhydrous Na₂SO₄ and evaporated under reduced pressure to obtain 8 g of 1-(((3-hydroxyethyl)imino)(phenyl)methyl)cyclopentan-1-ol. This material was stirred in dioxane (1 M), treated with HO/dioxane (1.05 eq.), and evaporated under reduced pressure to obtain 1-(((3-hydroxyethyl)imino)(phenyl) methyl)cyclopentan-1-ol hydrochloride. ¹H NMR (400 MHz, DMSO-d₆) δ 7.58-7.50 (m, 2H), 7.27 (dd, J=8.3, 6.3

Hz, 3H), 4.37 (s, 1H), 3.48 (td, J=7.4, 3.1 Hz, 2H), 3.17 (s, 1H), 2.40 (d, J=9.2 Hz, 1H), 1.71-1.62 (m, 2H), 1.59 (d, J=7.2 Hz, 2H), 1.58-1.46 (m, 2H), 1.25 (d, J=10.5 Hz, 2H).

Step 2: Preparation of 2-((2-hydroxyethyl)amino)-2-phenylcyclohexan-1-one (30rac)

To stirred Dowtherm (70 mL, 228.7 mmol), heated to 200° C. with an oil bath, was added in portions 1-(((3-hydroxyethyl)imino)(phenyl)methyl)cyclopentan-1-ol hydrochloride. The reaction mixture was heated to 180° C. for 15 min, cooled to RT, and diluted with CHCl$_3$ (200 mL) and water (120 mL). The aqueous layer was washed with CHCl$_3$ (2×150 mL) and evaporated under reduced pressure. The residue was recrystallized (5 mL of EtOH+few drops of ACN per 1 g of crude product) to obtain 2.7 g of 24(2-hydroxyethyl)amino)-2-phenylcyclohexan-1-one hydrochloride (30rac). $^1$H NMR (400 MHz, Chloroform-d) δ 7.55 (d, J=7.7 Hz, 2H), 7.43-7.32 (m, 3H), 7.32-7.23 (m, 2H), 5.41 (t, J=3.7 Hz, 1H), 3.91 (dd, J=10.7, 3.8 Hz, 1H), 3.85-3.73 (m, 2H), 2.94-2.81 (m, 1H), 2.64 (dd, J=13.7, 3.0 Hz, 1H), 2.21-2.06 (m, 2H), 1.94 (dt, J=12.6, 3.4 Hz, 2H), 1.86-1.68 (m, 2H), 1.53-1.47 (m, 1H), 1.31-1.18 (m, 1H).

Step 3: Preparation of (R)-2-((2-hydroxyethyl)amino)-2-phenylcyclohexan-1-one (30R) and (S)-2-((2-hydroxyethyl)amino)-2-phenylcyclohexan-1-one (30S)

To a solution of 2-((2-hydroxyethyl)amino)-2-phenylcyclohexan-1-one hydrochloride (1.7 g, 2 mmol) in dry methanol (20 mL) was added NaOH (0.3 g, 7 mmol) and the reaction mixture was stirred for 30 min at RT. The mixture was then filtered and the filtrate was concentrated in vacuo. The residue after evaporation was separated on a 250×20 mm, 5 μm Chiralpak AD-H column eluting with 99-1 Hexane-IPA at a flow rate of 15 mL/min Samples were separated and combined to give product freebases. These were treated in dioxane with 10% HCl in dioxane (5 mL) and evaporated to dryness to obtain ENT-1 2-((2-hydroxyethyl)amino)-2-phenylcyclohexan-1-one hydrochloride 0.268 g, t$_R$=9.953 min (for freebase) (assigned here as the R isomer, 30R); m/z [M+1-1]+216.2; $^1$H NMR (DMSO-d$_6$, 400 MHz) (for HCl): δ (ppm) 10.27 (s, 1H), 9.95 (s, 1H), 7.58 (d, J=7.6 Hz, 2H), 7.44 (t, 2H), 7.38 (t, J=5.8 Hz, 1H), 5.67 (br s, 1H), 4.01 (d, J=13.3 Hz, 1H), 3.93 (t, J=14.0, 14.0 Hz, 1H), 3.09 (d, J=15.6 Hz, 1H), 2.73 (m, 1H), 2.39 (m, 1H), 2.14 (m, 5H), 1.56 (m, 1H), 0.95 (m, 1H); and ENT-2 2-((2-hydroxyethyl)amino)-2-phenylcyclohexan-1-one hydrochloride 0.288 g, t$_R$=12.382 min (for freebase) (assigned here as the S isomer. 30S); m/z [M+1-1]+216.2; $^1$H NMR (DMSO-d$_6$, 400 MHz) (for HCl): δ (ppm) 10.24 (s, 1H), 9.97 (s, 1H), 7.58 (d, J=7.3 Hz, 2H), 7.46 (t, J=7.5, 7.5 Hz, 2H), 7.39 (t, J=7.6, 7.6 Hz, 1H), 5.67 (br s, 1H), 4.02 (d, J=15.3 Hz, 1H), 3.93 (t, J=12.6, 12.6 Hz, 1H), 3.09 (d, J=16.4 Hz, 1H), 2.73 (m, 1H), 2.39 (m, 1H), 2.14 (m, 5H), 1.55 (m, 1H), 0.96 (m, 1H).

Example 5: Preparation of Compound 38R and 38S

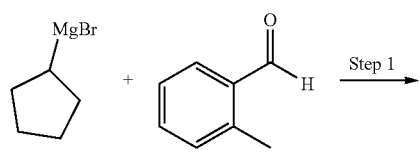

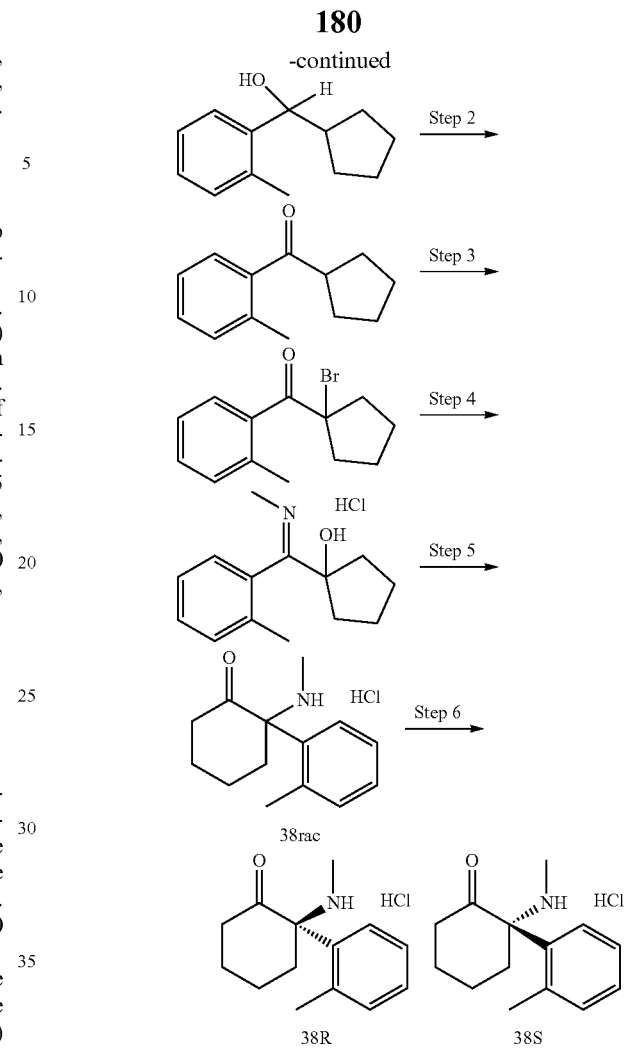

Step 1: Preparation of cyclopentyl(o-tolyl)methanol

To a THF solution of cyclopentylmagnesium bromide (0.8 M, 700 mL, 560 mmol, 1.5 eq.) was added dropwise a solution of 2-methylbenzaldehyde (37 g, 380 mmol) in THF (200 mL). The reaction mixture was stirred overnight at RT. The mixture was cooled with an ice-water bath and treated with a solution of NH$_4$Cl (50 g) in water (500 mL) dropwise. The resulting mixture was extracted with ethyl acetate (3×400 mL). The combined organic layers were washed with water, dried over anhydrous Na$_2$SO$_4$, and evaporated under reduced pressure. Purification of the residue via column chromatography on silica gel (500 g SiO$_2$/25 g of reaction mixture, hexanes/MTBE 20/1→1/1) afforded 25 g of cyclopentyl(o-tolyl)methanol (39.5% yield). $^1$H NMR (500 MHz, Chloroform-d) δ 7.46-7.40 (m, 1H), 7.26-7.19 (m, 1H), 7.16 (ddt, J=10.4, 5.6, 2.7 Hz, 2H), 4.72 (dd, J=8.2, 2.2 Hz, 1H), 2.45 (s, 3H), 2.29 (dt, J=8.0, 6.0 Hz, 2H), 1.89 (dtt, J=10.9, 8.4, 5.6 Hz, 1H), 1.78-1.68 (m, 1H), 1.68-1.60 (m, 2H), 1.60-1.43 (m, 3H), 1.24-1.13 (m, 1H).

Step 2: Preparation of cyclopentyl(o-tolyl)methanone

To a solution of cyclopentyl(o-tolyl)methanol (25 g, 150 mmol) in dry dichloromethane (250 mL), cooled with an ice-water bath, was added Dess-Martin Periodinane (DMP, 97.5 g, 230 mmol). The reaction mixture was stirred overnight at RT, diluted with an aqueous solution of sodium bicarbonate (75 g, 500 mL), and extracted with dichloromethane twice. The combined organic layers were dried over anhydrous $Na_2SO_4$ and evaporated under reduced pressure. Purification of the residue via column chromatography on silica gel (100 g $SiO_2$/10 g of reaction mixture, Hexane/DCM 10/1) afforded 16 g of cyclopentyl(o-tolyl)methanone (60% yield).

Step 3: Preparation of (1-bromocyclopentyl)(o-tolyl)methanone

To a solution of cyclopentyl(o-tolyl)methanone (16 g, 90 mmol) in a mixture of dry ethyl acetate (75 mL) and dry $CHCl_3$ (75 mL) was added copper(II) bromide (57 g, 257 mmol) and the reaction mixture was stirred under reflux overnight. The mixture was cooled, filtered and the filtrate concentrated in vacuo to obtain 20 g of (1-bromocyclopentyl)(o-tolyl)methanone (96% yield), which was used in the next step without further purification. $^1$H NMR (400 MHz, Chloroform-d) δ 7.74 (d, J=7.7 Hz, 1H), 7.32 (t, J=7.5 Hz, 1H), 7.27-7.14 (m, 2H), 2.36 (m, 7H), 2.05 (tt, J=9.6, 5.3 Hz, 2H), 1.81 (q, J=7.6 Hz, 2H).

Step 4: Preparation of 1-((methylimino)(o-tolyl)methyl)cyclopentan-1-ol hydrochloride A mixture of (1-bromocyclopentyl)(o-tolyl)methanone (15 g, 56.14 mmol) and a solution of methylamine in methanol (150 mL) was stirred at RT for 48 h. Upon completion, the mixture was evaporated under reduced pressure and the residue was diluted with water (300 mL) and ethyl acetate (300 mL). The separated organic layer was dried over anhydrous $Na_2SO_4$ and evaporated under reduced pressure to obtain 9.5 g of 1-((methylimino)(o-tolyl)methyl)cyclopentan-1-ol. This material in dioxane (1 M) was treated with HCl/dioxane (1.05 eq.) and evaporated under reduced pressure to obtain 11.1 g of the 1-((methylimino)(o-tolyl)methyl)cyclopentan-1-ol hydrochloride. $^1$H NMR (500 MHz, Chloroform-d) δ 7.26 (d, J=4.0 Hz, 3H), 6.95 (s, 1H), 2.95 (s, 3H), 2.14 (s, 3H), 1.91 (s, 2H), 1.86 (s, 1H), 1.81 (s, 1H), 1.67 (s, 3H), 1.25 (s, 1H).

Step 5: Preparation of 2-(methylamino)-2-(o-tolyl)cyclohexan-1-one (38rac)

To stirred Dowtherm (70 mL, 228.7 mmol), heated to 200° C. with an oil bath, was added in portions 1-((methylimino)(o-tolyl)methyl)cyclopentan-1-ol hydrochloride. The reaction mixture was heated to 180° C. for 15 min, cooled to RT, and diluted with $CHCl_3$ (250 mL) and water (150 mL). The aqueous layer was washed with $CHCl_3$ (2×200 mL) and evaporated under reduced pressure. The residue was recrystallized (5 ml of EtOH and a few drops of ACN per 1 g of crude product) to obtain 2.7 g of 2-(methylamino)-2-(o-tolyl)cyclohexan-1-one hydrochloride (38rac). $^1$H NMR (400 MHz, Chloroform-d) δ 7.45 (dd, J=7.5, 1.7 Hz, 1H), 7.21 (dtd, J=14.5, 7.2, 2.3 Hz, 2H), 7.14 (dd, J=7.3, 1.8 Hz, 1H), 3.05 (dd, J=15.2, 4.1 Hz, 1H), 2.37 (dd, J=7.9, 3.1 Hz, 1H), 2.13 (s, 3H), 2.04 (s, 3H), 2.01-1.96 (m, 1H), 1.83-1.70 (m, 3H), 1.54 (dq, J=14.2, 4.7 Hz, 1H).

Step 6: Preparation of (R)-2-(methylamino)-2-(o-tolyl)cyclohexan-1-one (38R) and (S)-2-(methylamino)-2-(o-tolyl)cyclohexan-1-one (38S)

To a solution of 2-(methylamino)-2-(o-tolyl)cyclohexan-1-one hydrochloride (1.4 g, 2 mmol) in dry methanol (20 mL) was added NaOH (0.3 g, 7 mmol) and the reaction mixture was stirred for 30 min at RT. The mixture was than filtered, and the filtrate was concentrated in vacuo to give the freebase. The residue after evaporation was separated on a 250×20 mm, 5 μm Chiralcel OJ-H column eluting with 95:2.5:2.5 hexane-IPA-MeOH at a flow rate of 15 mL/min Samples were separated and combined to give product freebases. The resulting freebases were dissolved in dioxane, treated with 10% HCl in dioxane (5 mL), and then evaporated to dryness to obtain ENT-1 2-(methylamino)-2-(o-tolyl)cyclohexan-1-one hydrochloride 0.494 g, $t_R$=11.012 min (for freebase) (assigned here as the S isomer, 38S); m/z [M+H]$^+$ 218.2; $^1$H NMR (DMSO-d$_6$, 400 MHz) (for HCl): δ (ppm) 9.65 (s, 1H), 8.95 (s, 1H), 7.67 (m, 1H), 7.39 (m, 2H), 7.30 (m, 1H), 3.33 (m, 1H), 2.41 (m, 1H), 2.31 (m, 1H), 2.15 (s, 3H), 2.09 (s, 3H), 1.98 (m, 1H), 1.83 (t, J=13.6, 13.6 Hz, 1H), 1.76 (d, J=12.7 Hz, 1H), 1.59 (m, 2H); and ENT-2 2-(methylamino)-2-(o-tolyl)cyclohexan-1-one hydrochloride 0.453 g; $t_R$=15.045 min (for freebase) (assigned here as the R isomer, 38R); m/z [M+H]$^+$ 218.2; $^1$H NMR (DMSO-d6, 400 MHz) (for HCl): δ (ppm) 9.67 (s, 1H), 8.94 (s, 1H), 7.67 (m, 1H), 7.40 (m, 2H), 7.31 (m, 1H), 3.35 (m, 1H), 2.41 (m, 1H), 2.32 (m, 1H), 2.15 (s, 3H), 2.10 (s, 3H), 1.99 (m, 1H), 1.83 (t, J=12.0, 12.0 Hz, 1H), 1.76 (d, J=15.3 Hz, 1H), 1.59 (m, 2H).

Example 6: Preparation of Compound 26R and 26S

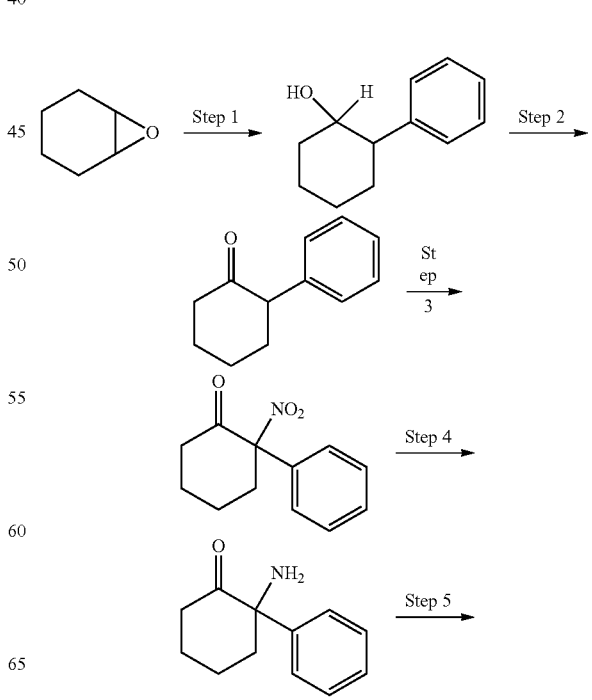

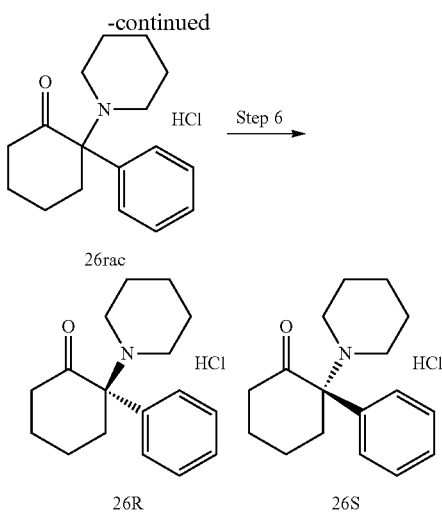

26rac 26R    26S

Step 1: Preparation of 2-phenylcyclohexan-1-ol

To a stirred solution of 7-oxabicyclo[4.1.0]heptane (107 g, 1090 mmol) in THF (1000 mL) was added CuI (20.76 g, 109 mmol). To the obtained mixture, cooled to 0° C., was added dropwise a solution of phenylmagnesium bromide in THF (1500 mL, 1200 mmol). The reaction mixture was stirred overnight at RT. The mixture was cooled to 0° C. and treated dropwise with a concentrated solution of $NH_4Cl$ (90 g, 1690 mmol) in water. The resulting mixture was evaporated to 1500 mL of total volume and diluted with MTBE. The organic layer was separated and the aqueous layer was extracted with additional MTBE. The combined organic layers were washed with brine 3 times, dried over anhydrous $Na_2SO_4$, and evaporated under reduced pressure to afford 120 g of 2-phenylcyclohexan-1-ol (62.5% yield). $^1$H NMR (400 MHz, Chloroform-d) δ 7.32 (t, J=7.5 Hz, 2H), 7.24 (dd, J=7.6, 2.6 Hz, 3H), 3.65 (td, J=10.0, 4.2 Hz, 1H), 2.41 (ddd, J=13.1, 9.9, 3.4 Hz, 1H), 2.14-2.05 (m, 1H), 1.85 (dd, J=12.2, 3.4 Hz, 2H), 1.79-1.70 (m, 1H), 1.59-1.27 (m, 6H).

Step 2: Preparation of 2-phenylcyclohexan-1-one

To a stirred solution of 2-phenylcyclohexan-1-ol (120 g, 680 mmol) in dry dichloromethane (1500 mL), cooled with an ice-water bath, was added in portions Dess-Martin Periodinane (DMP, 303 g, 715 mmol). The reaction mixture was stirred overnight at RT, poured into a mixture of $K_2CO_3$/ice (250 g, 2000 mL), stirred for 30 min, and filtered. The filtrate was extracted with dichloromethane twice. The combined organic layers were dried over anhydrous $Na_2SO_4$ and evaporated under reduced pressure. The residue was diluted with hexanes, refluxed and filtered. The filtrate was evaporated under reduced pressure to obtain 90 g of 2-phenylcyclohexan-1-one (69% yield). $^1$H NMR (400 MHz, Chloroform-d) δ 7.34-7.22 (m, 3H), 7.12 (d, J=7.0 Hz, 2H), 3.60 (d, J=9.3 Hz, 1H), 2.50 (s, 1H), 2.46 (d, J=7.6 Hz, 1H), 2.26 (s, 1H), 2.14 (s, 1H), 2.02 (d, J=19.8 Hz, 2H), 1.82 (s, 2H).

Step 3: Preparation of 2-nitro-2-phenylcyclohexan-1-one

To a solution of 2-phenylcyclohexan-1-one (90 g, 470 mmol) in 1,2-dichloroethane (1200 mL) was added ammonium cerium(IV) nitrate (524 g, 956 mmol) and copper(II) acetate (17.3 g, 95 mmol). The reaction mixture was stirred overnight at 60° C. then cooled to RT and filtered. The filtrate was washed with water twice, dried over anhydrous $Na_2SO_4$ and evaporated under reduced pressure to obtain 90 g of 2-nitro-2-phenylcyclohexan-1-one (87% yield).

Step 4: Preparation of 2-amino-2-phenylcyclohexan-1-one hydrochloride

To a solution of 2-nitro-2-phenylcyclohexan-1-one (90 g, 410 mmol) in acetic acid (1000 mL) was added zinc in 4 portions (each 26.8 g, 410 mmol) with an interval of 30 minutes. The reaction mixture was stirred overnight at RT, filtered and the filtrate was evaporated under reduced pressure. The residue was dissolved in dichloromethane, washed with a saturated aqueous $Na_2CO_3$ solution 4 times, acidified with HCl in dioxane, and evaporated under reduced pressure. Purification of the residue via column chromatography on silica gel (MTBE:MeOH (50:1→1:4)) afforded 16 g of 2-amino-2-phenylcyclohexan-1-one hydrochloride (71.1 mmol, 10.4% yield for 2 steps). $^1$H NMR (400 MHz, DMSO-$d_6$) δ 8.81 (s, 2H), 7.50 (dd, J=9.2, 3.7 Hz, 2H), 7.48-7.35 (m, 3H), 2.48 (s, 1H), 2.43-2.25 (m, 2H), 2.15 (td, J=13.9, 13.5, 4.2 Hz, 1H), 1.99-1.91 (m, 1H), 1.81 (d, J=11.7 Hz, 1H), 1.59 (dt, J=24.5, 8.6 Hz, 2H).

Step 5: Preparation of 2-phenyl-2-(piperidin-1-yl)cyclohexan-1-one (26rac)

To a solution of 2-amino-2-phenylcyclohexan-1-one hydrochloride (3.5 g, 15.5 mmol) in DMF was added $K_2CO_3$ (6.4 g, 46.5 mmol) and 1,5-dibromopentane (2.11 mL, 15.5 mmol). The reaction mixture was stirred overnight at 80° C., cooled to RT, and poured into water. The aqueous layer was extracted with ethyl acetate 4 times. The combined organic layers were washed with water 5 times, dried over anhydrous $Na_2SO_4$, and evaporated under reduced pressure. The residue was dissolved in dichloromethane (100 mL) and HCl in dioxane (50 mL) was added dropwise. The resulting mixture was stirred for 15 min and evaporated under reduced pressure. Purification of the residue via column chromatography on silica gel (MTBE:MeOH (50:1→1:4)) afforded 1.1 g of 2-phenyl-2-(piperidin-1-yl)cyclohexan-1-one hydrochloride (26rac) (24.2% yield). $^1$H NMR (400 MHz, DMSO-$d_6$) δ 9.87 (s, 1H), 7.57-7.51 (m, 3H), 7.45 (br s, 2H), 3.42 (d, J=11.7 Hz, 1H), 3.24 (d, J=13.7 Hz, 1H), 3.07 (d, J=11.4 Hz, 1H), 2.67 (q, J=11.1 Hz, 1H), 2.43-2.16 (m, 4H), 2.05-1.57 (m, 8H), 1.42 (m, 1H), 1.29-1.17 (m, 1H).

Step 6: Preparation of (R)-2-phenyl-2-(piperidin-1-yl)cyclohexan-1-one (26R) and (S)-2-phenyl-2-(piperidin-1-yl)cyclohexan-1-one (26S)

To a solution of 2-phenyl-2-(piperidin-1-yl)cyclohexan-1-one hydrochloride (1.1 g, 3.74 mmol) in dry methanol (20 mL) was added NaOH (0.15 g, 3.74 mmol) and the reaction mixture was stirred for 30 min at RT. The mixture was then filtered and the filtrate was concentrated in vacuo to give the freebase. The residue was separated on a 250×20 mm, 5 μm Chiralcel OJ-H column eluting with Hexane-IPA-MeOH 70-15-15 at a flow rate of 12 mL/min Samples were separated and combined to give product freebases. The resulting freebases were dissolved in dioxane, treated with 10% HCl in dioxane (5 mL), and evaporated to dryness to obtain 0.328 g of ENT-1 2-phenyl-2-(piperidin-1-yl)cyclohexan-1-one hydrochloride, $t_R$=9.303 min (for freebase) (assigned here as the S isomer, 26S); m/z [M+H]$^+$ 258.2; $^1$H NMR (DMSO-d$_6$, 500 MHz) (for HCl): δ (ppm) 9.79 (s, 1H), 7.58 (m, 3H), 7.48 (m, 2H), 3.45 (d, J=10.1 Hz, 1H), 3.27 (d, J=12.0 Hz, 1H), 3.08 (d, J=12.0 Hz, 1H), 2.72 (m, 1H), 2.42 (m, 2H), 2.30 (m, 2H), 2.05-1.57 (m, 8H), 1.47 (m, 1H), 1.27 (m, 1H); and 0.338 g of ENT-2 2-phenyl-2-(piperidin-1-yl)cyclohexan-1-one hydrochloride, $t_R$=12.153 min (for freebase) (assigned here as the R isomer, 26R); m/z [M+H]$^+$ 258.2; $^1$H NMR (DMSO-d$_6$, 500 MHz): δ (ppm) 10.04 (s, 1H), 7.57 (m, 3H), 7.49 (m, 2H), 3.45 (d, J=10.1 Hz, 1H), 3.28 (d, J=13.6 Hz, 1H), 3.14 (d, J=10.9 Hz, 1H), 2.70 (q, J=10.9, 10.9, 10.0 Hz, 1H), 2.42 (m, 2H), 2.30 (m, 2H), 2.04 (q, J=13.9, 13.9, 13.8 Hz, 1H), 1.93-1.57 (m, 7H), 1.43 (m, 1H), 1.25 (m, 1H).

Example 7: Preparation of Compounds 27R and 27S

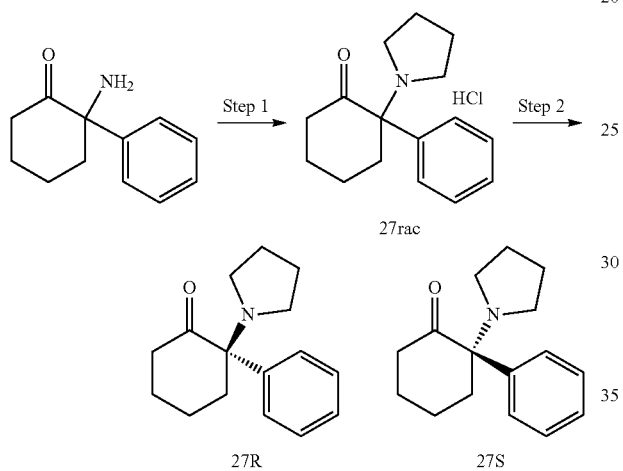

Step 1: Preparation of 2-phenyl-2-(pyrrolidin-1-yl)cyclohexan-1-one (27rac)

To a solution of 2-amino-2-phenylcyclohexan-1-one (4 g, 17.7 mmol, hydrochloride salt) in DMF was added K$_2$CO$_3$ (7.3 g, 53 mmol) and 1,4-dibromobutane (2.33 mL, 19.5 mmol). The reaction mixture was stirred overnight at 80° C., cooled to RT, and poured into water. The aqueous layer was extracted with ethyl acetate 4 times. The combined organic layers were washed with water 5 times, dried over anhydrous Na$_2$SO$_4$ and evaporated under reduced pressure. The residue was dissolved in dichloromethane (100 mL) and HCl in dioxane (50 mL) was added dropwise. The resulting mixture was stirred for 15 min and evaporated under reduced pressure. Purification of the residue via column chromatography on silica gel (MTBE:MeOH (50:1→1:4)) afforded 1.5 g of 2-phenyl-2-(pyrrolidin-1-yl)cyclohexan-1-one hydrochloride (27rac) (30.2% yield). m/z [M+H]$^+$ 244.2; $^1$H NMR (DMSO-d$_6$, 400 MHz): δ (ppm) 11.26 (s, 1H), 7.54 (m, 5H), 3.06 (m, 5H), 2.32 (m, 3H), 1.80 (m, 7H), 1.47 (q, J=13.5, 12.8, 12.8 Hz, 1H).

Step 2: Preparation of (R)-2-phenyl-2-(pyrrolidin-1-yl)cyclohexan-1-one (27R) and (S)-2-phenyl-2-(pyrrolidin-1-yl)cyclohexan-1-one (27S)

The HCl salt of 27rac was basified with aqueous NaHCO$_3$, extracted with CH$_2$Cl$_2$, and the organic extracts were concentrated to provide the freebase (850 mg). This material was separated into the enantiomers by SFC (column: Phenomenex-Cellulose-2 (250 mm*30 mm, 10 μm); mobile phase: A: CO$_2$, B: 0.1% NH$_3$H$_2$O in MeOH, B %: 36%; multi-injection process with 3 min spacing between injections) to afford ENT-1, RT=2.177 min (300 mg) (assigned here as the S isomer, 27S) and ENT-2, RT=2.438 min (316 mg) (assigned here as the R isomer, 27R). Retention times were determined using the following chiral analytical method: column: Lux Cellulose-2, 100×4.6 mm I.D., 3 μm; mobile phase: A: CO$_2$, B: MeOH (0.05% IPAm, v/v); gradient: (Time (min)/A %/B %), (0.0/95/5, 0.5/95/5, 2.0/60/40, 3.0/60/40, 3.6/95/5, 4.0/95/5); flow rate: 3.4 mL/min; column temp.: 35° C.; ABPR: 1800 psi.

Example 8: Preparation of Compounds 19R and 19S

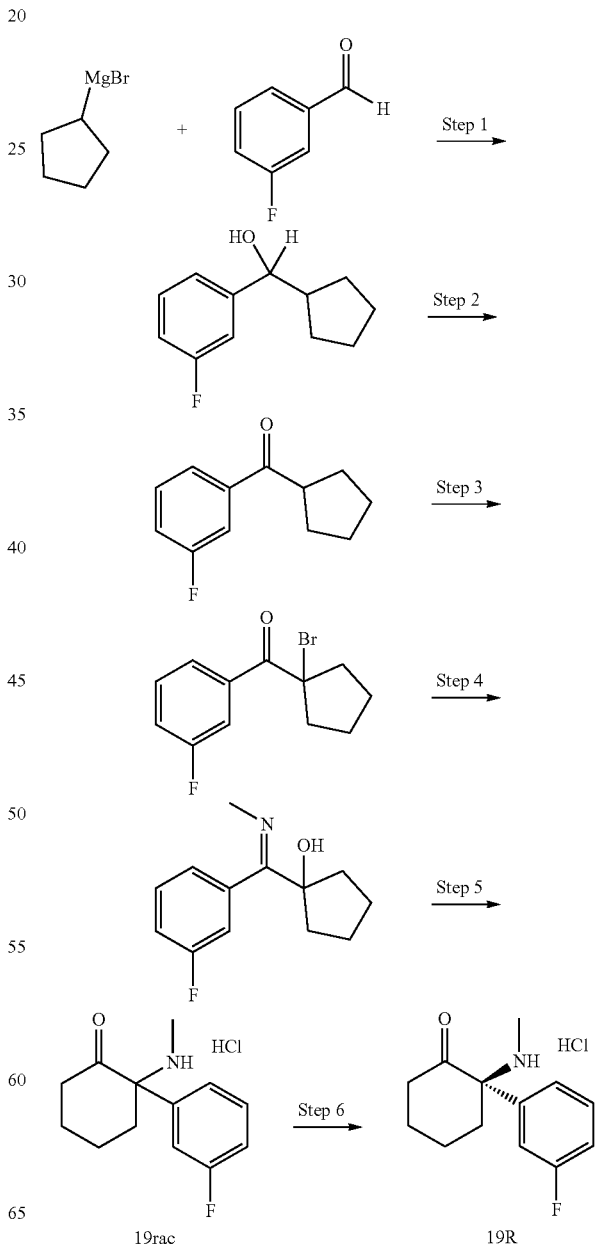

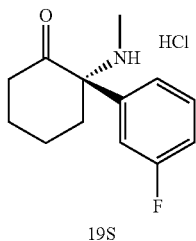

19S

Step 1: Preparation of cyclopentyl(3-fluorophenyl)methanol

To a solution of cyclopentylmagnesium bromide in THF (0.8 M, 700 mL, 560 mmol, 1.5 eq.) was added dropwise a solution of 3-fluorobenzaldehyde (39 g, 380 mmol) in THF (200 mL). The reaction mixture was stirred overnight at RT. To the mixture, cooled with an ice-water bath, was added dropwise a solution of NH₄Cl (50 g) in water (500 mL). The resulting mixture was extracted with ethyl acetate (3×400 mL). The combined organic layers were washed with water, dried over anhydrous Na₂SO₄ and evaporated under reduced pressure. Purification of the residue via column chromatography on silica gel (100 g SiO₂/10 g of reaction mixture, Hexane/DCM 10/1) afforded 23 g of cyclopentyl(3-fluorophenyl)methanol (39.5% yield).

Step 2: Preparation of cyclopentyl(3-fluorophenyl)methanone

To a solution of cyclopentyl(3-fluorophenyl)methanol (23 g, 150 mmol) in dry dichloromethane (250 mL), cooled with an ice-water bath, was added Dess-Martin Periodinane (DMP, 97.5 g, 230 mmol). The reaction mixture was stirred overnight at RT, diluted with an aqueous solution of sodium bicarbonate (75 g, 500 mL), and extracted with dichloromethane twice. The combined organic layers were dried over anhydrous Na₂SO₄ and evaporated under reduced pressure. Purification of the residue via column chromatography on silica gel (100 g SiO₂/10 g of reaction mixture, Hexane/DCM 10/1) afforded 16.5 g of cyclopentyl(3-fluorophenyl)methanone (57.3% yield).

Step 3: Preparation of (1-bromocyclopentyl)(3-fluorophenyl)methanone

To a solution of cyclopentyl(3-fluorophenyl)methanone (16.5 g, 86 mmol) in a mixture of dry ethyl acetate (90 mL) and dry CHCl₃ (90 mL) was added copper(II) bromide (58 g, 258 mmol) and the reaction mixture was stirred under reflux overnight. Upon completion, the mixture was filtered and the filtrate was concentrated in vacuo to obtain 21 g of (1-bromocyclopentyl)(3-fluorophenyl)methanone (90% yield), which was used in the next step without further purification. ¹H NMR (400 MHz, Chloroform-d) δ 7.94 (d, J=7.7 Hz, 1H), 7.82 (d, J=9.8 Hz, 1H), 7.41 (td, J=7.9, 5.4 Hz, 1H), 7.23 (dd, J=9.3, 7.0 Hz, 1H), 2.44 (dh, J=21.7, 7.6, 6.9 Hz, 4H), 2.05 (q, J=6.3, 5.5 Hz, 2H), 1.80 (q, J=7.4 Hz, 2H).

Step 4: Preparation of 1-((3-fluorophenyl)(methylimino)methyl)cyclopentan-1-ol hydrochloride A mixture of (1-bromocyclopentyl)(3-fluorophenyl)methanone (21 g, 77.5 mmol) and a solution of methylamine in methanol (200 mL) was stirred at RT for 48 h. The mixture was evaporated under reduced pressure and the residue was diluted with water (300 mL) and ethyl acetate (300 mL). The separated organic layer was dried over anhydrous Na₂SO₄ and evaporated under reduced pressure to obtain 14 g of 1-((3-fluorophenyl) (methylimino)methyl) cyclopentan-1-ol. This material in dioxane was diluted with HO/dioxane and evaporated under reduced pressure to obtain 16.3 g of the hydrochloride salt.

Step 5: Preparation of 2-(3-fluorophenyl)-2-(methylamino)cyclohexan-1-one (19rac)

To Dowtherm (100 mL, 326.7 mmol), heated to 200° C. with an oil bath, was added in portions 16 g 1-((3-fluorophenyl) (methylimino)methyl)cyclopentan-1-ol. The reaction mixture was heated to 180° C. for 15 min, cooled to RT, and diluted with CHCl₃ (250 mL) and water (150 mL). The aqueous layer was washed with CHCl₃ (2×200 mL) and evaporated under reduced pressure. The residue was recrystallized (5 mL of EtOH and a few drops of MeOH per 1 g of crude product) to obtain 3.9 g of 2-(3-fluorophenyl)-2-(methylamino)cyclohexan-1-one hydrochloride (19rac). ¹H NMR (500 MHz, DMSO-d₆) 9.49 (s, 2H), 7.59 (q, J=7.5 Hz, 1H), 7.37 (td, J=8.5, 2.4 Hz, 1H), 7.32 (d, J=10.0 Hz, 1H), 7.21 (d, J=7.8 Hz, 1H), 3.14 (dd, J=14.2, 3.1 Hz, 1H), 2.39 (d, J=13.5 Hz, 1H), 2.36-2.26 (m, 1H), 2.21-2.12 (m, 1H), 2.11 (s, 3H), 1.95 (ddd, J=12.6, 6.2, 3.1 Hz, 1H), 1.87-1.81 (m, 1H), 1.67-1.50 (m, 2H).

Step 6: Preparation of (R)-2-(3-fluorophenyl)-2-(methylamino)cyclohexan-1-one (19R) and (S)-2-(3-fluorophenyl)-2-(methylamino)cyclohexan-1-one (19S)

To a solution of 2-(3-fluorophenyl)-2-(methylamino)cyclohexan-1-one hydrochloride (1.9 g, 2.5 mmol) in dry methanol (20 mL) was added NaOH (0.35 g, 7.5 mmol) and the reaction mixture was stirred for 30 min at RT. The mixture was then filtered and the filtrate was concentrated in vacuo to provide the freebase. The residue after evaporation was separated on a ChiralPak IA 250×20 mm, 5 μm column eluting with Hexane-IPA-MeOH 90-5-5 at a flow rate of 12 mL/min Samples were separated and combined to give product freebases. The resulting freebases in dioxane were treated with 10% HCl in dioxane (5 mL) and evaporated to dryness to obtain ENT-1 2-(3-fluorophenyl)-2-(methylamino)cyclohexan-1-one hydrochloride 0.406 g, $t_R$=14.233 min (for freebase) (assigned here as the S isomer, 19S); m/z [M+H]⁺ 222.0; ¹H NMR (DMSO-d₆, 500 MHz) (for HCl): δ (ppm) 9.94 (s, 1H), 9.44 (s, 1H), 7.60 (q, J=7.6, 7.6, 7.5 Hz, 1H), 7.38 (t, J=8.1, 8.1 Hz, 1H), 7.31 (d, J=10.1 Hz, 1H), 7.20 (d, J=7.7 Hz, 1H), 3.13 (d, J=12.8 Hz, 1H), 2.40 (d, J=13.2 Hz, 1H), 2.31 (m, 1H), 2.13 (s, 3H), 2.07 (m, 1H), 1.96 (m, 1H), 1.85 (d, J=10.2 Hz, 1H), 1.59 (m, 2H); and 0.351 g of ENT-2 2-(3-fluorophenyl)-2-(methylamino)cyclohexan-1-one hydrochloride, $t_R$=18.439 (for freebase) (assigned here as the R isomer, 19R); m/z [M+H]⁺ 222.0; ¹H NMR (DMSO-d₆, 500 MHz) (for HCl): δ (ppm) 10.03 (s, 1H), 9.42 (s, 1H), 7.60 (q, J=7.3, 7.3, 6.6 Hz, 1H), 7.38 (t, J=8.3, 8.3 Hz, 1H), 7.31 (d, J=10.2 Hz, 1H), 7.20 (d, J=7.7 Hz, 1H), 3.14 (d, J=13.7 Hz, 1H), 2.40 (d, J=13.8 Hz, 1H), 2.31 (m, 1H), 2.11 (s, 3H), 2.11 (m, 1H), 1.96 (m, 1H), 1.85 (d, J=10.7 Hz, 1H), 1.59 (m, 2H).

Example 9: Preparation of Compounds 88R and 88S

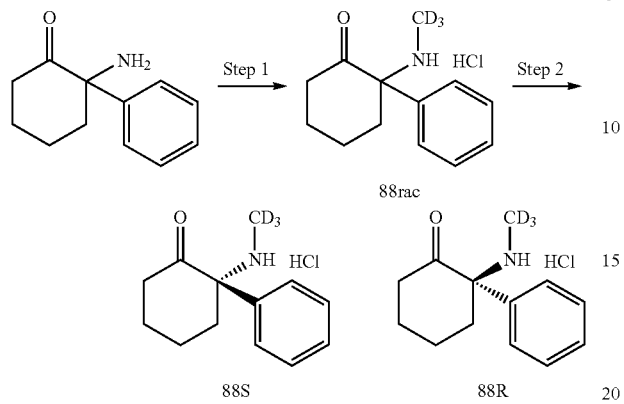

Step 1: Preparation of 2-((methyl-d₃)amino)-2-phenylcyclohexan-1-one (88rac)

To a solution of 2-amino-2-phenylcyclohexan-1-one hydrochloride (10 g, 44.3 mmol) in DMF was added $K_2CO_3$ (18.37 g, 133 mmol) and $CD_3I$ (3.3 mL, 53 mmol). The reaction mixture was stirred overnight at 80° C., cooled to RT, and poured into water. The aqueous layer was extracted with ethyl acetate 4 times. The combined organic layers were washed with water 5 times, dried over anhydrous $Na_2SO_4$, and evaporated under reduced pressure. The residue was dissolved in dichloromethane (100 mL) and HCl in dioxane (50 mL) was added dropwise. The resulting mixture was stirred for 15 min and evaporated under reduced pressure. Purification of the residue via column chromatography on silica gel (MTBE:MeOH (50:1→1:4)) afforded 1.7 g of 2-((methyl-d₃)amino)-2-phenylcyclohexan-1-one as hydrochloride salt (15.8% yield). $^1$H NMR (500 MHz, DMSO-d₆) δ 9.59 (s, 2H), 7.56-7.48 (m, 3H), 7.43-7.36 (m, 2H), 3.14 (dq, J=13.9, 3.2 Hz, 1H), 2.40-2.34 (m, 1H), 2.32-2.25 (m, 1H), 2.12 (td, J=13.4, 4.1 Hz, 1H), 1.95 (ddd, J=12.8, 6.3, 3.3 Hz, 1H), 1.88-1.81 (m, 1H), 1.66-1.52 (m, 2H).

Step 2: Preparation of (S)-2-((methyl-d₃)amino)-2-phenylcyclohexan-1-one (88S) and (R)-2-((methyl-d₃)amino)-2-phenylcyclohexan-1-one (88R)

To a solution of 2-((methyl-d₃)amino)-2-phenylcyclohexan-1-one (1.7 g, 7 mmol, hydrochloride salt) in dry methanol (20 mL) was added NaOH (0.28 g, 7 mmol) and the reaction mixture was stirred for 30 min at RT. The mixture was then filtered and the filtrate was concentrated in vacuo to provide the freebase. The residue after evaporation was separated on a ChiralPak AD 250×30 mm, 10 μm column eluting with Hexane-IPA-MeOH 95-5-5 at a flow rate of 40 mL/min Samples were separated and combined to give product freebases. The resulting freebases in dioxane were treated with 10% HCl in dioxane (5 mL) and evaporated to dryness to obtain 0.317 g of ENT-1 2-((methyl-d₃)amino)-2-phenylcyclohexan-1-one hydrochloride, $t_R$=14.656 min (for freebase) (assigned here as the R isomer, 88R); m/z [M+H]⁺ 207.1; $^1$H NMR (DMSO-d₆, 400 MHz) (for HCl) δ (ppm) 10.00 (s, 1H), 9.34 (s, 1H), 7.56 (m, J=6.6 Hz, 3H), 7.41 (d, J=6.9 Hz, 2H), 3.16 (m, J=13.8 Hz, 1H), 2.39 (d, J=13.5 Hz, 1H), 2.28 (m, 1H), 2.14 (t, J=13.1 Hz, 1H), 1.95 (m, 1H), 1.85 (d, J=11.0 Hz, 1H), 1.59 (m, 2H) and 0.315 g of ENT-2 2-((methyl-d₃)amino)-2-phenylcyclohexan-1-one hydrochloride, $t_R$=30.684 min (for freebase) (assigned here as the S isomer, 88S); m/z [M+H]⁺ 207.2; $^1$H NMR (DMSO-d₆, 400 MHz): δ (ppm) 10.01 (s, 1H), 9.34 (s, 1H), 7.54 (m, 3H), 7.41 (d, J=7.5 Hz, 2H), 3.15 (d, J=13.8 Hz, 1H), 2.39 (d, J=13.6 Hz, 1H), 2.29 (m, 1H), 2.14 (t, J=11.6, 11.6 Hz, 1H), 1.96 (m, 1H), 1.85 (d, J=11.8 Hz, 1H), 1.61 (m, 2H).

Example 10: Preparation of Compounds 86S and 86R

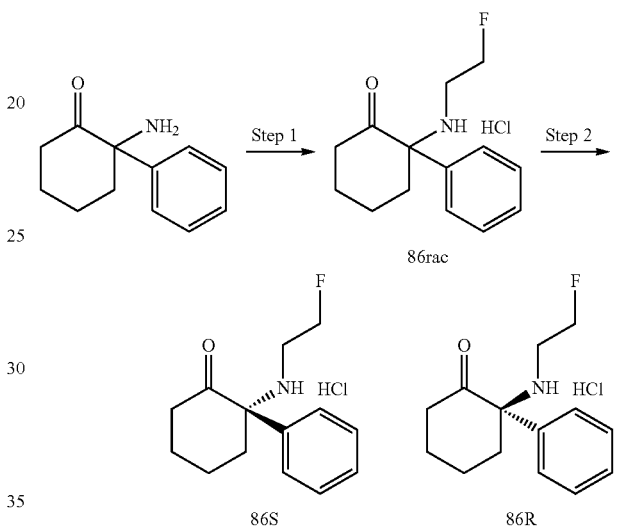

Step 1: Preparation of 2-((2-fluoroethyl)amino)-2-phenylcyclohexan-1-one (86rac)

To a solution of 2-amino-2-phenylcyclohexan-1-one (9 g, 40 mmol, hydrochloride salt) in DMF was added $K_2CO_3$ (16.5 g, 119.6 mmol) and 1-fluoro-2-iodoethane (4 mL, 47.9 mmol). The reaction mixture was stirred overnight at 80° C., cooled to RT, and poured into water. The aqueous layer was extracted with ethyl acetate 4 times. The combined organic layers were washed with water 5 times, dried over anhydrous $Na_2SO_4$, and evaporated under reduced pressure. The residue was dissolved in dichloromethane (100 mL) and HCl in dioxane (50 mL) was added dropwise. The resulting mixture was stirred for 15 min and evaporated under reduced pressure. Purification of the residue via column chromatography on silica gel (MTBE:MeOH (50:1→1:4)) afforded 1.8 g of 2-((2-fluoroethyl)amino)-2-phenylcyclohexan-1-one as the hydrochloride salt (86rac) (16.5% yield). $^1$H NMR (500 MHz, DMSO-d₆) (for freebase) δ 7.35 (m, 2H), 7.25 (m, 3H), 4.37 (t, J=5.1 Hz, 1H), 4.31-4.24 (m, 1H), 2.99 (dd, J=14.5, 2.9 Hz, 1H), 2.41 (m, 4H), 1.89-1.74 (m, 5H).

Step 2: Preparation of (S)-2-((2-fluoroethyl)amino)-2-phenylcyclohexan-1-one (86S) and (R)-2-((2-fluoroethyl)amino)-2-phenylcyclohexan-1-one (86R)

To a solution of 2-((2-fluoroethyl)amino)-2-phenylcyclohexan-1-one (1.8 g, 6.6 mmol, hydrochloride salt) in dry methanol (20 mL) was added NaOH (0.265 g, 6.6 mmol) and the reaction mixture was stirred for 30 min at RT. The mixture was then filtered and the filtrate was concentrated in vacuo to provide the freebase. The residue after evaporation was separated on a 250×20 mm, 5 μm Chiralpak AD-H Hexane-IPA-MeOH 98-1-1 flow rate 18 mL/min Samples were separated and combined to give product freebases. The resulting freebases in dioxane were treated with 10% HCl in dioxane (5 mL) and evaporated to dryness to obtain 0.324 g ENT-1 2-((2-fluoroethyl)amino)-2-phenylcyclohexan-1-one hydrochloride, $t_R$=14.667 min (for freebase) (assigned here as the R isomer, 86R); m/z [M+H]$^+$ 236.0; $^1$H NMR (DMSO-d$_6$, 500 MHz) (for HCl): δ (ppm) 9.77 (s, 1H), 9.57 (s, 1H), 7.55 (m, 3H), 7.44 (d, J=6.3 Hz, 2H), 4.60 (d, J=48.4 Hz, 2H), 3.17 (m, 1H), 2.89 (m, 1H), 2.74 (m, 1H), 2.38 (m, 2H), 2.15 (t, J=12.4, 12.4 Hz, 1H), 1.95 (d, J=14.8 Hz, 1H), 1.84 (d, J=15.9 Hz, 1H), 1.62 (m, 1H), 1.51 (m, 1H); and 0.310 g of ENT-2 2-((2-fluoroethyl)amino)-2-phenylcyclohexan-1-one hydrochloride, $t_R$=16.727 min (for freebase) (assigned here as the S isomer, 86S); m/z [M+H]$^+$ 236.0; $^1$H NMR (DMSO-d$_6$, 500 MHz) (for freebase): δ (ppm) 7.36 (t, J=7.6, 7.6 Hz, 2H), 7.27 (t, 1H), 7.23 (d, J=8.1 Hz, 2H), 4.36 (m, 2H), 2.84 (d, J=13.3 Hz, 1H), 2.39 (m, 4H), 1.95 (m, 1H), 1.83 (m, 2H), 1.72 (m, 2H).

Example 11: Preparation of Compounds 28R and 28S

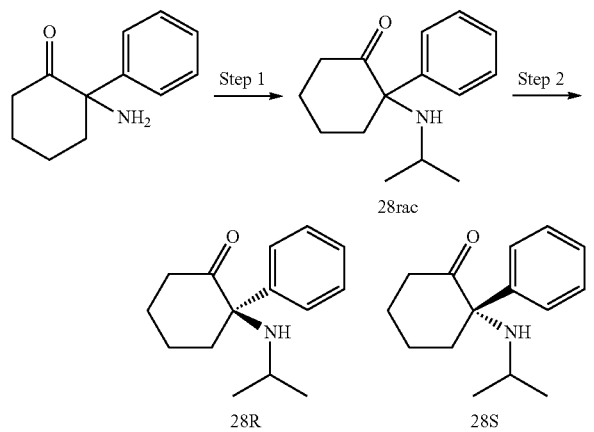

Step 1: Preparation of 2-(isopropylamino)-2-phenylcyclohexan-1-one (28rac)

A mixture of 2-amino-2-phenyl-cyclohexan-1-one (4 g, 21.14 mmol, 1 eq), 2-bromopropane (13.00 g, 105.68 mmol, 5 eq), KI (701.71 mg, 4.23 mmol, 0.2 eq), and K$_2$CO$_3$ (5.84 g, 42.27 mmol, 2 eq) in MeCN (10 mL) was stirred at 100° C. for 12 hrs. The mixture was cooled, filtered, concentrated, and then purified by prep-HPLC (column: Agela DuraShell C18 250*70 mm, 10 μm; mobile phase: A: water (10 mM NH$_4$HCO$_3$); B: ACN; B %: 25%-55%, 25 min) to afford 2-(isopropylamino)-2-phenylcyclohexan-1-one (1 g, 4.32 mmol, 20.45% yield) (28rac) as a white solid.

Step 2: Preparation of (R)-2-(isopropylamino)-2-phenylcyclohexan-1-one (28R) and (S)-2-(isopropylamino)-2-phenylcyclohexan-1-one (28S)

The racemate was separated by SFC (column: DAICEL CHIRALPAK AD (250 mm*30 mm, 10 μm); mobile phase: A: CO$_2$, B: 0.1% NH$_3$H$_2$O in EtOH, B %: 10%; multi-injection process with 5 min spacing between injections) to afford ENT-1 0.659 min (230 mg) as a white solid and ENT-2 1.111 min (250 mg) as a white solid. Retention times were determined using the following chiral analytical method: column: Chiralpak AD-3, 100×4.6 mm I.D., 3 μm; mobile phase: A: CO$_2$ B: EtOH (0.05% IPAm, v/v); gradient: (Time (min)/A %/B %), (0.0/95/5, 0.5/95/5, 2.0/60/40, 3.0/60/40, 3.6/95/5, 4.0/95/5); flow rate: 3.4 mL/min; column temp.: 35° C.; ABPR: 1800 psi.

ENT-1, RT=0.659 min (assigned here as the R isomer, 28R); LCMS R$_T$=1.630 min; MS calc.: 231.33, [M+H]$^+$=232.1; $^1$H NMR (400 MHz, CHLOROFORM-d) δ=7.41-7.34 (m, 2H), 7.31-7.25 (m, 3H), 2.96 (qd, J=2.8, 13.6 Hz, 1H), 2.48-2.35 (m, 2H), 2.33-2.23 (m, 2H), 1.98-1.68 (m, 5H), 0.91 (d, J=6.4 Hz, 3H), 0.75 (d, J=6.4 Hz, 3H); $^{13}$C NMR (101 MHz, CHLOROFORM-d) δ=211.62, 139.76, 129.11, 127.76, 127.54, 70.56, 43.44, 39.97, 38.01, 28.04, 26.04, 25.35, 22.88; ENT-2, RT=1.111 min (assigned here as the S isomer, 28S); LCMS R$_T$=1.636 min; MS calc.: 231.33, [M+H]$^+$=232.1; $^1$H NMR (400 MHz, CHLOROFORM-d) δ=7.41-7.33 (m, 2H), 7.32-7.23 (m, 3H), 3.01-2.92 (m, 1H), 2.49-2.35 (m, 2H), 2.32-2.25 (m, 2H), 1.97-1.68 (m, 5H), 0.91 (d, J=6.4 Hz, 3H), 0.75 (d, J=6.4 Hz, 3H); $^{13}$C NMR (101 MHz, CHLOROFORM-d) δ=211.62, 139.80, 129.09, 127.73, 127.52, 70.54, 43.39, 39.97, 38.04, 28.03, 26.08, 25.36, 22.88.

Example 12: Preparation of Compounds 84R, 84S, 11R and 11S

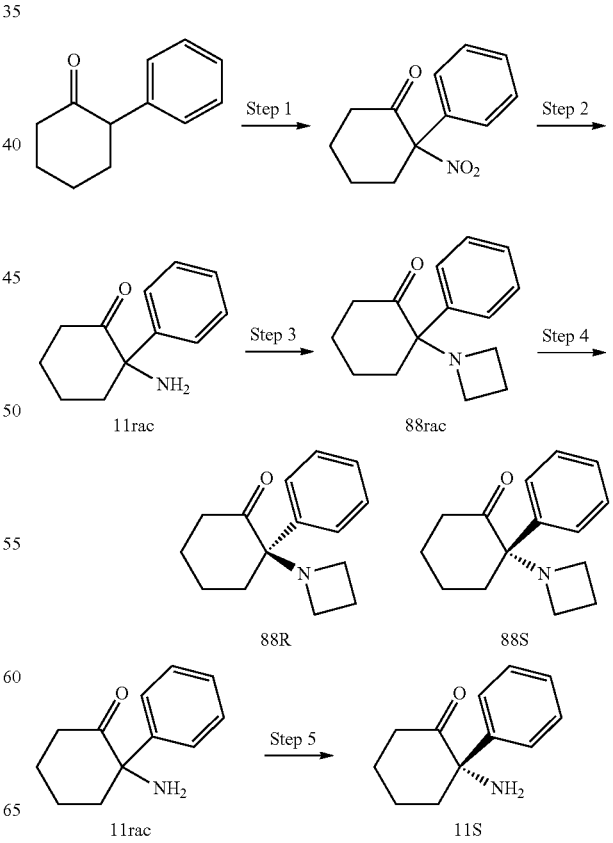

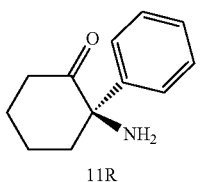

11R

Step 1: Preparation of 2-nitro-2-phenyl-cyclohexan-1-one

A mixture of 2-phenylcyclohexan-1-one (15 g, 86.09 mmol, 1 eq), CAN (94.39 g, 172.18 mmol, 85.81 mL, 2 eq) and Cu(OAc)$_2$ (3.13 g, 17.22 mmol, 0.2 eq) in DCE (150 mL) was stirred at 85° C. for 12 h. On completion, the mixture was filtered and concentrated. The residue was purified by silica gel (PE:EA=30:1) to afford 2-nitro-2-phenyl-cyclohexan-1-one (10 g, 45.61 mmol, 52.98% yield) as a yellow oil. $^1$H NMR (400 MHz, CHLOROFORM-d) δ ppm 7.50-7.45 (m, 3H), 7.36 (dd, J=2.8, 6.8 Hz, 2H), 3.08 (ddd, J=3.2, 10.8, 14.4 Hz, 1H), 2.97-2.85 (m, 1H), 2.74-2.64 (m, 1H), 2.61-2.52 (m, 1H), 2.00-1.88 (m, 3H), 1.84-1.75 (m, 1H).

Step 2: Preparation of 2-amino-2-phenyl-cyclohexan-1-one (11rac)

A mixture of 2-nitro-2-phenyl-cyclohexan-1-one (10 g, 45.61 mmol, 1 eq) and Zn (23.86 g, 364.90 mmol, 8 eq) in AcOH (100 mL) was stirred at 20° C. for 12 hr. On completion, the mixture was filtered and concentrated. The residue was dissolved in DCM, washed with sat. NaHCO$_3$, H$_2$O, and brine, dried over Na$_2$SO$_4$, filtered, and concentrated to afford 2-amino-2-phenyl-cyclohexan-1-one (7.5 g, 39.63 mmol, 86.88% yield) (11rac) as a brown oil. $^1$H NMR (400 MHz, CHLOROFORM-d) δ ppm 7.33-7.27 (m, 2H), 7.24-7.17 (m, 3H), 2.88-2.79 (m, 1H), 2.42-2.24 (m, 2H), 2.24-2.09 (m, 2H), 1.95-1.87 (m, 1H), 1.85-1.59 (m, 4H).

Step 3: Preparation of 2-(azetidin-1-yl)-2-phenyl-cyclohexan-1-one (84rac)

A mixture of 2-amino-2-phenyl-cyclohexan-1-one (2 g, 10.57 mmol, 1 eq), 1,3-dibromopropane (2.77 g, 13.74 mmol, 1.40 mL, 1.3 eq), KI (526.28 mg, 3.17 mmol, 0.3 eq), and K$_2$CO$_3$ (4.38 g, 31.70 mmol, 3 eq) in MeCN (30 mL) was stirred at 100° C. for 12 hrs. The mixture was cooled, filtered, and concentrated. The residue was purified by prep-HPLC (column: Agela DuraShell C18 250*70 mm, 10 μm; mobile phase: A:water (10 mM NH$_4$HCO$_3$), B: ACN; B %: 25%-55%, 20 min) to afford 2-(azetidin-1-yl)-2-phenyl-cyclohexan-1-one (1 g, 4.36 mmol, 41.26% yield) (84rac) as a white solid.

Step 4: Preparation of (R)-2-(azetidin-1-yl)-2-phenyl-cyclohexan-1-one (84R) and (S)-2-(azetidin-1-yl)-2-phenyl-cyclohexan-1-one (84S)

The racemate (84rac) was separated by SFC (column: DAICEL CHIRALPAK AD (250 mm*30 mm, 10 μm); mobile phase: A: CO$_2$, B: 0.1% NH$_3$H$_2$O in ETOH; B %: 15%; multi-injection process) to afford ENT-1 0.736 min (340 mg) as a white solid and ENT-2 0.831 min (370 mg) as a white solid. Retention times were determined using the following chiral analytical method: column: Chiralpak AD-3, 50×4.6 mm I.D., 3 μm; mobile phase: A: CO$_2$ B: EtOH (0.05% IPAm, v/v); Gradient: (Time (min)/A %/B %), (0.0/95/5, 0.2/95/5, 1.2/50/50, 2.2/50/50, 2.6/95/5, 3.0/95/5); flow rate: 3.4 mL/min; column temp.: 35° C.; ABPR: 1800 psi.

ENT-1, RT=0.736 min (assigned here as the R isomer, 84R); LCMS (R$_T$=1.534 min, MS calc.: 229.15, [M+H]$^+$=230.1); $^1$H NMR (400 MHz, CHLOROFORM-d) δ ppm 7.47-7.41 (m, 2H), 7.38-7.32 (m, 1H), 7.16 (d, J=7.6 Hz, 2H), 3.29 (q, J=7.2 Hz, 2H), 3.09 (q, J=6.8 Hz, 2H), 2.64 (qd, J=3.2, 14.0 Hz, 1H), 2.39-2.26 (m, 2H), 1.95-1.55 (m, 7H); $^{13}$C NMR (101 MHz, CHLOROFORM-d) δ ppm 212.19, 134.03, 128.54, 128.31, 128.21, 127.68, 72.74, 48.48, 40.57, 33.18, 28.09, 21.72, 17.39; ENT-2, RT=0.831 min (assigned here as the S isomer, 84S); LCMS (R$_T$=1.529 min, MS calc.: 229.15, [M+H]$^+$=230.1); $^1$H NMR (400 MHz, CHLOROFORM-d) δ ppm 7.49-7.40 (m, 2H), 7.39-7.32 (m, 1H), 7.16 (d, J=7.6 Hz, 2H), 3.30 (q, J=6.8 Hz, 2H), 3.10 (q, J=6.8 Hz, 2H), 2.65 (qd, J=3.2, 14.0 Hz, 1H), 2.39-2.26 (m, 2H), 1.94-1.52 (m, 7H); $^{13}$C NMR (101 MHz, CHLOROFORM-d) δ ppm 212.17, 134.01, 128.54, 128.39, 128.21, 127.69, 72.75, 48.49, 40.57, 33.18, 28.09, 21.72, 17.39.

Step 5: Preparation of (S)-2-amino-2-phenyl-cyclohexan-1-one (11S) and (R)-2-amino-2-phenyl-cyclohexan-1-one (11R)

Racemic 2-amino-2-phenyl-cyclohexan-1-one (11rac) was separated by SFC (column: DAICEL CHIRALPAK AD (250 mm*30 mm, 10 μm); mobile phase: A: CO$_2$, B: 0.1% NH$_3$ H$_2$O in MeOH]; B %: 42%; multi-injection process with 3.8 min spacing between injections) to afford ENT-1 1.691 min (370 mg, 1.96 mmol) as an off-white solid and ENT-2 2.135 min (340 mg, 1.80 mmol) as an off-white solid. Retention times were determined using the following chiral analytical method: column: Chiralpak AD-3, 100×4.6 mm I.D., 3 μm; mobile phase: A: CO$_2$, B: MeOH (0.05% IPAm, v/v); gradient: (Time (min)/A %/B %), (0.0/95/5, 0.5/95/5, 2.0/60/40, 3.0/60/40, 3.6/95/5, 4.0/95/5); flow rate: 3.4 mL/min; column temp.: 35° C.; ABPR: 1800 psi.

ENT-1, RT=1.691 min (assigned here as the S isomer, 11S); LCMS (R$_T$=1.360 min, MS calc.: 189.12, [M+H]$^+$=190.1); $^1$H NMR (400 MHz, CHLOROFORM-d) δ ppm 7.42-7.34 (m, 2H), 7.32-7.24 (m, 3H), 2.92-2.82 (m, 1H), 2.50-2.35 (m, 2H), 2.04-1.95 (m, 1H), 1.88 (s, 2H), 1.83-1.64 (m, 4H); $^{13}$C NMR (101 MHz, CHLOROFORM-d) δ ppm 213.60, 141.87, 129.24, 127.68, 126.09, 66.49, 39.85, 39.48, 28.18, 22.69; ENT-2, RT=2.135 min (assigned here as the R isomer, 11R) LCMS (R$_T$=1.387 min, MS calc.: 189.12, [M+H]$_+$=190.1); $^1$H NMR (400 MHz, CHLOROFORM-d) δ ppm 7.41-7.36 (m, 2H), 7.32-7.25 (m, 3H), 2.92-2.82 (m, 1H), 2.51-2.35 (m, 2H), 2.04-1.95 (m, 1H), 1.87 (s, 2H), 1.83-1.67 (m, 4H); $^{13}$C NMR (101 MHz, CHLOROFORM-d) δ ppm 213.54, 141.89, 141.88, 129.24, 127.69, 126.10, 66.50, 39.85, 39.50, 28.18, 22.70.

Example 13: Preparation of Compounds 114S and 114R

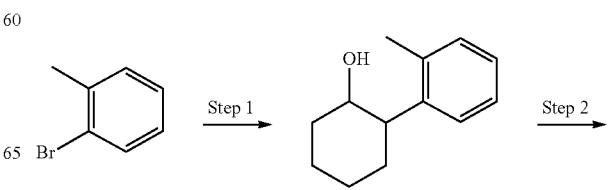

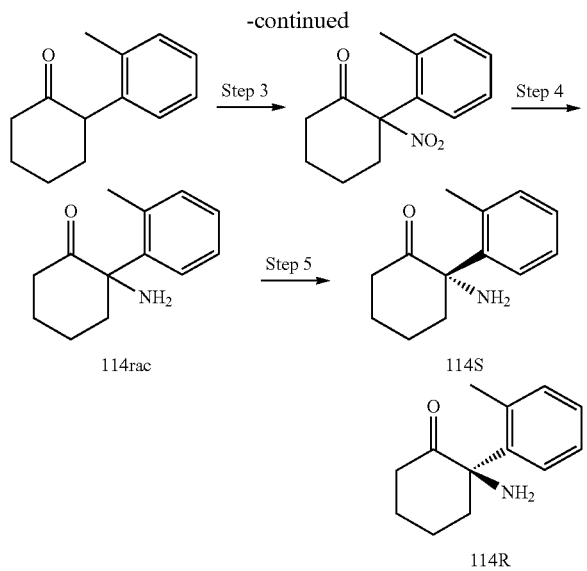

Step 1: Preparation of 2-(o-tolyl)cyclohexan-1-ol

A solution of 1-bromo-2-methyl-benzene (10 g, 58.47 mmol, 1 eq) in THF (100 mL) was cooled to −70° C. Then n-BuLi (2.5 M, 27 mL, 1.15 eq) was added. The mixture was stirred at −70° C. for 0.5 hr and then 7-oxabicyclo[4.1.0]heptane (6.31 g, 64.31 mmol, 1.1 eq) and $BF_3 \cdot Et_2O$ (9.13 g, 64.31 mmol, 1.1 eq) were added. The mixture was stirred at −70° C. for 1.5 hrs. On completion, the mixture was poured into sat. aq. $NH_4Cl$ (100 ml) and extracted with EA (50 ml×2). The combined organic extracts were washed with brine, dried over with $Na_2SO_4$, filtered, and concentrated. The residue was purified by silica gel (PE:EA=50:1-5:1) to afford 2-(o-tolyl)cyclohexan-1-ol (4 g, 21.02 mmol, 35.95% yield) as a colorless oil. $^1H$ NMR (400 MHz, CHLOROFORM-d) δ=7.28-7.24 (m, 1H), 7.23-7.08 (m, 3H), 3.82-3.73 (m, 1H), 2.83-2.72 (m, 1H), 2.37 (s, 3H), 2.14 (td, J=4.4, 8.8 Hz, 1H), 1.91-1.85 (m, 1H), 1.84-1.74 (m, 2H), 1.48-1.32 (m, 4H).

Step 2: Preparation of 2-(o-tolyl)cyclohexan-1-one

To a mixture of 2-(o-tolyl)cyclohexan-1-ol (3.5 g, 18.39 mmol, 1 eq) in DCM (15 mL) was added Dess-Martin Periodinane (DMP, 11.70 g, 27.59 mmol, 1.5 eq) in one portion at 0° C. under $N_2$. The mixture was stirred at 25° C. for 12 hrs. The mixture was filtered and the filtrate was washed with sat. aq. $Na_2SO_3$, sat. aq. $Na_2CO_3$, and brine, then dried over $Na_2SO_4$, filtered, and concentrated. The residue was purified by silica gel (PE:EA=50:1-8:1) to afford 2-(o-tolyl)cyclohexan-1-one (2.9 g, 15.40 mmol, 83.74% yield) as a colorless oil. $^1H$ NMR (400 MHz, CHLOROFORM-d) δ=7.26-7.13 (m, 4H), 3.86-3.77 (m, 1H), 2.62-2.48 (m, 2H), 2.33-2.21 (m, 5H), 2.10-2.05 (m, 2H), 1.94-1.80 (m, 2H).

Step 3: Preparation of 2-nitro-2-(o-tolyl)cyclohexan-1-one

A mixture of 2-(o-tolyl)cyclohexanone (2.4 g, 12.75 mmol, 1 eq), ceric ammonium nitrate (CAN, 13.98 g, 25.50 mmol, 2 eq), and $Cu(OAc)_2$ (463 mg, 2.55 mmol, 0.2 eq) in DCE (25 mL) was stirred at 85° C. for 12 hrs. The mixture was cooled, filtered, and concentrated. The residue was purified by column chromatography ($SiO_2$, Petroleum ether/Ethyl acetate=100/1 to 0/1) to afford 2-nitro-2-(o-tolyl)cyclohexan-1-one (1.2 g, 5.14 mmol, 40.35% yield) as a yellow oil. $^1H$ NMR (400 MHz, CHLOROFORM-d) δ=7.26-7.13 (m, 4H), 3.86-3.77 (m, 1H), 2.62-2.48 (m, 2H), 2.33-2.21 (m, 5H), 2.10-2.05 (m, 2H), 1.94-1.80 (m, 2H).

Step 4: Preparation of 2-amino-2-(o-tolyl)cyclohexan-1-one (114rac)

A mixture of 2-nitro-2-(o-tolyl)cyclohexan-1-one (2 g, 8.57 mmol, 1 eq) and Zn (3.92 g, 60.02 mmol, 7 eq) in AcOH (25 mL) was stirred at 20° C. for 12 hrs. The mixture was filtered and concentrated. The residue was dissolved with DCM, washed with sat. aq. $NaHCO_3$, $H_2O$, and brine, dried over $Na_2SO_4$, filtered, and concentrated to afford 2-amino-2-(o-tolyl)cyclohexan-1-one (900 mg, 4.43 mmol, 51.64% yield) (114rac) as a brown oil.

Step 5: Preparation of (S)-2-amino-2-(o-tolyl)cyclohexan-1-one (114S) and (R)-2-amino-2-(o-tolyl)cyclohexan-1-one (114R)

The racemate was separated by SFC (column: REGIS (s,$) WHELK-01 (250 mm*30 mm, 5 μm); mobile phase: A: $CO_2$, B: 0.1% $NH_3$ $H_2O$ in IPA; B %: 15%, multi-injection process with 10 min spacing between runs) to afford ENT-1 1.591 min (260 mg, 1.28 mmol) as a yellow oil and ENT-2 1.906 min (330 mg, 1.62 mmol) as a yellow oil. Retention times were determined using the following chiral analytical method: column: (S,S)-WHELK-01, 100×4.6 mm I.D., 3.5 μm; mobile phase: A: $CO_2$, B: IPA (0.05% IPAm, v/v); gradient: (Time (min)/A %/B %), (0.0/95/5, 0.5/95/5, 2.0/60/40, 3.0/60/40, 3.6/95/5, 4.0/95/5); flow rate: 3.4 mL/min; column temp.: 35° C.; ABPR: 1800 psi.

ENT-1, RT=1.591 min (assigned here as the S isomer, 114S); LCMS ($R_T$=1.448 min, MS calc.: 203.13, $[M+H]^+$=204.1); $^1H$ NMR (400 MHz, CHLOROFORM-d) δ=7.54 (d, J=7.6 Hz, 1H), 7.27-7.11 (m, 3H), 2.89 (dd, J=3.2, 14.4 Hz, 1H), 2.49-2.28 (m, 2H), 2.17-2.14 (m, 3H), 2.05-1.94 (m, 1H), 1.88-1.53 (m, 4H); $^{13}C$ NMR (101 MHz, CHLOROFORM-d) δ=215.34, 139.36, 136.72, 132.76, 127.86, 126.72, 126.39, 67.52, 43.67, 39.72, 30.04, 22.90, 20.93; ENT-2, RT=1.906 min (assigned here as the R isomer, 114R); LCMS ($R_T$=1.482 min, MS calc.: 203.13, $[M+H]^+$=204.1); $^1H$ NMR (400 MHz, CHLOROFORM-d) δ=7.54 (d, J=7.6 Hz, 1H), 7.27-7.11 (m, 3H), 2.89 (dd, J=3.2, 14.4 Hz, 1H), 2.49-2.28 (m, 2H), 2.17-2.14 (m, 3H), 2.05-1.94 (m, 1H), 1.88-1.53 (m, 4H); $^{13}C$ NMR (101 MHz, CHLOROFORM-d) δ=215.34, 139.36, 136.72, 132.76, 127.86, 126.72, 126.39, 67.52, 43.67, 39.72, 30.04, 22.90, 20.93.

Example 14: Preparation of Compounds 31S and 31R

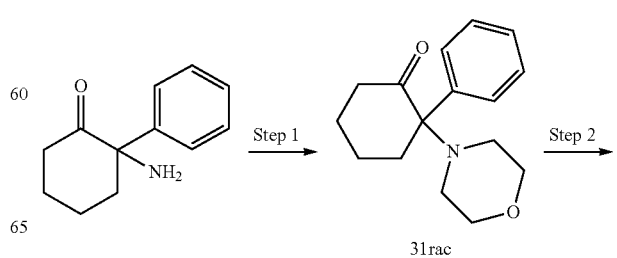

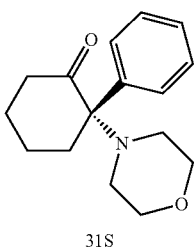
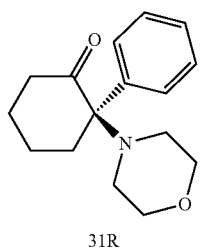

31S          31R

Step 1: Preparation of 2-morpholino-2-phenylcyclohexan-1-one (31rac)

A mixture of 2-amino-2-phenyl-cyclohexan-1-one (2 g, 10.57 mmol, 1 eq), 1-bromo-2-(2-bromoethoxy)ethane (7.35 g, 31.70 mmol, 3.97 mL, 3 eq), $K_2CO_3$ (4.38 g, 31.70 mmol, 3 eq), and KI (526 mg, 3.17 mmol, 0.3 eq) in MeCN (50 mL) was stirred at 80° C. for 12 hrs. The mixture was cooled, filtered, and concentrated. The residue was purified by prep-HPLC (column: Agela DuraShell C18 250*70 mm, 10 μm; mobile phase: A: water (0.05% $NH_3H_2O$+10 mM $NH_4HCO_3$), B: ACN; B %: 20%-55%, 30 min) to afford 2-morpholino-2-phenylcyclohexan-1-one (1.1 g, 4.24 mmol, 40.14% yield) as a white solid.

Step 2: Preparation of (S)-2-morpholino-2-phenyl-cyclohexan-1-one (31S) and (R)-2-morpholino-2-phenylcyclohexan-1-one (31R)

The racemate was separated by SFC (column: REGIS (R,R)WHELK-01 (250 mm*25 mm, 10 μm); mobile phase: A: $CO_2$, B: 0.1% $NH_3H_2O$ in IPA; B %: 38%, multi-injection process with 6 min spacing between injections) to afford ENT-1 1.950 min (434 mg) as a white solid and ENT-2 2.276 min (474 mg) as a white solid. Retention times were determined using the following chiral analytical method: column: (S,S)-WHELK-01, 100×4.6 mm I.D., 3.5 μm; mobile phase: A: $CO_2$, B: IPA (0.05% IPAm, v/v); gradient: (Time (min)/A %/B %), (0.0/95/5, 0.5/95/5, 2.0/60/40, 3.0/60/40, 3.6/95/5, 4.0/95/5); flow rate: 3.4 mL/min; column temp.: 35° C.; ABPR: 1800 psi.

ENT-1, RT=1.950 min (assigned here as the S isomer, 31S); LCMS ($R_T$=1.425 min, MS calc.: 259.34, $[M+H]^+$=260.1); $^1H$ NMR (400 MHz, CHLOROFORM-d) δ=7.41-7.36 (m, 2H), 7.32 (d, J=7.2 Hz, 1H), 7.28-7.24 (m, 2H), 3.73-3.63 (m, 4H), 2.59-2.42 (m, 4H), 2.41-2.31 (m, 3H), 2.23 (ddd, J=3.6, 10.8, 14.0 Hz, 1H), 1.97-1.85 (m, 3H), 1.82-1.67 (m, 2H); $^{13}C$ NMR (101 MHz, CHLOROFORM-d) δ=211.12, 135.80, 128.59, 128.23, 127.66, 74.52, 67.57, 47.47, 40.84, 31.98, 28.24, 22.17; ENT-2, RT=2.276 min; (assigned here as the R isomer, 31R); LCMS ($R_T$=1.439 min, MS calc.: 259.34, $[M+H]^+$=260.1); $^1H$ NMR (400 MHz, CHLOROFORM-d) δ=7.42-7.36 (m, 2H), 7.34-7.29 (m, 1H), 7.28-7.23 (m, 2H), 3.73-3.63 (m, 4H), 2.52 (br s, 1H), 2.59-2.42 (m, 1H), 2.40-2.30 (m, 3H), 2.28-2.18 (m, 1H), 1.97-1.85 (m, 2H), 1.82-1.66 (m, 2H); $^{13}C$ NMR (101 MHz, CHLOROFORM-d) δ=211.12, 135.77, 128.59, 128.23, 127.67, 74.54, 67.55, 47.47, 40.85, 31.98, 28.24, 22.17.

Example 15: Preparation of Compounds 117rac and 18rac

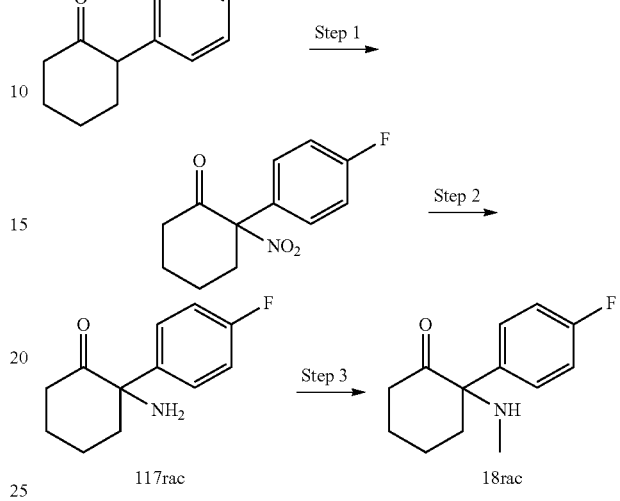

Step 1: Preparation of 2-(4-fluorophenyl)-2-nitrocyclohexan-1-one

A mixture of 2-(4-fluorophenyl)cyclohexan-1-one (5 g, 26.01 mmol, 1 eq), ceric ammonium nitrate (CAN, 28.52 g, 52.02 mmol, 2 eq), and $Cu(OAc)_2$ (945 mg, 5.20 mmol, 0.2 eq) in DCE (50 mL) was stirred at 85° C. for 12 hrs. The mixture was cooled, filtered and concentrated. The residue was purified by column chromatography ($SiO_2$, Petroleum ether/Ethyl acetate=100/1 to 0/1) to afford 2-(4-fluorophenyl)-2-nitrocyclohexan-1-one (2.5 g, 10.54 mmol, 40.52% yield) as a yellow oil. $^1H$ NMR (400 MHz, CHLOROFORM-d) δ=7.47-7.29 (m, 2H), 7.22-7.04 (m, 2H), 3.12 (ddd, J=3.6, 10.0, 14.0 Hz, 1H), 2.86-2.76 (m, 1H), 2.75-2.62 (m, 1H), 2.61-2.47 (m, 1H), 2.08-1.86 (m, 3H), 1.80 (dt, J=3.6, 9.2 Hz, 1H).

Step 2: Preparation of 2-amino-2-(4-fluorophenyl)cyclohexan-1-one (117rac)

A mixture of 2-(4-fluorophenyl)-2-nitrocyclohexan-1-one (3 g, 12.65 mmol, 1 eq) and Zn (19.85 g, 303.51 mmol, 24 eq) in AcOH (25 mL) was stirred at 20° C. for 12 hrs. The mixture was cooled, filtered, and concentrated. The residue was dissolved in DCM, washed with sat. $NaHCO_3$, $H_2O$, and brine, dried over $Na_2SO_4$, filtered, and concentrated. The residue was purified by silica gel (PE:EA=50:1-8:1) to afford 2-amino-2-(4-fluorophenyl)cyclohexan-1-one (1.5 g, 7.24 mmol, 57.23% yield) (117rac) as a brown oil. LCMS ($R_T$=1.336 min, MS calc.: 207.11, $[M+H]^+$=208.1) $^1H$ NMR (400 MHz, CHLOROFORM-d) δ=7.26-7.19 (m, 2H), 7.11-7.01 (m, 2H), 2.87-2.73 (m, 1H), 2.50-2.42 (m, 1H), 2.41-2.29 (m, 1H), 2.04-1.96 (m, 1H), 1.93 (s, 2H), 1.83-1.63 (m, 4H); $^3C$ NMR (101 MHz, CHLOROFORM-d) δ=213.28, 163.27, 160.82, 137.67, 137.63, 127.99, 127.91, 116.16, 115.95, 65.93, 39.71, 28.08, 22.61

Step 3: Preparation of 2-(4-fluorophenyl)-2-(methylamino)cyclohexan-1-one (18rac)

A mixture of 2-amino-2-(4-fluorophenyl)cyclohexan-1-one (1.3 g, 6.27 mmol, 1 eq) and methyl trifluoromethanesulfonate (1.03 g, 6.27 mmol, 1 eq) in hexafluoroisopropanol (HFIP, 130 mL) was stirred at 0-25° C. for 12 hrs under N₂ atmosphere. The mixture was filtered and concentrated. The residue was adjusted to pH=7 with sat. Na₂CO₃ (20 ml). The aqueous phase was extracted with EA (50 mL×2). The combined organic phase was washed with brine (50 mL×2), dried with anhydrous Na₂SO₄, filtered, and concentrated in vacuo. The residue was purified by prep-HPLC (column: Welch Xtimate C18 250*70 mm, 10 μm; mobile phase: A: water (0.05% NH₃H₂O), B: ACN; B %: 18%-48%, 32 min) to afford 2-(4-fluorophenyl)-2-(methylamino)cyclohexan-1-one (590 mg, 4.02 mmol, 42.45% yield) (18rac) as a white solid. LCMS (R$_T$=1.415 min, MS calc.: 221.12, [M+H]⁺=222.1); ¹H NMR (400 MHz, CHLOROFORM-d) δ=7.26-7.17 (m, 2H), 7.07 (br t, J=8.4 Hz, 2H), 2.92-2.74 (m, 1H), 2.50-2.26 (m, 3H), 2.12-1.93 (m, 4H), 1.90-1.63 (m, 4H); ¹³C NMR (101 MHz, CHLOROFORM-d) δ=211.15, 163.20, 160.75, 134.68, 134.65, 128.99, 128.91, 115.79, 115.58, 69.37, 39.70, 35.85, 28.87, 27.70, 22.21.

Example 16: Preparation of Compounds 118rac and 23rac

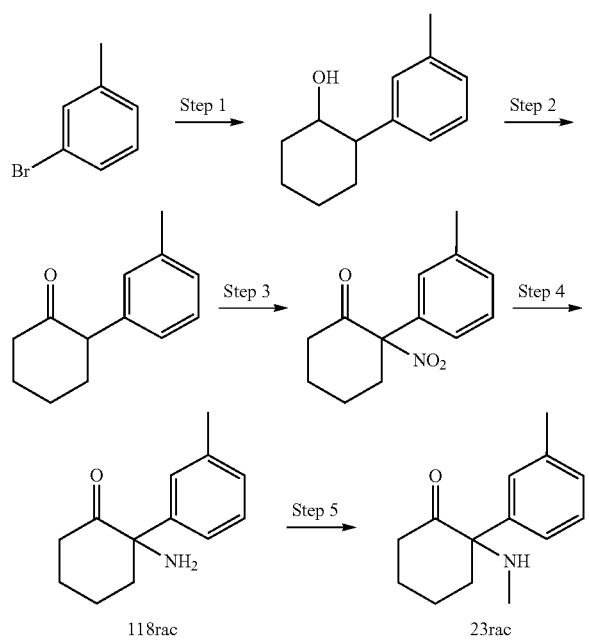

Step 1: Preparation of 2-(m-tolyl)cyclohexan-1-ol

A mixture of 1-bromo-3-methyl-benzene (15 g, 87.70 mmol, 10.64 mL, 1 eq) in THF (150 mL) was cooled to −70° C. Then n-BuLi (2.5 M, 38.59 mL, 1.1 eq) was added. The mixture was stirred at −70° C. for 0.5 hr and then 7-oxabicyclo[4.1.0]heptane (9.47 g, 96.47 mmol, 9.76 mL, 1.1 eq) and BF₃·Et₂O (13.69 g, 96.47 mmol, 11.91 mL, 1.1 eq) were added. The mixture was stirred at −70° C. for 1.5 hrs. The mixture was poured into sat. aq. NH₄Cl (200 ml) and extracted with EA (100 ml×2). The organic layer was washed with brine, dried over Na₂SO₄, filtered, and concentrated. The residue was purified by silica gel (PE: EA=100:1-10:1) to afford 2-(m-tolyl)cyclohexan-1-ol (13 g, 68.32 mmol, 77.9% yield) as a colorless oil. ¹H NMR (400 MHz, CHLOROFORM-d) δ=7.33-7.28 (m, 1H), 7.16-7.09 (m, 3H), 3.72 (dt, J=4.0, 10.0 Hz, 1H), 2.50-2.44 (m, 1H), 2.41 (s, 3H), 2.22-2.14 (m, 1H), 1.92 (br d, J=10.8 Hz, 2H), 1.83 (br d, J=12.4 Hz, 1H), 1.61-1.36 (m, 4H).

Step 2: Preparation of 2-(m-tolyl)cyclohexan-1-one

To a mixture of 2-(m-tolyl)cyclohexan-1-ol (13 g, 68.32 mmol, 1 eq) in DCM (50 mL) was added Dess-Martin Periodinane (43.47 g, 102.48 mmol, 31.73 mL, 1.5 eq) in several portions at 0° C. (maintaining the temperature at 0° C. during addition). Then the mixture was stirred at 20° C. for 12 hrs. The mixture was filtered and the filtrate was washed with sat. aq. Na₂SO₃, sat. aq. Na₂CO₃, and brine, dried over Na₂SO₄, filtered, and concentrated. The residue was purified by silica gel chromatography (PE:EA=1:0-5:1) to afford 2-(m-tolyl)cyclohexan-1-one (13 g, crude) as a white solid. ¹H NMR (400 MHz, CHLOROFORM-d) δ 7.26-7.21 (m, 1H), 7.10-7.06 (m, 1H), 6.98-6.93 (m, 2H), 3.62-3.55 (m, 1H), 2.58-2.44 (m, 2H), 2.35 (s, 3H), 2.31-2.23 (m, 1H), 2.21-2.13 (m, 1H), 2.08-1.97 (m, 2H), 1.90-1.83 (m, 2H).

Step 3: Preparation of 2-(m-tolyl)-2-nitro-cyclohexan-1-one

A mixture of 2-(m-tolyl)cyclohexan-1-one (11 g, 58.43 mmol, 1 eq), ceric ammonium nitrate (CAN, 64.06 g, 116.86 mmol, 58.24 mL, 2 eq), and Cu(OAc)₂ (2.12 g, 11.69 mmol, 0.2 eq) in DCE (200 mL) was stirred at 85° C. for 12 hrs. The mixture was cooled and filtered and the filter cake was washed by EtOAc (80 mL×μL). The filtrate was concentrated under vacuum to give a residue that was purified by silica gel chromatography (SiO₂, PE/EtOAc=10/1) to afford 2-(m-tolyl)-2-nitro-cyclohexan-1-one (3 g, 12.86 mmol, 22.01% yield) as a yellow oil. ¹H NMR (400 MHz, CHLOROFORM-d) δ=7.39-7.33 (m, 1H), 7.28 (br s, 1H), 7.18-7.13 (m, 2H), 3.06 (ddd, J=3.2, 10.7, 14.3 Hz, 1H), 2.96-2.86 (m, 1H), 2.74-2.64 (m, 1H), 2.62-2.52 (m, 1H), 2.40 (s, 3H), 1.99-1.88 (m, 3H), 1.78 (ddd, J=3.6, 6.6, 10.4 Hz, 1H).

Step 4: Preparation of 2-amino-2-(m-tolyl)cyclohexan-1-one (118rac)

To a mixture of 2-(m-tolyl)-2-nitro-cyclohexan-1-one (2.5 g, 10.72 mmol, 1 eq) in AcOH (30 mL) was added Zn (16.82 g, 257.22 mmol, 24 eq) over 1 hr and the mixture was then stirred at 20° C. for 12 hrs. On completion, the mixture was filtered and the filtrate was concentrated. The residue was dissolved with DCM (10 ml), adjusted to pH=8 with sat. Na₂CO₃, and extracted with DCM (10 mL×2). The organic phase was dried over Na₂SO₄, filtered, and concentrated to afford 2-amino-2-(m-tolyl)cyclohexan-1-one (1.90 g, 9.35 mmol, 87.21% yield) (118rac) as a yellow oil. LCMS (R$_T$=1.629 min, MS calc.: 203.3, [M+H]⁺=204.1); ¹H NMR (400 MHz, CHLOROFORM-d) δ=7.30-7.27 (m, 1H), 7.11 (d, J=7.6 Hz, 1H), 7.09-7.05 (m, 2H), 2.91-2.83 (m, 1H), 2.49-2.41 (m, 2H), 2.36 (s, 3H), 2.07-1.94 (m, 1H), 1.80-1.650 (m, 4H); ¹³C NMR (101 MHz, CHLOROFORM-d) δ=213.83, 141.84, 139.01, 129.14, 128.46, 126.79, 123.08, 66.50, 39.94, 39.49, 28.24, 22.78, 21.57.

Step 5: Preparation of 2-(methylamino)-2-(m-tolyl) cyclohexan-1-one (23rac)

A mixture of 2-amino-2-(m-tolyl)cyclohexan-1-one (1.34 g, 6.59 mmol, 1 eq) in hexafluoroisopropanol (HFIP, 140 mL) was added methyl trifluoromethanesulfonate (1.08 g, 6.59 mmol, 721.15 uL, 1 eq) at 0° C. Then the mixture was stirred at 25° C. for 12 hrs under N2 atmosphere. The mixture was filtered and concentrated. The residue was adjusted to pH=7 with aq. $Na_2CO_3$ solution (30 mL). The aqueous phase was extracted with EA (100 mL×2). The combined organic phase was washed with brine (100 mL×2), dried with anhydrous $Na_2SO_4$, filtered, and concentrated in vacuo. The residue was purified by prep-HPLC (column: Agela DuraShell C18 250*70 mm, 10 μm; mobile phase: A: water (0.05% $NH_3H_2O$+10 mM $NH_4HCO_3$), B: ACN; B %: 29%-59%, 20 min) to afford 2-(methylamino)-2-(m-tolyl)cyclohexan-1-one (742 mg, 3.41 mmol, 51.8% yield) (23rac) as a brown oil. LCMS (RT=1.551 min, MS calc.: 217.3, [M+H]$^+$=218.1); $^1$H NMR (400 MHz, CHLOROFORM-d) δ=7.28-7.19 (m, 1H), 7.11-6.95 (m, 3H), 2.86 (td, J=2.4, 5.4 Hz, 1H), 2.43-2.30 (m, 2H), 2.34 (br s, 3H), 2.05 (s, 3H), 1.97-1.87 (m, 1H), 1.87-1.62 (m, 4H); $^{13}$C NMR (101 MHz, CHLOROFORM-d) δ=211.63, 138.66, 138.55, 128.63, 128.30, 127.73, 124.18, 69.86, 39.88, 35.28, 28.94, 27.81, 22.34, 21.62.

Example 17: Preparation of Compounds 120rac and 119rac

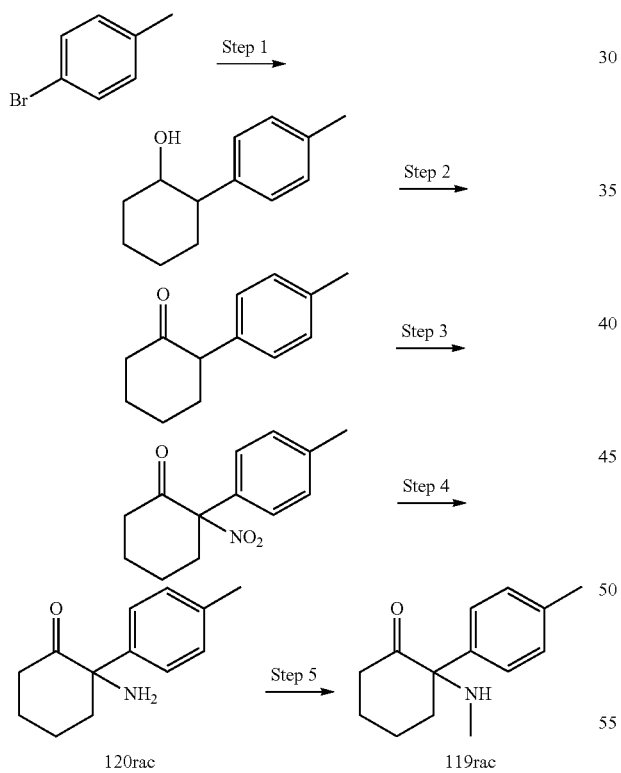

Step 1: Preparation of 2-(p-tolyl)cyclohexan-1-ol

To a solution of 1-bromo-4-methyl-benzene (15 g, 87.70 mmol, 10.79 mL, 1 eq) in THF (200 mL) was cooled to −70° C. Then n-BuLi (2.5 M, 38.59 mL, 1.1 eq) was added. The mixture was stirred at −70° C. for 0.5 hr and then 7-oxabicyclo[4.1.0]heptane (9.47 g, 96.47 mmol, 9.76 mL, 1.1 eq) and $BF_3.Et_2O$ (13.69 g, 96.47 mmol, 11.91 mL, 1.1 eq) were added. The mixture was stirred at −70° C. for 1.5 hrs. On completion, the reaction was quenched with sat. aq. NH$_4$Cl (40 ml) slowly and then extracted with EtOAc (50 mL×3). The combined organic phase was washed with brine (50 mL), dried over $Na_2SO_4$, filtered, and concentrated in vacuo. The residue was purified by silica gel chromatography (Petroleum ether/Ethyl acetate=100/1, 5/1) to afford 2-(p-tolyl)cyclohexan-1-ol (13 g, 68.32 mmol, 77.9% yield) as a white solid. $^1$H NMR (400 MHz, CHLOROFORM-d) δ=7.18-7.13 (m, 4H), 3.69-3.61 (m, 1H), 2.44-2.37 (m, 1H), 2.35 (s, 3H), 2.16-2.09 (m, 1H), 1.91-1.82 (m, 2H), 1.80-1.73 (m, 1H), 1.55-1.31 (m, 4H).

Step 2: Preparation of 2-(p-tolyl)cyclohexan-1-one

To a mixture of 2-(p-tolyl)cyclohexan-1-ol (13 g, 68.32 mmol, 1 eq) in $CH_2Cl_2$ (50 mL) was added Dess-Martin Periodinane (43.47 g, 102.48 mmol, 31.73 mL, 1.5 eq) in several portions at 0° C. (maintaining the temperature at 0° C. during addition). Then the mixture was stirred at 20° C. for 12 hrs. The mixture was filtered. The filtrate was washed with sat. aq. $Na_2SO_3$, sat. aq. $Na_2CO_3$, and brine, dried over $Na_2SO_4$, filtered, and concentrated. The residue was purified by silica gel chromatography (PE:EA=50:1-5:1) to afford 2-(p-tolyl)cyclohexan-1-one (12.01 g, 63.82 mmol, 93.41% yield) as a white solid. $^1$H NMR (400 MHz, CHLOROFORM-d) δ=7.20-7.13 (m, 2H), 7.08-7.02 (m, 2H), 3.63-3.55 (m, 1H), 2.58-2.42 (m, 2H), 2.35 (s, 3H), 2.32-2.23 (m, 1H), 2.20-2.12 (m, 1H), 2.08-1.98 (m, 2H), 1.90-1.81 (m, 2H).

Step 3: Preparation of 2-nitro-2-(p-tolyl)cyclohexan-1-one

A mixture of 2-(p-tolyl)cyclohexan-1-one (11 g, 58.43 mmol, 1 eq), ceric ammonium nitrate (CAN, 64.06 g, 116.86 mmol, 58.24 mL, 2 eq), and $Cu(OAc)_2$ (2.12 g, 11.69 mmol, 0.2 eq) in DCE (150 mL) was stirred at 85° C. for 12 hrs. The reaction mixture was cooled, filtered, and the filtrate was concentrated. The residue was purified by column chromatography ($SiO_2$, PE/EA=1/O to 0/1) to afford 2-nitro-2-(p-tolyl)cyclohexan-1-one (5.98 g, 25.64 mmol, 43.88% yield) as a yellow oil. $^1$H NMR (400 MHz, CHLOROFORM-d) δ=7.36-7.27 (m, 4H), 3.10 (ddd, J=3.6, 10.9, 14.4 Hz, 1H), 2.99-2.89 (m, 1H), 2.76-2.65 (m, 1H), 2.65-2.54 (m, 1H), 2.44 (s, 3H), 2.05-1.92 (m, 3H), 1.86-1.73 (m, 1H).

Step 4: Preparation of 2-amino-2-(p-tolyl)cyclohexan-1-one (120rac)

To a solution of 2-nitro-2-(p-tolyl)cyclohexan-1-one (4.98 g, 21.35 mmol, 1 eq) in AcOH (40 mL) was added Zn (33.50 g, 512.38 mmol, 24 eq) at 0° C. The mixture was stirred at 25° C. for 12 hrs. On completion, the mixture was filtered and concentrated. The residue was adjusted to pH=7 with aq. $Na_2CO_3$ solution (150 mL). The aqueous phase was extracted with DCM (200 mL×2) and the combined organics were dried over anhydrous $Na_2SO_4$, filtered, and concentrated in vacuo. The residue was purified by column chromatography ($SiO_2$, PE/EA=1/O to 0/1) to afford 2-amino-2-(p-tolyl)cyclohexan-1-one (1.3 g, 6.40 mmol, 29.95% yield) (120rac) as a yellow oil. LCMS (R$_T$=1.618 min, MS calc.: 203.3, [M+H]$^+$=204.1); $^1$H NMR (400 MHz, CHLOROFORM-d) δ=7.14 (q, J=8.4 Hz, 4H), 2.90-2.75 (m, 1H), 2.48-2.35 (m, 2H), 2.32 (s, 3H), 1.96 (br s, 3H), 1.83-1.52

(m, 4H); ¹³C NMR (101 MHz, CHLOROFORM-d) δ=213.76, 138.92, 137.49, 129.93, 126.04, 66.28, 39.83, 39.53, 28.22, 22.76, 20.99.

Step 5: Preparation of 2-(methylamino)-2-(p-tolyl) cyclohexan-1-one (119rac)

A mixture of 2-amino-2-(p-tolyl)cyclohexan-1-one (583 mg, 2.87 mmol, 1 eq) in hexafluoroisopropanol (HFIP, 60 mL) was added methyl trifluoromethanesulfonate (470.65 mg, 2.87 mmol, 313.76 uL, 1 eq) at 0° C. Then the mixture was stirred at 25° C. for 12 hrs under $N_2$ atmosphere. The mixture was filtered and concentrated. The residue was adjusted to pH=7 with sat. aq. $Na_2CO_3$ solution (100 mL). The aqueous phase was extracted with EA (100 mL×2). The combined organic phase was washed with brine (100 mL×1), dried with anhydrous $Na_2SO_4$, filtered, and concentrated in vacuo. The residue was purified by prep-HPLC (column: Welch Xtimate C18 250*70 mm, 10 μm; mobile phase: A: water (0.05% $NH_3H_2O$), B: ACN; B %: 10%-45%, 35 min) to afford 2-(methylamino)-2-(p-tolyl)cyclohexan-1-one (398.86 mg, 1.84 mmol, 64.00% yield) (119rac) as a yellow oil. LCMS ($R_T$=1.574 min, MS calc.: 217.3, [M+H]⁺=218.1); ¹H NMR (400 MHz, CHLOROFORM-d) δ=7.21-7.17 (m, 2H), 7.16-7.10 (m, 2H), 2.92-2.83 (m, 1H), 2.44-2.36 (m, 2H), 2.35 (s, 3H), 2.04 (s, 3H), 2.01-1.91 (m, 1H), 1.86-1.68 (m, 4H); ¹³C NMR (101 MHz, CHLOROFORM-d) δ=211.35, 137.45, 129.60, 127.17, 69.80, 39.76, 35.30, 28.87, 27.78, 22.31, 21.04.

Example 18: Preparation of Compounds 25R and 25S

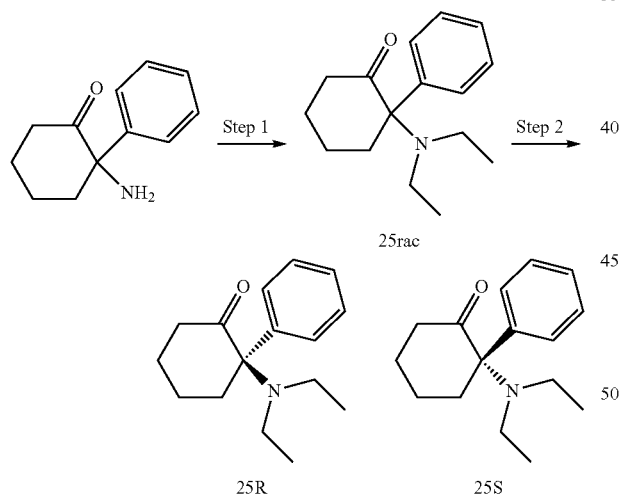

Step 1: Preparation of 2-(diethylamino)-2-phenylcyclohexan-1-one (25rac)

A mixture of 2-amino-2-phenyl-cyclohexan-1-one (5 g, 26.42 mmol, 1 eq), iodoethane (20.60 g, 132.10 mmol, 10.57 mL, 5 eq) and $K_2CO_3$ (10.95 g, 79.26 mmol, 3 eq) in MeCN (50 mL) was stirred at 100° C. for 12 hrs. The mixture was filtered and concentrated. The residue was purified by prep-HPLC (mobile phase: A: water (10 mM $NH_4HCO_3$), B: ACN; B %: 35%-70%, 20 min) to afford 2-(diethylamino)-2-phenylcyclohexan-1-one (3 g, 12.23 mmol, 46.28% yield) (25rac) as a yellow oil. ¹H NMR (400 MHz, CHLOROFORM-d) δ=7.32-7.16 (m, 5H), 2.60-2.51 (m, 1H), 2.47 (q, J=7.2 Hz, 4H), 2.41-2.17 (m, 3H), 1.92-1.65 (m, 3H), 1.63-1.47 (m, 1H), 0.90 (t, J=7.2 Hz, 6H).

Step 2: Preparation of (R)-2-(diethylamino)-2-phenylcyclohexanone (25R) and (S)-2-(diethylamino)-2-phenylcyclohexanone (25S)

The racemate was separated by SFC (column: DAICEL CHIRALCEL OJ (250 mm*30 mm, 10 μm); mobile phase: A: $CO_2$, B: 0.1% $NH_3H_2O$ in IPA; B %: 11%, multi-injection process with 5 min spacing between injections) to afford ENT-1 1.103 min (343 mg) as a yellow oil and ENT-2 1.300 min (373 mg) as a yellow oil. Retention times were determined using the following chiral analytical method: column: Chiralcel OJ-3, 100×4.6 mm I.D., 3 μm; mobile phase: A: $CO_2$ B: IPA (0.05% IPAm, v/v); gradient: (Time (min)/A %/B %), (0.0/95/5, 0.5/95/5, 2.0/60/40, 3.0/60/40, 3.6/95/5, 4.0/95/5); flow rate: 3.4 mL/min; column temp.: 35° C.; ABPR: 1800 psi.

ENT-1, RT=1.103 min (assigned here as the S isomer, 25S); LCMS ($R_T$=1.456 min, MS calc.: 245.18, [M+H]⁺=246.1); ¹H NMR (400 MHz, CHLOROFORM-d) δ=7.31-7.20 (m, 4H), 7.20-7.14 (m, 1H), 2.58-2.48 (m, 1H), 2.43 (q, J=7.2 Hz, 4H), 2.37-2.14 (m, 3H), 1.91-1.63 (m, 3H), 1.60-1.48 (m, 1H), 0.93-0.79 (m, 6H); ¹³C NMR (101 MHz, CHLOROFORM-d) δ=212.94, 139.77, 128.71, 128.04, 127.25, 45.89, 41.27, 35.08, 27.85, 22.46, 16.85; ENT-2, RT=1.300 min (assigned here as the R isomer, 25R); LCMS (RT=1.514 min, MS calc.: 245.18, [M+H]⁺=246.1); ¹H NMR (400 MHz, CHLOROFORM-d) δ=7.34-7.21 (m, 4H), 7.20-7.14 (m, 1H), 2.59-2.48 (m, 1H), 2.43 (q, J=7.2 Hz, 4H), 2.36-2.13 (m, 3H), 1.92-1.62 (m, 3H), 1.60-1.48 (m, 1H), 0.96-0.80 (m, 6H); ¹³C NMR (101 MHz, CHLOROFORM-d) δ=212.96, 139.77, 128.71, 128.04, 127.25, 45.89, 41.28, 35.09, 27.85, 22.46, 16.85.

Example 19: Preparation of Compound 128mix

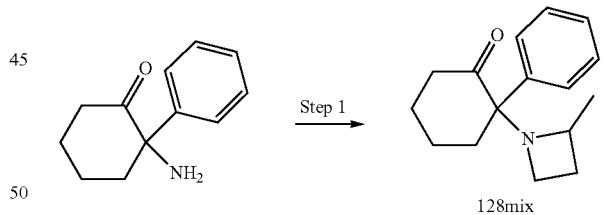

Step 1: Preparation of 2-(2-methylazetidin-1-yl)-2-phenylcyclohexan-1-one (128mix)

A mixture of 2-amino-2-phenyl-cyclohexan-1-one (200 mg, 1.06 mmol, 1 eq), 1,3-dibromobutane (296.63 mg, 1.37 mmol, 1.3 eq), KI (52.63 mg, 317.04 umol, 0.3 eq), and $K_2CO_3$ (438.16 mg, 3.17 mmol, 3 eq) in MeCN (2 mL) was stirred at 100° C. for 12 hrs. The mixture was cooled, filtered, and concentrated. The residue was purified by prep-HPLC (mobile phase: A: water (0.05% $NH_3H_2O$+10 mM $NH_4HCO_3$), B: ACN; B %: 25%-55%, 8 min) to afford 2-(2-methylazetidin-1-yl)-2-phenylcyclohexan-1-one as a mixture of all 4 diastereomers, (50 mg, 205.47 umol, 19.44% yield) (128mix) as a yellow oil. LCMS ($R_T$=1.542 min, MS calc.: 243.16, [M+H]⁺=244.1); $^1$H NMR (400 MHz, CHLOROFORM-d) (partial integrals due to mixture of isomers) δ=7.50-7.29 (m, 3H), 7.25-7.15 (m, 2H), 3.65 (br d, J=4.8 Hz, 0.5H), 3.51-3.33 (m, 1H), 3.29-3.16 (m, 0.5H), 3.10 (br d, J=6.0 Hz, 1H), 2.79-2.54 (m, 1H), 2.50-2.24 (m, 2H), 1.93-1.80 (m, 3H), 1.76-1.44 (m, 4H), 1.02-0.76 (m, 3H).

Example 20: Preparation of Compound 129rac

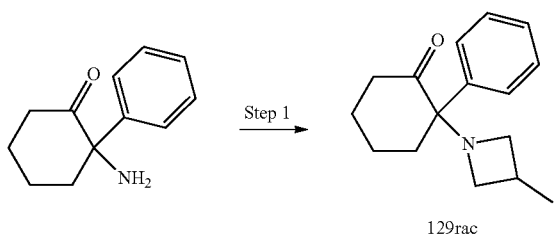

Step 1: Preparation of 2-(3-methylazetidin-1-yl)-2-phenyl-cyclohexan-1-one (129rac)

A mixture of 2-amino-2-phenyl-cyclohexan-1-one (300 mg, 1.59 mmol, 1 eq), 1,3-dibromo-2-methyl-propane (444.94 mg, 2.06 mmol, 1.3 eq), KI (78.94 mg, 475.55 umol, 0.3 eq), and K₂CO₃ (657.24 mg, 4.76 mmol, 3 eq) in MeCN (5 mL) was stirred at 100° C. for 12 hrs. The mixture was cooled, filtered, and concentrated. The residue was purified by prep-HPLC (mobile phase: A: water (10 mM NH₄HCO₃), B: ACN; B %: 30%-50%, 8 min) to afford 2-(3-methylazetidin-1-yl)-2-phenyl-cyclohexan-1-one (16 mg, 65.09 umol, 4.11% yield, 99% purity) (129rac) as a white solid. LCMS (R$_T$=1.602 min, MS calc.: 243.16, [M+H]⁺=244.1); $^1$H NMR (400 MHz, METHANOL-d4) δ=7.55-7.47 (m, 2H), 7.46-7.40 (m, 1H), 7.27-7.18 (m, 2H), 3.56-3.48 (m, 1H), 3.31-3.26 (m, 1H), 2.92-2.84 (m, 1H), 2.81-2.69 (m, 2H), 2.47-2.21 (m, 3H), 1.99-1.91 (m, 1H), 1.84-1.55 (m, 4H), 0.84 (d, J=6.8 Hz, 3H).

Example 21. Metabolic Stability in Human Liver Microsomes

Disclosed compounds were tested for stability in human liver microsomes (HLM), with the results summarized in Table 2. For some of the compounds, stability was tested under two microsomal incubation conditions, one with normal enzymatic activity (low activity) and one with higher enzymatic loading, longer incubation time, and lower compound concentration (high activity) intended to increase metabolic lability. Disclosed compounds exhibited greater metabolic stability than ketamine in this model under both conditions.

Drugs. Compounds were tested as the racemates (indicated by "rac" nomenclature) or pure enantiomers (indicated by "R" or "S" nomenclature).

HLM Stability (Low Activity). Pooled HLM from adult male and female donors (XenoTech H0630) were used. Microsomal incubations were carried out in 96-well plates in 5 aliquots of 40 μL, each (one for each time point). Liver microsomal incubation medium consisted of PBS (100 mM, pH 7.4), MgCl₂ (3.3 mM), NADPH (3 mM), glucose-6-phosphate (5.3 mM), and glucose-6-phosphate dehydrogenase (0.67 units/mL), with 0.42 mg of liver microsomal protein per mL. Control incubations were performed by replacing the NADPH-cofactor system with PBS. Test compounds (2 μM, final solvent concentration 1.6%) were incubated with microsomes at 37° C., shaking at 100 rpm. Incubations were performed in duplicate. Five time points over 40 minutes were analyzed. The reactions were stopped by adding 12 volumes of 90% acetonitrile-water to incubation aliquots, followed by protein sedimentation by centrifugation at 5500 rpm for 3 minutes. Supernatants were analyzed for parent compound remaining using a fit-for-purpose liquid chromatography-tandem mass spectrometry (LC-MS/MS) method, with authentic samples of each analyte used for identity confirmation.

HLM Stability (Low Activity, Alternative Method). Pooled HLM from adult male and female donors (Corning 452117) were used. Microsomal incubations were carried out in multi-well plates. Liver microsomal incubation medium consisted of PBS (100 mM, pH 7.4), MgCl₂ (1 mM), and NADPH (1 mM), with 0.50 mg of liver microsomal protein per mL. Control incubations were performed by replacing the NADPH-cofactor system with PBS. Test compounds (1 μM, final solvent concentration 1.0%) were incubated with microsomes at 37° C. with constant shaking. Six time points over 60 minutes were analyzed, with 60 μL aliquots of the reaction mixture being drawn at each time point. The reaction aliquots were stopped by adding 180 μL of cold (4° C.) acetonitrile containing 200 ng/mL tolbutamide and 200 ng/mL labetalol as internal standards (IS), followed by shaking for 10 minutes, and then protein sedimentation by centrifugation at 4000 rpm for 20 minutes at 4° C. Supernatant samples (80 μL) were diluted with water (240 μL) and analyzed for parent compound remaining using a fit-for-purpose liquid chromatography-tandem mass spectrometry (LC-MS/MS) method.

HLM Stability (High Activity). Pooled HLM from adult male and female donors (XenoTech H0630) were used. Microsomal incubations were carried out in 96-well plates in 5 aliquots of 40 μL, each (one for each time point). Liver microsomal incubation medium consisted of PBS (100 mM, pH 7.4), MgCl₂ (3.3 mM), NADPH (3 mM), glucose-6-phosphate (5.3 mM), and glucose-6-phosphate dehydrogenase (0.67 units/mL), with 1.0 mg of liver microsomal protein per mL. Control incubations were performed by replacing the NADPH-cofactor system with PBS. Test compounds (1 μM, final solvent concentration 1.6%) were incubated with microsomes at 37° C., shaking at 100 rpm. Incubations were performed in duplicate. Five time points over 60 minutes were analyzed. The reactions were stopped by adding 12 volumes of 90% acetonitrile-water to incubation aliquots, followed by protein sedimentation by centrifugation at 5500 rpm for 3 minutes. Supernatants were analyzed for parent compound remaining using a fit-for-purpose liquid chromatography-tandem mass spectrometry (LC-MS/MS) method, with authentic samples of each analyte used for identity confirmation.

Data Analysis. The elimination constant ($k_{el}$), half-life ($t_{1/2}$) and intrinsic clearance ($Cl_{int}$) were determined in a plot of ln(AUC) versus time, using linear regression analysis.

TABLE 2

Intrinsic clearance (Cl$_{int}$) and half-life (t$_{1/2}$) of ketamine and analogs in the presence of HLM under 2 incubation conditions. NT = not tested.

| Compound Number (rac = racemic) | Structure | Condition 1 (Low Activity) | | Condition 2 (High Activity) | |
|---|---|---|---|---|---|
| | | Cl$_{int}$ (μL/min/mg) | t$_{1/2}$ (min) | Cl$_{int}$ (μL/min/mg) | t$_{1/2}$ (min) |
| rac-ketamine | 2-Cl-phenyl cyclohexanone with NHMe | 21 | 78.6 | 19 | 36.8 |
| 78rac | 2-Cl-phenyl cyclohexanone with NH$_2$ | 7 | 257 | 4 | 182 |
| 14rac | phenyl cyclohexanone with NHMe | 5 | 328 | 2 | 367 |
| 14R | (R)-phenyl cyclohexanone with NHMe | NT | NT | 1 | 586 |
| 14S | (S)-phenyl cyclohexanone with NHMe | NT | NT | 2 | 371 |
| 1rac | phenyl cyclohexanone with NHEt | 13 | 133 | 2 | 299 |
| 11rac | phenyl cyclohexanone with NH$_2$ | 2 | 803 | 1 | 534 |
| 11R | (R)-phenyl cyclohexanone with NH$_2$ | NT | NT | 3 | 198.7 |

TABLE 2-continued

Intrinsic clearance (Cl$_{int}$) and half-life (t$_{1/2}$) of ketamine and analogs in the presence of HLM under 2 incubation conditions. NT = not tested.

| Compound Number (rac = racemic) | Structure | Condition 1 (Low Activity) | | Condition 2 (High Activity) | |
|---|---|---|---|---|---|
| | | Cl$_{int}$ (µL/min/mg) | t$_{1/2}$ (min) | Cl$_{int}$ (µL/min/mg) | t$_{1/2}$ (min) |
| 11S | | NT | NT | 4 | 194.8 |
| 35rac | | 10 | 171 | 5 | 148 |
| 4rac | | 1 | 2590 | 1 | 819 |
| 3rac | | 19 | 87.5 | 5 | 150 |
| 2rac | | 6 | 291 | 3 | 199 |
| 38R | | NT | NT | 6 | 111 |
| 38S | | NT | NT | 6 | 109.5 |

TABLE 2-continued

Intrinsic clearance (Cl$_{int}$) and half-life (t$_{1/2}$) of ketamine and analogs in the presence of HLM under 2 incubation conditions. NT = not tested.

| Compound Number (rac = racemic) | Structure | Condition 1 (Low Activity) | | Condition 2 (High Activity) | |
|---|---|---|---|---|---|
| | | Cl$_{int}$ (μL/min/mg) | t$_{1/2}$ (min) | Cl$_{int}$ (μL/min/mg) | t$_{1/2}$ (min) |
| 29rac | | NT | NT | 5 | 140.0 |
| 29R | | <9.6* | >145* | NT | NT |
| 29S | | <9.6* | >145* | NT | NT |
| 30R | | NT | NT | 30 | 23.0 |
| 30S | | NT | NT | 61 | 11.4 |
| 19R | | NT | NT | 5 | 136.1 |

TABLE 2-continued

Intrinsic clearance (Cl$_{int}$) and half-life (t$_{1/2}$) of ketamine and analogs in the presence of HLM under 2 incubation conditions. NT = not tested.

| Compound Number (rac = racemic) | Structure | Condition 1 (Low Activity) | | Condition 2 (High Activity) | |
|---|---|---|---|---|---|
| | | Cl$_{int}$ (µL/min/mg) | t$_{1/2}$ (min) | Cl$_{int}$ (µL/min/mg) | t$_{1/2}$ (min) |
| 19S | 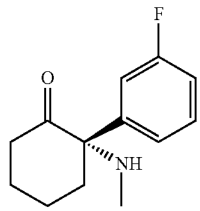 [SMILES: CN[C@]1(c2cccc(F)c2)CCCCC1=O] | NT | NT | 7 | 95.7 |
| 26R | 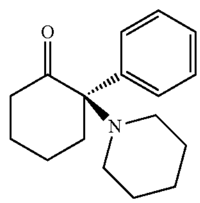 [SMILES: O=C1CCCC[C@]1(c1ccccc1)N1CCCCC1] | NT | NT | 11 | 63.2 |
| 26S | 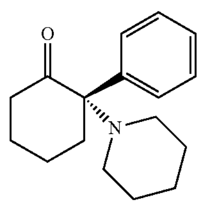 [SMILES: O=C1CCCC[C@@]1(c1ccccc1)N1CCCCC1] | NT | NT | 7 | 101.0 |
| 27rac | 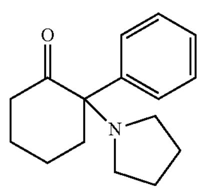 [SMILES: O=C1CCCCC1(c1ccccc1)N1CCCC1] | NT | NT | 3 | 232.0 |
| 27R | 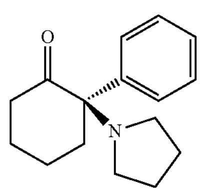 [SMILES: O=C1CCCC[C@]1(c1ccccc1)N1CCCC1] | <9.6* | >145* | NT | NT |
| 27S | 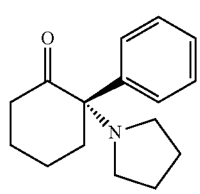 [SMILES: O=C1CCCC[C@@]1(c1ccccc1)N1CCCC1] | <9.6* | >145* | NT | NT |
| 86R | 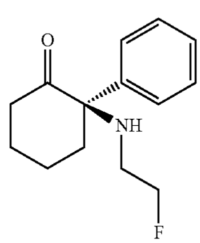 [SMILES: O=C1CCCC[C@@]1(NCCF)c1ccccc1] | NT | NT | 12 | 55.8 |

TABLE 2-continued

Intrinsic clearance ($Cl_{int}$) and half-life ($t_{1/2}$) of ketamine and analogs in the presence of HLM under 2 incubation conditions. NT = not tested.

| Compound Number (rac = racemic) | Structure | Condition 1 (Low Activity) | | Condition 2 (High Activity) | |
|---|---|---|---|---|---|
| | | $Cl_{int}$ (μL/min/mg) | $t_{1/2}$ (min) | $Cl_{int}$ (μL/min/mg) | $t_{1/2}$ (min) |
| 86S | 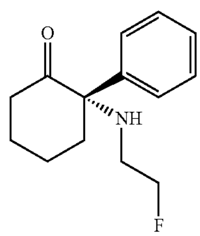 [SMILES: O=C1CCCC[C@]1(NCCF)c1ccccc1] | NT | NT | 11 | 61.9 |
| 88R | 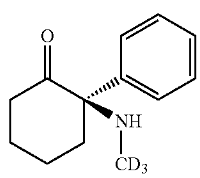 | NT | NT | 4 | 175.0 |
| 88S | 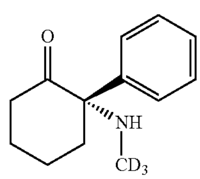 [SMILES: [2H]C([2H])([2H])N[C@]1(c2ccccc2)CCCCC1=O] | NT | NT | 4 | 166.9 |
| 84R | 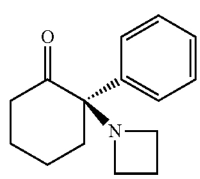 [SMILES: O=C1CCCC[C@]1(c1ccccc1)N1CCC1] | NT | NT | 4 | 165.0 |
| 84S | 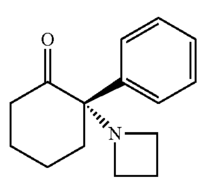 [SMILES: O=C1CCCC[C@@]1(c1ccccc1)N1CCC1] | NT | NT | 4 | 165.4 |
| 28R | 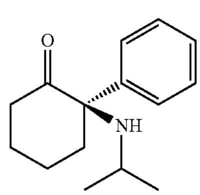 [SMILES: CC(C)N[C@@]1(c2ccccc2)CCCCC1=O] | 20* | 69.4* | NT | NT |
| 28S | 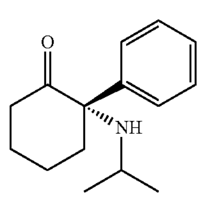 [SMILES: CC(C)N[C@]1(c2ccccc2)CCCCC1=O] | 18.1* | 76.6* | NT | NT |

TABLE 2-continued

Intrinsic clearance (Cl$_{int}$) and half-life (t$_{1/2}$) of ketamine and analogs in the presence of HLM under 2 incubation conditions. NT = not tested.

| Compound Number (rac = racemic) | Structure | Condition 1 (Low Activity) | | Condition 2 (High Activity) | |
|---|---|---|---|---|---|
| | | Cl$_{int}$ (μL/min/mg) | t$_{1/2}$ (min) | Cl$_{int}$ (μL/min/mg) | t$_{1/2}$ (min) |
| 31R | | 30.3* | 45.7* | NT | NT |
| 31S | | 22.7* | 61* | NT | NT |
| 114R | | <9.6* | >145* | NT | NT |
| 114S | | <9.6* | >145* | NT | NT |
| 120rac | | <9.6* | >145* | NT | NT |
| 117rac | | <9.6* | >145* | NT | NT |
| 118rac | | <9.6* | >145* | NT | NT |

TABLE 2-continued

Intrinsic clearance (Cl$_{int}$) and half-life (t$_{1/2}$) of ketamine and analogs in the presence of HLM under 2 incubation conditions. NT = not tested.

| Compound Number (rac = racemic) | Structure | Condition 1 (Low Activity) | | Condition 2 (High Activity) | |
|---|---|---|---|---|---|
| | | Cl$_{int}$ (µL/min/mg) | t$_{1/2}$ (min) | Cl$_{int}$ (µL/min/mg) | t$_{1/2}$ (min) |
| 18rac | 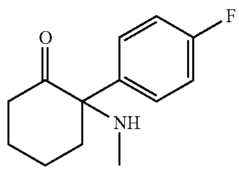 [SMILES: CNC1(c2ccc(F)cc2)CCCCC1=O] | <9.6* | >145* | NT | NT |
| 23rac | 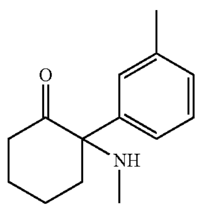 [SMILES: CNC1(c2cccc(C)c2)CCCCC1=O] | 10.4* | 133.4* | NT | NT |
| 119rac | 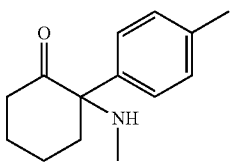 [SMILES: CNC1(c2ccc(C)cc2)CCCCC1=O] | <9.6* | >145* | NT | NT |
| 128mix | 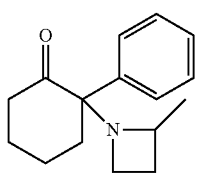 [SMILES: CC1CCN1C1(c2ccccc2)CCCCC1=O] | 15.9* | 87* | NT | NT |
| 129rac | 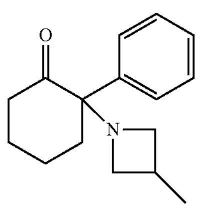 [SMILES: CC1CN(C2(c3ccccc3)CCCCC2=O)C1] | 10.4* | 133.9* | NT | NT |
| 25R | 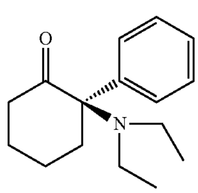 [SMILES: CCN(CC)[C@@]1(c2ccccc2)CCCCC1=O] | 28.3* | 49.0* | NT | NT |
| 25S | 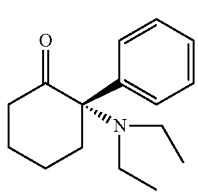 [SMILES: CCN(CC)[C@]1(c2ccccc2)CCCCC1=O] | 33.0* | 42.0* | NT | NT |

*Data collected using "Low Activity, Alternative Method".

Example 22. Metabolic Stability in Mouse Liver Microsomes

Disclosed compounds were tested for stability in mouse liver microsomes (MLM), with the results summarized in Table 3. Two microsomal incubation conditions were variously used, one with normal enzymatic activity (low activity) and one with higher enzymatic loading (high activity) intended to increase metabolic lability. Disclosed compounds exhibited greater metabolic stability than ketamine in this model under both conditions.

Drugs. Compounds were tested as the racemates (indicated by "rac" nomenclature) or pure enantiomers (indicated by "R" or "S" nomenclature).

MLM Stability (Low Activity). Pooled MLM from male CD-1 mice (XenoTech M1000) were used. Microsomal incubations were carried out in multi-well plates. Liver microsomal incubation medium consisted of PBS (100 mM, pH 7.4), $MgCl_2$ (1 mM), and NADPH (1 mM), with 0.50 mg of liver microsomal protein per mL. Control incubations were performed by replacing the NADPH-cofactor system with PBS. Test compounds (1 μM, final solvent concentration 1.0%) were incubated with microsomes at 37° C. with constant shaking. Six time points over 60 minutes were analyzed, with 60 μL aliquots of the reaction mixture being drawn at each time point. The reaction aliquots were stopped by adding 180 μL of cold (4° C.) acetonitrile containing 200 ng/mL tolbutamide and 200 ng/mL labetalol as internal standards (IS), followed by shaking for 10 minutes, and then protein sedimentation by centrifugation at 4000 rpm for 20 minutes at 4° C. Supernatant samples (80 μL) were diluted with water (240 μL) and analyzed for parent compound remaining using a fit-for-purpose liquid chromatography-tandem mass spectrometry (LC-MS/MS) method.

MLM Stability (High Activity). Pooled MLM from male BALB/c mice (XenoTech M3000) were used. Microsomal incubations were carried out in 96-well plates in 5 aliquots of 40 μL each (one for each time point). Liver microsomal incubation medium consisted of PBS (100 mM, pH 7.4), $MgCl_2$ (3.3 mM), NADPH (3 mM), glucose-6-phosphate (5.3 mM), and glucose-6-phosphate dehydrogenase (0.67 units/mL), with 1.0 mg of liver microsomal protein per mL. Control incubations were performed by replacing the NADPH-cofactor system with PBS. Test compounds (1 μM, final solvent concentration 1.6%) were incubated with microsomes at 37° C., shaking at 100 rpm. Incubations were performed in duplicate. Five time points over 60 minutes were analyzed. The reactions were stopped by adding 9 volumes of 90% acetonitrile-water to incubation aliquots, followed by protein sedimentation by centrifugation at 5500 rpm for 3 minutes. Supernatants were analyzed for parent compound remaining using a fit-for-purpose liquid chromatography-tandem mass spectrometry (LC-MS/MS) method, with authentic samples of each analyte used for identity confirmation.

Data Analysis. The elimination constant ($k_{el}$), half-life ($t_{1/2}$) and intrinsic clearance ($Cl_{int}$) were determined in a plot of ln(AUC) versus time, using linear regression analysis.

TABLE 3

Intrinsic clearance ($Cl_{int}$) and half-life ($t_{1/2}$) of ketamine and analogs in the presence of MLM under 2 incubation conditions. NT = not tested.

| Compound Number (rac = racemic) | Structure | Condition 1 (Low Activity) | | Condition 2 (High Activity) | |
|---|---|---|---|---|---|
| | | $Cl_{int}$ (μL/min/mg) | $t_{1/2}$ (min) | $Cl_{int}$ (μL/min/mg) | $t_{1/2}$ (min) |
| rac-ketamine | 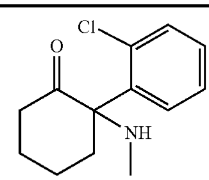 | NT | NT | 75 | 9.3 |
| 14R | 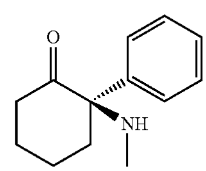 | NT | NT | 4 | 196.8 |
| 14S | 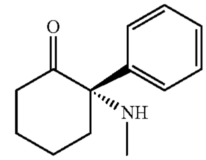 | NT | NT | 3 | 262.9 |
| 38R | 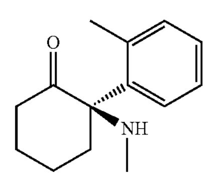 [SMILES: CN[C@@]1(c2ccccc2C)CCCCC1=O] | NT | NT | 23 | 30 |

TABLE 3-continued

Intrinsic clearance (Cl$_{int}$) and half-life (t$_{1/2}$) of ketamine and analogs in the presence of MLM under 2 incubation conditions.
NT = not tested.

| Compound Number (rac = racemic) | Structure | Condition 1 (Low Activity) | | Condition 2 (High Activity) | |
|---|---|---|---|---|---|
| | | Cl$_{int}$ (μL/min/mg) | t$_{1/2}$ (min) | Cl$_{int}$ (μL/min/mg) | t$_{1/2}$ (min) |
| 38S | 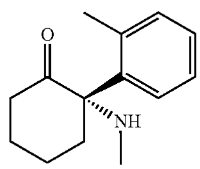 [SMILES: CN[C@]1(c2ccccc2C)CCCCC1=O] | NT | NT | 31 | 22.4 |
| 29rac | 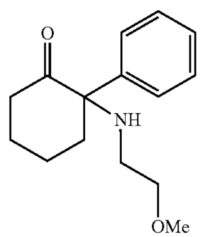 [SMILES: COCCNC1(c2ccccc2)CCCCC1=O] | NT | NT | 41 | 17.0 |
| 29R | 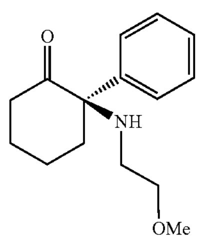 [SMILES: COCCN[C@@]1(c2ccccc2)CCCCC1=O] | 46.1 | 30.1 | NT | NT |
| 29S | 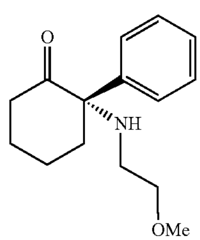 [SMILES: COCCN[C@]1(c2ccccc2)CCCCC1=O] | 35.8 | 35.7 | NT | NT |
| 30R | 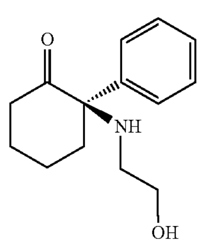 [SMILES: O=C1CCCC[C@@]1(NCCO)c1ccccc1] | NT | NT | 106 | 6.5 |
| 30S | 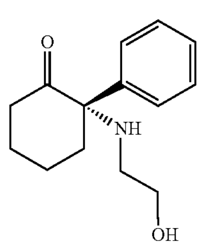 [SMILES: O=C1CCCC[C@]1(NCCO)c1ccccc1] | NT | NT | 162 | 4.3 |

TABLE 3-continued

Intrinsic clearance (Cl$_{int}$) and half-life (t$_{1/2}$) of ketamine and analogs in the presence of MLM under 2 incubation conditions. NT = not tested.

| Compound Number (rac = racemic) | Structure | Condition 1 (Low Activity) | | Condition 2 (High Activity) | |
|---|---|---|---|---|---|
| | | Cl$_{int}$ (μL/min/mg) | t$_{1/2}$ (min) | Cl$_{int}$ (μL/min/mg) | t$_{1/2}$ (min) |
| 19R | 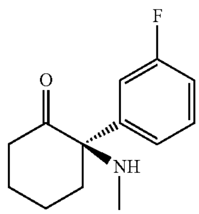 [SMILES: CN[C@@]1(c2cccc(F)c2)CCCCC1=O] | NT | NT | 12 | 59.9 |
| 19S | 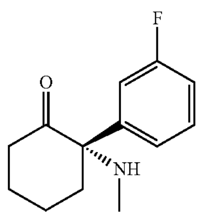 [SMILES: CN[C@]1(c2cccc(F)c2)CCCCC1=O] | NT | NT | 11 | 60.5 |
| 26R | 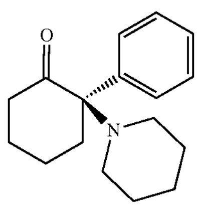 [SMILES: O=C1CCCC[C@]1(c1ccccc1)N1CCCCC1] | NT | NT | 65 | 10.6 |
| 26S | 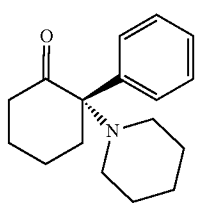 [SMILES: O=C1CCCC[C@@]1(c1ccccc1)N1CCCCC1] | NT | NT | 56 | 12.3 |
| 27rac | 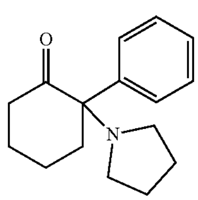 [SMILES: O=C1CCCCC1(c1ccccc1)N1CCCC1] | NT | NT | 20 | 35.0 |
| 27R | 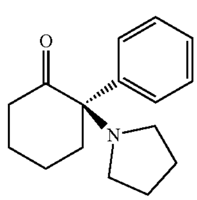 [SMILES: O=C1CCCC[C@]1(c1ccccc1)N1CCCC1] | 34.3 | 40.4 | NT | NT |
| 27S | 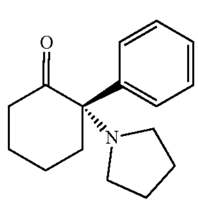 [SMILES: O=C1CCCC[C@@]1(c1ccccc1)N1CCCC1] | 33.8 | 41.0 | NT | NT |

TABLE 3-continued

Intrinsic clearance ($Cl_{int}$) and half-life ($t_{1/2}$) of ketamine and analogs in the presence of MLM under 2 incubation conditions.
NT = not tested.

| Compound Number (rac = racemic) | Structure | Condition 1 (Low Activity) | | Condition 2 (High Activity) | |
|---|---|---|---|---|---|
| | | $Cl_{int}$ (µL/min/mg) | $t_{1/2}$ (min) | $Cl_{int}$ (µL/min/mg) | $t_{1/2}$ (min) |
| 86R | 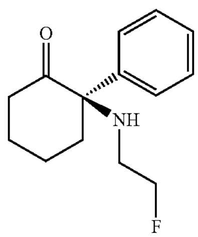 [SMILES: O=C1CCCC[C@@]1(NCCF)c1ccccc1] | NT | NT | 113 | 6.2 |
| 86S | 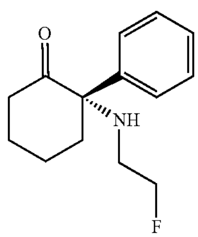 [SMILES: O=C1CCCC[C@]1(NCCF)c1ccccc1] | NT | NT | 82 | 8.5 |
| 88R | 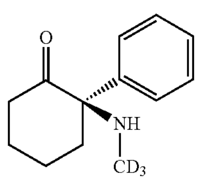 | NT | NT | 7 | 105.7 |
| 88S | 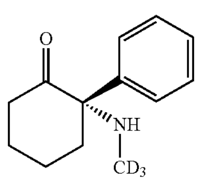 [SMILES: [2H]C([2H])([2H])N[C@]1(c2ccccc2)CCCCC1=O] | NT | NT | 6 | 111.4 |
| 84R | 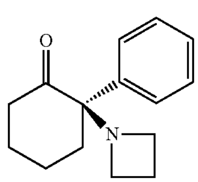 [SMILES: O=C1CCCC[C@]1(c1ccccc1)N1CCC1] | NT | NT | 30 | 22.7 |
| 84S | 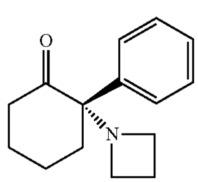 [SMILES: O=C1CCCC[C@@]1(c1ccccc1)N1CCC1] | NT | NT | 36 | 19.3 |
| 11R | 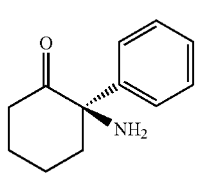 [SMILES: N[C@@]1(c2ccccc2)CCCCC1=O] | <9.6 | >145 | 4 | 169.1 |

TABLE 3-continued

Intrinsic clearance (Cl$_{int}$) and half-life (t$_{1/2}$) of ketamine and analogs in the presence of MLM under 2 incubation conditions.
NT = not tested.

| Compound Number (rac = racemic) | Structure | Condition 1 (Low Activity) | | Condition 2 (High Activity) | |
|---|---|---|---|---|---|
| | | Cl$_{int}$ (μL/min/mg) | t$_{1/2}$ (min) | Cl$_{int}$ (μL/min/mg) | t$_{1/2}$ (min) |
| 11S | 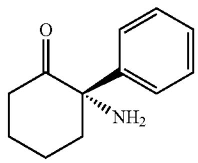 [SMILES: N[C@]1(c2ccccc2)CCCCC1=O] | <9.6 | >145 | 3 | 217.2 |
| 28R | 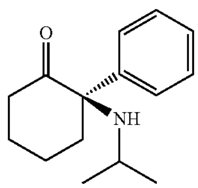 [SMILES: CC(C)N[C@@]1(c2ccccc2)CCCCC1=O] | 122.7 | 11.3 | NT | NT |
| 28S | 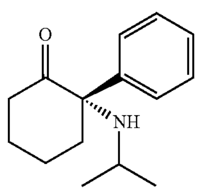 [SMILES: CC(C)N[C@]1(c2ccccc2)CCCCC1=O] | 94 | 14.8 | NT | NT |
| 31R | 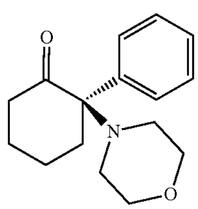 [SMILES: O=C1CCCC[C@]1(c1ccccc1)N1CCOCC1] | 123.9 | 11.2 | NT | NT |
| 31S | 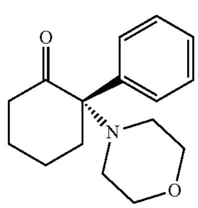 [SMILES: O=C1CCCC[C@@]1(c1ccccc1)N1CCOCC1] | 128 | 10.8 | NT | NT |
| 114R | 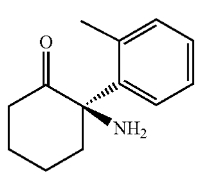 | 31.7 | 43.7 | NT | NT |
| 114S | 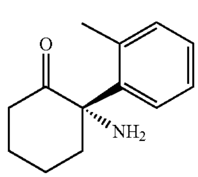 | 17.1 | 80.9 | NT | NT |

TABLE 3-continued

Intrinsic clearance (Cl$_{int}$) and half-life (t$_{1/2}$) of ketamine and analogs in the presence of MLM under 2 incubation conditions. NT = not tested.

| Compound Number (rac = racemic) | Structure | Condition 1 (Low Activity) | | Condition 2 (High Activity) | |
|---|---|---|---|---|---|
| | | Cl$_{int}$ (μL/min/mg) | t$_{1/2}$ (min) | Cl$_{int}$ (μL/min/mg) | t$_{1/2}$ (min) |
| 120rac | 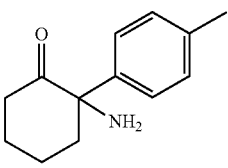 | 12.4 | 112.1 | NT | NT |
| 117rac | 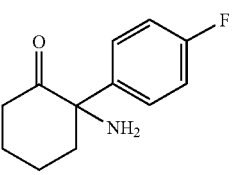 [SMILES: NC1(c2ccc(F)cc2)CCCCC1=O] | <9.6 | >145 | NT | NT |
| 118rac | 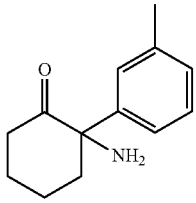 | 16.4 | 84.4 | NT | NT |
| 18rac | 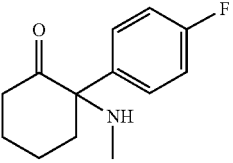 [SMILES: CNC1(c2ccc(F)cc2)CCCCC1=O] | 13.7 | 100.9 | NT | NT |
| 23rac | 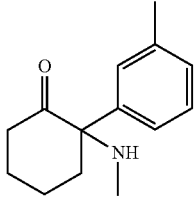 | 26.3 | 52.7 | NT | NT |
| 119rac | 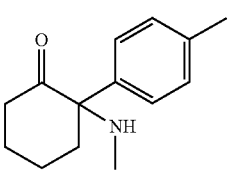 [SMILES: CNC1(c2ccc(C)cc2)CCCCC1=O] | 18.4 | 75.5 | NT | NT |
| 128mix | 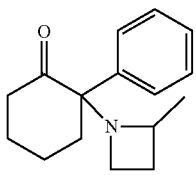 [SMILES: CC1CCN1C1(c2ccccc2)CCCCC1=O] | 68.3 | 20.3 | NT | NT |

TABLE 3-continued

Intrinsic clearance (Cl$_{int}$) and half-life (t$_{1/2}$) of ketamine and analogs in the presence of MLM under 2 incubation conditions.
NT = not tested.

| Compound Number (rac = racemic) | Structure | Condition 1 (Low Activity) | | Condition 2 (High Activity) | |
|---|---|---|---|---|---|
| | | Cl$_{int}$ (μL/min/mg) | t$_{1/2}$ (min) | Cl$_{int}$ (μL/min/mg) | t$_{1/2}$ (min) |
| 129rac | | 149.4 | 9.3 | NT | NT |
| 25R | | 162.6 | 8.5 | NT | NT |
| 25S | | 161.2 | 8.6 | NT | NT |

Example 23. Metabolic Stability in Rat Liver Microsomes

Figure 2:
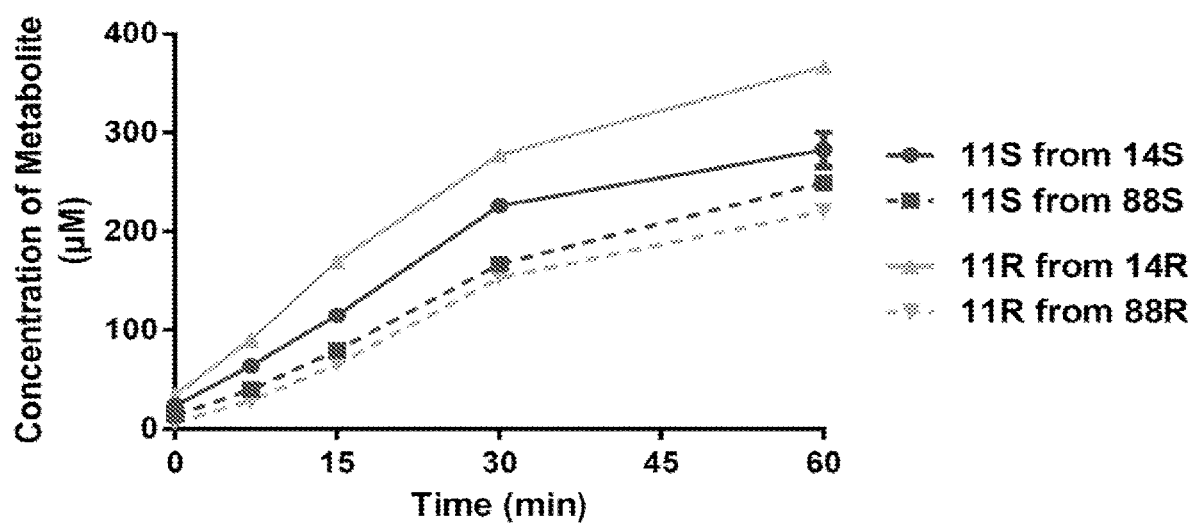
FIG. 2. Deuteration of compounds 14R and 14S at the N-methyl group, as in compounds 88R and 88S, respectively, attenuated formation of the metabolites 11R and 11S, respectively, in rat liver microsomes (RLM). The effect of deuteration was more pronounced with the R isomers. Compounds 88R and 88S were incubated with RLM under the High Activity conditions and concentrations of 11R and 11S formed, respectively, were determined by LC-MS/MS. All data points represent the mean±SEM of two incubations.

Disclosed compounds were tested for stability in rat liver microsomes (RLM), with the results summarized in Table 4. Two microsomal incubation conditions were variously used, one with normal enzymatic activity (low activity) and one with higher enzymatic loading (high activity) intended to increase metabolic lability. Disclosed compounds exhibited greater metabolic stability than ketamine in this model under both conditions. Further, deuterated compounds 88R and 88S exhibited increased metabolic stability and decreased formation of their respective metabolites 11R and 11S, compared to their non-deuterated counterparts 14R and 14S (Table 4 and FIG. 2). These effects on metabolism were more pronounced for the R isomers.

Drugs. Compounds were tested as the racemates (indicated by "rac" nomenclature) or pure enantiomers (indicated by "R" or "S" nomenclature).

RLM Stability (Low Activity). Pooled RLM from male Sprague Dawley rats (XenoTech R1000) were used. Microsomal incubations were carried out in multi-well plates. Liver microsomal incubation medium consisted of PBS (100 mM, pH 7.4), MgCl$_2$ (1 mM), and NADPH (1 mM), with 0.50 mg of liver microsomal protein per mL. Control incubations were performed by replacing the NADPH-cofactor system with PBS. Test compounds (1 μM, final solvent concentration 1.0%) were incubated with microsomes at 37° C. with constant shaking. Six time points over 60 minutes were analyzed, with 60 μL aliquots of the reaction mixture being drawn at each time point. The reaction aliquots were stopped by adding 180 μL of cold (4° C.) acetonitrile containing 200 ng/mL tolbutamide and 200 ng/mL labetalol as internal standards (IS), followed by shaking for 10 minutes, and then protein sedimentation by centrifugation at 4000 rpm for 20 minutes at 4° C. Supernatant samples (80 μL) were diluted with water (240 μL) and analyzed for parent compound remaining using a fit-for-purpose liquid chromatography-tandem mass spectrometry (LC-MS/MS) method.

RLM Stability (High Activity). Pooled RLM from male Sprague Dawley rats (XenoTech R1000, lot #1910100) were used. Microsomal incubations were carried out in 96-well plates in 5 aliquots of 40 μL each (one for each time point). Liver microsomal incubation medium consisted of PBS (100 mM, pH 7.4), MgCl$_2$ (3.3 mM), NADPH (3 mM), glucose-6-phosphate (5.3 mM), and glucose-6-phosphate dehydrogenase (0.67 units/mL), with 1.0 mg of liver microsomal protein per mL. Control incubations were performed by replacing the NADPH-cofactor system with PBS. Test compounds (1 μM, final solvent concentration 1.6%) were incubated with microsomes at 37° C., shaking at 100 rpm. Incubations were performed in duplicate. Five time points over 60 minutes were analyzed. The reactions were stopped by adding 9 volumes of 90% acetonitrile-water to incubation aliquots, followed by protein sedimentation by centrifugation at 5500 rpm for 3 minutes. Supernatants were analyzed for parent compound remaining using a fit-for-purpose liquid chromatography-tandem mass spectrometry (LC-MS/MS) method, with authentic samples of each analyte used for identity confirmation.

This condition was also used for experiments measuring the formation of metabolite 11R from compounds 14R and 88R and formation of metabolite 11S from compounds 14S and 88S. The concentrations of 11R and 11S formed during the incubations were quantified using a fit-for-purpose liquid chromatography-tandem mass spectrometry (LC-MS/MS) method, with authentic samples of each analyte used for calibration and identity confirmation.

Data Analysis. The elimination constant ($k_{el}$), half-life ($t_{1/2}$) and intrinsic clearance ($Cl_{int}$) were determined in a plot of ln(AUC) versus time, using linear regression analysis.

TABLE 4

Intrinsic clearance ($Cl_{int}$) and half-life ($t_{1/2}$) of ketamine and analogs in the presence of RLM under 2 incubation conditions. NT = not tested.

| Compound Number (rac = racemic) | Structure | Condition 1 (Low Activity) | | Condition 2 (High Activity) | |
|---|---|---|---|---|---|
| | | $Cl_{int}$ (µL/min/mg) | $t_{1/2}$ (min) | $Cl_{int}$ (µL/min/mg) | $t_{1/2}$ (min) |
| rac-ketamine | | NT | NT | 151 | 4.6 |
| 14R | | NT | NT | 38 | 18.2 |
| 14S | | NT | NT | 22 | 31.6 |
| 29rac | | NT | NT | 39 | 17.6 |
| 29R | | 43.0 | 32.2 | NT | NT |
| 29S | | 43.6 | 31.8 | NT | NT |

TABLE 4-continued

Intrinsic clearance (Cl$_{int}$) and half-life (t$_{1/2}$) of ketamine and analogs in the presence of RLM under 2 incubation conditions.
NT = not tested.

| Compound Number (rac = racemic) | Structure | Condition 1 (Low Activity) | | Condition 2 (High Activity) | |
| --- | --- | --- | --- | --- | --- |
| | | Cl$_{int}$ (μL/min/mg) | t$_{1/2}$ (min) | Cl$_{int}$ (μL/min/mg) | t$_{1/2}$ (min) |
| 19R | | NT | NT | 59 | 11.7 |
| 19S | | NT | NT | 37 | 18.8 |
| 27rac | | 39.1 | 35.4 | NT | NT |
| 27R | | 24.8 | 55.9 | NT | NT |
| 27S | | 25.8 | 53.7 | NT | NT |
| 88R | | NT | NT | 18 | 39.6 |
| 88S | | NT | NT | 13 | 52.8 |

TABLE 4-continued

Intrinsic clearance (Cl$_{int}$) and half-life (t$_{1/2}$) of ketamine and analogs in the presence of RLM under 2 incubation conditions.
NT = not tested.

| Compound Number (rac = racemic) | Structure | Condition 1 (Low Activity) | | Condition 2 (High Activity) | |
|---|---|---|---|---|---|
| | | Cl$_{int}$ (μL/min/mg) | t$_{1/2}$ (min) | Cl$_{int}$ (μL/min/mg) | t$_{1/2}$ (min) |
| 84R | 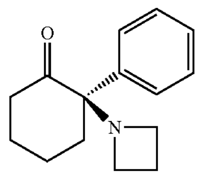 [SMILES: O=C1CCCC[C@]1(c1ccccc1)N1CCC1] | NT | NT | 32 | 21.8 |
| 84S | 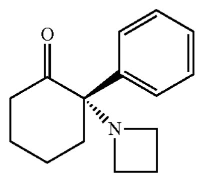 [SMILES: O=C1CCCC[C@@]1(c1ccccc1)N1CCC1] | NT | NT | 23 | 30.3 |
| 11R | 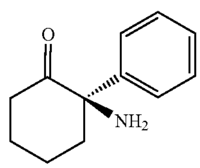 [SMILES: N[C@@]1(c2ccccc2)CCCCC1=O] | NT | NT | 7 | 103.4 |
| 11S | 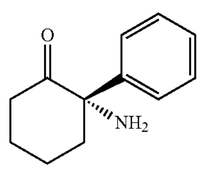 [SMILES: N[C@]1(c2ccccc2)CCCCC1=O] | NT | NT | 6 | 108.9 |
| 28R | 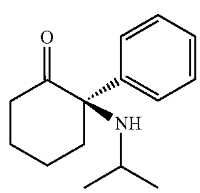 [SMILES: CC(C)N[C@@]1(c2ccccc2)CCCCC1=O] | 52.6 | 26.3 | NT | NT |
| 28S | 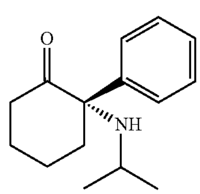 [SMILES: CC(C)N[C@]1(c2ccccc2)CCCCC1=O] | 73.4 | 18.9 | NT | NT |
| 31R | 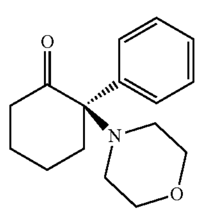 [SMILES: O=C1CCCC[C@]1(c1ccccc1)N1CCOCC1] | 203.7 | 6.8 | NT | NT |

TABLE 4-continued

Intrinsic clearance (Cl$_{int}$) and half-life (t$_{1/2}$) of ketamine and analogs in the presence of RLM under 2 incubation conditions. NT = not tested.

| Compound Number (rac = racemic) | Structure | Condition 1 (Low Activity) | | Condition 2 (High Activity) | |
|---|---|---|---|---|---|
| | | Cl$_{int}$ (µL/min/mg) | t$_{1/2}$ (min) | Cl$_{int}$ (µL/min/mg) | t$_{1/2}$ (min) |
| 31S | 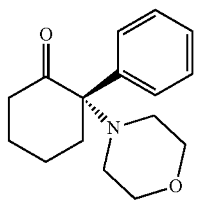 [SMILES: O=C1CCCC[C@@]1(c1ccccc1)N1CCOCC1] | 143.8 | 9.6 | NT | NT |
| 114R | 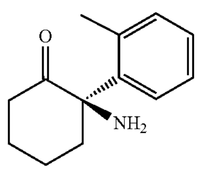 | 50.3 | 27.6 | NT | NT |
| 114S | 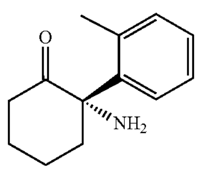 | 54.5 | 25.4 | NT | NT |
| 120rac | 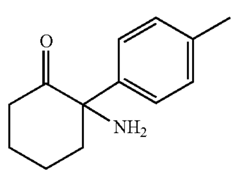 | 379.8 | 3.6 | NT | NT |
| 117rac | 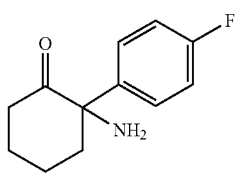 [SMILES: NC1(c2ccc(F)cc2)CCCCC1=O] | <9.6 | >145 | NT | NT |
| 118rac | 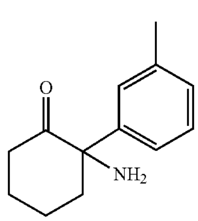 | 191.7 | 7.2 | NT | NT |
| 18rac | 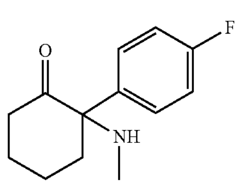 [SMILES: CNC1(c2ccc(F)cc2)CCCCC1=O] | 19.6 | 70.6 | NT | NT |

TABLE 4-continued

Intrinsic clearance (Cl$_{int}$) and half-life (t$_{1/2}$) of ketamine and analogs in the presence of RLM under 2 incubation conditions.
NT = not tested.

| Compound Number (rac = racemic) | Structure | Condition 1 (Low Activity) | | Condition 2 (High Activity) | |
|---|---|---|---|---|---|
| | | Cl$_{int}$ (µL/min/mg) | t$_{1/2}$ (min) | Cl$_{int}$ (µL/min/mg) | t$_{1/2}$ (min) |
| 23rac | 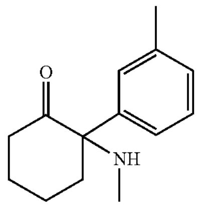 [SMILES: CNC1(c2cccc(C)c2)CCCCC1=O] | 389.5 | 3.6 | NT | NT |
| 119rac | 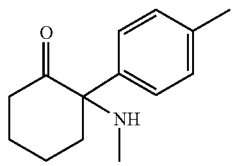 [SMILES: CNC1(c2ccc(C)cc2)CCCCC1=O] | 416.7 | 3.3 | NT | NT |
| 128mix | 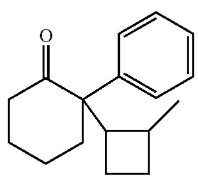 [SMILES: CC1CCC1C1(c2ccccc2)CCCCC1=O] | 50.6 | 27.4 | NT | NT |
| 129rac | 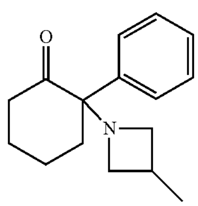 [SMILES: CC1CN(C2(c3ccccc3)CCCCC2=O)C1] | 57.5 | 24.1 | NT | NT |
| 25R | 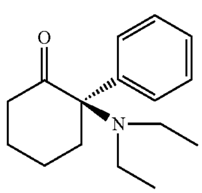 [SMILES: CCN(CC)[C@@]1(c2ccccc2)CCCCC1=O] | 90.3 | 15.3 | NT | NT |
| 25S | 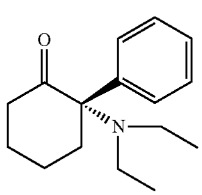 [SMILES: CCN(CC)[C@]1(c2ccccc2)CCCCC1=O] | 95.4 | 14.5 | NT | NT |

Example 24. Oral Bioavailability in Mice

In mice, disclosed compounds demonstrated improved absolute oral bioavailability (F), longer half-life (t$_{1/2}$), higher maximal concentrations (C$_{max}$), and higher absolute exposure as quantified by area under the curve (AUC), compared to ketamine in both plasma (Table 5) and brain (Table 6).

Method A:
Animals. Male CD-1 mice were used in these studies Animals were randomly assigned to treatment groups and were fasted for 4 h before dosing.

Drugs. Test compounds were dissolved in normal saline (ketamine) or de-ionized water (other compounds) and administered intravenously (iv) or orally (po) at a dose of 10 mg/kg (calculated based on freebase) and at a volume of 5 mL/kg body weight. Compounds were tested as the racemates (indicated by "rac" nomenclature) or pure enantiomers (indicated by "R" or "S" nomenclature).

Sample Collection and Bioanalysis. Blood samples were collected under 2,2,2-tribromoethanol anesthesia (150 mg/kg, ip) from the orbital sinus at 0.083, 0.25, 0.5, 1, 2, 4, 8 and 24 h (4 animals per time point) into microcontainers containing $K_2$EDTA Immediately after collection of blood, mice were euthanized by cervical dislocation and brain samples were collected at the same time points. All samples were immediately processed, flash-frozen, and stored at −70° C. until subsequent analysis. Plasma samples were separated by centrifugation of whole blood and aliquots (50 μL) were mixed with 200 μL of internal standard solution (400 ng/mL in 1:1 v/v $CH_3CN$:MeOH). After mixing by pipetting and centrifuging for 4 min at 6000 rpm, 0.5 μL of each supernatant was analyzed for drug using a fit-for-purpose liquid chromatography-tandem mass spectrometry (LC-MS/MS) method, with authentic samples of each analyte used for calibration and identification. Brain samples (weight 100 mg±1 mg) were dispersed in 500 μL, of internal standard solution (400 ng/mL in 4:1 v/v MeOH:water) using zirconium oxide beads (115 mg±5 mg) in The Bullet Blender® homogenizer for 30 s at speed 8. After homogenization, the samples were centrifuged for 4 min at 14,000 rpm and 0.5 μL of each supernatant was analyzed for drug using a fit-for-purpose LC-MS/MS method, with authentic samples of each analyte used for calibration and identification.

Data Analysis. The drug concentrations of samples below the lower limit of quantitation (LLOQ) were designated as zero. Pharmacokinetic data analysis was performed using noncompartmental, bolus injection or extravascular input analysis models in WinNonlin 5.2 (PharSight). Data points below LLOQ were presented as missing to improve validity of t112 calculations.

Method B:

Animals. Male CD-1 mice were used in these studies Animals were randomly assigned to treatment groups and were fasted for 4 h before oral dosing.

Drugs. Test compounds were dissolved in a vehicle consisting of normal saline (compounds 19S and 88R) or a mixture of 5% v/v N-methyl-2-pyrrolidone, 5% v/v Solutol HS-15, and 90% v/v normal saline (compounds 11S, 11R, 114S, and 114R). They were then administered intravenously (iv) or orally (po) at a dose of 10 mg/kg (calculated based on freebase) and at a volume of 5 mL/kg body weight. Compounds were tested as the racemates (indicated by "rac" nomenclature) or pure enantiomers (indicated by "R" or "S" nomenclature).

Sample Collection and Bioanalysis. Blood samples (approximately 60 μL) were collected under light isoflurane anesthesia (Surgivet®) from the retro orbital plexus at 0.08, 0.25, 0.5, 1, 2, 4, 8, and 24 h (4 animals per time point) Immediately after blood collection, plasma was harvested by centrifugation at 4000 rpm for 10 min at 4° C. and samples were stored at −70±10° C. until bioanalysis. Following blood collection, animals were immediately sacrificed, the abdominal vena-cava was cut open, and the whole body was perfused from the heart using 10 mL of normal saline, and brain samples were collected from all animals After isolation, brain samples were rinsed three times in ice-cold normal saline (for 5-10 seconds/rinse using ~5-10 mL normal saline in disposable petri dish for each rinse) and dried on blotting paper. Brain samples were homogenized using ice-cold phosphate-buffered saline (pH 7.4). Total homogenate volume was three times the tissue weight. All homogenates were stored at −70±10° C. until bioanalysis. For bioanalysis, 25 μL aliquots of plasma/brain study samples or spiked plasma/brain calibration standards were added to individual pre-labeled micro-centrifuge tubes followed by 100 μL of an internal standard solution (glipizide, 500 ng/mL in acetonitrile) except for blanks, where 100 μL of acetonitrile was added. Samples were vortexed for 5 minutes and then centrifuged for 10 minutes at 4000 rpm at 4° C. Following centrifugation, 100 μL of each clear supernatant was transferred to a 96 well plate and analyzed with a fit-for-purpose LC-MS/MS method, with authentic samples of each analyte used for calibration and identification.

Data Analysis. Pharmacokinetic parameters were estimated using the non-compartmental analysis tool of Phoenix® WinNonlin software (Ver 8.0).

TABLE 5

Selected pharmacokinetic parameters of ketamine and analogs in plasma of CD-1 mice.

| Compound Number (rac = racemic) | Structure | Method | $C_{max}$ (po) (ng/mL) | $AUC_{0-inf}$(iv) (ng*min/mL)* | $AUC_{0-inf}$(po) (ng*min/mL)* | $t_{1/2\ (iv)}$ (min) | $t_{1/2}$ (po) (min) | F (%) |
|---|---|---|---|---|---|---|---|---|
| rac-ketamine | (Cl-phenyl cyclohexanone NHMe) | A | 253 | 38,000 | 5,810 | 8.46 | 11.5 | 15 |
| 35rac | (F-phenyl cyclohexanone NHMe) | A | 618 | 77,900 | 21,800 | 15.1 | 19.7 | 28 |

TABLE 5-continued
Selected pharmacokinetic parameters of ketamine and analogs in plasma of CD-1 mice.
| Compound Number (rac = racemic) | Structure | Method | $C_{max}$ (po) (ng/mL) | $AUC_{0-inf}$ (iv) (ng*min/mL)* | $AUC_{0-inf}$ (po) (ng*min/mL)* | $t_{1/2\ (iv)}$ (min) | $t_{1/2}$ (po) (min) | F (%) |
|---|---|---|---|---|---|---|---|---|
| 14rac | 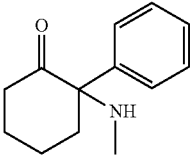 | A | 930 | 116,000 | 55,200 | 33.7 | 42.3 | 48 |
| 14R | 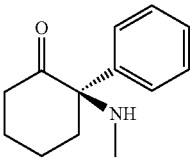 | A | 1700 | 211,000 | 84,400 | 70.5 | 55.3 | 40 |
| 14S | 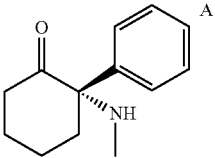 | A | 951 | 131,000 | 59,600 | 142 | 176 | 45.5 |
| 4rac | 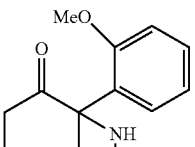 | A | 958 | 99,200 | 51,000 | 20.6 | 42.6 | 51 |
| 2rac | 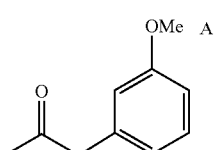 | A | 135 | 65,900 | 3,770 | 17.9 | 14.0 | 6 |
| 19S | 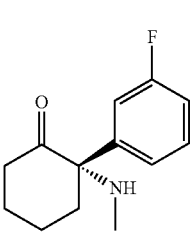 [SMILES: CN[C@]1(c2cccc(F)c2)CCCCC1=O] | B | 442 | 67,686 | 40,257 | 114 | 137 | 59 |
| 88R | 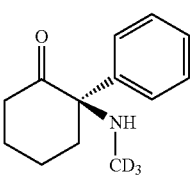 | B | 621 | 91,793 | 43,052 | 34.2 | 82.8 | 47 |

TABLE 5-continued

Selected pharmacokinetic parameters of ketamine and analogs in plasma of CD-1 mice.

| Compound Number (rac = racemic) | Structure | Method | $C_{max}$ (po) (ng/mL) | $AUC_{0-inf}$ (iv) (ng*min/mL)* | $AUC_{0-inf}$ (po) (ng*min/mL)* | $t_{1/2\ (iv)}$ (min) | $t_{1/2}$ (po) (min) | F (%) |
|---|---|---|---|---|---|---|---|---|
| 11S | 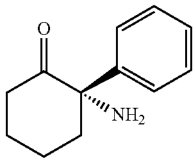 [SMILES: N[C@]1(c2ccccc2)CCCCC1=O] | B | 2128 | 205,480 | 251,829 | 63.6 | — | 123 |
| 11R | 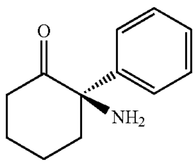 [SMILES: N[C@@]1(c2ccccc2)CCCCC1=O] | B | 1430 | 334,448 | 252,830 | 66.6 | 144.6 | 76 |
| 114S | 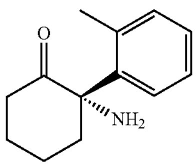 | B | 746 | 45,430 | 88,327 | 80.4 | 79.2 | 194 |
| 114R | 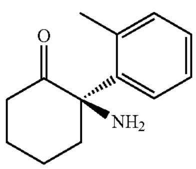 | B | 319 | 19,529 | 25,793 | 45.0 | 76.8 | 132 |

*For parameters determined by method B, AUC values represent $AUC_{0-last}$ and calculated F is based on these values rather than on $AUC_{0-inf}$.

TABLE 6

Selected pharmacokinetic parameters of ketamine and analogs in brains of CD-1 mice.

| Compound Number (rac = racemic) | Structure | Method | $C_{max}$ (po) (ng/g) | $AUC_{0-inf}$ (iv) (ng*min/g)* | $AUC_{0-inf}$ (po) (ng*min/g)* | $t_{1/2}$ (iv) (min) | $t_{1/2}$ (po) (min) | F (%)** |
|---|---|---|---|---|---|---|---|---|
| rac-ketamine | 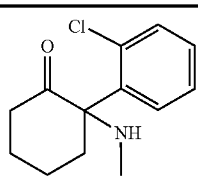 | A | 521 | 97,000 | 6,030 | 8.66 | 12.2 | 6.2 |
| 35rac | 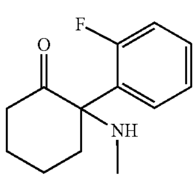 | A | 1,840 | 186,000 | 34,200 | 16.1 | 19.1 | 18 |
| 14rac | 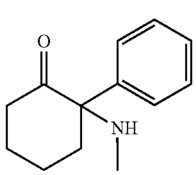 | A | 3,150 | 457,000 | 192,000 | 28.1 | 39.4 | 42 |

TABLE 6-continued

Selected pharmacokinetic parameters of ketamine and analogs in brains of CD-1 mice.

| Compound Number (rac = racemic) | Structure | Method | $C_{max}$ (po) (ng/g) | $AUC_{0\text{-}inf}$ (iv) (ng*min/g)* | $AUC_{0\text{-}inf}$ (po) (ng*min/g)* | $t_{1/2}$ (iv) (min) | $t_{1/2}$ (po) (min) | F (%)** |
|---|---|---|---|---|---|---|---|---|
| 14R | 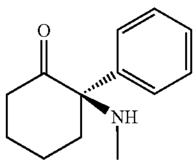 | A | 3640 | 548,000 | 192,000 | 716 | 44.1 | 35 |
| 14S | 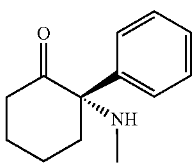 | A | 3480 | 507,000 | 166,000 | 127 | 104 | 33 |
| 4rac | 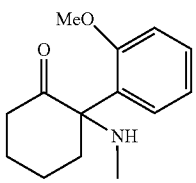 [SMILES: CNC1(c2ccccc2OC)CCCCC1=O] | A | 1,900 | 292,000 | 135,000 | 19.9 | 45.9 | 46 |
| 2rac | 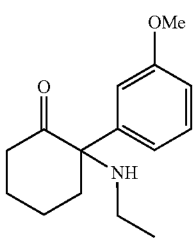 [SMILES: CCNC1(c2cccc(OC)c2)CCCCC1=O] | A | 420 | 279,000 | 11,800 | 16.1 | 16.6 | 4 |
| 19S | 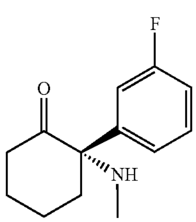 [SMILES: CN[C@]1(c2cccc(F)c2)CCCCC1=O] | B | 436 | 171,028 | 23,552 | 116 | 141 | 14 |
| 88R | 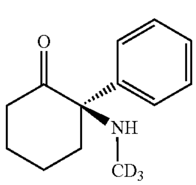 [SMILES: [2H]C([2H])([2H])N[C@@]1(c2ccccc2)CCCCC1=O] | B | 3095 | 334,518 | 143,445 | 36.0 | 79.8 | 43 |
| 11S | 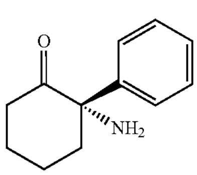 [SMILES: N[C@]1(c2ccccc2)CCCCC1=O] | B | 2187 | 434,023 | 292,247 | 42.0 | — | 67 |

TABLE 6-continued

Selected pharmacokinetic parameters of ketamine and analogs in brains of CD-1 mice.

| Compound Number (rac = racemic) | Structure | Method | $C_{max}$ (po) (ng/g) | $AUC_{0-inf}$(iv) (ng*min/g)* | $AUC_{0-inf}$(po) (ng*min/g)* | $t_{1/2}$ (iv) (min) | $t_{1/2}$ (po) (min) | F (%)** |
|---|---|---|---|---|---|---|---|---|
| 11R | (structure) | B | 1474 | 621,341 | 220,091 | 70.2 | 114 | 35 |
| 114S | (structure) | B | 825 | 244,634 | 86,338 | — | — | 35 |
| 114R | (structure) | B | 683 | 155,752 | 38,185 | 19.2 | 67.2 | 25 |

*For parameters determined by method B, AUC values represent $AUC_{0-last}$ and calculated F is based on these values rather than on $AUC_{0-inf}$.
**Calculated based on brain exposure.

Example 25. Exposure After Intraperitoneal Administration in Mice

In mice, intraperitoneal (ip) administration of compounds 14R and 14S at 3.16 mg/kg resulted in values of maximal concentration ($C_{max}$) and absolute exposure as quantified by area under the curve (AUC) that were comparable to, or higher than, those achieved by ketamine after the higher dose of 10 mg/kg, in both plasma (Table 7) and brain (Table 8). Accordingly, exposure to 14R and 14S is much higher than ketamine after ip administration when scaled for dose equivalency. Further, exposure (AUC) to 14R was roughly 2-fold higher than exposure to 14S after the same dose, suggesting greater metabolic stability for the R isomer.

Animals. Male CD-1 mice were used in these studies Animals were randomly assigned to treatment groups and were fasted for 4 h before dosing.

Drugs. Test compounds (HCl salts) were dissolved in de-ionized water and administered intraperitoneally (ip) at the indicated doses (calculated based on freebase) and at a volume of 5 mL/kg body weight. Compounds were tested as the racemates (indicated by "rac" nomenclature) or pure enantiomers (indicated by "R" or "S" nomenclature), as indicated.

Pharmacokinetics. Blood samples were collected under 2,2,2-tribromoethanol anesthesia (150 mg/kg, ip) from the orbital sinus at 0.083, 0.25, 0.5, 1, and 2 h (ketamine, 4 animals per time point) or 0.083, 0.25, 0.5, 1, 2, 4, and 8 h (14R and 14S, 4 animals per time point) into microcontainers containing $K_2EDTA$ Immediately after collection of blood, mice were euthanized by cervical dislocation and brain samples were collected at the same time points. All samples were immediately processed, flash-frozen, and stored at −70° C. until subsequent analysis. Plasma samples were separated by centrifugation of whole blood and aliquots (50 μL) were mixed with 200 μL, of internal standard solution (400 ng/mL in 1:1 v/v $CH_3CN$:MeOH). After mixing by pipetting and centrifuging for 4 min at 6000 rpm, 0.5 μL of each supernatant was analyzed for drug using a fit-for-purpose liquid chromatography-tandem mass spectrometry (LC-MS/MS) method, with authentic samples of each analyte used for calibration and identification. Brain samples (weight 200 mg±1 mg) were dispersed in 800 μL of internal standard solution (400 ng/mL in 4:1 v/v MeOH:water) using zirconium oxide beads (115 mg±5 mg) in The Bullet Blender® homogenizer for 30 s at speed 8. After homogenization, the samples were centrifuged for 4 min at 14,000 rpm and 0.5 μL of each supernatant was analyzed for drug using a fit-for-purpose LC-MS/MS method, with authentic samples of each analyte used for calibration and identification.

Data Analysis. The drug concentrations of samples below the lower limit of quantitation (LLOQ) were designated as zero. Pharmacokinetic data analysis was performed using noncompartmental, bolus injection or extravascular input analysis models in WinNonlin 5.2 (PharSight). Data points below LLOQ were presented as missing to improve validity of t1l2 calculations.

TABLE 7

Selected pharmacokinetic parameters of ketamine and analogs in plasma of CD-1 mice after ip administration.

| Compound Number (rac = racemic) | Structure | Dose, ip (mg/kg) | $C_{max}$ (ng/mL) | $AUC_{0-inf}$ (ng*min/mL) |
|---|---|---|---|---|
| rac-ketamine | [structure] | 10 | 822 | 22,900 |
| 14R | [structure] | 3.16 | 1,010 | 42,200 |
| 14S | [structure] | 3.16 | 875 | 23,100 |

TABLE 8

Selected pharmacokinetic parameters of ketamine and analogs in brains of CD-1 mice after ip administration.

| Compound Number (rac = racemic) | Structure | Dose, ip (mg/kg) | $C_{max}$ (ng/mL) | $AUC_{0-inf}$ (ng*min/mL) |
|---|---|---|---|---|
| rac-ketamine | [structure] | 10 | 2,250 | 43,500 |
| 14R | [structure] | 3.16 | 3,320 | 152,000 |
| 14S | [structure] | 3.16 | 3,370 | 73,000 |

Example 26. Oral Bioavailability in Rats

In rats, compounds disclosed herein demonstrated improved absolute oral bioavailability (F), longer half-life ($t_{1/2}$), higher maximal concentrations ($C_{max}$), and higher absolute exposure as quantified by area under the curve (AUC), compared to ketamine in plasma (Table 9). These studies also showed that deuteration of the N-methyl group, as in compound 88R, increased the oral bioavailability of this compound compared to its non-deuterated counterpart 14R. Formation of the metabolite 11R from 88R was also reduced compared to formation of the same metabolite from the non-deuterated compound 14R after oral administration (Table 10).

Method A:

Animals. Male Sprague Dawley rats were used in these studies Animals were randomly assigned to treatment groups and were fasted overnight before oral dosing.

Drugs. The test compound was dissolved in normal saline and administered intravenously (iv) or orally (po) at a dose of 10 mg/kg (calculated based on freebase) and at a volume of 5 mL/kg body weight. The compound was tested as the racemate (indicated by "rac" nomenclature).

Sample Collection and Bioanalysis. Blood samples were collected through external jugular vein (via cannulation) at 0.083, 0.25, 0.5, 1, 2, 4, 8 and 24 h post-dose (total 8 time points/rat, 4 rats per administration route). At each time point, ~0.2 mL of blood was withdrawn and transferred into a pre-labeled 0.5 mL of micro centrifuge tube containing 4 μL of 200 mM $K_2EDTA$ solution as anticoagulant and mixed gently by inverting the tube to facilitate mixing of anticoagulant with the blood. Blood samples were kept on ice until centrifugation. The collected blood samples were centrifuged at 4000 rpm for 10 min at 4° C. Plasma samples were separated after centrifugation, transferred into pre-labeled tubes, and stored at −70° C. until bioanalysis. For bio analysis, 50 μL aliquots of plasma study samples or calibration standards were added to pre-labeled eppendorf tubes and 10 μL of an internal standard solution (diclofenac, 5 μg/mL in 50:50 v/v methanol:water) was added. Samples were quenched with 500 μL of precipitation solution (0.1% v/v formic acid in acetonitrile) and vortexed. All the samples were centrifuged at 14,000 rpm for 10 minutes at 4° C. Following centrifugation, 5 μL of each clear supernatant was analyzed with a fit-for-purpose LC-MS/MS method, with authentic samples of the analyte used for calibration and identification.

Data Analysis. Pharmacokinetic parameters were estimated using the non-compartmental analysis tool of Phoenix® WinNonlin software (Ver 8.1). The drug concentrations of samples below the lower limit of quantitation (LLOQ) were designated as zero.

Method B:

Animals. Male Sprague Dawley rats were used in these studies. Animals were randomly assigned to treatment groups and were fasted overnight before oral dosing.

Drugs. Test compounds were dissolved in a vehicle consisting of normal saline (compounds 14R, 88R, 29rac, and 27rac) or a mixture of 5% v/v N-methyl-2-pyrrolidone, 5% v/v Solutol HS-15, and 90% v/v normal saline (compounds 84R and 84S). They were then administered intravenously (iv) or orally (po) at a dose of 10 mg/kg (calculated based on freebase) and at a volume of 5 mL/kg body weight. Compounds were tested as the racemates (indicated by "rac" nomenclature) or pure enantiomers (indicated by "R" or "S" nomenclature).

Sample Collection and Bioanalysis. Blood samples (approximately 120 μL) were collected under light isoflurane anesthesia (Surgivet®) from the retro orbital plexus at 0.08, 0.25, 0.5, 1, 2, 4, 8, and 24 h (total 8 time points/rat, 4 rats per administration route per compound). Immediately after blood collection, plasma was harvested by centrifugation at 4000 rpm for 10 min at 4° C. and samples were stored at −70±10° C. until bioanalysis. For bioanalysis, 25 μL aliquots of plasma study samples or spiked plasma calibration standards were added to individual pre-labeled micro-centrifuge tubes followed by 100 μL of an internal standard solution (glipizide, 500 ng/mL in acetonitrile) except for blanks, where 100 μL of acetonitrile was added. Samples were vortexed for 5 minutes and then centrifuged for 10 minutes at 4000 rpm at 4° C. Following centrifugation, 100 μL of each clear supernatant was transferred to a 96 well plate and analyzed with a fit-for-purpose LC-MS/MS method, with authentic samples of each analyte used for calibration and identification. In the case of compounds 14R and 88R, their metabolite 11R was also quantified in plasma samples.

Data Analysis. Pharmacokinetic parameters were estimated using the non-compartmental analysis tool of Phoenix® WinNonlin software (Ver 8.0).

TABLE 9

Selected pharmacokinetic parameters of ketamine and analogs in plasma of Sprague Dawley rats.

| Compound Number (rac = racemic) | Structure | Method | $C_{max}$ (po) (ng/mL) | $AUC_{0-last}$ (iv) (ng*min/mL) | $AUC_{0-last}$ (po) (ng*min/mL) | $t_{1/2}$ (iv) (min) | $t_{1/2}$ (po) (min) | F (%) |
|---|---|---|---|---|---|---|---|---|
| rac-ketamine | 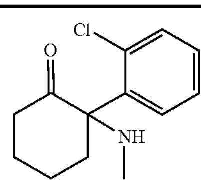 | A | 190 | 80,400 | 7,260 | 41.6 | 33.7 | 9 |
| 14R | 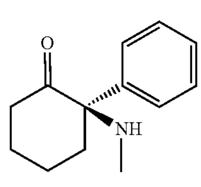 | B | 235 | 117,619 | 14,245 | 37.8 | 30.6 | 12 |
| 88R | 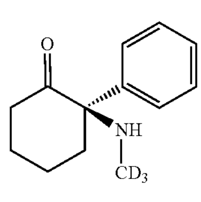 [SMILES: [2H]C([2H])([2H])N[C@@]1(c2ccccc2)CCCCC1=O] | B | 393 | 100,385 | 20,079 | 59.4 | 45.6 | 20 |

TABLE 9-continued

Selected pharmacokinetic parameters of ketamine and analogs in plasma of Sprague Dawley rats.

| Compound Number (rac = racemic) | Structure | Method | $C_{max}$ (po) (ng/mL) | $AUC_{0-last}$ (iv) (ng*min/mL) | $AUC_{0-last}$ (po) (ng*min/mL) | $t_{1/2}$ (iv) (min) | $t_{1/2}$ (po) (min) | F (%) |
|---|---|---|---|---|---|---|---|---|
| 29rac | 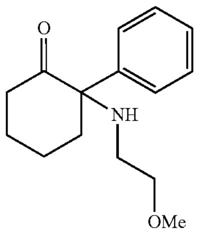 [SMILES: COCCNC1(c2ccccc2)CCCCC1=O] | B | 321 | 102,565 | 21,157 | 66.0 | 69.0 | 21 |
| 27rac | 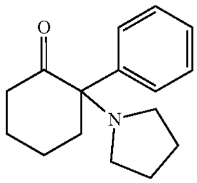 [SMILES: O=C1CCCCC1(c1ccccc1)N1CCCC1] | B | 197 | 102,710 | 33,808 | 97.2 | 145.2 | 33 |
| 84R | 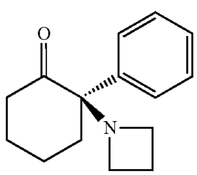 [SMILES: O=C1CCCC[C@]1(c1ccccc1)N1CCC1] | B | 15.5 | 22,140 | 713 | 37.2 | 27 | 3 |
| 84S | 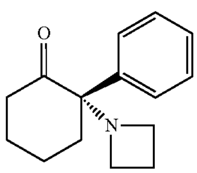 [SMILES: O=C1CCCC[C@@]1(c1ccccc1)N1CCC1] | B | 69.8 | 28,920 | 4,620 | 46.2 | 37.2 | 16 |

TABLE 10

Exposure to metabolite 11R after administration of compounds 14R and 88R at 10 mg/kg, iv or po, in plasma of Sprague Dawley rats.

| Compound Administered and Route | Method | $C_{max}$ 11R (ng/mL) | $AUC_{0-last}$ 11R (ng*min/mL) |
|---|---|---|---|
| 14R, iv | B | 229 | 153, 254 |
| 14R, po | B | 1334 | 169, 634 |
| 88R, iv | B | 179 | 131, 031 |
| 88R, po | B | 1090 | 118, 615 |

Example 27. NMDA Receptor Binding

The binding affinities of disclosed compounds the MK-801 binding site of the N-methyl-D-aspartate receptor (NMDAR) were determined in radioligand binding experiments (Table 11). Values shown for racemic ketamine (rac-ketamine) and its enantiomers are drawn from the literature (Ebert et al. 1997). Generally, the R enantiomers of compounds of the present invention exhibited weaker binding affinity for NMDAR, suggesting reduced dissociative side effects for these compounds compared to their corresponding S enantiomers or racemates. In contrast, the S isomers, in light of their higher potency at NMDAR, may have higher potency as anesthetics. For example, compound 14R displayed weaker NMDAR binding than rac-ketamine, (R)-ketamine, (S)-ketamine, and 14S, suggesting that it is likely to have less pronounced dissociative side effects than these compound at equimolar doses. Many of the compounds of the invention exhibited affinity in the ideal range of 1-5 μM, including, for example, 14R, 11S, 88R, 27rac, 29rac, 19S, 114S, and 18rac. In certain cases, the R isomer exhibited activity in the target affinity range, in other cases the S isomer was more desirable, and in some cases, both stereoisomers or the racemate fell in the desired range. Indeed, the eudysmic ratio for each pair of enantiomers was quite variable, in some cases being <2, while in other cases it ranged up to ~10.

TABLE 11

Binding affinity at the MK-801 site of NMDAR.

| Compound (rac = racemic) | NMDAR $K_i$ ± SEM (μM) | Method |
|---|---|---|
| rac-ketamine | 0.53 ± 0.078* | NA |
| (R)-ketamine | 1.4 ± 0.1* | NA |
| (S)-ketamine | 0.30 ± 0.013* | NA |
| 14rac | 0.76 | A |
| 14R | 4.5 | B |
| 14S | 0.69 | B |

TABLE 11-continued

Binding affinity at the MK-801 site of NMDAR.

| Compound (rac = racemic) | NMDAR $K_i$ ± SEM (μM) | Method |
|---|---|---|
| 35rac | 1.82 | A |
| 35R | 3.91 ± 0.40 | A |
| 35S | 0.79 ± 0.21 | A |
| 38R | 0.74 | B |
| 38S | 0.24 | B |
| 4rac | 35 | A |
| 78rac | 4.0 | A |
| 16rac | 2.0 | A |
| 11rac | 1.4 | A |
| 11R | 9.4 | B |
| 11S | 1.2 | B |
| 12rac | 1.3 | A |
| 3rac | 0.99 | A |
| 1rac | 0.30 | A |
| 29rac | 4.4 | B |
| 29R | >23 | B |
| 29S | 8.2 | B |
| 19R | 6.8 | B |
| 19S | 2.1 | B |
| 26R | 3.7 | B |
| 26S | 0.52 | B |
| 27rac | 1.1 | B |
| 27R | 3.1 | B |
| 27S | 1.1 | B |
| 86R | 7.1 | B |
| 86S | 1.3 | B |
| 88R | 3.4 | B |
| 88S | 0.80 | B |
| 84R | 2.3 | B |
| 84S | 1.3 | B |
| 114R | >23 | B |
| 114S | 2.5 | B |
| 30R | >23 | B |
| 30S | 23 | B |
| 28R | >23 | B |
| 28S | 3.0 | B |
| 31R | >23 | B |
| 31S | >23 | B |
| 120rac | 23 | B |
| 117rac | 8.4 | B |
| 118rac | 4.5 | B |
| 18rac | 4.5 | B |
| 23rac | 4.6 | B |
| 119rac | 16.7 | B |
| 25R | 5.5 | B |
| 25S | 5.2 | B |
| 128mix** | 1.9 | B |
| 129rac | 0.52 | B |

*Ebert et.al. 1997
**Mixture of all 4 diastereomers

Radioligand Binding—Method A. Affinity of the test compounds for NMDAR was determined in radioligand binding experiments with [³H]MK-801 by Eurofins Panlabs, Inc., using methods adapted from the literature (Javitt et al. 1987; Reynolds et al. 1989) and under the conditions described in Table 12.

TABLE 12

NMDAR radioligand binding experimental parameters for Method A.

| | |
|---|---|
| Receptor Source | Wistar rat brain (minus cerebellum) |
| Vehicle | 1.0% DMSO |
| Incubation Time | 3 h |
| Incubation Temperature | 25° C. |
| Incubation Buffer | 5 mM Tris-HCl, pH 7.4 |
| Ligand | 5.0 nM [³H]MK-801 |
| Non-Specific Ligand | 10.0 μM (+)-MK-801 |
| Specific Binding | 90%* |

TABLE 12-continued

NMDAR radioligand binding experimental parameters for Method A.

| | |
|---|---|
| $K_d$ | 12.0 nM* |
| $B_{max}$ | 1.30 pmol/mg protein* |

*historical values

Radioligand Binding—Method B. Affinity of the test compounds for NMDAR was determined in radioligand binding experiments with [³H]MK-801 by WuXi AppTec (Hong Kong) Limited, under the conditions described in Table 13.

TABLE 13

NMDAR radioligand binding experimental parameters for Method B.

| | |
|---|---|
| Receptor Source | male Sprague Dawley rat cortex |
| Incubation Time | 1 h |
| Incubation Temperature | 25° C. |
| Incubation Buffer | 50 mM Tris-HCl, pH 7.4 |
| Ligand | 5.0 nM [³H]MK-801 |
| Non-Specific Ligand | 10.0 μM (+)-MK-801 |

Example 28. Activity at Monoamine Transporters

The ability of the compounds of the present invention to inhibit uptake of monoamines by the serotonin transporter (SERT), norepinephrine transporter (NET), dopamine transporter (DAT), and vesicular monoamine transporter 2 (VMAT2) (collectively monoamine transporters, MATs) was measured using fluorescent substrate uptake assays in transfected cells (Table 14). The binding affinities of select compounds were also determined in radioligand displacement assays at SERT, NET, and/or DAT (Table 14). Activity was generally greatest with compounds containing a cyclic moiety on the amine. For example, compounds 26, 27, and 84 all exhibited $IC_{50}$s for monoamine uptake of <10 μM at one or more of the tested MATs. The activity of compound 27S was particularly noteworthy, as it exhibited an $IC_{50}$ of 0.041 μM at SERT. However, there were notable exceptions to the trend of greater MAT inhibitory activity for cyclic amines, as the enantiomers of compound 31, containing a morpholine ring, exhibited almost no activity at MATs. Considering that inhibitors of MATs are well known to have antidepressant and anxiolytic effects and are among the most commonly prescribed drugs for mood disorders (e.g. fluoxetine, sertraline, venlafaxine, imipramine, etc.), blockade of MATs by certain compounds of the present invention is expected to synergize with their NMDAR inhibition to increase therapeutic activity for treating depression and related disorders. Indeed, such synergy between these two mechanisms of action has been demonstrated in animal models (Ates-Alagoz and Adej are 2013). Further, a compound with sufficient potency at both targets might be envisioned as a replacement for two separate drugs targeting a MAT and NMDAR individually. For example, a compound such as 27S, with significant affinity at both SERT and NMDAR, might replace a combination of a selective serotonin reuptake inhibitor (SSRI), such as fluoxetine, and an NMDAR antagonist, such as ketamine, with a single therapeutic agent. Further, the ability to tune the ratio between MATs and NMDAR and among the different MATs themselves is useful to obtain the optimal therapeutic profile depending on the intended clinical indication. For example, compounds with greater selectivity for NMDAR, such as 14R, 11S, 88R, 29rac, 19S, 114S, or 18rac, might be preferred treatments for patients who are intolerant of the side effects of MAT inhibitors. Alternatively, compounds with significant inhibitory activity at DAT, such as 26R or 28S, might be useful treatments for psychostimulant abuse.

in the absence of an inhibitor and 2) a masking dye that inhibits the fluorescence of dye 1 in the extracellular compartment. Therefore, the overall fluorescence of the system increases as the fluorescent dye is transported into the cells.

TABLE 14

Uptake inhibition activity and binding affinity at monoamine transporters.

| Compound | % Uptake Inhibition @ 10 µM (Uptake IC$_{50}$, µM) | | | | $K_i$ (µM) | | |
|---|---|---|---|---|---|---|---|
| | SERT | NET | DAT | VMAT2 | SERT | NET | DAT |
| 38R | 41.5 | 20.3 | −2.2 | 2.9 | — | — | — |
| 38S | 39.7 | 2.7 | 8.3 | −11.2 | — | — | — |
| 14S | 17.0 (30.6) | 1.8 | −4.5 | 7.4 | 45.1 | — | — |
| 14R | 19.3 (45.5) | 1.7 | −4.5 | 6.2 | 40.0 | — | — |
| 30R | 1.2 | 3.5 | 8.5 | 16.3 | — | — | — |
| 30S | 51.9 | 22.3 | 18.7 | 23.2 | — | — | — |
| 29 | 10.0 | 3.9 | 9.6 | 13.7 | — | — | — |
| 29S | −12.9 | 4.0 | 13.7 | −10.5 | | | |
| 29R | 19.6 | −16.0 | −7.1 | −31.9 | | | |
| 19R | 20.9 | 8.8 | −10.7 | 11.0 | — | — | — |
| 19S | 20.6 | 10.3 | 18.1 | −0.87 | — | — | — |
| 26R | 30.4 (>100) | 19.5 (23.7) | 58.0 (5.0) | −12.3 | 22.5 | >87.4 | 70.4 |
| 26S | 42.95 (44.0) | 16.1 (8.9) | 33.7 (16.4) | 22.9 | 8.2 | >87.4 | 79.5 |
| 27rac | 88.6 (0.45) | 40.8 (4.9) | 49.5 (6.5) | 60.4 (11.2) | 0.11 | 11.5 | 55.1 |
| 27S | (0.041) | (8.5) | (10.9) | (19.3) | — | — | — |
| 27R | (2.1) | (17.3) | (21.0) | (18.1) | — | — | — |
| 86S | 14.1 | 12.2 | 20.8 | −5.5 | — | — | — |
| 86R | 7.1 | 11.4 | 13.6 | −8.9 | — | — | — |
| 88S | 28.2 | 21.6 | 18.6 | −6.0 | — | — | — |
| 88R | 25.9 | 10.6 | 7.9 | 20.2 | — | — | — |
| 84R | 75.2 (0.80) | 29.1 (15.4) | 28.2 (19.4) | 14.1 (98.2) | 0.60 | 77.8 | >94.7 |
| 84S | 91.9 (0.94) | 34.9 (29.7) | 32.2 (19.5) | 10.9 (>100) | 0.72 | 53.8 | 91.4 |
| 11S | −2.6 | 14.8 | 10.1 | −17.4 | — | — | — |
| 11R | 0.19 | 10.4 | −11.8 | 14.4 | — | — | — |
| 28R | 37.2 (7.3) | 11.4 | 16.5 | −11.4 | 8.6 | — | — |
| 28S | 22.0 (8.5) | 48.7 (4.7) | 58.0 (1.3) | −32.7 | 12.3 | 13.5 | 6.0 |
| 31S | −7.9 | 1.6 | 16.9 | −5.5 | — | — | — |
| 31R | −1.2 | 1.3 | 9.8 | −3.4 | — | — | — |
| 114S | −4.0 | 10.4 | −15.2 | −15.9 | — | — | — |
| 114R | 23.4 | 7.7 | 6.2 | −14.0 | — | — | — |
| 120rac | 27.5 | 7.1 | 5.3 | 41.0 | — | — | — |
| 117rac | −0.91 | 5.0 | 6.8 | 17.1 | — | — | — |
| 118rac | 16.9 | 19.5 | 23.8 | 36.6 | — | — | — |
| 18rac | 25.2 | 16.0 | 21.4 | 20.2 | — | — | — |
| 23rac | −1.0 | 8.0 | 8.5 | 16.0 | — | — | — |
| 119rac | 42.0 | 5.0 | 10.3 | 48.1 | — | — | — |
| 128mix | 81.9 | −2.9 | 19.2 | 23.4 | — | — | — |
| 129rac | 28.0 | 10.6 | 35.8 | 31.9 | — | — | — |
| 25S | 45.6 | −0.13 | 24.9 | 1.7 | — | — | — |
| 25R | 26.9 | 20.8 | 20.8 | −10.3 | — | — | — |

Uptake Inhibition. The ability of test compounds to block monoamine uptake by SERT, NET, DAT, and VMAT2 was determined using the Neurotransmitter Transporter Uptake Assay Kit manufactured by Molecular Devices (Cat #R8173). Briefly, stably transfected cells expressing the MAT of interest (HEK293 cells for SERT and NET; CHO cells for DAT) were grown and plated into 384-well plates at a concentration of 20,000 cells per well. Plates were then incubated for 16-20 h at 37° C. and 5% $CO_2$. The medium was then aspirated and replaced with 25 µL of assay buffer (20 mM HEPES in HBSS, containing 0.1% BSA) containing the test compounds at the appropriate concentrations. Plates were then centrifuged at 300 rpm for 15 s and then incubated at 37° C. for 30 minutes. At this time, 25 µL of the proprietary fluorescent dye solution was added, the plates were incubated at 37° C. for 60 minutes, and then fluorescence was quantified on a plate reader (excitation wavelength=440 nm, emission wavelength=520 nm). The proprietary dye solution contains a mixture of 1) a fluorescent dye that mimics the endogenous substrates of MATs and is thereby actively transported to the intracellular compartment In the presence of an inhibitor of the MAT under study, uptake of the dye is reduced, and therefore, the fluorescence is also decreased, allowing this inhibition to be quantified.

Radioligand Binding. Affinity of the test compounds for SERT, NET, and DAT was determined in radioligand binding experiments with [$^3$H]imipramine, [$^3$]nisoxetine, and [$^3$H]WIN35,428, respectively, by WuXi AppTec (Hong Kong) Limited, under the conditions described in Table 15.

TABLE 15

SERT, NET, and DAT radioligand binding experimental parameters.

| SERT | |
|---|---|
| Receptor Source | HEK293 cells stably expressing SERT |
| Incubation Time | 1 h |
| Incubation Temperature | 25° C. |
| Incubation Buffer | 50 mM Tris-HCl pH 7.4, 120 mM NaCl, 5 mM KCl |
| Ligand | 2.0 nM [$^3$H]imipramine |
| Non-Specific Ligand | 10.0 µM imipramine |

TABLE 15-continued

SERT, NET, and DAT radioligand binding experimental parameters.

| NET | |
| --- | --- |
| Receptor Source | HEK293 cells stably expressing NET |
| Incubation Time | 2 h |
| Incubation Temperature | 4° C. |
| Incubation Buffer | 50 mM Tris-HCl pH 7.4, 120 mM NaCl, 5 mM KCl |
| Ligand | 1.0 nM [$^3$H]nisoxetine |
| Non-Specific Ligand | 10.0 μM protriptyline |

| DAT | |
| --- | --- |
| Receptor Source | CHO-K1 cells stably expressing DAT |
| Incubation Time | 2 h |
| Incubation Temperature | 4° C. |
| Incubation Buffer | 50 mM Tris-HCl pH 7.4, 100 mM NaCl |
| Ligand | 12.5 nM [$^3$H]WIN35, 428 |
| Non-Specific Ligand | 10.0 μM BTCP |

Figures 3A, 3B, 3C, 3D, 3E, 3F, 3G:
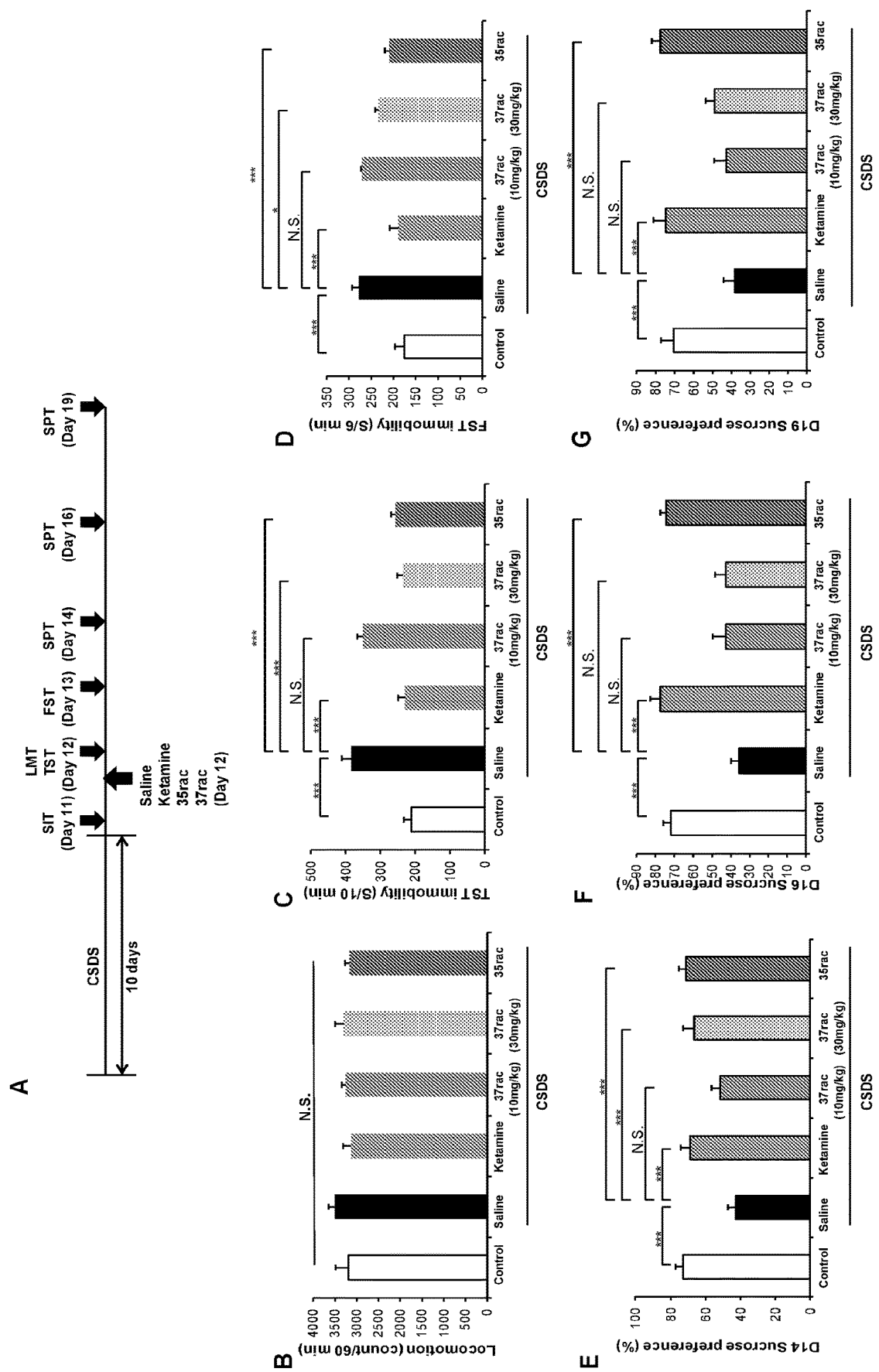
FIG. 3A-3G. shows the antidepressant-like effects of 35rac as compared to racemic ketamine and superior to 37rac in mice susceptible to a depression-like phenotype after chronic social defeat stress (CSDS). (3A) The schedule of the CSDS model, drug treatment, and behavioral tests. CSDS was performed from day 1 to day 10, and social interaction test (SIT) was performed on day 11. Saline (10 mL/kg), racemic ketamine (10 mg/kg), 37rac (10 mg/kg and 30 mg/kg), or 35rac (10 mg/kg) were administered i.p. to CSDS-susceptible mice on day 12. Locomotion (LMT) and tail suspension test (TST) were performed 1 and 3 h after injection, respectively. Forced swim test (FST) was performed 1 day after injection. Sucrose preference test (SPT) was performed 2, 4, and 7 days after injection. (3B) LMT (one-way ANOVA, F5,50=0.691, P=0.633). (3C) TST ($F_{5,50}$=15.481, P<0.001). (3D) FST ($F_{5,50}$=10.343, P<0.001). (3E) SPT on day 14 ($F_{5,50}$=6.670, P<0.001). (3F) SPT on day 16 ($F_{5,50}$=14.962, P<0.001). (3G) SPT on day 19 ($F_{5,50}$=11.310, P<0.001). Data are shown as mean±S.E.M. (n=8-12). *p<0.05, p<0.01, *p<0.001. ns=not significant, p>0.05.
Figures 4A, 4B, 4C, 4D, 4E, 4F, 4G:
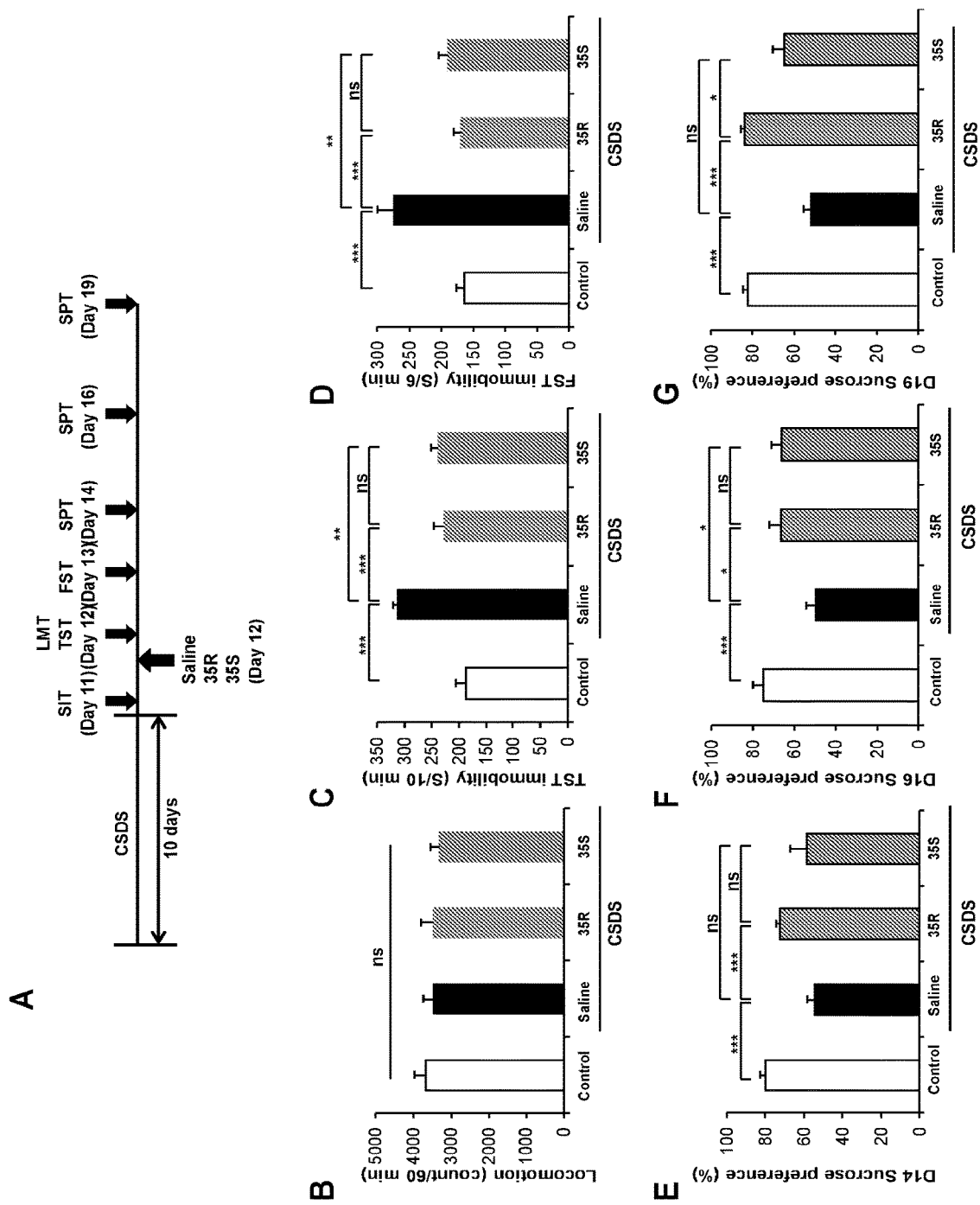
FIG. 4A-4G. shows the antidepressant-like effects of 35R vs. 35S in mice susceptible to a depression-like phenotype after chronic social defeat stress (CSDS). (4A) The schedule of the CSDS model, drug treatment, and behavioral tests. CSDS was performed from day 1 to day 10, and social interaction test (SIT) was performed on day 11. Saline (10 mL/kg), 35R (14.4 mg/kg), or 35S (14.4 mg/kg) were administered i.p. to CSDS-susceptible mice on day 12. Locomotion (LMT) and tail suspension test (TST) were performed 1 and 3 h after injection, respectively. Forced swim test (FST) was performed 1 day after injection. Sucrose preference test (SPT) was performed 2, 4, and 7 days after injection. (4B) LMT (one-way ANOVA: $F_{3,28}$=0.296, p=0.828). (4C) TST ($F_{3,28}$=12.550, p<0.001). (4D) FST ($F_{3,28}$=10.551, p<0.001). (4E) SPT on day 14 ($F_{3,28}$=7.062, p<0.001). (4F) SPT on day 16 ($F_{3,28}$=5.864, p<0.001). (4G) SPT on day 19 ($F_{3,28}$=17.874, p<0.001). Data are shown as mean±S.E.M. (n=8). *p<0.05, p<0.01, *p<0.001. ns=not significant, p>0.05.

Example 29. Effects on Behavioral Tests After Chronic Social Defeat Stress in Mice In mice, compound 35rac reversed the pro-depressive effects induced by chronic social defeat stress (CSDS) in several behavioral tests (FIG. 3). This antidepressant-like activity was observed at the same dose (10 mg/kg, i.p.) as was effective with racemic ketamine Compound 37rac was not effective at this dose level in the same model and even at a 3-fold higher dose (30 mg/kg, i.p.), was only partially effective (FIG. 3). Further, the enantiomers of compound 35, 35R and 35S, induced antidepressant-like effects in the same CSDS model (FIG. 4). Notably, the antidepressant-like effects of the 35R enantiomer were more robust and longer lasting than the 35S enantiomer when each drug was given at the same dose. At the same time, despite equipotent antidepressant activity, compound 35R displayed weaker NMDAR binding than compounds 35S and 35rac, racemic ketamine, and R-ketamine (see above Example 27), suggesting that it may possesses a superior separation between dissociative side effects (driven by potency of binding at NMDAR) and therapeutic effects in depression.

Animals. Male adult C57BL/6 mice, aged 8 weeks (body weight 20-25 g, Japan SLC, Inc., Hamamatsu, Japan) and male adult CD1 mice, aged 13-15 weeks (body weight>40 g, Japan SLC, Inc., Hamamatsu, Japan) were used in the experiments. Animals were housed under controlled temperatures and 12-hour light/dark cycles (lights on between 07:00-19:00 h), with ad libitum food and water. The protocol was approved by the Chiba University Institutional Animal Care and Use Committee (Permission number: 29-397 and 30-397). This study was carried out in strict accordance with the recommendations in the Guide for the Care and Use of Laboratory Animals of the National Institutes of Health. All efforts were made to minimize suffering.

Drugs and Drug Administration. Racemic ketamine hydrochloride for injection was obtained as a commercial solution (Ketalar®, ketamine hydrochloride, Daiichi Sankyo Pharmaceutical Ltd., Tokyo, Japan) and administered intraperitoneally (i.p.) at a dose of 10 mg/kg. Compounds 35rac and 37rac were synthesized as described above (Example 1) and administered i.p. as the HCl salts at doses of 10 mg/kg (35rac and 37rac) and 30 mg/kg (37rac only). The enantiomers of compound 35, 35R and 35S, were synthesized as described above (Example 1) and administered i.p. as the hydrogen tartrate salts 35R-L-tartrate and 35S-D-tartrate at a dose of 14.4 mg/kg (equivalent to 10 mg/kg of the HCl salt). Doses were selected based on prior literature with ketamine and its enantiomers (Yang et al. 2015; Zhang et al. 2014).

Chronic Social Defeat Stress (CSDS) Model. The social defeat procedure was performed as previously reported (Berton et al. 2006; Golden et al. 2011; Ren et al. 2016; Yang et al. 2015; Zhang et al. 2015). Every day the C57BL/6 mice were exposed to a different CD1 aggressor mouse for 10 min, and this was repeated for 10 days. When the social defeat session ended, the resident C57 mouse and the intruder CD1 mouse were each housed in one half of a cage separated by a perforated Plexiglas divider to allow visual, olfactory, and auditory contact for the remainder of the 24-h period. At 24 h after the last social defeat session, all mice were housed individually. On day 11, a social interaction test (SIT) was performed to identify subgroups of mice that were susceptible and unsusceptible to social defeat stress. This was accomplished by placing mice in an interaction test box (42×42 cm) with an empty wire mesh cage (10×4.5 cm) located at one end. The movement of the mice was tracked for 2.5 min, followed by 2.5 min in the presence of an unfamiliar aggressor confined in the wire mesh cage. The duration of the subject's presence in the "interaction zone" (defined as the 8-cm-wide area surrounding the wire mesh cage) was recorded by a stopwatch. The interaction ratio was calculated as time spent in the interaction zone with an aggressor/time spent in the interaction zone without an aggressor. An interaction ratio of 1 was set as the cutoff: mice with scores <1 were defined as "susceptible" to social defeat stress and those with scores >1 were defined as "unsusceptible". Only susceptible mice were used in the subsequent experiments.

Behavioral Tests. Behavioral tests were performed as previously reported previously (Ren et al. 2016; Yang et al. 2015; Zhang et al. 2015).

Locomotion (LMT): Locomotor activity was measured in experimental cages (length×width×height: 560×560×330 mm) by an animal movement analysis system SCANET MV-40 (MELQUEST Co., Ltd., Toyama, Japan). The cumulative activity was recorded for 60 minutes. Cages were cleaned between testing sessions.

Tail suspension test (TST): A small piece of adhesive tape was placed approximately 2 cm from the tip of the tail. A single hole was punched in the tape and mice were hung individually, on a hook. The immobility time was recorded for 10 minutes. Mice were considered immobile only when they hung passively and completely motionless.

Forced swimming test (FST): The FST was tested by an automated forced-swim apparatus SCANET MV-40 (MELQUEST Co., Ltd., Toyama, Japan). Mice were placed individually in a cylinder (diameter: 23 cm; height: 31 cm) containing 15 cm of water, maintained at 23±1° C. The activity of each mouse was recorded for 6 minutes Immobility time was calculated by the apparatus analysis software from activity time as (total time)—(active time).

Sucrose preference test (SPT): Mice were exposed to water and 1% sucrose solution for 48 h, followed by 4 hours of water and food deprivation and then a 1-hour exposure to two identical bottles, one containing water, and the other containing 1% sucrose solution. The bottles containing water and sucrose solution were weighed before and at the end of this 1-hour test period and the sucrose preference was determined as (sucrose solution consumed)/(sucrose solution consumed+water consumed).

Statistical Analysis. The data points shown are the mean±standard error of the mean (SEM). Analysis was performed using PASW Statistics 20 (formerly SPSS Statistics; SPSS). Comparisons between groups were performed using the one-way analysis of variance (ANOVA), followed by post-hoc Fishers Least Significant Difference (LSD) test. P-values of less than 0.05 were considered statistically significant.

Example 30. Forced Swim Test in Mice—30-Minute Pre-Treatment

Figure 5:
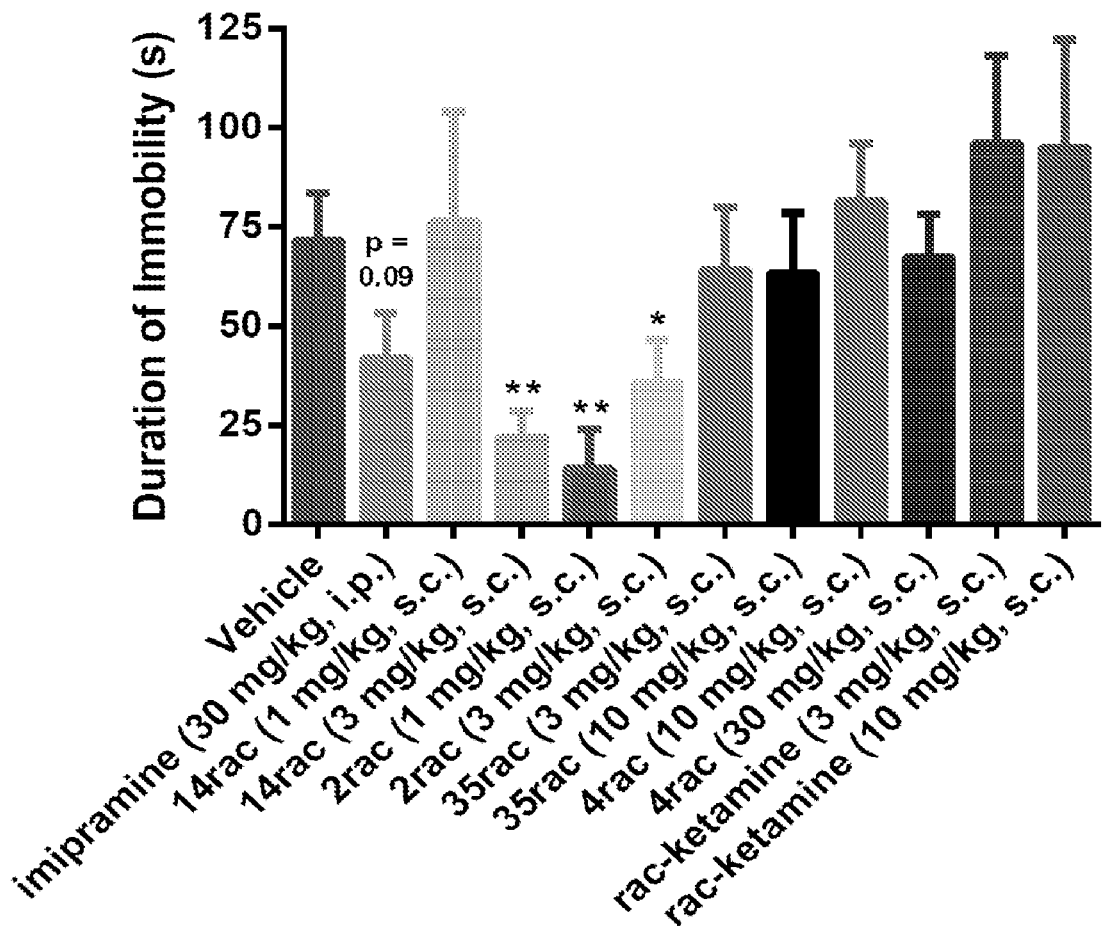
FIG. 5. shows the results of 2rac and 14rac in a forced swim test model. Mice were treated with drug at the indicated doses and 30 minutes later, were placed in the FST tank and cumulative duration of immobility was quantified over the entire 6-minute test session. Compounds 2rac and 14rac reduced time immobile and had a stronger effect than the control antidepressant imipramine. The other tested compounds had no effect. Unpaired, two-tailed t tests (not corrected for multiple comparisons): **p<0.01, *p<0.05, relative to vehicle. n=10 per treatment. All values are expressed as the mean±SEM.

Racemic compounds 2rac and 14rac induced antidepressant-like effects in the forced swim test (FST) in mice with a 30-minute pre-treatment time (FIG. 5). Specifically, the compounds reduced immobility time relative to vehicle control, indicative of an antidepressant-like effect. The reductions in immobility seen with 2rac and 14rac were also of a greater magnitude than the effect of the control antidepressant imipramine In contrast, racemic ketamine (rac-ketamine) and compounds 4rac and 35rac did not have effects in this test, even at higher doses than were effective with 2rac and 14rac.

Animals. Male Swiss Webster mice, aged 4-5 weeks (body weight 25-30 g, Envigo) were used in the experiments Animals were housed in groups of 4-5 under controlled temperatures and 12-hour light/dark cycles, with ad libitum food (Teklad 7001 rodent diet) and water. These studies were carried out in strict accordance with the recommendations in the Guide for the Care and Use of Laboratory Animals of the National Institutes of Health. All efforts were made to minimize suffering.

Drugs and Drug Administration. Imipramine hydrochloride was administered intraperitoneally (i.p.) at a dose of 30 mg/kg. Other compounds were tested as the racemates (indicated by "rac" nomenclature) and were administered subcutaneously (s.c.) as the hydrochloride salts. Normal saline was used as the vehicle and all compounds were administered at a volume of 10 mL/kg, 30 minutes before behavioral testing.

Forced Swim Test (FST). Group size was n=10 per treatment Animals were acclimated to the testing room 30 minutes prior to behavioral testing. Mice were placed individually in a cylinder of water measuring 5 inches wide by 10 inches tall and maintained at 24-25° C. The activity of each mouse was recorded for 6 minutes using Noldus Ethovision tracking software, with periods of inactivity being automatically quantified.

Statistical Analysis. The data points shown are the mean±standard error of the mean (SEM). Analysis was performed using GraphPad Prism 6. Indicated statistical comparisons represent the results of unpaired, two-tailed t tests relative to vehicle (not corrected for multiple comparisons).

Example 31. Forced Swim Test in Mice—2-h Pre-Treatment

Figure 6:
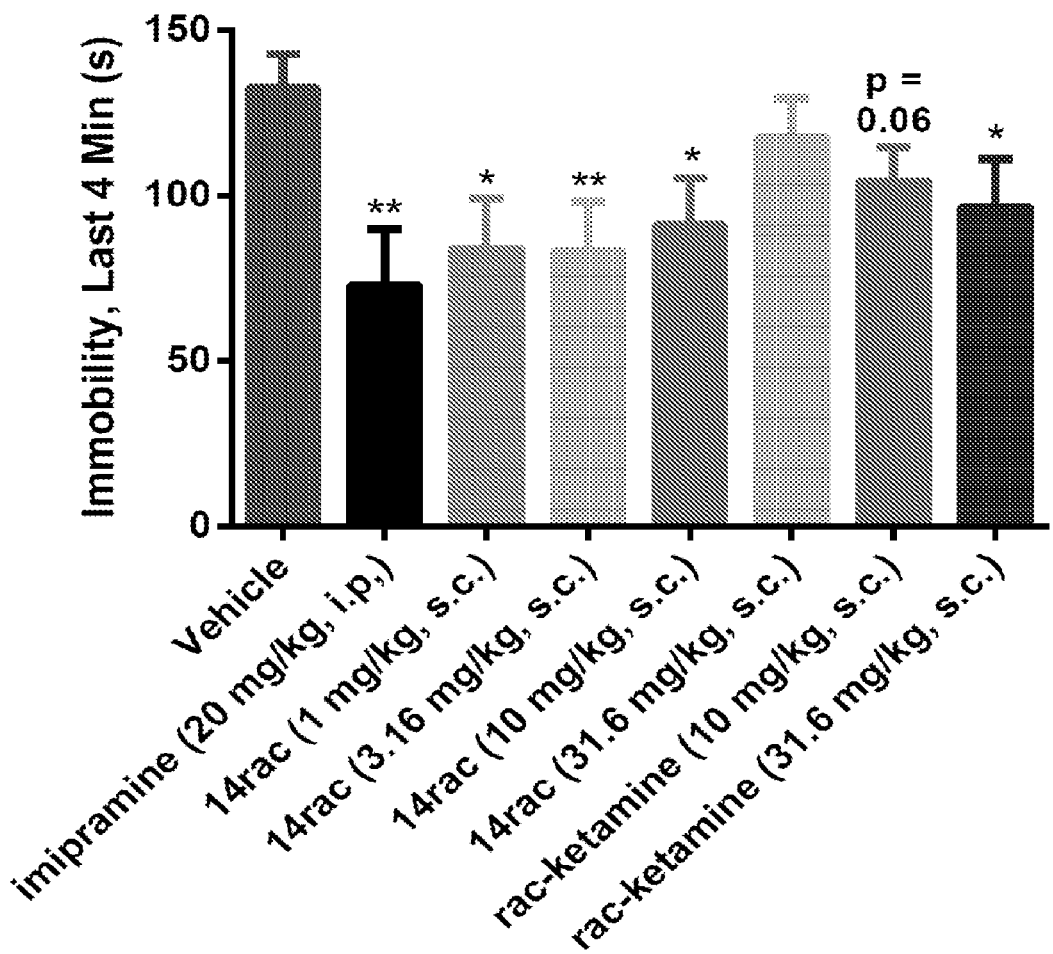
FIG. 6. shows the antidepressant-like effects of compound 14rac in a forced swim test (FST). Mice were treated with drug at the indicated doses and 2 h later, were placed in the FST tank and cumulative duration of immobility was quantified over the last 4 minutes of the test session. Compound 14rac reduced time immobile and had a stronger and more potent effect than racemic ketamine (rac-ketamine) Unpaired, two-tailed t tests (not corrected for multiple comparisons): **p<0.01, *p<0.05, relative to vehicle. n=10 per treatment except for vehicle and rac-ketamine groups, which represent n=20 per treatment. All values are expressed as the mean±SEM.

Racemic compound 14rac induced antidepressant-like effects in the forced swim test (FST) in mice with a 2-h pre-treatment time (FIG. 6). Specifically, the compound reduced immobility time relative to vehicle control, indicative of an antidepressant-like effect. The reduction in immobility seen with 14rac was of a similar magnitude to that seen with the control antidepressant imipramine and greater than that of racemic ketamine (rac-ketamine) Further, compound 14rac was at least 30-fold more potent than rac-ketamine at reducing immobility in this test.

Animals. Male CD-1 mice, aged ~8 weeks (body weight ~25-30 g), were used in the experiments. Animals were singly housed under controlled temperatures and 12-hour light/dark cycles, with ad libitum food and water. These studies were carried out in strict accordance with the recommendations in the European Convention for the Protection of Vertebrate Animals Used for Experimental and Other Scientific Purposes. All efforts were made to minimize suffering.

Drugs and Drug Administration. Imipramine hydrochloride was administered intraperitoneally (i.p.) at a dose of 20 mg/kg. Other compounds were tested as the racemates (indicated by "rac" nomenclature) and were administered subcutaneously (s.c.) with doses calculated based on the freebase. Normal saline was used as the vehicle and all compounds were administered at a volume of 5 mL/kg, 2 h before behavioral testing.

Forced Swim Test (FST). Group size was n=10 per treatment, except for vehicle and rac-ketamine groups, which represented n=20 per treatment. Mice were placed individually in a glass cylinder measuring 19 cm wide by 30 cm tall and filled with 24° C. water to a depth of 18 cm. The activity of each mouse was video recorded during each 6-minute session and total immobility time was scored during the last 4 minutes of the session. The water was changed between each mouse to avoid any influence on behavior.

Statistical Analysis. The data points shown are the mean±standard error of the mean (SEM). Analysis was performed using GraphPad Prism 6. Indicated statistical comparisons represent the results of unpaired, two-tailed t tests relative to vehicle (not corrected for multiple comparisons).

Example 32. Forced Swim Test in Rats

Figure 7:
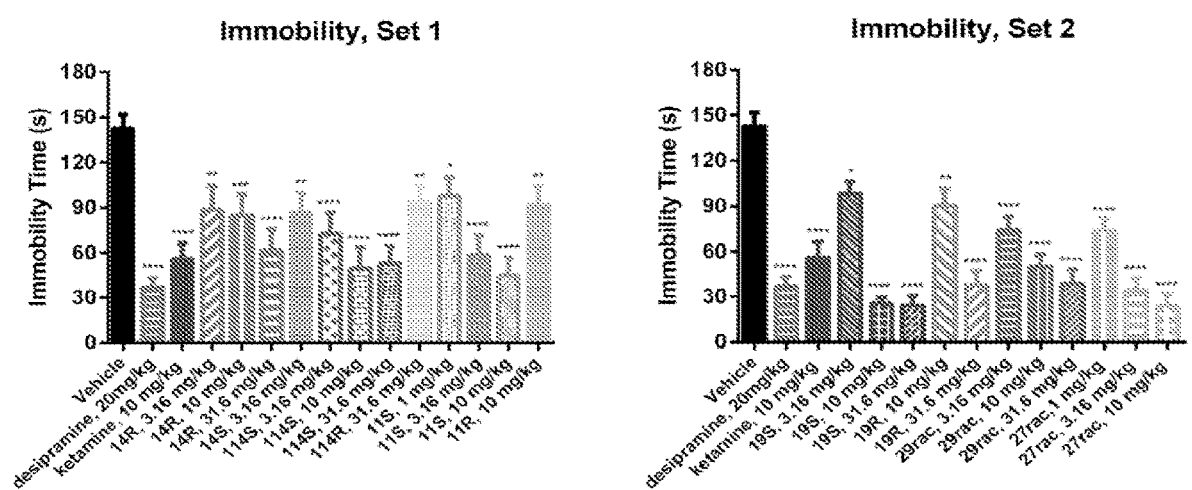
FIG. 7. indicates activity of compounds on the duration or immobility in the forced swim test (FST) in rats at 23.5 h post treatment. For clarity, the data has been divided into two panels, but these represent the same experiment, with the vehicle, desipramine, and ketamine groups being the same in the two panels. One-way ANOVA: $F_{25,254}$=9.163, p<0.0001. **p<0.0001, *p<0.001, **p<0.01, *p<0.05 relative to vehicle. n=10 per treatment except for vehicle and desipramine groups, which represent n=20 per treatment. All values are expressed as the mean±SEM.
Figure 8:
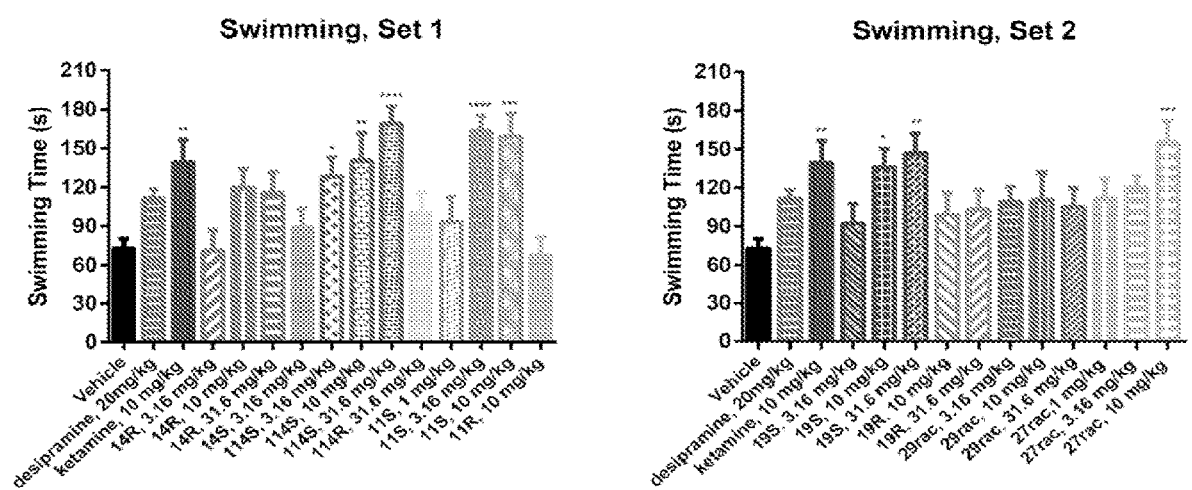
FIG. 8. shows certain disclosed compounds and their effect on swimming behavior in the forced swim test (FST) in rats at 23.5 h post treatment. For clarity, the data has been divided into two panels, but these represent the same experiment, with the vehicle, desipramine, and ketamine groups being the same in the two panels. One-way ANOVA: $F_{25,254}$=3.862, p<0.0001. **p<0.0001, *p<0.001, **p<0.01, *p<0.05 relative to vehicle. n=10 per treatment except for vehicle and desipramine groups, which represent n=20 per treatment. All values are expressed as the mean±SEM.
Figure 9:
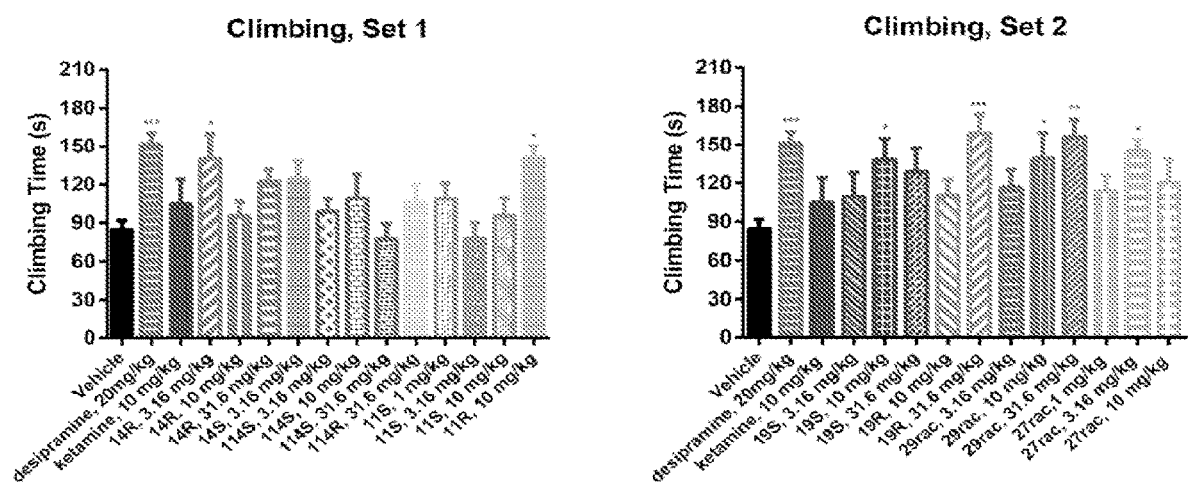
FIG. 9. shows certain disclosed compounds and their effect on increased climbing behavior in the forced swim test (FST) in rats at 23.5 h post treatment. For clarity, the data has been divided into two panels, but these represent the same experiment, with the vehicle, desipramine, and ketamine groups being the same in the two panels. One-way ANOVA: $F_{25,254}$=3.048, p<0.0001. *p<0.001, p<0.01, *p<0.05 relative to vehicle. n=10 per treatment except for vehicle and desipramine groups, which represent n=20 per treatment. All values are expressed as the mean±SEM.

Disclosed compounds induced antidepressant-like effects in the forced swim test (FST) in rats with a 23.5-h pre-treatment time (FIGS. 7-9). Specifically, the compounds reduced immobility time relative to vehicle control, indicative of an antidepressant-like effect. These effects on immobility were observed 23.5 hours after a single compound administration, a time point at which most or all of the drug has been cleared from the systemic circulation. Additionally, certain compounds induced increases in swimming (FIG. 8) and/or climbing (FIG. 9) behavior during the test.

Animals. Male Sprague Dawley rats, aged 8-10 weeks, were used in the experiments. Animals were housed in groups of 2 under controlled temperature (22±3° C.) and relative humidity (30-70%) conditions, with 12-hour light/dark cycles, and with ad libitum food and water. These studies were carried out in strict accordance with the requirements of the Committee for the Purpose of Control and Supervision of Experiments on Animals (CPCSEA), India. All efforts were made to minimize suffering.

Drugs and Drug Administration. Test compounds, saline vehicle, and the positive control desipramine were administered subcutaneously (s.c.), with doses calculated based on the freebase. The ketamine used was racemic. The stereochemistry of other compounds used was as indicated. Normal saline was used as the vehicle for compounds provided as the HCl salt, while saline acidified with 1-2 molar equivalents of HCl was used as the vehicle for compounds provided as the freebase (to form the soluble HCl salt in situ). All compounds were administered at a volume of 5 mL/kg. Test compounds and vehicle were administered 0.5 h after the start of the training swim (Swim 1) and 23.5 h before the test swim (Swim 2). Desipramine was administered 3 times, at 23.5 h, 5 h, and 1 h before the test swim (Swim 2), each time at a dose of 20 mg/kg.

Forced Swim Test (FST). Animals were randomized based on body weight, and it was ensured that inter-group variations were minimal and did not exceed ±20% of the mean body weight across the groups. Group size was n=10 per treatment, except for the vehicle and desipramine groups, which were n=20. Rats were handled for about 2 min daily for the 5 days prior to the beginning of the experimental procedure. On the first day of the experiment (i.e. Day 0), post randomization, training swim sessions (Swim 1) were conducted between 12:00 and 18:00 h with all animals by placing rats in individual glass cylinders (46 cm tall×20 cm in diameter) containing 23-25° C. water 30 cm deep for 15 minutes. At the conclusion of Swim 1, animals were dried with paper towels, placed in heated drying cages for 15 minutes, and then returned to their home cages Animals were then administered the appropriate drug or vehicle treatment(s), as described above. For clarity, a compound administration time of 23.5 h before Swim 2 means 0.5 h after the start of Swim 1 and 0.25 h after the completion of Swim 1 (i.e. immediately after return to the home cage). On Day 1 (i.e. 24 h after start of Swim 1), animals performed the test swim (Swim 2) for a period of 5 min but otherwise under the same conditions as Swim 1. During all swim sessions, the water was changed between each animal.

Behavioral scoring was conducted by observers who were blind to the treatment groups. Animals were continuously observed during Swim 2 and the total time spent engaging in the following behaviors was recorded: immobile, swimming, and climbing. A rat was judged to be immobile when it remained floating in the water without struggling and was making only those movements necessary to keep its head above water. A rat was judged to be swimming when it made active swimming motions, more than necessary to merely maintain its head above water (e.g. moving around in the cylinder). A rat was judged to be climbing when it made active movements with its forepaws in and out of the water, usually directed against the walls.

Statistical Analysis. The data points shown are the mean±standard error of the mean (SEM). Analysis was performed using GraphPad Prism 6. Comparisons between groups were performed using the one-way analysis of variance (ANOVA), followed by Dunnett's test for comparisons to vehicle.

Example 33. Conditioned Place Preference in Mice

Figure 10:
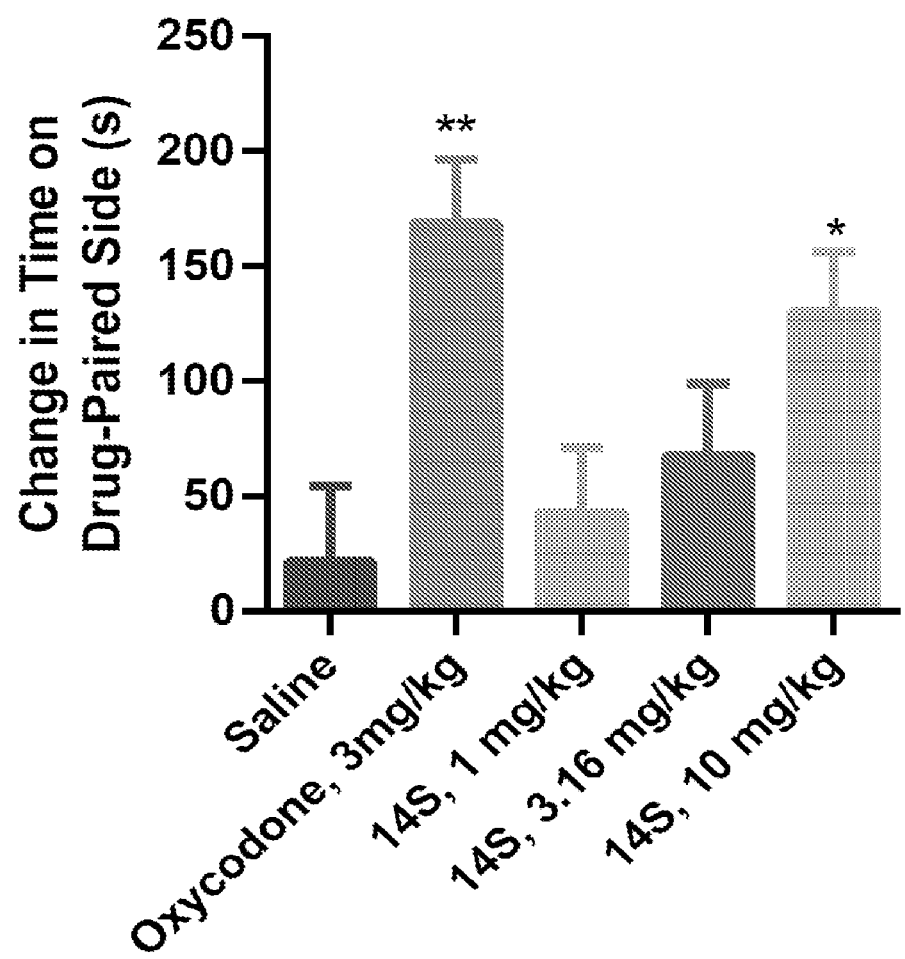
FIG. 10. Compound 14S induced significant preference in the conditioned place preference assay in mice. One-way ANOVA: $F_{4,45}$=4.399, p=0.0044. **p<0.01, *p<0.05 relative to saline vehicle. n=10 per treatment. All values are expressed as the mean±SEM.
Figure 11:
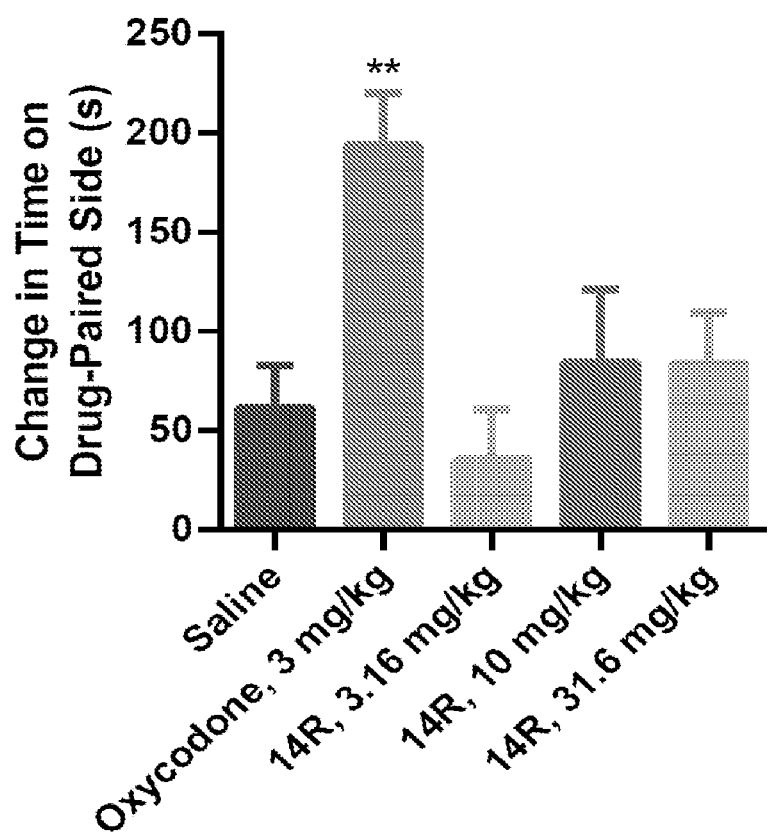
FIG. 11. Compound 14R induced neither preference nor aversion in the conditioned place preference assay in mice. One-way ANOVA: $F_{4,43}$=4.559, p=0.0037. **p<0.01 relative to saline vehicle. n=10 per treatment. All values are expressed as the mean±SEM.

In the conditioned place preference model of abuse liability in mice, compound 14S induced a dose-dependent and significant preference of similar magnitude to the opioid agonist control oxycodone (FIG. 10). In contrast, compound 14R induced neither preference nor aversion (FIG. 11), even at doses up to 3-fold higher than the dose that elicited preference with 14S.

Animals. Male C57BL/6 mice, 5-8 weeks of age, (body weight 25-30 g; Envigo, Indianapolis, Ind., USA) were housed 5 per polycarbonate tub with soft bedding in a temperature- and humidity-controlled vivarium. Mice were maintained under a 12-h light/dark cycle with lights on at 06:00. Food and water were available ad libitum Animals acclimated to the vivarium 1 week prior to experimental manipulations.

Drugs and Drug Administration. Test compounds and saline vehicle were administered subcutaneously (s.c.), with doses calculated based on the HCl salt, while the positive control oxycodone was administered intraperitoneally (i.p.), with the dose calculated based on the HCl salt. Normal saline was used as the vehicle. All compounds were administered at a volume of 10 mL/kg. Test compounds, positive control, or vehicle were administered immediately before the start of each conditioning session.

Conditioned Place Preference. Reward and/or aversion was assessed in conditioned place preference chambers (Model MED-CPP-3013; Med Associates, St. Albans, Vt.). Each chamber (16.75×12.70 cm) has two stimulus-distinct conditioning chambers (wall color and flooring texture) separated by a third central start chamber. Manual guillotine doors permit confinement/access to individual chambers.

Group size was n=10 per treatment. Mice were habituated to the chambers for 15 minutes. The following day, the mice were placed back into the chambers for 15 minutes to establish baselines preferences. Drugs were then administered over 6 total, 45-minute conditioning trials whereby the drug of interest is paired to the compartment less preferred (based on baseline score) during 3 conditioning trials (S+) and the vehicle is paired to the preferred compartment (based on baseline score) during 3 conditioning trials (S−). Final drug preference is assessed in a 15-minute post-conditioning trial and is calculated by subtracting the time in the drug-paired compartment at baseline from the time in the drug-paired compartment post-conditioning, with positive values reflecting reward and negative values reflecting aversion.

For all trials, time spent in chambers as well as movement was quantified by infrared photobeam detectors and calculated by Med-PC IV software. Movement was defined as consecutive beam breaks within in a chamber to detect forward locomotion. The test apparatus was thoroughly cleaned with 70% ethanol solution after each trial.

Statistical Analysis. The data points shown are the mean±standard error of the mean (SEM). Analysis was performed using GraphPad Prism 6. Comparisons between groups were performed using the one-way analysis of variance (ANOVA), followed by Dunnett's test for comparisons to vehicle.

Example 34. Effects of Additional Compounds in the Forced Swim Test in Mice

Additional compounds of the present invention are tested in the acute forced swim test (FST) in mice according to the procedures described in Example 30 and 31. Test compounds or vehicle are administered to groups of mice and 30 minutes or 2 h later, duration of immobility is recorded during a 6-minute test swim.

Example 37. Effects of Additional Compounds in the Forced Swim Test in Rats

Additional compounds of the present invention are tested in the forced swim test (FST) in rats using the general procedure of Detke (Detke et al. 1995), but modified such that test compounds are administered only once, 23.5 h before the test swim, as further described in Example 32.

Example 38. Synthesis of Additional Compounds

Additional compounds of the present invention may be prepared and separated into their enantiomers by standard methods known to those skilled in the art of organic synthesis, for example, those presented in Examples 1-20 and additional procedures shown in Schemes 2-5. It should be understood that the relationship between a particular enantiomer of a given basic compound and the necessary enantiomer of a selected chiral acid used for its resolution (as the diastereomeric salt) is compound specific and thus, such relationships exemplified in Scheme 2 are only representative. The enantiomers of a particular compound may also be separated by chiral chromatography using methods well known in the art.

Scheme 2. Preparation and chiral resolution of additional compounds.

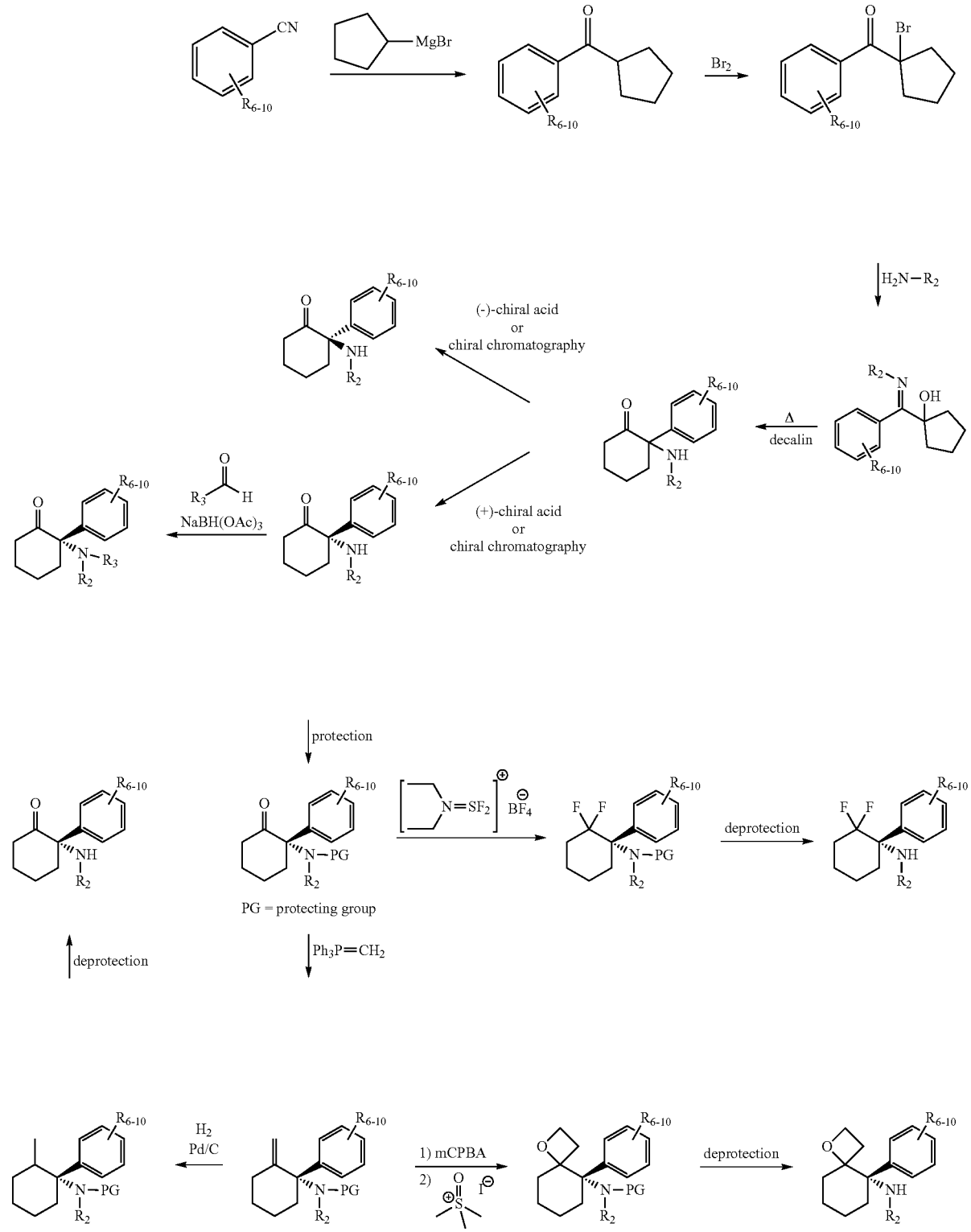

Scheme 3
Preparation of compounds containing a thiophene or thiazole moiety.

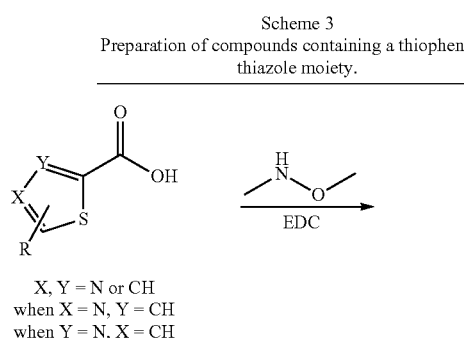

X, Y = N or CH
when X = N, Y = CH
when Y = N, X = CH

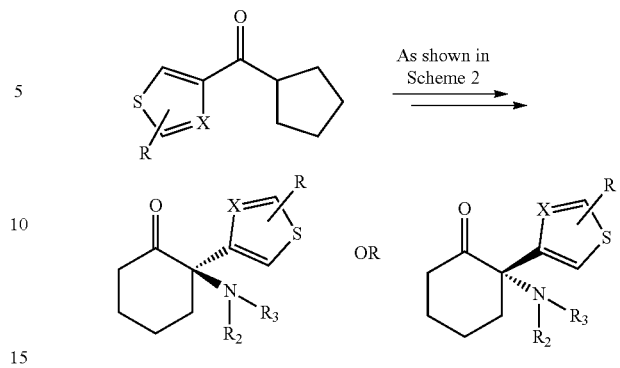

Scheme 4. Preparation of compounds containing a cyclic amine moiety.

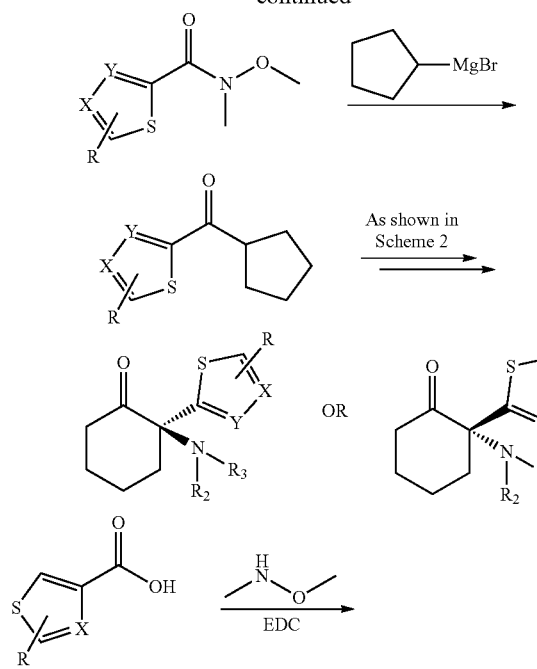

Scheme 5.
Preparation of compounds deuterated at the position alpha to the ketone.

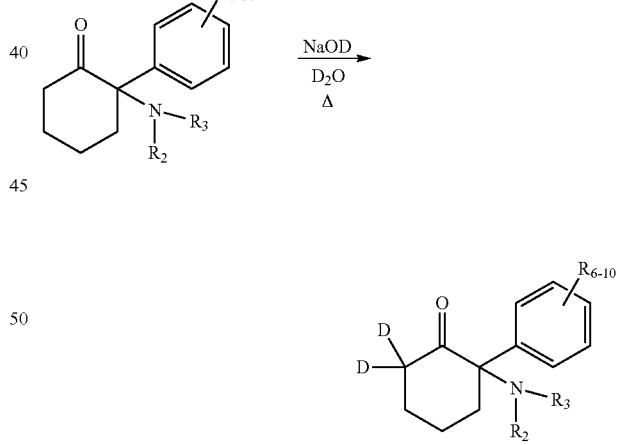

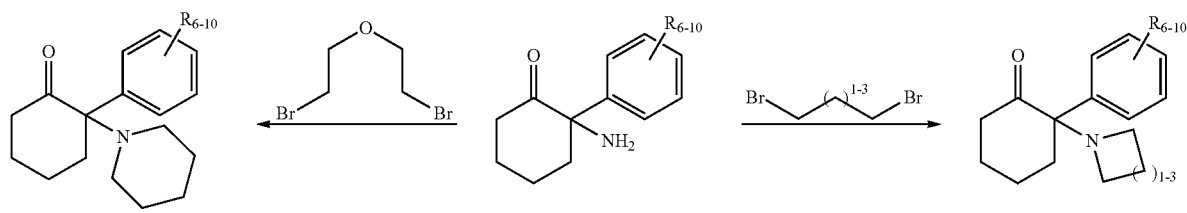

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:
1. A compound represented by:
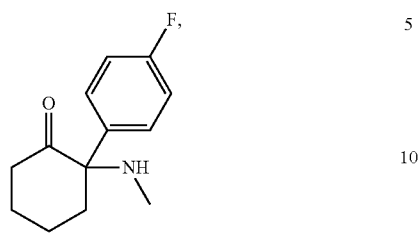
or a pharmaceutically acceptable salt thereof.
2. A pharmaceutical composition comprising a compound of claim 1 and a pharmaceutically acceptable excipient.
* * * * *